US007262318B2

(12) United States Patent
Hamanaka et al.

(10) Patent No.: US 7,262,318 B2
(45) Date of Patent: Aug. 28, 2007

(54) SUBSTITUTED HETEROARYL- AND PHENYLSULFAMOYL COMPOUNDS

(75) Inventors: Ernest S. Hamanaka, Gales Ferry, CT (US); Marcus E. Kehrli, Jr., Ames, IA (US)

(73) Assignee: Pfizer, Inc., New York, NY (US)

( * ) Notice: Subject to any disclaimer, the term of this patent is extended or adjusted under 35 U.S.C. 154(b) by 394 days.

(21) Appl. No.: 11/012,139

(22) Filed: Dec. 16, 2004

(65) Prior Publication Data

US 2005/0228015 A1 Oct. 13, 2005

Related U.S. Application Data

(60) Provisional application No. 60/552,114, filed on Mar. 10, 2004.

(51) Int. Cl.
*C07C 321/00* (2006.01)
*A61K 8/64* (2006.01)
*A01N 65/00* (2006.01)

(52) U.S. Cl. ............... 560/17; 424/70.5; 514/71
(58) Field of Classification Search ........... 560/17; 424/70.5; 514/71
See application file for complete search history.

(56) References Cited

U.S. PATENT DOCUMENTS

| | | | |
|---|---|---|---|
| 3,658,990 A | 4/1972 | Werner | 424/228 |
| 3,806,542 A | 4/1974 | Werner | 260/518 |
| 3,812,104 A | 5/1974 | Werner | 260/239.6 |
| 3,843,662 A | 10/1974 | Holland | 260/293.73 |
| 3,879,402 A | 4/1975 | Holland | 260/293.73 |
| 3,929,803 A | 12/1975 | Holland | 260/293.62 |
| 4,495,439 A | 1/1985 | Shimoma et al. | 313/412 |
| 5,413,892 A | 5/1995 | Matsuura et al. | 430/110 |
| 6,063,173 A | 5/2000 | Torii et al. | 106/31.17 |
| 6,200,995 B1 | 3/2001 | De la Brouse-Elwood et al. | 514/347 |
| 6,316,450 B1 | 11/2001 | Bromidge et al. | 514/253.05 |
| 6,528,528 B2 | 3/2003 | Connor et al. | 514/312 |
| 6,583,157 B2 | 6/2003 | McGee et al. | 514/312 |
| 6,620,827 B2 | 9/2003 | De la Brouse-Elwood et al. | 514/347 |
| 6,653,332 B2 | 11/2003 | Jaen et al. | 514/347 |
| 2003/0187001 A1 | 10/2003 | Calderwood et al. | 514/265.1 |
| 2004/0102500 A1 | 5/2004 | Cano et al. | 514/384 |
| 2004/0235212 A1 | 11/2004 | Ishizaki | 438/46 |
| 2004/0254160 A1 | 12/2004 | Starke et al. | 514/211.09 |
| 2005/0014833 A1 | 1/2005 | Clark et al. | 514/561 |
| 2005/0020684 A1 | 1/2005 | Brooks et al. | 514/562 |
| 2005/0288340 A1 | 12/2005 | Hamanaka | 514/365 |

FOREIGN PATENT DOCUMENTS

| | | |
|---|---|---|
| CH | 558789 | 2/1975 |
| EP | 0068407 | 1/1983 |
| EP | 0068408 | 1/1983 |
| GB | 2090136 | 7/1982 |
| GB | 0378179 | 2/2003 |
| JP | 0216543 | 1/1990 |
| JP | 200189412 | 4/2001 |
| WO | WO9938845 | 8/1999 |
| WO | WO 0174786 | 10/2001 |
| WO | WO 0182916 | 11/2001 |
| WO | WO 0238553 | 5/2002 |
| WO | WO 02100813 | 12/2002 |
| WO | WO 03016265 | 2/2003 |
| WO | WO 03020710 | 3/2003 |
| WO | WO 03043997 | 5/2003 |
| WO | WO 03087044 | 10/2003 |
| WO | WO0182916 A2 * | 8/2006 |

OTHER PUBLICATIONS

*English language equivalent to JP 02-16543.
Spain, J. N., et al., *Tri-State Dairy Nutrition Conference*, pp. 13-34, (2001).
Douglas, G. N., et al., Lipid metabolism and production by Holstein cows fed control or high fat diets at restricted or ad libitum Intakes during the dry period, *J. Dairy Science*, vol. 81, Suppl. 1, p. 295, (1998).
English language translation of JP 2001-89412.
* Equivalent to WO 99/38845.
**Equivalent to WO 01/842916.
*Equivalent to WO 02/38553.
**Equivalent to WO 03/043997.
***Equivalent to WO 03/020710.
****Equivalent to WO 03/016265.
*****Equivalent to WO 02/100813.

* cited by examiner

*Primary Examiner*—Samuel A Barts
*Assistant Examiner*—Lalitha Nagubandi
(74) *Attorney, Agent, or Firm*—Gregg C. Benson; Lisa A. Samuels

(57) ABSTRACT

The present invention is directed at substituted heteroaryl- and phenylsulfamoyl compounds, pharmaceutical compositions containing such compounds and the use of such compounds as peroxisome proliferator activator receptor (PPAR) agonists. PPAR alpha activators, pharmaceutical compositions containing such compounds and the use of such compounds to elevate certain plasma lipid levels, including high density lipoprotein-cholesterol and to lower certain other plasma lipid levels, such as LDL-cholesterol and triglycerides and accordingly to treat diseases which are exacerbated by low levels of HDL cholesterol and/or high levels of LDL-cholesterol and triglycerides, such as atherosclerosis and cardiovascular diseases, in mammals, including humans. The compounds are also useful for the treatment of negative energy balance (NEB) and associated diseases in ruminants.

13 Claims, 1 Drawing Sheet

SUBSTITUTED HETEROARYL- AND PHENYLSULFAMOYL COMPOUNDS

BACKGROUND OF INVENTION

The present invention relates to substituted heteroaryl- and phenylsulfamoyl-compounds, pharmaceutical compositions containing such compounds and the use of such compounds as peroxisome proliferator activator receptor (PPAR) agonists. The subject compounds are particularly useful as PPARα agonists and to treat atherosclerosis, hypercholesterolemia, hypertriglyceridemia, diabetes, obesity, osteoporosis and Syndrome X (also known as metabolic syndrome) in mammals, including humans. The compounds are also useful for the treatment of negative energy balance (NEB) and associated diseases in ruminants.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, gives rise to development of the "fibrous plaque," which consists of accumulated intimal smooth muscle cells laden with lipid and surrounded by extra-cellular lipid, collagen, elastin and proteoglycans. These cells plus matrix form a fibrous cap that covers a deeper deposit of cell debris and more extra-cellular lipid. The lipid is primarily free and esterified cholesterol. The fibrous plaque forms slowly, and is likely in time to become calcified and necrotic, advancing to the "complicated lesion," which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Additional independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes could be improved. The use of insulin typically requires multiple daily doses. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and in more severe cases, insulin. However, the clinically available hypoglycemic agents can have side effects that limit their use. In the case of insulin dependent diabetes mellitus (Type I), insulin is usually the primary course of therapy.

Thus, although there are a variety of anti-atherosclerosis and diabetes therapies, there is a continuing need and a continuing search in this field of art for alternative therapies.

Moreover, negative energy balance (NEB) is a problem frequently encountered in ruminants particularly dairy cows. NEB may be experienced at any time during the cows life but it is particularly prevalent during the transition period. The ruminant transition period is defined as the period spanning late gestation to early lactation. This is sometimes defined as from 3 weeks before to three weeks after parturition, but has been expanded to 30 days prepartum to 70 days postpartum (J N Spain and W A Scheer, Tri-State Dairy Nutrition Conference, 2001, 13).

Energy balance is defined as energy intake minus energy output and an animal is described as being in negative energy balance if energy intake is insufficient to meet the demands on maintenance and production (eg milk). A cow in NEB has to find the energy to meet the deficit from its body reserves. Thus cows in NEB tend to lose body condition and liveweight, with cows that are more energy deficient tending to lose condition and weight at a faster rate.

It is important that the mineral and energy balance and overall health of the cow is managed well in the transition period, since this interval is critically important to the subsequent health, production, and profitability in dairy cows.

Long chain fatty acids (or non esterified fatty acids, NEFAs) are also mobilised from body fat. NEFAs, already elevated from around 7 days prepartum, are a significant source of energy to the cow during the early postpartum period, and the greater the energy deficit the higher the concentration of NEFA in the blood. Some workers suggest that in early lactation (Bell and references therein—see above) mammary uptake of NEFAs accounts for some milk fat synthesis. The circulating NEFAs are taken up by the liver and are oxidised to carbon dioxide or ketone bodies, including 3-hydroxybutyrate, by mitochondria, or reconverted via esterification into triglycerides and stored. In non-ruminant mammals it is thought that entry of NEFAs into the mitochondria is controlled by the enzyme carnitine palmitoyltransferase (CPT-1) however, some studies have shown that in ruminants there is little change in activity of CPT-1 during the transition period (G. N. Douglas, J. K. Drackley, T. R. Overton, H. G. Bateman, J. Dairy Science, 1998, Supp 1, 81, 295). Furthermore, the capacity of the ruminant liver for synthesising very low density lipoproteins to export triglycerides from the liver is limited.

Significantly, if NEFA uptake by the bovine liver becomes excessive, accumulation of ketone bodies can lead to ketosis, and excessive storage of triglycerides may lead to fatty liver. Fatty liver can lead to prolonged recovery for other disorders, increased incidence of health problems, and development of "downer cows" that die.

Thus, fatty liver is a metabolic disease of ruminants, particularly high producing dairy cows, in the transition period that negatively impacts disease resistance (abomasal displacement, lameness), immune function (mastitits, metritis), reproductive performance (oestrus, calving interval, foetal viability, ovarian cysts, metritis, retained placenta), and milk production (peak milk yield, 305 day milk yield). Fatty liver has largely developed by the day after parturition and precedes an induced (secondary) ketosis. It usually results from increased esterification of NEFA absorbed from blood coupled with the low ability of ruminant liver to secrete triglycerides as very low-density lipoproteins.

By improving energy balance, or by treating the negative energy balance, the negative extent of the sequelae will be reduced. This is addressed by the compounds of the present invention.

SUMMARY OF THE INVENTION

The present invention is directed to compounds of Formula I

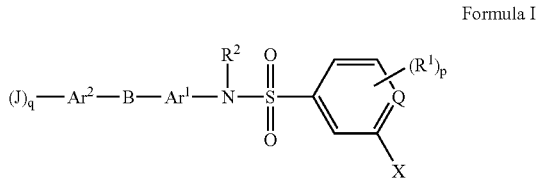

Formula I or a prodrug of said compound or a pharmaceutically acceptable salt of said compound or prodrug, wherein Q is carbon;

each $R^1$ is independently hydrogen, halo, $(C_1-C_5)$alkyl optionally substituted with one or more halo or with $(C_1-C_3)$ alkoxy, $(C_1-C_5)$alkoxy optionally substituted with one to eleven halo, $(C_1-C_5)$alkylthio optionally substituted with one or more halo, or $R^1$ in conjunction with the two adjacent carbon atoms forms a $C_5-C_6$ fused fully saturated, partially unsaturated or fully unsaturated five or six membered carbocyclic ring wherein each carbon in the carbon chain may optionally be replaced with one heteroatom selected from oxygen and sulfur;

$R^2$ is hydrogen or $(C_1-C_5)$alkyl optionally substituted with $C_1-C_3$ alkoxy;

X is —$COOR^4$, —O—$(CR^3{}_2)$—$COOR^4$, —S—$(CR^3{}_2)$—$COOR^4$, —$CH_2$—$(CR^5{}_w)$—$COOR^4$, 1H-tetrazol-5-yl-E- or thiazolidinedione-5-yl-G-; wherein w is 0, 1 or 2; E is $(CH_2)_r$ and r is 0, 1, 2 or 3, and G is $(CH_2)_s$ or methylidene and s is 0 or 1;

each $R^3$ is independently hydrogen, $(C_1-C_4)$alkyl optionally substituted with one to nine halo or with $(C_1-C_3)$alkoxy optionally substituted with one or more halo, or $R^3$ and the carbon to which it is attached form a 3, 4, 5, or 6 membered carbocyclic ring;

$R^4$ is H, $(C_1-C_4)$alkyl; benzyl or p-nitrobenzyl;

each $R^5$ is independently hydrogen, $(C_1-C_4)$alkyl optionally substituted with one to nine halo or with $(C_1-C_3)$alkoxy, $(C_1-C_4)$alkoxy optionally substituted with one to nine halo, $(C_1-C_4)$alkylthio optionally substituted with one to nine halo or with $(C_1-C_3)$alkoxy, or $R^5$ and the carbon to which it is attached form a 3, 4, 5, or 6 membered carbocyclic ring wherein any carbon of a 5- or 6-membered ring may be replaced by an oxygen atom;

$Ar^1$ is phenyl or phenyl fused to a member selected from thiazolyl, furanyl, oxazolyl, pyridine, pyrimidine, phenyl, or thienyl wherein $Ar^1$ is optionally mono-, di- or tri-substituted independently with: halo, $(C_1-C_3)$alkyl optionally substituted with one to nine halo or $(C_1-C_3)$alkoxy optionally substituted with one to nine halo or $(C_1-C_3)$alkylthio optionally substituted with one to nine halo;

B is a bond, CO, $(CY_2)_n$, CYOH, CY=CY, —L—$(CY_2)_n$—, —$(CY_2)_n$—L—, —L—$(CY_2)_2$—L—, NY—OC— —CONY—, —$SO_2NY$—, —NY—$SO_2$— wherein each L is independently O, S, SO, or $SO_2$, each Y is independently hydrogen or $(C_1-C_3)$ alkyl, and n is 0, 1, 2 or 3;

$Ar^2$ is a bond, phenyl, phenoxybenzyl, phenoxyphenyl, benzyloxyphenyl, benzyloxybenzyl, pyrimidinyl, pyridinyl, pyrazolyl, imidazolyl, thiazolyl, thiadiazolyl, oxazolyl, oxadiazolyl or phenyl fused to a ring selected from the group consisting of: phenyl, pyrimidinyl, thienyl, furanyl, pyrrolyl, thiazolyl, oxazolyl, pyrazolyl, and imidazolyl;

each J is independently hydrogen, hydroxy, halo, $(C_1-C_8)$ alkyl optionally substituted with one to eleven halo, $(C_1-C_8)$ alkoxy optionally substituted with one to eleven halo, $(C_1-C_8)$alkylthio optionally substituted with one to eleven halo, $(C_3-C_7)$cycloalkyl, $(C_3-C_7)$cycloalkoxy, $(C_3-C_7)$cycloalkylthio, or phenyl optionally substituted with one to four substituents from the group consisting of: halo, $(C_1-C_3)$ alkyl optionally substituted with one to five halo, $(C_1-C_3)$ alkoxy optionally substituted with one to five halo, $(C_1-C_3)$ alkylthio optionally substituted with one to five halo;

p and q are each independently 0, 1, 2 or 3; and with the provisos:

a) if $Ar^1$ is phenyl, B is a bond, $Ar^2$ is a bond or phenyl, and X is —COOH then q is other than 0 and J is other than hydrogen, halo, $(C_1-C_8)$alkyl or unsubstituted phenyl;

b) if $Ar^1$ is phenyl, B is not a bond, $Ar^2$ is phenyl and X is —$COOR^4$ then B is attached to $Ar^1$ para to $NR^2$; and c) if B is O, S, SO, NH, CO, $CH_2$ or $SO_2$ then $R^1$ is not H.

The present application also is directed to methods for treating dyslipidemia, obesity, overweight condition, hypertriglyceridemia, hyperlipidemia, hypoalphalipoproteinemia, metabolic syndrome, diabetes mellitus (Type I and/or Type II), hyperinsulinemia, impaired glucose tolerance, insulin resistance, diabetic complications, atherosclerosis, hypertension, coronary heart disease, hypercholesterolemia, inflammation, osteoporosis, thrombosis, peripheral vascular disease, cognitive dysfunction, or congestive heart failure in a mammal by administering to a mammal in need of such treatment a therapeutically effective amount of a compound of any of claims 1-13, or a prodrug of said compound or a pharmaceutically acceptable salt of said compound or prodrug.

The present application also is directed to pharmaceutical compositions which comprises a therapeutically effective amount of a compound of formula I, or a prodrug of said compound or a pharmaceutically acceptable salt of said compound or prodrug and a pharmaceutically acceptable carrier, vehicle or diluent.

In addition, the present application is directed to pharmaceutical combination compositions comprising: a therapeutically effective amount of a composition comprising a first compound, said first compound being a compound of formula I, or a prodrug of said compound or a pharmaceutically acceptable salt of said compound or prodrug;

a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor, a bile acid sequestrant, or a prodrug of said compound or a pharmaceutically acceptable salt of said compound or prodrug; and a pharmaceutically acceptable carrier, vehicle or diluent.

Moreover, the present invention is directed to methods for treating atherosclerosis in a mammal comprising administering to a mammal in need of treatment thereof;

a first compound, said first compound being a compound of formula I, or a prodrug of said compound or a pharmaceutically acceptable salt of said compound or prodrug; and a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor or a bile acid sequestrant wherein the amounts of first and second compounds result in a therapeutic effect.

Furthermore, the present application also is directed to kits for achieving a therapeutic effect in a mammal comprising packaged in association a first therapeutic agent comprising a therapeutically effective amount of a compound of the formula I, or a prodrug of said compound or a pharmaceutically acceptable salt of said compound or prodrug and a pharmaceutically acceptable carrier, a second therapeutic agent comprising a therapeutically effective amount of an HMG CoA reductase inhibitor, a CETP inhibitor, a cholesterol absorption inhibitor, a cholesterol synthesis inhibitor, a fibrate, niacin, slow-release niacin, a combination of niacin and lovastatin, an ion-exchange resin, an antioxidant, an ACAT inhibitor or a bile acid sequestrant and a pharmaceutically acceptable carrier and directions for administration of said first and second agents to achieve the therapeutic effect.

Another aspect of the present invention is the use of a compound of formula I, in the manufacture of a medicament for the palliative, prophylactic or curative treatment of negative energy balance in ruminants.

Another aspect of the invention is the use of a compound of formula I, in the manufacture of a medicament for the palliative, prophylactic or curative treatment of negative energy balance or a ruminant disease associated with negative energy balance in ruminants, wherein the excessive accumulation of triglycerides in liver tissue is prevented or alleviated, and/or the excessive elevation of non-esterified fatty acid levels in serum is prevented or alleviated.

Another aspect of the invention is where the ruminant disease associated with negative energy balance in ruminants, as mentioned in the aspects of the invention herein, includes one or more diseases selected independently from fatty liver syndrome, dystocia, immune dysfunction, impaired immune function, toxification, primary and secondary ketosis, downer cow syndrome, indigestion, inappetence, retained placenta, displaced abomasum, mastitis, (endo-)-metritis, infertility, low fertility and lameness, preferably fatty liver syndrome, primary ketosis, downer cow syndrome, (endo-)-metritis and low fertility.

Another aspect of the invention is the use of a compound of formula I, in the improvement of fertility, including decreased return to service rates, normal oestrus cycling, improved conception rates, and improved foetal viability.

Another aspect of the invention is the use of a compound of formula I, in the manufacture of a medicament for the management of effective homeorhesis to accommodate parturition and lactogenesis.

Another aspect of the invention is the use of a compound of formula I, in the manufacture of a medicament for improving or maintaining the functioning of the ruminant liver and homeostatic signals during the transition period.

In one aspect of the invention, the compound of formula I is administered during the period from 30 days prepartum to 70 days postpartum.

In another aspect of the invention, the compound of formula I is administered prepartum and, optionally, also at parturition.

In yet another aspect of the invention, the compound of formula I is administered postpartum.

In yet another aspect of the invention, the compound of formula I is administered at parturition.

More preferably, the compound of formula I is administered during the period from 3 weeks prepartum to 3 weeks postpartum.

In another aspect of the invention, the compound of formula I is administered up to three times during the first seven days postpartum.

Preferably, the compound of formula I is administered once during the first 24 hours postpartum.

In another aspect of the invention, the compound of formula I is administered prepartum and up to four times postpartum.

In another aspect of the invention, the compound of formula I is administered at parturition and then up to four times postpartum.

Another aspect of the invention is the use of the compound of formula I in the manufacture of a medicament for the palliative, prophylactic or curative treatment of negative energy balance in ruminants and to increase ruminant milk quality and/or milk yield. In a preferred aspect of the invention, the milk quality increase is seen in a reduction in the levels of ketone bodies in ruminant milk.

In another aspect of the invention, peak milk yield is increased.

Preferably, the ruminant is a cow or sheep.

In another aspect of the invention, an overall increase in ruminant milk yield is obtained during the 305 days of the bovine lactation period.

In another aspect of the invention, an overall increase in ruminant milk yield is obtained during the first 60 days of the bovine lactation period.

Preferably, the overall increase in ruminant milk yield, or the increase in peak milk yield, or the increase in milk quality, is obtained from a dairy cow.

In another aspect of the invention, the increase in ruminant milk quality and/or milk yield is obtained after administration of a compound of formula I to a healthy ruminant.

In another aspect of the invention, there is provided a compound of formula I, for use in veterinary medicine.

The present application also is directed to compounds having a Formula II

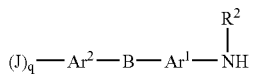

Formula II or a pharmaceutically acceptable salt thereof, wherein
$R^2$ is hydrogen or $(C_1-C_4)$alkyl;

$Ar^1$ is phenyl optionally mono-, di- or tri-substituted independently with: halo, $(C_1-C_3)$alkyl optionally substituted with one to five halo or $(C_1-C_3)$alkoxy optionally substituted with one to five halo or $(C_1-C_3)$alkyllthio optionally substituted with one to five halo;

B is $(CY_2)_n$, O, S; —$CH_2S$— or —$CH_2O$ and n is 1 or 2;

$Ar^2$ is phenyl or phenyl fused to a ring selected from the group consisting of: phenyl, pyrimidinyl, thienyl, furanyl, pyrrolyl, thiazolyl, oxazolyl, pyrazolyl, and imidazolyl;

each J is independently hydrogen, hydroxy; halo; $(C_1-C_8)$ alkyl optionally substituted with one to eleven halo; $(C_1-C_8)$ alkoxy optionally substituted with one to eleven halo; $(C_1-C_8)$alkylthio optionally substituted with one to eleven halo; $(C_3-C_7)$cycloalkyl; $(C_3-C_7)$cycloalkoxy; $(C_3-C_7)$cycloalkylthio; or phenyl optionally substituted with one or more: halo or $(C_1-C_3)$alkyl optionally substituted with one to five halo or $(C_1-C_3)$alkoxy optionally substituted with one to five halo or $(C_1-C_3)$alkylthio optionally substituted with one to five halo; and q is 0, 1, 2 or 3.

It is to be understood that both the foregoing general description and the following detailed description are exemplary and explanatory only and are not restrictive of the invention, as claimed.

DETAILED DESCRIPTION OF THE INVENTION

Figure 1:
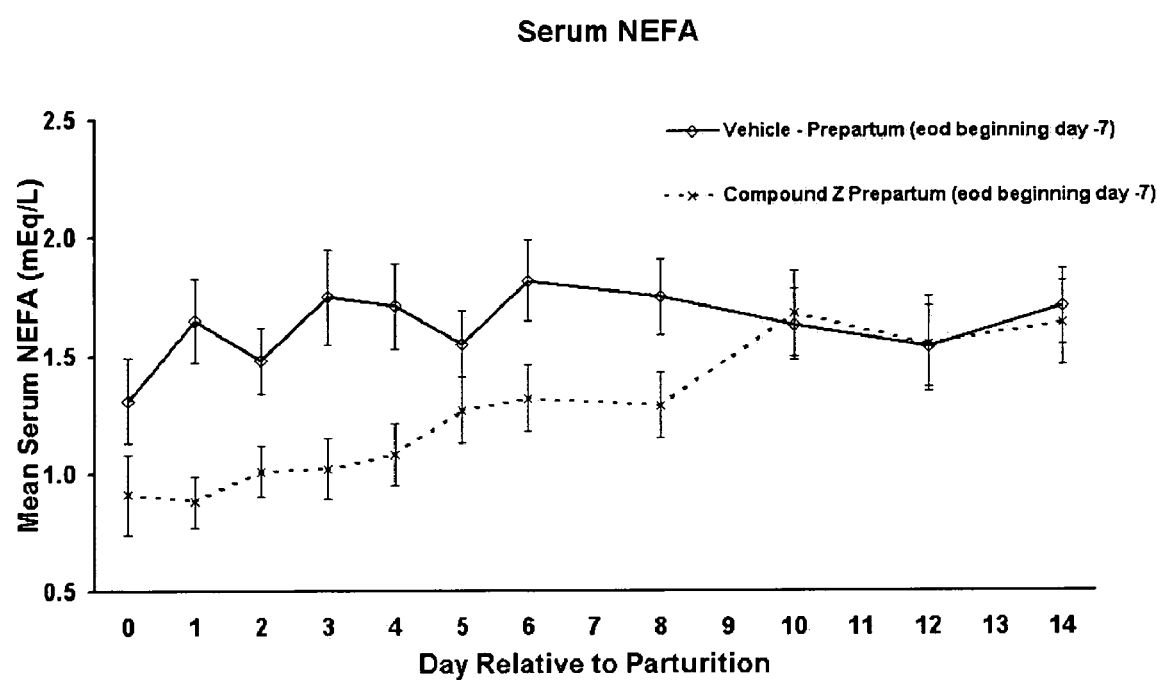
FIG. 1 shows the serum NEFA levels for transition cows administered with compound Z,: 2-Methyl-5-(4'-trifluoromethoxy-biphenyl-4-ylsulfamoyl)-benzoic acid (EXAMPLE 193), compared to controls.

The present invention may be understood more readily by reference to the following detailed description of exemplary embodiments of the invention and the examples included therein.

Before the present compounds, compositions and methods are disclosed and described, it is to be understood that this invention is not limited to specific synthetic methods of making that may of course vary. It is also to be understood that the terminology used herein is for the purpose of describing particular embodiments only and is not intended to be limiting.

The present invention also relates to the pharmaceutically acceptable acid addition salts of compounds of the present invention. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)) salts.

The invention also relates to base addition salts of the compounds of the present invention. The chemical bases that may be used as reagents to prepare pharmaceutically acceptable base salts of those compounds of the present invention that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The chemist of ordinary skill will recognize that certain compounds of this invention will contain one or more atoms that may be in a particular stereochemical or geometric configuration, giving rise to stereoisomers and configurational isomers. All such isomers and mixtures thereof are included in this invention. Hydrates and solvates of the compounds of this invention are also included.

Where the compounds of the present invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the present invention possess one or more stereogenic centers and no stereochemistry is given in the name or structure, it is understood that the name or structure is intended to encompass all forms of the compound, including the racemic form.

The compounds of this invention may contain olefin-like double bonds. When such bonds are present, the compounds of the invention exist as cis and trans configurations and as mixtures thereof. The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

Alpha and Beta refer to the orientation of a substituent with reference to the plane of the ring. Beta is above the plane of the ring and Alpha is below the plane of the ring.

This invention also includes isotopically-labeled compounds, which are identical to those described by Formulas I and II, except for the fact that one or more atoms are replaced by one or more atoms having specific atomic mass or mass numbers. Examples of isotopes that can be incorporated into compounds of the invention include isotopes of hydrogen, carbon, nitrogen, oxygen, sulfur, fluorine, and chlorine such as $^2H$, $^3H$, $^{13}C$, $^{14}C$, $^{15}N$, $^{18}O$, $^{17}O$, $^{18}F$, and $^{36}Cl$ respectively. Compounds of the present invention, prodrugs thereof, and pharmaceutically acceptable salts of the compounds or of the prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated (i.e., $^3H$), and carbon-14 (i.e., $^{14}C$), isotopes are particularly preferred for their ease of preparation and detectability. Further, substitution with heavier isotopes such as deuterium (i.e., $^2$H), can afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out the procedures disclosed in the schemes and/or in the Examples below, by substituting a readily available isotopically labeled reagent for a non-isotopically labeled reagent.

In this specification and in the claims that follow, reference will be made to a number of terms that shall be defined to have the following meanings:

The "transition period" means from 30 days prepartum to 70 days postpartum

The term "treating", "treat", "treats" or "treatment" as used herein includes prophylactic, palliative and curative treatment.

"Negative energy balance" as used herein means that energy via food does not meet the requirements of maintenance and production (milk).

The term "cow" as used herein includes heifer, primiparous and multiparous cow.

"Healthy ruminant" means where the ruminant does not show signs of the following indications: fatty liver syndrome, dystocia, immune dysfunction, impaired immune function, toxification, primary and secondary ketosis, downer cow syndrome, indigestion, inappetence, retained placenta, displaced abomasum, mastitis, (endo-)-metritis, infertility, low fertility and/or lameness.

Milk "quality" as used herein refers to the levels in milk of protein, fat, lactose, somatic cells, and ketone bodies. An increase in milk quality is obtained on an increase in fat, protein or lactose content, or a decrease in somatic cell levels or ketone bodies levels.

An increase in milk yield can mean an increase in milk solids or milk fat or milk protein content, as well as, or instead of, an increase in the volume of milk produced.

"Excessive accumulation of triglycerides" as used herein means greater than the physiological triglyceride content of 10% w/w in liver tissue.

"Excessive elevation of non-esterified fatty acid levels in serum" as used herein means non-esterified fatty acid levels of greater than 800 μmol/L in serum.

Unless otherwise specified, "prepartum" means 3 weeks before calving until the day of calving.

Unless otherwise specified, "postpartum" means from when the newborn is "expelled" from the uterus to 6 weeks after the newborn was expelled from the uterus.

"At parturition" means the 24 hours after the newborn was expelled from the uterus.

"Periparturient" means the period from the beginning of the prepartum period, to the end of the postpartum period.

The term "treating", "treat" or "treatment" as used herein includes preventative (e.g., prophylactic) and palliative treatment.

As used herein, "therapeutically effective amount of a compound" means an amount that is effective to exhibit therapeutic or biological activity at the site(s) of activity in a mammalian subject, without undue adverse side effects (such as undue toxicity, irritation or allergic response), commensurate with a reasonable benefit/risk ratio when used in the manner of the present invention.

The term "cerebrovascular disease", as used herein, is selected, but not limited to, the group consisting of ischemic attacks (e.g., transient), ischemic stroke (transient), acute stroke, cerebral apoplexy, hemorrhagic stroke, neurologic deficits post-stroke, first stroke, recurrent stroke, shortened recovery time after stroke and provision of thrombolytic therapy for stroke. Preferable patient populations include patients with or without pre-existing stroke or coronary heart disease.

The term "coronary artery disease", as used herein, is selected, but not limited to, the group consisting of atherosclerotic plaque (e.g., prevention, regression, stablilization), vulnerable plaque (e.g., prevention, regression, stabilization), vulnerable plaque area (reduction), arterial calcification (e.g., calcific aortic stenosis), increased coronary artery calcium score, dysfunctional vascular reactivity, vasodilation disorders, coronary artery spasm, first myocardial infarction, myocardia re-infarction, ischemic cardiomyopathy, stent restenosis, PTCA restenosis, arterial restenosis, coronary bypass graft restenosis, vascular bypass restenosis, decreased exercise treadmill time, angina pectoris/chest pain, unstable angina pectoris, exertional dyspnea, decreased exercise capacity, ischemia (reduce time to), silent ischemia (reduce time to), increased severity and frequency of ischemic symptoms, reperfusion after thrombolytic therapy for acute myocardial infarction.

The term "hypertension", as used herein, is selected, but not limited to, the group consisting of lipid disorders with hypertension, systolic hypertension and diastolic hypertension.

The term "ventricular dysfunction", as used herein, is selected, but not limited to, the group consisting of systolic dysfunction, diastolic dysfunction, heart failure, congestive heart failure, dilated cardiomyopathy, idiopathic dilated cardiomyopathy, and non-dilated cardiomopathy.

The term "cardiac arrhythmia", as used herein, is selected, but not limited to, the group consisting of atrial arrhythmias, supraventricular arrhythmias, ventricular arrhythmias and sudden death syndrome.

The term "pulmonary vascular disease", as used herein, is selected, but not limited to, the group consisting of pulmonary hypertension, peripheral artery block, and pulmonary embolism.

The term "peripheral vascular disease", as used herein, is selected, but not limited to, the group consisting of peripheral vascular disease and claudication.

The term "vascular hemostatic disease", as used herein, is selected, but not limited to, the group consisting of deep venous thrombosis, vaso-occlusive complications of sickle cell anemia, varicose veins, pulmonary embolism, transient ischemic attacks, embolic events, including stroke, in patients with mechanical heart valves, embolic events, including stroke, in patients with right or left ventricular assist devices, embolic events, including stroke, in patients with intra-aortic balloon pump support, embolic events, including stroke, in patients with artificial hearts, embolic events, including stroke, in patients with cardiomyopathy, embolic events, including stroke, in patients with atrial fibrillation or atrial flutter.

The term "diabetes", as used herein, refers to any of a number of diabetogenic states including type I diabetes, type II diabetes, Syndrome X, Metabolic syndrome, lipid disorders associated with insulin resistance, impaired glucose tolerance, non-insulin dependent diabetes, microvascular diabetic complications, reduced nerve conduction velocity, reduced or loss of vision, diabetic retinopathy, increased risk of amputation, decreased kidney function, kidney failure, insulin resistance syndrome, pluri-metabolic syndrome, central adiposity (visceral)(upper body), diabetic dyslipidemia, decreased insulin sensitization, diabetic retinopathy/neuropathy, diabetic nephropathy/micro and macro angiopathy and micro/macro albuminuria, diabetic cardiomyopathy, diabetic gastroparesis, obesity, increased hemoglobin glycoslation (including HbA1C), improved glucose control, impaired renal function (dialysis, endstage) and hepatic function (mild, moderate, severe).

The terms "inflammatory disease, autoimmune disorders and other systemic diseases", as used herein, are selected, but not limited to, the group consisting of multiple sclerosis, rheumatoid arthritis, osteoarthritis, irritable bowel syndrome, irritable bowel disease, Crohn's disease, colitis, vasculitis, lupus erythematosis, sarcoidosis, amyloidosis, apoptosis, and disorders of the complement systems.

The term "cognitive dysfunction", as used herein, is selected, but not limited to, the group consisting of dementia secondary to atherosclerosis, transient cerebral ischemic attacks, neurodegeneration (including Parkinson's, Huntington's disease, amyloid deposition and amylotrophic lateral sclerosis), neuronal deficient, and delayed onset or procession of Alzheimer's disease.

"Metabolic syndrome," also known as "Syndrome X," refers to a common clinical disorder that is defined as the presence of increased insulin concentrations in association with other disorders including viceral obesity, hyperlipidemia, dyslipidemia, hyperglycemia, hypertension, and potentially hyperuricemis and renal dysfunction.

By "pharmaceutically acceptable" is meant the carrier, diluent, excipients, and/or salt must be compatible with the other ingredients of the formulation, and not deleterious to the recipient thereof.

"Compounds" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. By "tautomers" is meant chemical compounds that may exist in two or more forms of different structure (isomers) in equilibrium, the forms differing, usually, in the position of a hydrogen atom. Various types of tautomerism can occur, including keto-enol, ring-chain and ring-ring tautomerism. The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the compounds of the present invention include but are not limited to those having a carboxyl moiety wherein the free hydrogen is replaced by $(C_1–C_4)$alkyl, $(C_2–C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1–C_2)$alkylamino$(C_2–C_3)$alkyl (such as β-dimethylaminoethyl), carbamoyl-$(C_1–C_2)$alkyl, N,N-di$(C_1–C_2)$alkylcarbamoyl-$(C_1–C_2)$alkyl and piperidino-, pyrrolidino- or morpholino$(C_2–C_3)$alkyl.

The following paragraphs describe exemplary ring(s) for the generic ring descriptions contained herein.

Exemplary five to six membered aromatic rings optionally having one or two heteroatoms selected independently from oxygen, nitrogen and sulfur include phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl.

Exemplary partially saturated, fully saturated or fully unsaturated five to eight membered carbocyclic rings optionally having one to four heteroatoms selected independently from oxygen, sulfur and nitrogen include cyclopentyl, cyclohexyl, cycloheptyl, cyclooctyl and phenyl.

Further exemplary five membered carbocyclic rings include 2H-pyrrolyl, 3H-pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered carbocyclic rings include 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl. Further exemplary seven membered rings include azepinyl, oxepinyl, and thiepinyl.

Further exemplary eight membered carbocyclic rings include cyclooctyl, cyclooctenyl and cyclooctadienyl.

Exemplary bicyclic rings consisting of two fused partially saturated, fully saturated or fully unsaturated five or six membered rings, taken independently, optionally having one to four heteroatoms selected independently from nitrogen, sulfur and oxygen include indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

The carbon atom content of various hydrocarbon-containing moieties is indicated by a prefix designating the minimum and maximum number of carbon atoms in the moiety, i.e., the prefix $C_i–C_j$ indicates a moiety of the integer "i" to the integer "j" carbon atoms, inclusive. Thus, for example, $C_1–C_3$ alkyl refers to alkyl of one to three carbon atoms, inclusive, or methyl, ethyl, propyl and isopropyl, and all isomeric forms and straight and branched forms thereof.

By "aryl" is meant an optionally substituted six-membered aromatic ring, including polyaromatic rings. Examples of aryl include phenyl, naphthyl and biphenyl.

"Heteroaryl" as used herein means an optionally substituted five- or six-membered aromatic ring, including polyaromatic rings where appropriate carbon atoms are substituted by nitrogen, sulfur or oxygen. Examples of heteroaryl include pyridine, pyrimidine, thiazole, oxazole, quinoline, quinazoline, benzothiazole and benzoxazole.

By "halo" or "halogen" is meant chloro, bromo, iodo, or fluoro.

By "alkyl" is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl. This term also includes a saturated hydrocarbon (straight chain or branched) wherein a hydrogen atom is removed from each of the terminal carbons.

"Alkenyl" referred to herein may be linear or branched, and they may also be cyclic (e.g. cyclobutenyl, cyclopentenyl, cyclohexenyl) or bicyclic or contain cyclic groups. They contain 1–3 carbon-carbon double bonds, which can be cis or trans.

By "alkoxy" is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

The term "HMG CoA reductase inhibitor" is selected, but not limited to, the group consisting of lovastatin, simvastatin, pravastatin, fluindostatin, velostatin, dihydrocompactin, compactin, fluvastatin, atorvastatin, glenvastatin, dalvastatin, carvastatin, crilvastatin, bervastatin, cerivastatin, rosuvastatin, pitavastatin, mevastatin, or rivastatin, or a pharmaceutically acceptable salt thereof.

The term "antihypertensive agent" is selected, but not limited to, a calcium channel blocker (including, but not limited to, verapamil, diltiazem, mibefradil, isradipine, lacidipine, nicardipine, nifedipine, nimodipine, nisoldipine, nitrendipine, avanidpine, amlodipine, amlodipine besylate, manidipine, cilinidipine, lercanidipine and felodipine), an ACE inhibitor (including, but not limited to, benazepril, captopril, enalapril, fosinopril, lisinopril, perindopril, quinapril, trandolapri, ramipril, zestril, zofenopril, cilaapril, temocapril, spirapril, moexipril, delapril, imidapril, ramipril, terazosin, urapidin, indoramin, amolsulalol, and alfuzosin), an A-II antagonist (including, but not limited to, losartan, irbesartan, telmisartan and valsartan), a diuretic (including, but not limited to, amiloride, and bendroflumethiazide), a beta-adrenergic receptor blocker (such as carvedilol) or an alpha-adrenergic receptor blocker (including, but not limited to, doxazosin, prazosin, and trimazosin), or a pharmaceutically acceptable salt of such compounds.

In one embodiment of the present invention, p is 1 or 2 and $R^1$ is bonded to Q.

In another embodiment of the present invention, $Ar^1$ is:

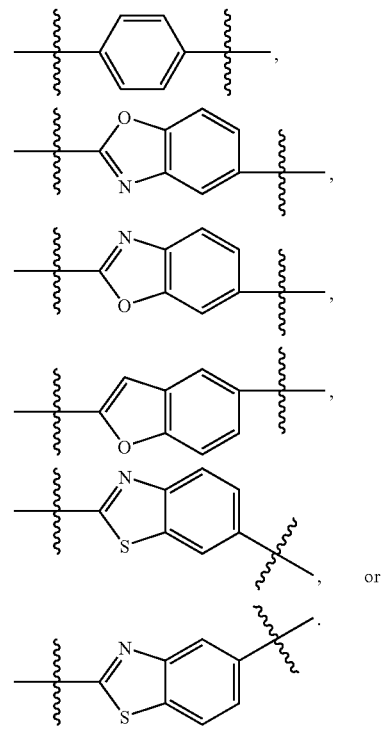

In another embodiment of the present invention, $Ar^2$ is

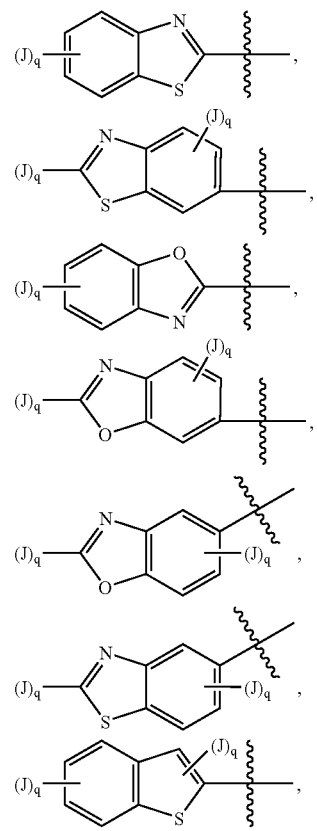

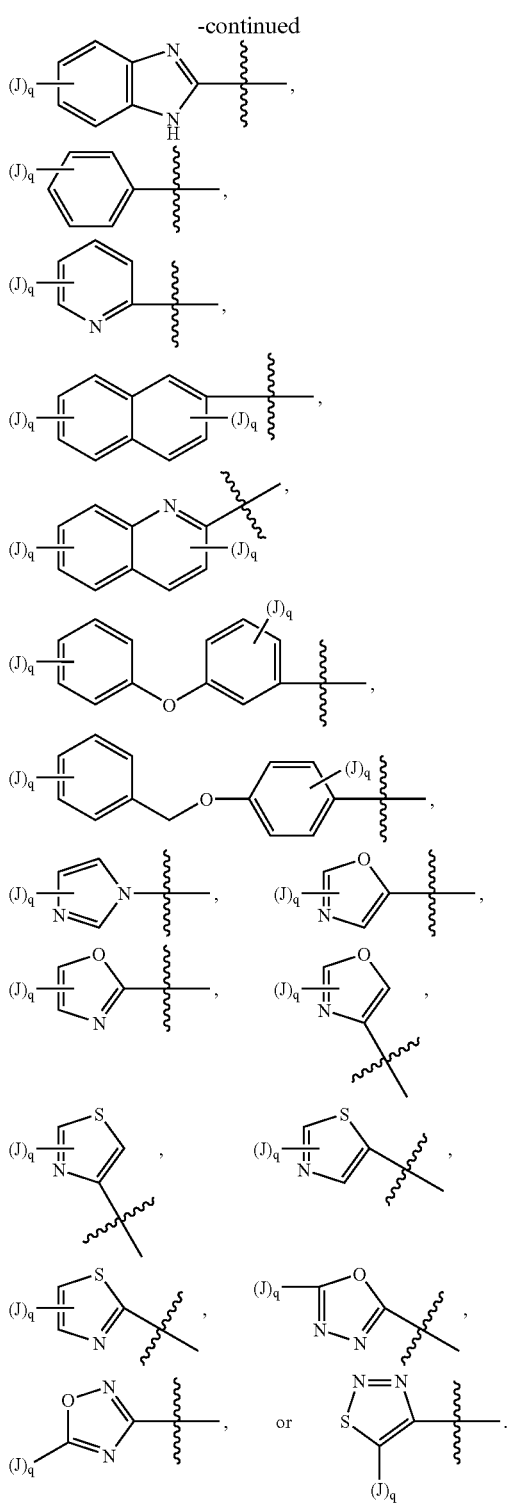

In another embodiment of the present invention,

Ar$^1$ is phenyl or phenyl fused to oxazolyl or thiazolyl; and

Ar$^2$ is phenyl or phenyl fused to a ring selected from the group consisting of: phenyl, pyridinyl, thienyl, thiazolyl, oxazolyl, and imidazolyl.

In another embodiment of the present invention, halo is fluoro.

In another embodiment of the present invention, B is a bond or —L—(CY$_2$)$_n$— or —(CY$_2$)$_n$—L—, and L is O or S, and n is 0, 1 or 2.

In another embodiment of the present invention,

X is —COOR$^4$;

B is a bond;

Ar$^1$ is phenyl or phenyl fused to oxazolyl or thiazolyl; and

Ar$^2$ is phenyl or phenyl fused to a ring selected from the group consisting of: phenyl, pyridinyl, thienyl, thiazolyl, oxazolyl, and imidazolyl.

In another embodiment of the present invention,

X is —COOR$^4$;

B is —L—(CY$_2$)$_n$— or —(CY$_2$)$_n$—L—, and L is O or S, and n is 0, 1 or 2;

Ar$^1$ is phenyl or phenyl fused to oxazolyl or thiazolyl; and

Ar$^2$ is phenyl or phenyl fused to a ring selected from the group consisting of: phenyl, pyridinyl, thienyl, thiazolyl, oxazolyl, and imidazolyl.

In another embodiment of the present invention,

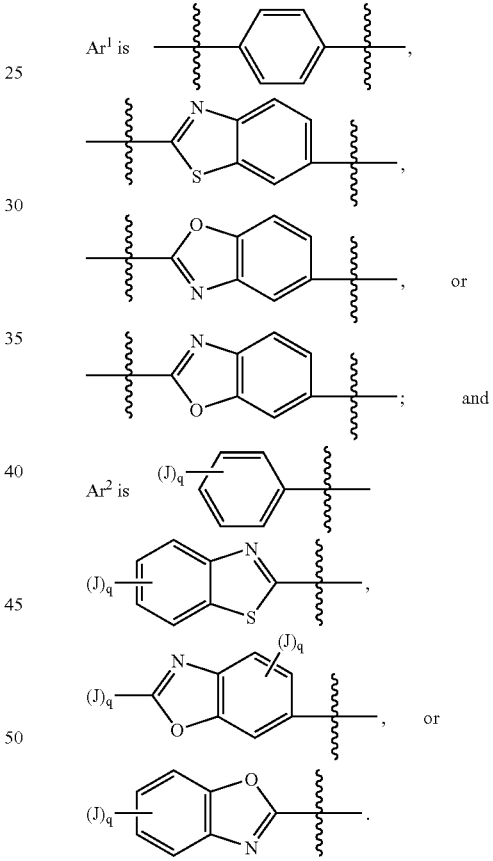

In another embodiment of the present invention, q is 1 or 2 and each J is independently halo, (C$_1$–C$_3$)alkyl optionally substituted with one to three halo, or (C$_1$–C$_3$)alkoxy optionally substituted with one to three halo.

In another embodiment of the present invention, p is 1 and R$^4$ is H or (C$_1$–C$_3$)alkyl.

In another embodiment of the present invention, L is S and n is 1.

In another embodiment of the present invention, the compound of formula I is selected from the group consisting of:

2-Methyl-5-[4-(5-methyl-benzooxazol-2-yl)-phenylsulfamoyl]benzoic acid;
5-[4-(5-Chloro-benzooxazol-2-yl)-phenylsulfamoyl]-2-methyl-benzoic acid;
2-Methyl-5-[4-(4-trifluoromethyl-benzylsulfanyl)-phenylsulfamoyl]-benzoic acid;
5-[4-(4-tert-Butyl-benzylsulfanyl)-phenylsulfamoyl]-2-methyl-benzoic acid;
2-Ethyl-5-[4-(5-methyl-benzooxazol-2-yl)-phenylsulfamoyl]-benzoic acid;
5-[4-(4-Ethyl-benzylsulfanyl)-phenylsulfamoyl]-2-methyl-benzoic acid;
5-[4-(3,4-Difluoro-benzylsulfanyl)-phenylsulfamoyl]-2-methyl-benzoic acid;
5-[4-(3,4-Dimethyl-benzylsulfanyl)-phenylsulfamoyl]-2-methyl-benzoic acid;
5-[4-(5,7-Difluoro-benzothiazol-2-ylmethylsulfanyl)-phenylsulfamoyl]-2-methyl-benzoic acid;
2,3-Dimethyl-5-(4'-trifluoromethoxy-biphenyl-4-ylsulfamoyl)-benzoic acid;
2-Ethyl-5-[4-(4-trifluoromethoxy-benzylsulfanyl)-phenylsulfamoyl]-benzoic acid;
2-Ethyl-5-(4'-trifluoromethoxy-biphenyl-4-ylsulfamoyl)-benzoic acid;
2-Isopropyl-5-[2-(4-trifluoromethoxy-phenyl)-benzooxazol-5-ylsulfamoyl]-benzoic acid; and
2-Methyl-5-(4'-trifluoromethoxy-biphenyl-4-ylsulfamoyl)-benzoic acid;

or a prodrug of said compound or a pharmaceutically acceptable salt of said compound or prodrug In another embodiment of the present invention, the compound of formula I is selected from the group consisting of:
2-Ethyl-5-[4-(6-methyl-benzothiazol-2-yl)-phenylsulfamoyl]-benzoic acid;
2-Methyl-5-(4'-trifluoromethyl-biphenyl-4-ylsulfamoyl)-benzoic acid;
2-asopropyl-5-[propyl-(4'-trifluoromethoxy-biphenyl-4-yl)-sulfamoyl]-benzoic acid;
2-Methyl-5-[(4'-propoxy-biphenyl4-yl)-propyl-sulfamoyl]-benzoic acid;
2-Methyl-5-(4'-propoxy-biphenyl-4-ylsulfamoyl)-benzoic acid;
2-Ethyl-5-[4-(4-trifluoromethoxy-benzylsulfanyl)-phenylsulfamoyl]-benzoic acid;
5-(4'-tert-Butyl-biphenyl-4-ylsulfamoyl)-2-methyl-benzoic acid;
5-[4-(4-Chloro-benzylsulfanyl)-phenylsulfamoyl]-2-methyl-benzoic acid;
2-Methyl-5-[4-(3-trifluoromethoxy-benzylsulfanyl)-phenylsulfamoyl]-benzoic acid;
2-Methyl-5-[2-(4-trifluoromethyl-phenyl)-benzooxazol-5-ylsulfamoyl]-benzoic acid;
2-Methyl-5-[4-(5-phenyl-benzooxazol-2-yl)-phenylsulfamoyl]-benzoic acid; and
2-Isopropyl-5-[4-(5-methyl-benzooxazol-2-yl)-phenylsulfamoyl]-benzoic acid;

or a prodrug of said compound or a pharmaceutically acceptable salt of said compound or prodrug.

In one embodiment of the methods of the present invention, atherosclerosis is treated.

In one embodiment of the methods of the present invention, peripheral vascular disease is treated.

In one embodiment of the methods of the present invention, dyslipidemia is treated.

In one embodiment of the methods of the present invention, diabetes is treated.

In one embodiment of the methods of the present invention, hypoalphalipoproteinemia is treated.

In one embodiment of the methods of the present invention, hypercholesterolemia is treated.

In one embodiment of the methods of the present invention, hypertriglyceridemia is treated.

In one embodiment of the methods of the present invention, obesity is treated.

In one embodiment of the methods of the present invention, osteoporosis is treated.

In one embodiment of the methods of the present invention, metabolic syndrome is treated.

In another embodiment of the present invention, the pharmaceutical composition is for the treatment of atherosclerosis in a mammal which comprises an atherosclerosis treating amount of a compound of formula I, or a prodrug of said compound or a pharmaceutically acceptable salt of said compound or prodrug and a pharmaceutically acceptable carrier, vehicle or diluent.

In one embodiment of the pharmaceutical combination compositions, methods and kits of the present invention, the second compound is an HMG-CoA reductase inhibitor or a CETP inhibitor.

In one embodiment of the pharmaceutical combination compositions, methods and kits of the present invention, the second compound is rosuvastatin, rivastatin, pitavastatin, lovastatin, simvastatin, pravastatin, fluvastatin, atorvastatin or cerivastatin or a prodrug of said compound or a pharmaceutically acceptable salt of said compound or prodrug.

In one embodiment of the pharmaceutical combination compositions, methods and kits of the present invention, the second compound is [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

In one embodiment of the pharmaceutical combination compositions, methods and kits of the present invention, the composition further comprises a cholesterol absorption inhibitor.

In one embodiment of the pharmaceutical combination compositions, methods and kits of the present invention, the cholesterol absorption inhibitor is ezetimibe.

In one embodiment of the pharmaceutical combination compositions, methods and kits of the present invention, the composition further comprises an antihypertensive agent.

In one embodiment of the pharmaceutical combination compositions, methods and kits of the present invention, said antihypertensive agent is a calcium channel blocker, an ACE inhibitor, an A-II antagonist, a diuretic, a beta-adrenergic receptor blocker or an alpha-adrenergic receptor blocker.

In one embodiment of the pharmaceutical combination compositions, methods and kits of the present invention, the antihypertensive agent is a calcium channel blocker, said calcium channel blocker being verapamil, diltiazem, mibefradil, isradipine, lacidipine, nicardipine, nifedipine, nimodipine, nisoldipine, nitrendipine, avanidpine, amlodipine, amlodipine besylate, manidipine, cilinidipine, lercanidipine or felodipine or a prodrug of said compound or a pharmaceutically acceptable salt of said compound or prodrug.

In another embodiment of the present invention, the compound of formula II is:
4-(5-Chloro-benzooxazol-2-yl)-phenylamine;
4-(4-Trifluoromethyl-benzylsulfanyl)-phenylamine;
4-(4-tert-Butyl-benzylsulfanyl)-phenylamine;
4-(4-Ethyl-benzylsulfanyl)-phenylamine;
4-(3,4-Difluoro-benzylsulfanyl)-phenylamine;
4-(3,4-Dimethyl-benzylsulfanyl)-phenylamine;
4-(5,7-Difluoro-benzothiazol-2-ylmethylsulfanyl)-phenylamine;
4'-Trifluoromethoxy-biphenyl-4-ylamine;
4-(4-Trifluoromethoxy-benzylsulfanyl)-phenylamine; or
4-Trifluoromethoxy-phenyl)-benzooxazol-5-ylamine;

or a pharmaceutically acceptable salt thereof.

In general, the compounds of this invention can be made by processes that include processes analogous to those known in the chemical arts, particularly in light of the description contained herein. Certain processes for the manufacture of the compounds of this invention are provided as further features of the invention and are illustrated by the following reaction schemes. Other processes may be described in the experimental section.

The Reaction Schemes herein described are intended to provide a general description of the methodology employed in the preparation of many of the Examples given. However, it will be evident from the detailed descriptions given in the Experimental section that the modes of preparation employed extend further than the general procedures described herein. In particular, it is noted that the compounds prepared according to these Schemes may be modified further to provide new Examples within the scope of this invention. For example, an ester functionality may be reacted further using procedures well known to those skilled in the art to give another ester, an amide, an acid, a carbinol or a ketone.

As an initial note, in the preparation of compounds of the present invention, it is noted that some of the preparation methods useful for the preparation of the compounds described herein may require protection of remote functionality (e.g., primary amine, secondary amine, carboxyl in intermediates). The need for such protection will vary depending on the nature of the remote functionality and the conditions of the preparative methods and can be readily determined by one of ordinary skill in the art. The use of such protection/deprotection methods is also within the ordinary skill in the art. For a general description of protecting groups and their use, see T. W. Greene, *Protective Groups in Organic Synthesis*, John Wiley & Sons, New York, 1991.

For example, in the reaction schemes below, certain compounds contain primary amines or carboxylic acid functionalities, which may interfere with reactions at other sites of the molecule if left unprotected. Accordingly, such functionalities may be protected by an appropriate protecting group, which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the compound.

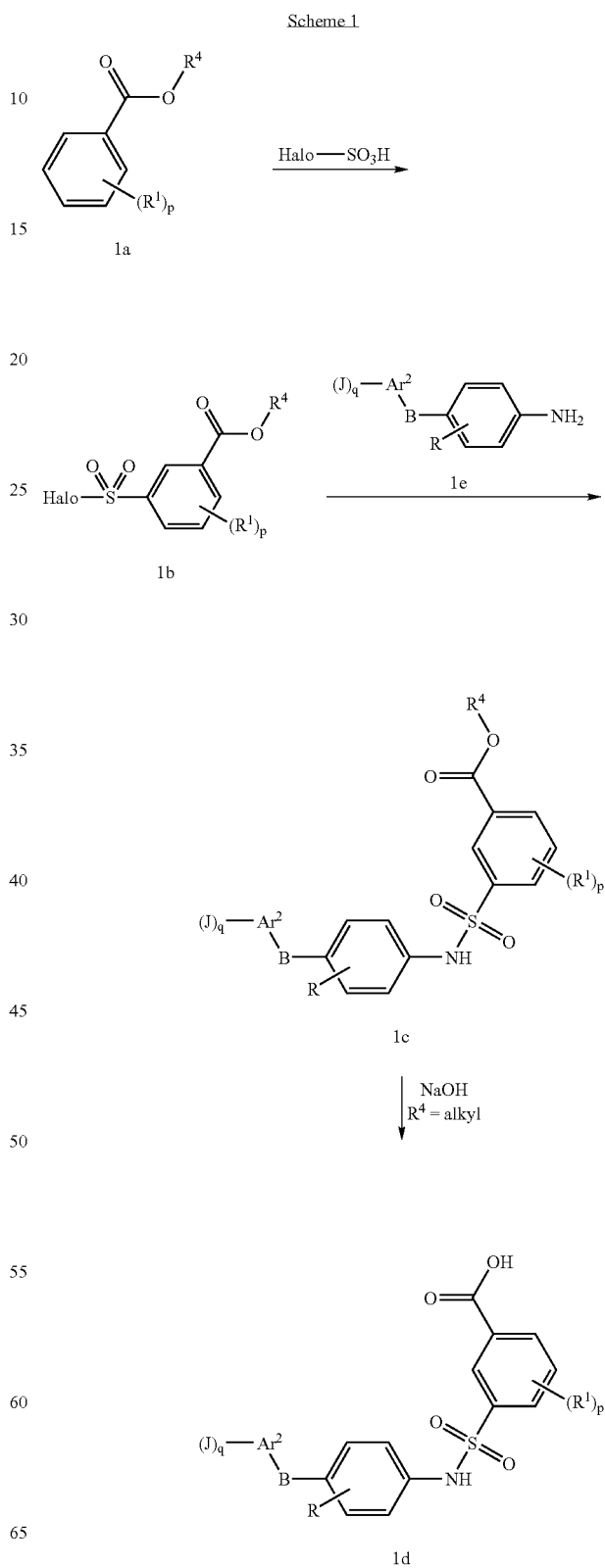

According to reaction Scheme 1, the compounds of formula 1d, which are compounds of formula I wherein X is —COOR$^4$, R$^2$ is H, R (optionally present) is halo, alkyl, alkoxy or alkylthio and R$^1$, B, Ar$^2$, J, p and q are as described above are prepared by procedures well known in the art. For example, treatment of the benzoic acid or ester 1a (which are commercially available or are known in the literature or may be prepared according to methods familiar to those skilled in the art) with chlorosulfonic acid (halo is chloro) at temperatures between about 90 and 110° C., preferably 100° C., for a period of about 15 min to 3 hr, preferably 2.5 hr for the acid and 15 min for the ester, leads to the halogenated sulfonyl 1b.

The reaction of sulfonyl chloride 1b with appropriately substituted anilines 1e (preparation of anilines 1e described in Schemes 4, 5, 6, 7 and 8) to form the sulfanilides 1c may be performed under reaction conditions well known to those skilled in the art. For example, the reaction of sulfonyl chloidel 1b and an aniline 1e may be performed in an inert solvent such as tetrahydrofuran, dimethylformamide or a mixture of acetone and water, in the presence of a base such as pyridine, potassium carbonate or sodium carbonate, at temperatures between 20° C. and 65° C., preferably at room temperature for a period of about 10 to 36 hr, preferably about 20 hr. If 1b is a chlorosulfonyl benzoic ester (R$^4$=CH$_3$), it may be preferable to perform the reaction in an organic solvent such as tetrahydrofuran in the presence of an amine base such pyridine and triethylamine.

The ester product 1c may be converted to the benzoic acid 1d by hydrolysis with an alkali metal hydroxide, preferably sodium hydroxide, in a mixture of an alcohol, preferably methanol, and water at a temperature of about 50 to 100° C. preferably at reflux temperature, for a period of about 2 to 30 hr.

Scheme 2

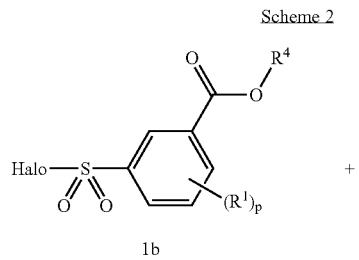

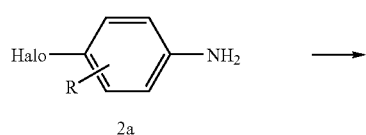

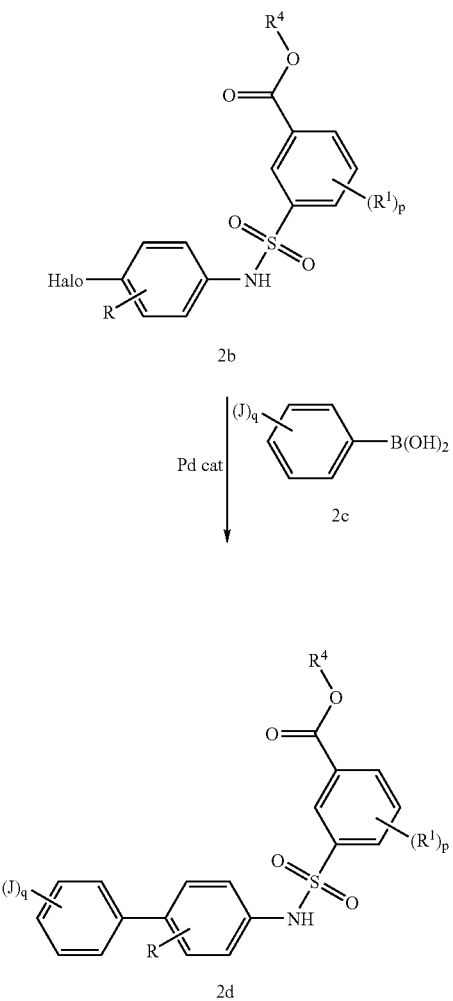

According to reaction Scheme 2, the desired Formula I compounds wherein X is —COOR$^4$, R$^2$ is H, B is a bond, Ar$^2$ is phenyl, R (optionally present) is halo, alkyl, alkoxy or alkylthio, and R$^1$, J, p and q are as described above, are prepared by reacting a halogenated sulfonyl (wherein halo is chloro) 1b and 4-haloaniline 2a (wherein halo is bromo or iodo) in an inert solvent such as tetrahydrofuran or a solvent mixture such as acetone and water, in the presence of an amine base such as pyridine/triethylamine or an inorganic base such as potassium carbonate or sodium carbonate, at a temperature of about 20° C. to 50° C., preferably room temperature, for a period of about 20 hr to form the halogenated sulfanilide 2b.

Reaction of the halogenated sulfanilide 2b in a solvent such as tetrahydrofuran, dioxane, dimethoxyethane or dioxane/water with an appropriately substituted benzene boronic acid derivative 2c under palladium catalysis in the presence of a base such as potassium carbonate, cesium carbonate or sodium carbonate, at temperatures between 80° C. and 110° C., preferably at reflux, for 6–30 hr, preferably 20 hr, using procedures known to those skilled in the art, leads to the biphenylsulfanilide 2d. Further palladium catalysts, phosphine ligands, solvents, bases and reaction temperatures that can be used are exemplified in Chemical Reviews 102, 1359 (2002). For example, reaction of bromosulfanilide as the halogenated sulfanilide 2b with an arylboronic acid 2c in the presence of a catalytic amount of dichloro[1,1'-bis(diphenylphosphino)ferrocene]palladium(II) dichloromethane adduct and 1,1'-bis(diphenylphosphino)ferrocene, with potassium carbonate as base and aqueous dioxane as solvent, yields biphenylanilide 2d. As shown in Scheme 1, the ester group of compound 2d (X, —COOR$^4$) may be converted to an acid group by basic hydrolysis.

The n-alkyl sulfanilide ester 3b may be converted to acid 3c by basic hydrolysis such as the reaction conditions previously exemplified in Scheme 1.

Schemes 4, 5, 6, 7 and 8 describe the preparation of anilines 1e, used in the synthesis shown in Scheme 1. Alternatively, the anilines 1e in Scheme 1 are commercially available or are known in the literature or may be prepared according to procedures well known in the art.

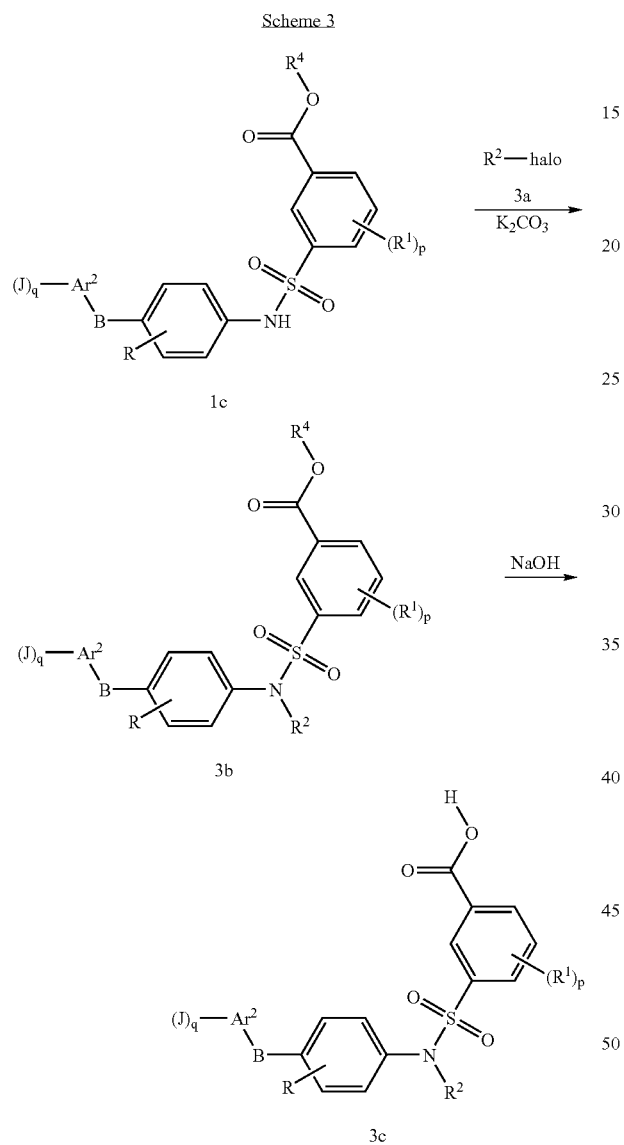

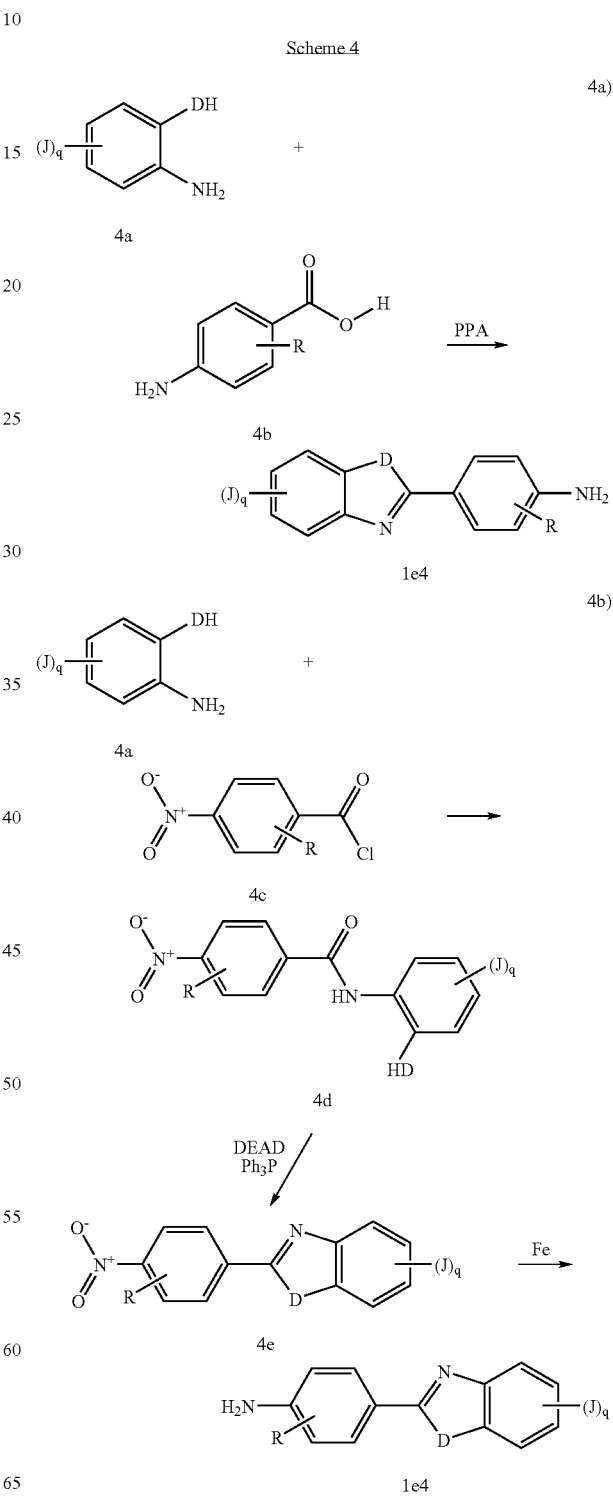

According to reaction Scheme 3, the desired Formula I compounds wherein X is —COOR$^4$, R$^2$ is alkyl, R (optionally present) is halo, alkyl, alkoxy or alkylthio, and R$^1$, R$^2$, B, Ar$^2$, J, p and q are as described above, are prepared by treating a sulfanilide 1c with an appropriate halogenated alkyl (wherein halo is bromo or iodo) 3a or with an alkyl sulfonate in the presence of an alkali metal carbonate such as potassium, sodium or cesium carbonate in an inert solvent such as acetone or dimethylformamide at temperatures between 60° C. and 80° C., preferably acetone at reflux temperature to yield the n-alkyl sulfanilide ester 3b.

The desired Formula 1e compounds wherein $R^2$ is hydrogen, R (optionally present) is halo, alkyl, alkoxy or alkylthio, B is a bond, $Ar^2$ is a phenyl ring fused to an imidazole, oxazole, or thiazole ring (D is N, O or S) and J and q are as described above, may be prepared by 4a and 4b (Scheme 4) or by similar synthetic routes familiar to those skilled in the art.

In Scheme 4a, a 2-aminophenol, 2-aminothiophenol or 2-aminoaniline derivative 4a is heated with an appropriately substituted 4-aminobenzoic acid 4b in polyphosphoric acid at about 170° C. to 200° C. for 4–10 hr, preferably 190° C. for 6 hr, to yield the corresponding 4-benzoxazol-2-yl-phenylamine, 4-benzothiazol-2-yl-phenylamine, or 4-benzimidazol-2-yl-phenylamine derivatives 1e4.

Alternatively, as outlined in Scheme 4b, acylation of a 2-aminophenol, 2-aminothiophenol or 2-aminoaniline derivative 4a with 4-nitrobenzoyl chloride or 4-nitrobenzoyl bromide 4c, in an inert solvent such as methylene chloride, in the presence of an amine base such as 4-dimethylaminopyridine, at a temperature of 20° C. to 50° C. for 10–30 hr, preferably at room temperature for 20 hr, yields the corresponding benzamide 4d.

Under the acylation reaction conditions, the thiophenol derivative 4d (D=S) spontaneously cyclizes to the benzothiazole derivative 4e (D=S). The phenol derivative 4d (D=O) may be cyclized to the benzoxazole derivative 4e (D=O) by treatment with diethyl azodicarboxylate (DEAD) and triphenylphosphine ($Ph_3P$), in a solvent such as tetrahydrofuran, dimethylformamide, methylene chloride or dioxane, preferably tetrahydrofuran at 15° C. to 35° C. for 10–30 hr, preferably at room temperature overnight.

The nitro group in 4e may be reduced to form the aniline 1e4 by procedures familiar to those skilled in the art. For example, heating the nitro compound 4e with iron powder and calcium chloride in aqueous alcohol such as ethanol at about 60° C. to 100° C. for 4 to 10 hr, preferably at reflux for 5 hr yields the aniline 1e4. Other reducing reagents such as iron and acetic acid, zinc and aqueous hydrochloric acid and catalytic hydrogenation are exemplified in Richard Larock, *Comprehensive Organic Transformations*, VCH Publishers, New York, 1989 412.

Acylation of commercially available 5-(4-nitrophenyl)-1H-tetrazole 5a with an acyl chloride 5b in pyridine at room temperature, followed by heating at 60° C. for 1 hr and at 100° C. for 2 hr, yields 2-(4-nitrophenyl)-1,3,4-oxadiazole 5c.

Reduction of the nitro group to amine by methods known to those skilled in the art yields the aniline 1e5. For example, the reduction may be performed, as previously shown in Scheme 4b, with iron powder and calcium chloride in aqueous ethanol.

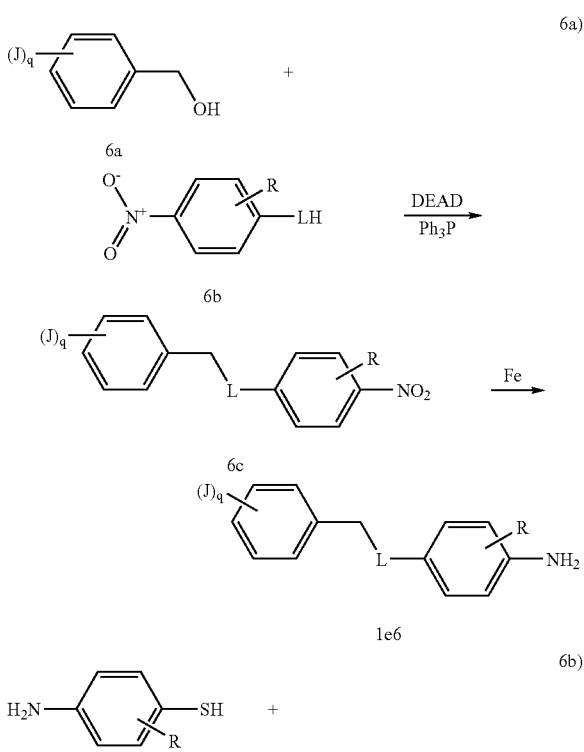

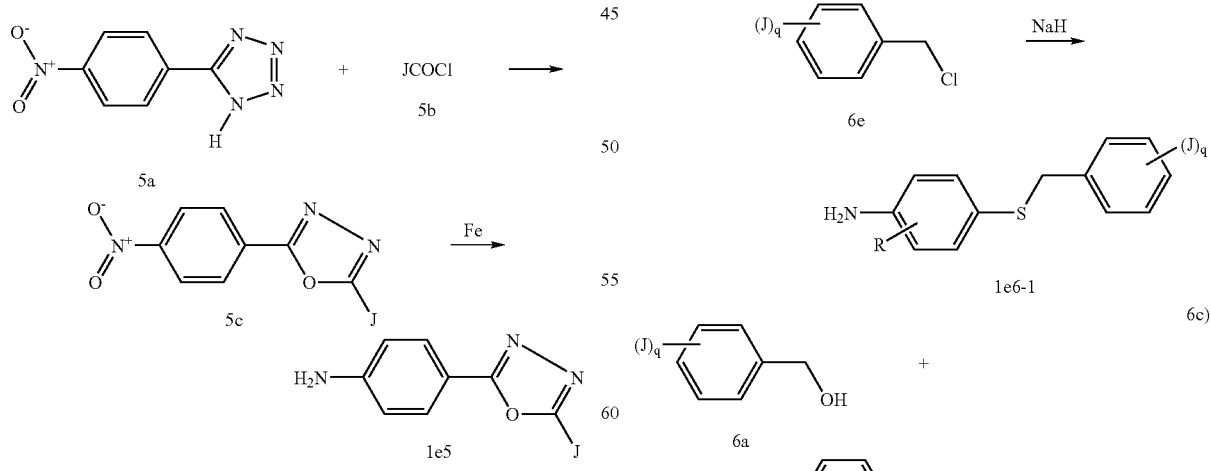

The desired Formula 1e5 compounds wherein $R^2$ is hydrogen, B is a bond, $Ar^2$ is an oxadiazole ring and J is as described above, may be prepared by Scheme 5 or by similar synthetic routes familiar to those skilled in the art.

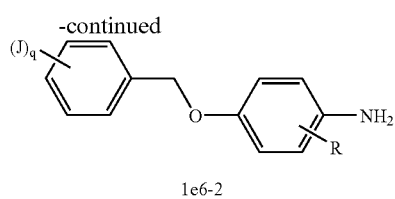

1e6-2

The desired Formula 1e6 compounds wherein $R^2$ is hydrogen, R (optionally present) is halo, alkyl, alkoxy or alkylthio, B is —L—CH$_2$— or —CH$_2$—L—, Ar$^2$ is phenyl and J and q are as described above, may be prepared by the synthesis depicted in 6a, 6b and 6c of Scheme 6 or by similar synthetic routes familiar to those skilled in the art.

Benzyloxynitrobenzene or benzylsulfanylnitrobenzene derivatives (6c) may be prepared by the Mitsunobu reaction, for example, by the reaction of 4-nitrophenol or 4-nitrothiophenol 6b with an appropriate benzyl alcohol 6a, in the presence of diethyl azodicarboxylate (DEAD) and triphenylphosphine (Ph$_3$P), in a solvent such as tetrahydrofuran, dimethylformamide, methylene chloride or dioxane, at about 15° C. to 35° C. for about 10 to 30 hr, preferably in tetrahydrofuran at room temperature overnight (Scheme 6a). The reaction conditions, solvents, temperature and reaction time for the Mitsunobu reaction are reviewed in *Organic Reactions*, Vol 42, 1992, 335, John Wiley, 2002. Reduction of the nitro group of 6c by methods known to those skilled in the art, including those exemplified in Scheme 4b, yields the corresponding aniline 1e6.

For example, in Scheme 6b, benzylsulfanylaniline 1e6-1 may be synthesized by treating 4-aminothiophenol 6d with an appropriately substituted benzyl chloride 6e in the presence of a base such as sodium hydride, cesium carbonate or sodium tert-butoxide, in a solvent such as tetrahydrofuran, dimethylformamide or dimethoxyethane, preferably tetrahydrofuran, at a temperature of about 20° C. to 70° C. for about 8 to 30 hr, preferably at room temperature overnight.

4-Benzyloxyaniline 1e6-2 may be prepared by the Mitsunobu reaction (Scheme 6c), wherein the reaction of 4-aminophenol 6f with an appropriate benzyl alcohol 6a, in a solvent such as tetrahydrofuran, is mediated by diethyl azodicarboxylate (DEAD) and triphenylphosphine (Ph$_3$P), at room temperature overnight as exemplified for 6c.

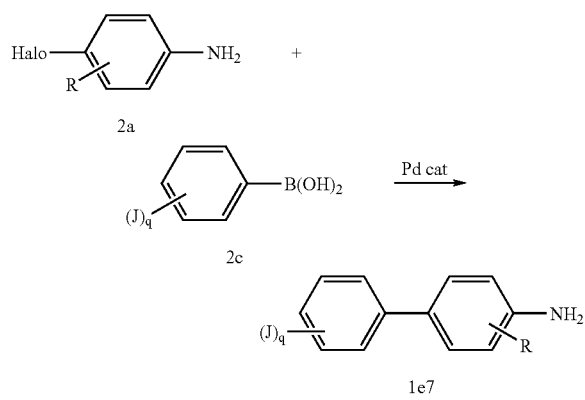

The desired Formula 1e compounds wherein $R^2$ is hydrogen, R (optionally present) is halo, alkyl, alkoxy or alkylthio, B is a bond, Ar$^2$ is phenyl and J and q are as described above, may be prepared by the synthesis depicted in Scheme 7 or by similar synthetic routes familiar to those skilled in the art.

Biphenylamine derivatives 1e7 may be synthesized by a Suzuki coupling of 4-haloaniline 2a wherein halo is bromo or iodo and an appropriately substituted benzene boronic acid derivative 2c, using procedures known to those skilled in the art as exemplified in Scheme 2c. Benzene boronic acid derivatives 2c are commercially available or may be readily prepared by literature methods known to those skilled in the art as exemplified in Scheme 2c. For example, reaction of 4-bromoaniline with an arylboronic acid 2c in the presence of a catalytic amount of dichloro[1,1'-bis(diphenylphosphino)ferrocene]palladium(II) dichloromethane adduct and 1,1'-bis(diphenylphosphino)ferrocene, with potassium carbonate as base and aqueous dioxane as solvent, at reflux temperature overnight yields biphenylamine derivative 1e7.

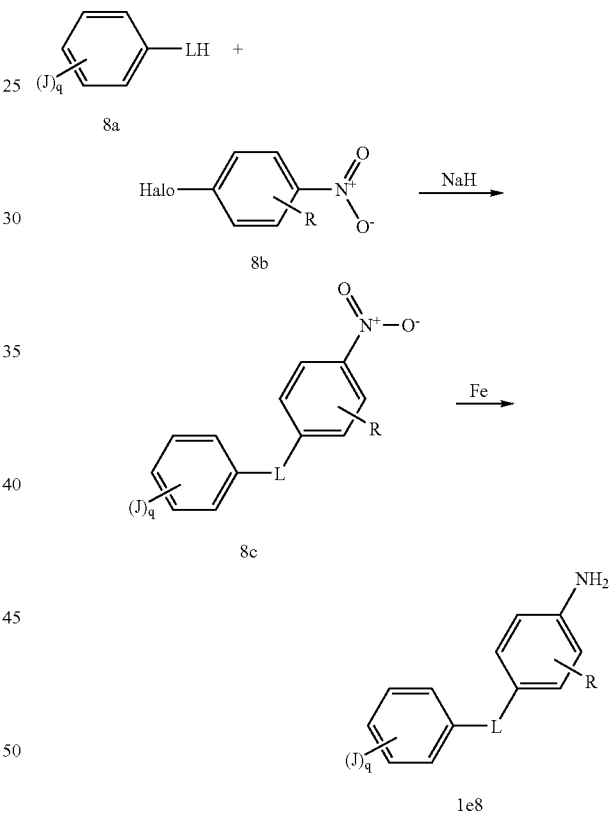

The desired Formula 1e compounds wherein $R^2$ is hydrogen, R (optionally present) is halo, alkyl, alkoxy or alkylthio, B is L, Ar$^2$ is phenyl and J and q are as described above, may be prepared by the synthesis depicted in Scheme 8 or by similar synthetic routes familiar to those skilled in the art.

Phenoxyaniline and phenylsulfanylaniline derivatives 1e8 (Scheme 8) may be prepared by reaction of 4-halonitrobenzene 8b, wherein halo is chloro, bromo or iodo, with an appropriate phenol or thiophenol 8a in the presence of a base such sodium hydride, sodium tert-butoxide or cesium carbonate in an inert solvent such as dimethylformamide, tetrahydrofuran or dimethoxyethane, at about 60° C. to 90°

C. for about 10 to 30 hr, preferably at 80° C. overnight yields the nitro derivative 8c. Aniline 1e8 may be produced by reducing the nitro derivative 8c, using procedures known to those skilled in the art, such as those previously exemplified in Scheme 4b.

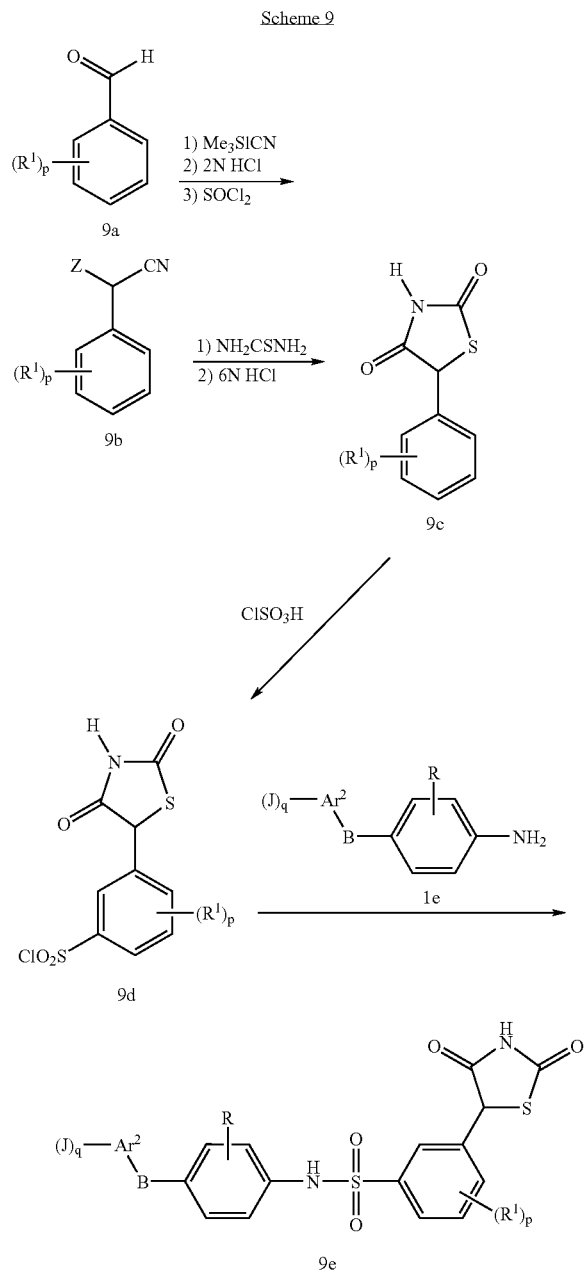

C. to 30° C. for about 15 to 30 hr, preferably in methylene chloride at room temperature overnight to yield the cyanohydrin 9b (Z=OH).

The cyanohydrin 9b (Z=OH) is converted to the chlorocyanide 9b (Z=Cl) with thionyl chloride in chloroform or methylene chloride at about 30° C. to 65° C. for about 30 to 60 min, preferably in chloroform at reflux temperature for 45 min. Reaction of chlorocyanide 9b (Z=Cl) with thiourea in an alcoholic solvent such as ethanol at about 60° C. to 80° C. for about 4 to 10 hr, preferably in ethanol at reflux temperature for 5 hr followed, by hydrolysis of the intermediate iminothiazolidinone with aqueous acid at about 95° C. to 120° C. for about 4 to 10 hr, preferably 6N aqueous hydrochloric acid at reflux temperature for 5 hr leads to the thiazolidinedione 9c.

Alternatively, appropriate benzaldehyde 9a is treated with sodium cyanide in a mixture of water, acetic acid and ethylene glycol monomethyl ether at room temperature for 1.5 hr followed by the addition of thiourea and concentrated hydrochloric acid and heating at about 100° C. for 18 hr to yield thiazolidinedione 9c (Chem. Pharm. Bull., 45, 1984 (1997).

Heating thiazolidinedione 9c in neat chlorosulfonic acid at about 90° C. to 110° C. for about 15 to 30 min, preferably at 100° C. for 15 min yields sulfonyl chloride 9d. Reaction of sulfonyl chloride 9d with appropriately substituted anilines 1e using procedures known to those skilled in the art, such as the reaction described in Scheme 1, leads to the desired thiazolidinedione derivatives 9e.

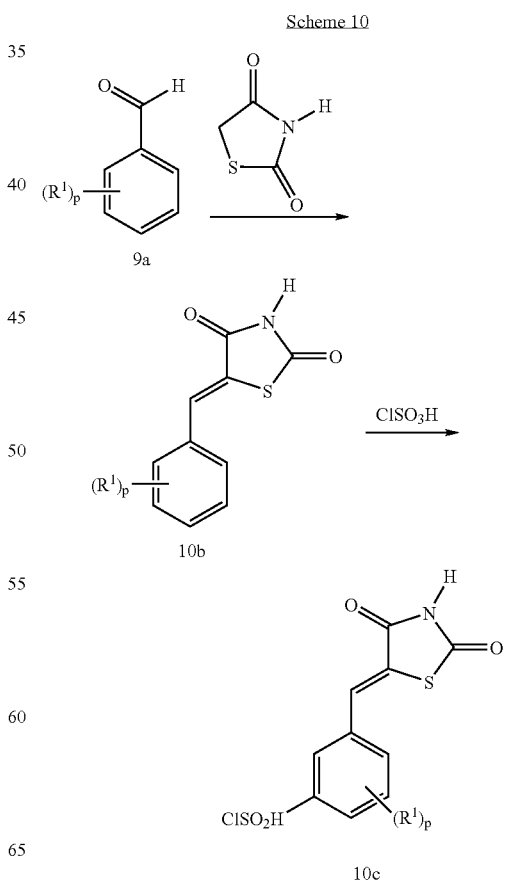

Compounds of Formula I wherein X is thiazolidinedione-5-yl-G-, G is $(CH_2)_s$, s is 0, $R^2$ is H, R (optionally present) is halo, alkyl, alkoxy or alkylthio and $R^1$, B, $Ar^2$, J, p and q are as described above, may be prepared by the synthetic sequence outlined in Scheme 9, as taught by J. Med. Chem., 29, 773 (1986) and Chem. Pharm. Bull., 30, 3601 (1982). An appropriately substituted benzaldehyde 9a is treated with trimethylsilyl cyanide and a catalytic amount of zinc iodide in anhydrous methylene chloride or chloroform at about 20°

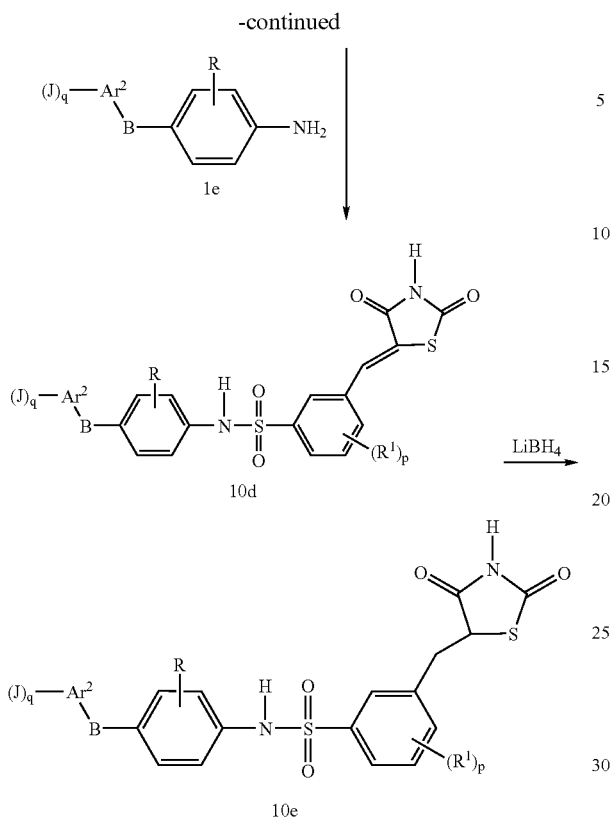

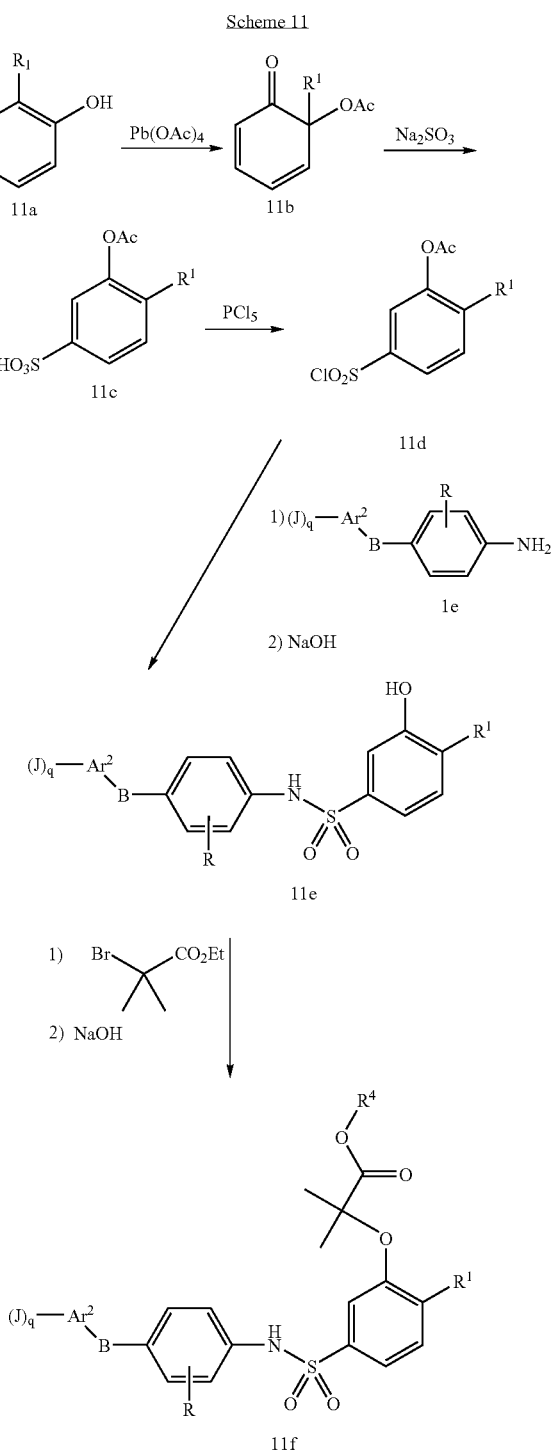

Scheme 11

Compounds of Formula I wherein X is thiazolidinedione-5-yl-G-, G is methylidine or $(CH_2)_s$ and s is 1, $R^2$ is H, R (optionally present) is halo, alkyl, alkoxy or alkylthio and $R^1$, B, $Ar^2$, J, p and q are as described above, may be synthesized by the reaction sequence outlined in Scheme 10, as taught by Chem. Pharm. Bull., 45, 1984 (1997). Condensation of an appropriately substituted benzaldehyde 9a and thiazolidinedione mediated by piperidine in acetic acid or ethanol or ammonium acetate in acetic acid at about 110° C. to 120° C. for about 8 to 30 hr, preferably piperidine in acetic acid at reflux for about 20 hr, or by piperidine and benzoic acid in toluene at reflux for about 3 to 10 hr leads to benzylidene thiazolidinedione 10b.

Heating thiazolidinedione 10b in neat chlorosulfonic acid at about 90° C. to 110° C. for about 15 to 25 min, preferably about 100° C. for 15 min yields sulfonyl chloride 10c.

Reaction of sulfonyl chloride 10c with appropriately substituted anilines 1e using procedures known to those skilled in the art, such as the process described in Scheme 1, leads to benzylidene thiazolidinedione derivatives 10d.

Reduction of the olefinic bond of 10d using methods familiar to those skilled in the art, such as lithium borohydride in pyridine/tetrahydrofuran at about 65° C. to 90° C. for about 2 to 6 hr or sodium borohydride/lithium chloride in pyridine/tetrahydrofuran at about 65° C. to 90° C. for about 3 to 6 hr, or catalytic hydrogenation with 10% Pd—C in 1,4-dioxane or methanol at about 50 to 60 psi for about 36 to 60 hr, preferably lithium borohydride in pyridine/tetrahydrofuran at reflux for 3 hr, yields the desired thiazolidinedione derivative 10e.

Compounds of Formula I, wherein X is —O—$(CR^3{}_2)$—$COOR^4$, $R^3$ is $CH_3$, $R^1$ is alkyl, $R^2$ is H, R (optionally present) is halo, alkyl, alkoxy or alkylthio and, B, $Ar^2$, J and q are as described above, may be prepared by the synthetic route outlined in Scheme 11 as taught by Monat. Chem. 99, 2048 (1968). The reaction of substituted phenol 11a with lead tetraacetate in acetic acid at about 20° C. to 30° C. for about 3 to 6 hr, preferably at room temperature for 3 hr yields quinol acetate 11b.

Upon treatment with sodium sulfite in water at about 20° C. to 30° C. for about 3 to 6 hr, preferably room temperature for 3 hr, quinol acetate 11b is converted to sulfonic acid 11c.

Sulfonyl chloride 11d is prepared by heating sulfonic acid 11c with phosphorus pentachloride at about 110° C. to 130° C. for about 25 to 55 min, preferably about 120° C. for about 30 min.

Reaction of sulfonyl chloride 11d with appropriately substituted anilines 1e using procedures known to those skilled in the art, such as the process described in Scheme 1, followed by alkaline hydrolysis of the acetate yields sulfonamide 11e.

Alkylation of sulfonamide 11e with ethyl 2-bromoisobutyrate and potassium carbonate in dimethylformamide or ethanol at about 80° C. to 100° C. for about 12 to 24 hr, preferably dimethylformamide at about 95° C. for about 18 hr, followed by basic hydrolysis of the product, leads to the desired acid 11f.

Scheme 12

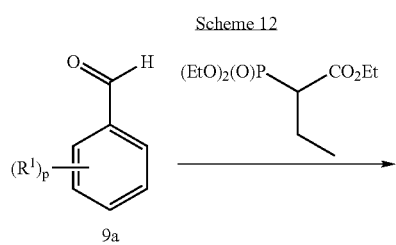

9a

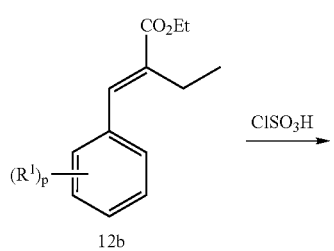

12b

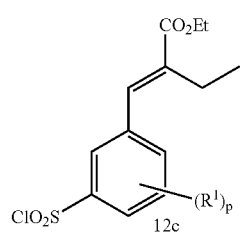

12c

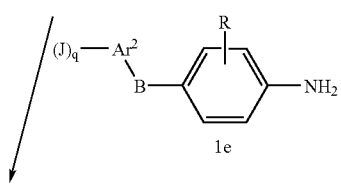

1e

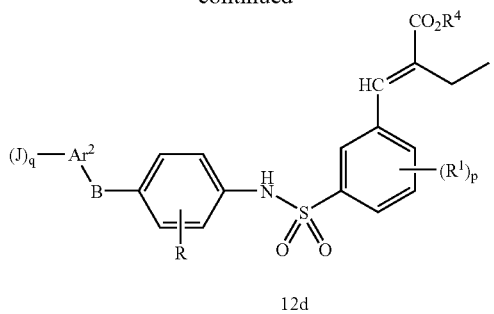

12d

1) Mg/MeOH
2) NaOH

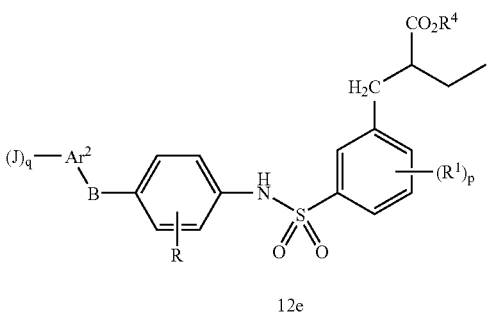

12e

Compounds of Formula I wherein X is —CH²(CR$^5_w$)—COOR$^4$ and R$^5$ is CH$_3$CH$_2$, w is 1, R$^2$ is H, R (optionally present) is halo, alkyl, alkoxy or alkylthio and R$^1$, B, Ar$^2$, J, p and q are as described above, may be synthesized by the reaction sequence outlined in Scheme 12. Reaction of an appropriately substituted benzaldehyde 9a with the carbanion formed from triethyl-2-phosphonobutyrate and potassium t-butoxide or sodium hydride in tetrahydrofuran or dimethoxyethane at about 20° C. to 30° C. for about 2 to 5 hr, preferably at room temperature for 3 hr, yields olefinic ester 12b.

Ester 12b is converted to sulfonyl chloride 12c by heating in chlorosulfonic acid at about 55° C. to 70° C. for about 15–25 min, preferably at about 60° C. for about 15 min.

Reaction of sulfonyl chloride 12c with appropriately substituted anilines 1e using methods know to those skilled in the art, such as the process described in Scheme 1, yields sulfonamide 12d.

Reduction of the olefinic bond of 12c using procedures known to those skilled in the art, such as magnesium in methanol or ethanol at about 60° C. to 85° C. until the magnesium is consumed, or catalytic hydrogenation with 10% Pd—C in 1,4-dioxane or methanol at about 50 to 60 psi for about 36 to 60 hr, preferably magnesium in methanol at about 65° C., followed by alkaline hydrolysis of the product, yields the desired acid 12e.

Scheme 13

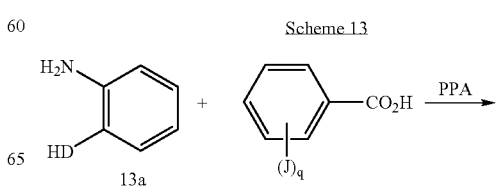

13a

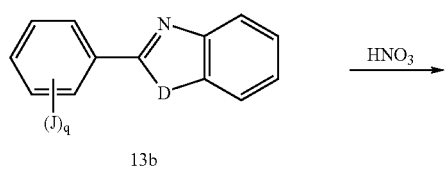

13b

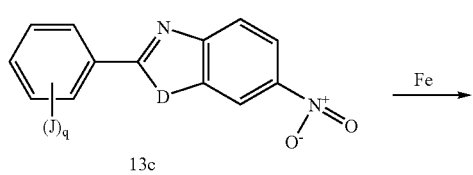

13c

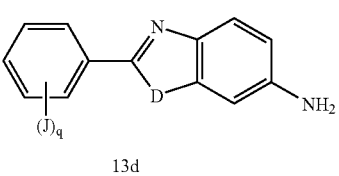

13d

The compounds of Formula 1 wherein $Ar^1$ is other than phenyl may be prepared by the reaction sequence outlined in Scheme 1 by replacing aniline 1e with anilines fused to a member selected from thiazolyl, furanyl, oxazolyl, pyridine, pyrimidine, phenyl or thienyl which are prepared from intermediates that are commercially available or known in the literature by methods known to those skilled in the art.

For example, Scheme 13 depicts a process wherein $Ar^1$ is benzooxazole or benzothiazole, B is a bond, $Ar^2$ is phenyl, and J and q are as defined above. In the first step of Scheme 13, a 2-aminophenol or 2-aminothiophenol (wherein D is O or S) 13a is reacted with an appropriate benzoic acid in polyphosphoric acid at about 190° C. for about 6 hr as exemplified in Scheme 4a yields the benzoxazole or benzothiazole 13b. Nitration of 13b with concentrated nitric acid and sulfuric acid at about 75° C. for about 30 min and at about 100° C. for about 1 hr leads to the nitro derivative 13c, which is reduced to the desired aminobenzoxazole or aminobenzothiazole 13d using procedures shown in Scheme 4b.

Scheme 14

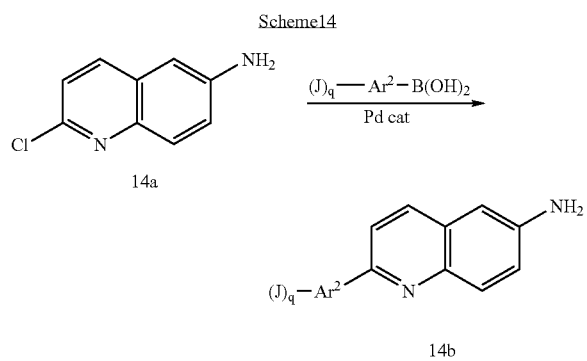

Compounds wherein $Ar^1$ is quinoline, B is a bond, $Ar^2$ is phenyl, and J and q are as defined above may be prepared,
for example, from chloroquinoline 14a, which is known in the literature [J. Amer. Chem. Soc., 60, 2104 (1938)], by reaction with an appropriate aryl- or alkylboronic acid using methods exemplified in Scheme 2.

Scheme 15

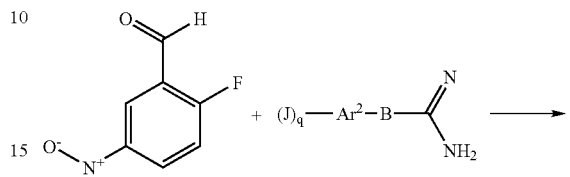

15a 15b

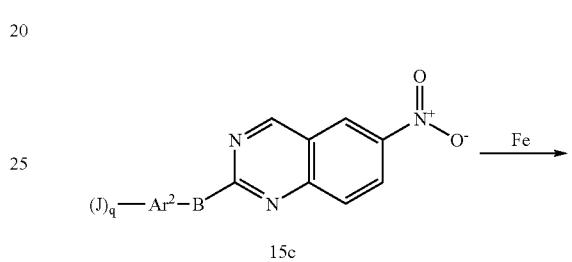

15c

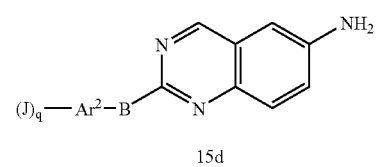

15d

Compounds wherein $Ar^1$ is quinazoline, and B, $Ar^2$, J, and q are as defined above may be prepared, for example, by the method described in Synlett, p. 1993 (1999). Reaction of an appropriate amidine 15b with nitrobenzaldehyde 15a in acetonitrile in the presence of potassium carbonate and molecular sieves at reflux temperature for about 5 to 10 hr yields the nitroquinazoline 15c. Reduction of 15c to the desired amine 15d may be carried out by the methods described in Scheme 4b.

Scheme 16

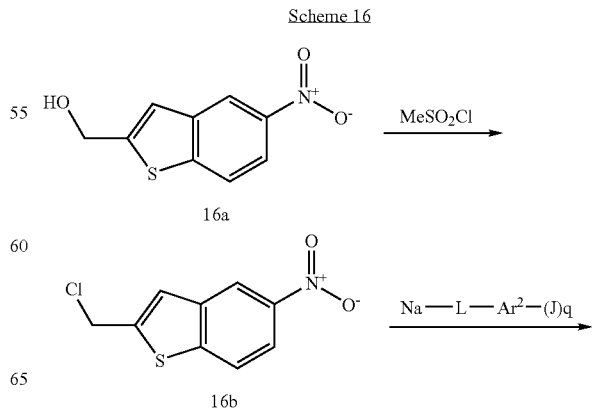

16a

16b

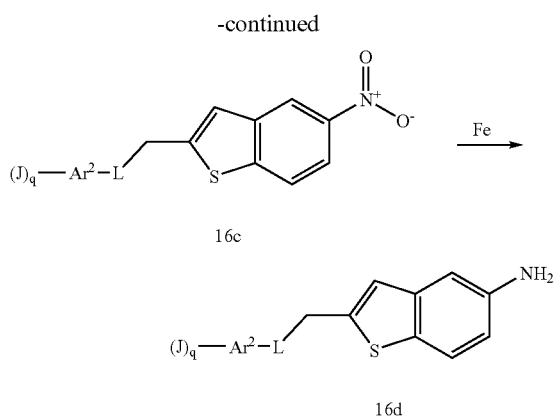

16c

16d

Compounds wherein Ar[1] is benzothiophene, B is —L—CH$_2$—, L is O or S, and Ar[2], J, and q are as defined above may be prepared, for example, from hydroxymethylbenzothiophene 16a, which is known in the literature (J. Heterocycl. Chem., 20, 129 (1983)). Reaction of 16a with methanesulphonyl chloride and pyridine in methylene chloride, as taught by J. Med. Chem., 35, 457 (1992), at room temperature overnight leads to chloromethylbenzothiophene 16b. Treatment of 16b with an appropriate alcohol or mercaptan in the presence of a base such as sodium hydride or sodium tert-butoxide in an inert solvent such as tetrahydrofuran, dimethoxyethane or dimethylformamide at about 20° C. to 60° C. for about 6 to 30 hr, preferably at room temperature overnight, yields the nitro derivative 16c. Reduction of 16c to the desired amine 16d may be performed by the methods described in Scheme 4b.

Scheme 17

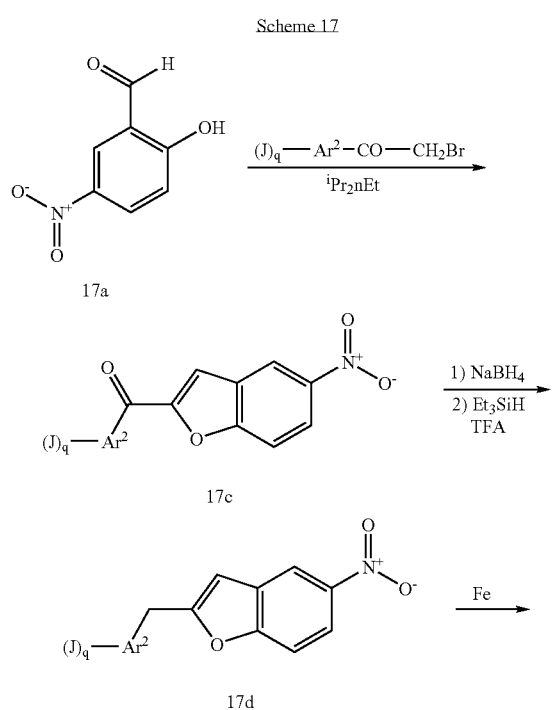

17a

17c

17d

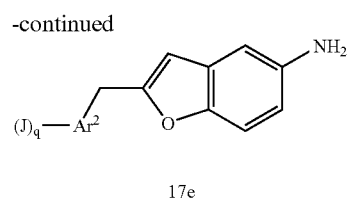

17e

Compounds wherein Ar[1] is benzofuran, B is CH$_2$, and Ar[2], J, and q are as defined above may be prepared as taught by J. Med. Chem., 39, 3897 (1996), for example, by the reaction of 5-nitrosalicylaldehyde 17a with an appropriate bromomethyl arylketone and a base such as diisopropylethylamine, potassium fluoride or potassium carbonate in a solvent such as dimethylformamide, ethanol or acetone, at a temperature of about 75 to 95° C., for about 3 to 24 hr, preferably diisopropylethylamine in dimethylformide at 92° C. for 4 hr. The ketone 17c is reduced to the corresponding alcohol with sodium borohydride in methanol, which is converted to the nitro compound 17d with triethylsilane in trifluoroacetic acid. Reduction of 17d to the desired amine may be carried out by the methods described in Scheme 4b.

The compounds of this invention may also be used in conjunction with other pharmaceutical agents (e.g., LDL-cholesterol lowering agents, triglyceride lowering agents) for the treatment of the disease/conditions described herein. For example, they may be used in combination with a HMG-CoA reductase inhibitor, a cholesterol synthesis inhibitor, a cholesterol absorption inhibitor, a CETP inhibitor, a MTP/Apo B secretion inhibitor, another PPAR modulator and other cholesterol lowering agents such as a fibrate, niacin, an ion-exchange resin, an antioxidant, an ACAT inhibitor, and a bile acid sequestrant. Other pharmaceutical agents would also include the following: a bile acid reuptake inhibitor, an ileal bile acid transporter inhibitor, an ACC inhibitor, an antihypertensive (such as NORVASC®), a selective estrogen receptor modulator, a selective androgen receptor modulator, an antibiotic, an antidiabetic (such as metformin, a PPARγ activator, a sulfonylurea, insulin, an aldose reductase inhibitor (ARI) and a sorbitol dehydrogenase inhibitor (SDI)), and aspirin (acetylsalicylic acid). A slow-release form of niacin is available and is known as Niaspan. Niacin may also be combined with other therapeutic agents such as statins, i.e. lovastatin, which is an HMG-CoA reductase inhibitor and described further below. This combination therapy is known as ADVICOR® (Kos Pharmaceuticals Inc.) In combination therapy treatment, both the compounds of this invention and the other drug therapies are administered to mammals (e.g., humans, male or female) by conventional methods.

Any HMG-CoA reductase inhibitor may be used in the combination aspect of this invention. The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. The following paragraphs describe exemplary statins.

The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455–509 and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus *Aspergillus*, such as lovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP-491226A (the disclosure of which is incorporated by reference) discloses certain pyridyldihydroxyheptenoic acids, such as cerivastatin. In addition, U.S. Pat. No. 5,273,995 (the disclosure of which is incorporated by reference) discloses certain 6-[2-(substituted-pyrrol-1-yl)alkyl]pyran-2-ones such as atorvastatin and any pharmaceutically acceptable form thereof (i.e. LIPITOR®). Additional HMG-CoA reductase inhibitors include rosuvastatin and pitavastatin.

Atorvastatin calcium (i.e., atorvastatin hemicalcium), disclosed in U.S. Pat. No. 5,273,995, which is incorporated herein by reference, is currently sold as Lipitor® and has the formula

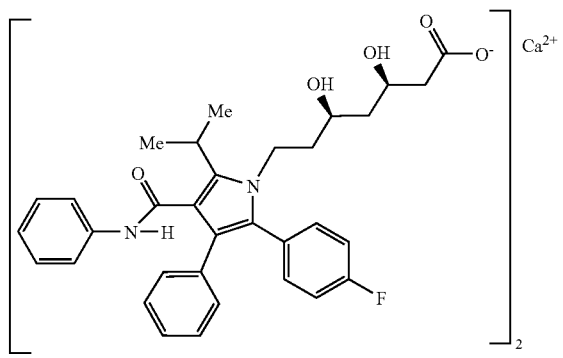

Atorvastatin calcium is a selective, competitive inhibitor of HMG-CoA. As such, atorvastatin calcium is a potent lipid lowering compound. The free carboxylic acid form of atorvastatin may exist predominantly as the lactone of the formula

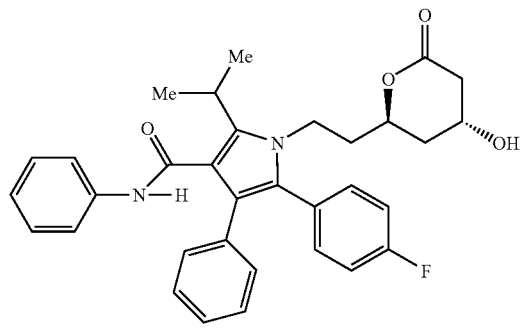

and is disclosed in U.S. Pat. No. 4,681,893, which is incorporated herein by reference.

Statins also include such compounds as rosuvastatin disclosed in U.S. Pat. No. RE 37,314 E, pitivastatin disclosed in EP 304063 B1 and U.S. Pat. No. 5,011,930, simvastatin, disclosed in U.S. Pat. No. 4,444,784, which is incorporated herein by reference; pravastatin, disclosed in U.S. Pat. No. 4,346,227 which is incorporated herein by reference; cerivastatin, disclosed in U.S. Pat. No. 5,502,199, which is incorporated herein by reference; mevastatin, disclosed in U.S. Pat. No. 3,983,140, which is incorporated herein by reference; velostatin, disclosed in U.S. Pat. No. 4,448,784 and U.S. Pat. No. 4,450,171, both of which are incorporated herein by reference; fluvastatin, disclosed in U.S. Pat. No. 4,739,073, which is incorporated herein by reference; compactin, disclosed in U.S. Pat. No. 4,804,770, which is incorporated herein by reference; lovastatin, disclosed in U.S. Pat. No. 4,231,938, which is incorporated herein by reference; dalvastatin, disclosed in European Patent Application Publication No. 738510 A2; fluindostatin, disclosed in European Patent Application Publication No. 363934 A1; and dihydrocompactin, disclosed in U.S. Pat. No. 4,450,171, which is incorporated herein by reference.

Any HMG-CoA synthase inhibitor may be used in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth Enzymol. 1975; 35:155–160: Meth. Enzymol. 1985; 110:19–26 and references cited therein). A variety of these compounds are described and referenced below, however other HMG-CoA synthase inhibitors will be known to those skilled in the art. U.S. Pat. No. 5,120,729 (the disclosure of which is hereby incorporated by reference) discloses certain beta-lactam derivatives. U.S. Pat. No. 5,064,856 (the disclosure of which is hereby incorporated by reference) discloses certain spiro-lactone derivatives prepared by culturing a microorganism (MF5253). U.S. Pat. No. 4,847,271 (the disclosure of which is hereby incorporated by reference) discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression may be used in the combination aspect of this invention. These agents may be HMG-CoA reductase transcription inhibitors that block the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such compounds may cause this effect by decreasing levels of SREBP (sterol receptor binding protein) by inhibiting the activity of site-1 protease (S1P) or agonizing the oxzgenal receptor or SCAP. Such regulation is readily determined by those skilled in the art according to standard assays (Meth. Enzymol. 1985; 110:9–19). Several compounds are described and referenced below, however other inhibitors of HMG-CoA reductase gene expression will be known to those skilled in the art. U.S. Pat. No. 5,041,432 (the disclosure of which is incorporated by reference) discloses certain 15-substituted lanosterol derivatives. Other oxygenated sterols that suppress synthesis of HMG-CoA reductase are discussed by E. I. Mercer (Prog.Lip. Res. 1993;32:357–416).

Any compound having activity as a CETP inhibitor can serve as the second compound in the combination therapy aspect of the present invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art, for example, those disclosed in commonly assigned U.S. Pat. No. 6,140,343 and commonly assigned U.S. Pat. No. 6,197,786. CETP inhibitors disclosed in these patents include compounds, such as [2R,4S]4-[(3, 5-bis-trifluoromethyl-benzyl)-methoxycarbonyl-amino]-2-ethyl-6-trifluoromethyl-3,4-dihydro-2H-quinoline-1-carboxylic acid ethyl ester, which is also known as torcetrapib. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.,* 49(8): 815–816 (1996), and *Bioorg. Med. Chem. Lett.;* 6:1951–1954 (1996), respectively.

Any other PPAR modulator may be used in the combination aspect of this invention. In particular, modulators of PPARβ and/or PPARγ may be useful incombination with compounds of the present invention.

Any MTP/Apo B (microsomal triglyceride transfer protein and or apolipoprotein B) secretion inhibitor may be used in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R. 1992; Science 258:999). A variety of these compounds are described and referenced below however other MTP/Apo B secretion inhibitors will be known to those skilled in the art, including imputapride (Bayer) and additional compounds such as those disclosed in WO 96/40640 and WO 98/23593, (two exemplary publications).

For example, the following MTP/Apo B secretion inhibitors are particularly useful:

4'-trifluoromethyl-biphenyl-2-carboxylic acid [2-(1H-[1, 2,4,]triazol-3-ylmethyl)-1,2,3,4-tetrahydro-isoquinolin-6-yl]-amide;

4'-trifluoromethyl-biphenyl-2-carboxylic acid [2-(2-acetylamino-ethyl)-1,2,3,4-tetrahydro-isoquinolin-6-yl]-amide;

(2-{6-[(4'-trifluoromethyl-biphenyl-2-carbonyl)-amino]-3,4-dihydro-1H-isoquinolin-2-yl}-ethyl)-carbamic acid methyl ester;

4'-trifluoromethyl-biphenyl-2-carboxylic acid [2-(1H-imidazol-2-ylmethyl)-1,2,3,4-tetrahydro-isoquinolin-6-yl]-amide;

4'-trifluoromethyl-biphenyl-2-carboxylic acid [2-(2,2-diphenyl-ethyl)-1,2,3,4-tetrahydro-isoquinolin-6-yl]-amide; and 4'-trifluoromethyl-biphenyl-2-carboxylic acid [2-(2-ethoxy-ethyl)-1,2,3,4-tetrahydro-isoquinolin-6-yl]-amide.

(S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide;

(S)-2-[(4'-Trifluoromethyl-biphenyl-2-carbonyl)-amino]-quinoline-6-carboxylic acid (pentylcarbamoyl-phenyl-methyl)-amide;

1H-indole-2-carboxamide, 1-methyl-N-[(1S)-2-[methyl (phenylmethyl)amino]-2-oxo-1-phenylethyl]-5-[[[4'-(trifluoromethyl)[1,1'-biphenyl]-2-yl]carbonyl]amino]; and N-[(1 S)-2-(benzylmethylamino)-2-oxo-1-phenylethyl]-1-methyl-5-[[[4'-(trifluoromethyl)biphenyl-2-yl]carbonyl] amino]-1H-indole-2-carboxamide.

Any squalene synthetase inhibitor may be used in the combination aspect of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (Meth. Enzymol. 1969; 15: 393–454 and Meth. Enzymol. 1985; 110: 359–373 and references contained therein). A variety of these compounds are described in and referenced below however other squalene synthetase inhibitors will be known to those skilled in the art. U.S. Pat. No. 5,026,554 (the disclosure of which is incorporated by reference) discloses fermentation products of the microorganism MF5465 (ATCC 74011) including zaragozic acid. A summary of other patented squalene synthetase inhibitors has been compiled (Curr. Op. Ther. Patents (1993) 861–4).

Any squalene epoxidase inhibitor may be used in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta 1984; 794:466–471). A variety of these compounds are described and referenced below, however other squalene epoxidase inhibitors will be known to those skilled in the art. U.S. Pat. Nos. 5,011,859 and 5,064,864 (the disclosures of which are incorporated by reference) disclose certain fluoro analogs of squalene. EP publication 395,768 A (the disclosure of which is incorporated by reference) discloses certain substituted allylamine derivatives. PCT publication WO 9312069 A (the disclosure of which is hereby incorporated by reference) discloses certain amino alcohol derivatives. U.S. Pat. No. 5,051,534 (the disclosure of which is hereby incorporated by reference) discloses certain cyclopropyloxy-squalene derivatives.

Any squalene cyclase inhibitor may be used as the second component in the combination aspect of this invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (FEBS Lett. 1989;244:347–350.). In addition, the compounds described and referenced below are squalene cyclase inhibitors, however other squalene cyclase inhibitors will also be known to those skilled in the art. PCT publication WO9410150 (the disclosure of which is hereby incorporated by reference) discloses certain 1,2,3,5,6,7,8,8a-octahydro-5,5,8(beta)-trimethyl-6-isoquinolineamine derivatives, such as N-trifluoroacetyl-1,2,3,5,6,7,8,8a-octahydro-2-allyl-5,5,8(beta)-trimethyl-6(beta)-isoquinolineamine. French patent publication 2697250 (the disclosure of which is hereby incorporated by reference) discloses certain beta, beta-dimethyl-4-piperidine ethanol derivatives such as 1-(1,5,9-trimethyldecyl)-beta,beta-dimethyl-4-piperidineethanol Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors, however, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below, however other squalene epoxidase/squalene cyclase inhibitors will be known to those skilled in the art. U.S. Pat. Nos. 5,084,461 and 5,278,171 (the disclosures of which are incorporated by reference) disclose certain azadecalin derivatives. EP publication 468,434 (the disclosure of which is incorporated by reference) discloses certain piperidyl ether and thio-ether derivatives such as 2-(1-piperidyl)pentyl isopentyl sulfoxide and 2-(1-piperidyl)ethyl ethyl sulfide. PCT publication WO 9401404 (the disclosure of which is hereby incorporated by reference) discloses certain acyl-piperidines such as 1-(1-oxopentyl-5-phenylthio)-4-(2-hydroxy-1-methyl)-ethyl)piperidine. U.S. Pat. No. 5,102,915 (the disclosure of which is hereby incorporated by reference) discloses certain cyclopropyloxy-squalene derivatives.

The compounds of the present invention can also be administered in combination with naturally occurring compounds that act to lower plasma cholesterol levels. These naturally occurring compounds are commonly called nutraceuticals and include, for example, garlic extract and niacin. A slow-release form of niacin is available and is known as Niaspan. Niacin may also be combined with other therapeutic agents such as lovastatin, or another HMG-CoA reductase inhibitor. This combination therapy with lovastatin is known as ADVICOR™ (Kos Pharmaceuticals Inc.).

Any cholesterol absorption inhibitor can be used as an additional in the combination aspect of the present invention. The term cholesterol absorption inhibition refers to the ability of a compound to prevent cholesterol contained within the lumen of the intestine from entering into the intestinal cells and/or passing from within the intestinal cells into the lymph system and/or into the blood stream. Such cholesterol absorption inhibition activity is readily determined by those skilled in the art according to standard assays (e.g., J. Lipid Res. (1993) 34: 377–395). Cholesterol absorption inhibitors are known to those skilled in the art and are described, for example, in PCT WO 94/00480. An example of a cholesterol absorption inhibitor is ZETIA™ (ezetimibe) (Schering-Plough/Merck).

Any ACAT inhibitor may be used in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.*, 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity. Examples of ACAT inhibitors include compounds such as Avasimibe (Pfizer), CS-505 (Sankyo) and Eflucimibe (Eli Lilly and Pierre Fabre).

A lipase inhibitor may be used in the combination therapy aspect of the present invention. A lipase inhibitor is a compound that inhibits the metabolic cleavage of dietary triglycerides or plasma phospholipids into free fatty acids and the corresponding glycerides (e.g. EL, HL, etc.). Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a glyceride and fatty acid. In the intestine, the resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Methods Enzymol. 286: 190–231).

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., Methods Enzymol. 286: 190–231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92, 125 (1987). Such gastric lipase inhibition activity is readily determined by those skilled in the art according to standard assays (e.g., Methods Enzymol. 286: 190–231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen*, 562, 205–229 (1949).

A variety of pancreatic lipase inhibitors are described herein below. The pancreatic lipase inhibitors lipstatin, (2S,3S,5S,7Z,10Z)-5-[(S)-2-formamido-4-methyl-valeryloxy]-2-hexyl-3-hydroxy-7,10-hexadecanoic acid lactone, and tetrahydrolipstatin (orlistat), (2S,3S,5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed in U.S. Pat. No. 4,598,089. For example, tetrahydrolipstatin is prepared as described in, e.g., U.S. Pat. Nos. 5,274,143; 5,420,305; 5,540,917; and 5,643,874. The pancreatic lipase inhibitor, FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151. The pancreatic lipase inhibitor, valilactone, and a process for the preparation thereof by the microbial cultivation of *Actinomycetes* strain MG147-CF2, are disclosed in Kitahara, et al., *J. Antibiotics,* 40 (11), 1647–1650 (1987). The pancreatic lipase inhibitors, ebelactone A and ebelactone B, and a process for the preparation thereof by the microbial cultivation of *Actinomycetes* strain MG7-G1, are disclosed in Umezawa, et al., *J. Antibiotics,* 33, 1594–1596 (1980). The use of ebelactones A and B in the suppression of monoglyceride formation is disclosed in Japanese Kokai 08-143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fibric acid derivatives, such as Atromid®, Lopid® and Tricor®.

Diabetes can be treated by administering to a patient having diabetes (especially Type II), insulin resistance, impaired glucose tolerance, metabolic syndrome, or the like, or any of the diabetic complications such as neuropathy, nephropathy, retinopathy or cataracts, a therapeutically effective amount of a compound of the present invention in combination with other agents (e.g., insulin) that can be used to treat diabetes. This includes the classes of anti-diabetic agents (and specific agents) described herein.

Any glycogen phosphorylase inhibitor can be used as the second agent in combination with a compound of the present invention. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem. 41 (1998) 2934–2938). A variety of glycogen phosphorylase inhibitors are known to those skilled in the art including those described in WO 96/39384 and WO 96/39385.

Any aldose reductase inhibitor can be used in combination with a compound of the present invention. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, *Diabetes,* 29:861–864 (1980). "Red Cell Sorbitol, an Indicator of Diabetic Control"). A variety of aldose reductase inhibitors are known to those skilled in the art, such as those described in U.S. Pat. No. 6,579,879, which includes 6-(5-chloro-3-methyl-benzofuran-2-sulfonyl)-2H-pyridazin-3-one.

Any sorbitol dehydrogenase inhibitor can be used in combination with a compound of the present invention. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem (2000) 280: 329–331). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase.

Any glucosidase inhibitor can be used in combination with a compound of the present invention. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry (1969) 8: 4214).

A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Methods Enzymol. (1955) 1: 149). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R, 3R,4R,5S)-3,4,5-trihydroxy-2-(hydroxymethyl)piperidino]-α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed in U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor AI-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing aminosugars related thereto are disclosed in U.S. Pat. No. 4,273,765.

Additional anti-diabetic compounds, which can be used as the second agent in combination with a compound of the present invention, includes, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDE5, inhibitors of GSK-3, glucagon antagonists, inhibitors of f-1,6-BPase(Metabasis/Sankyo), GLP-1/analogs (AC 2993, also known as exendin-4), insulin and insulin mimetics (Merck natural products). Other examples would include PKC-β inhibitors and AGE breakers.

The compounds of the present invention can be used in combination with other anti-obesity agents. Any anti-obesity agent can be used as the second agent in such combinations and examples are provided herein. Such anti-obesity activity is readily determined by those skilled in the art according to standard assays known in the art.

Suitable anti-obesity agents include phenylpropanolamine, ephedrine, pseudoephedrine, phentermine, β$_3$ adrenergic receptor agonists, apolipoprotein-B secretion/microsomal triglyceride transfer protein (apo-B/MTP) inhibitors, MCR-4 agonists, cholecystokinin-A (CCK-A) agonists, monoamine reuptake inhibitors (e.g., sibutramine), sympathomimetic agents, serotoninergic agents, cannabinoid-1 (CB-1) receptor antagonists (e.g., rimonabant (SR-141,716A)), dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), bombesin agonists, anorectic agents (e.g., a bombesin agonist), Neuropeptide-Y antagonists, thyroxine, thyromimetic agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine™), human agouti-related proteins (AGRP), ghrelin receptor antagonists, histamine 3 receptor antagonists or inverse agonists, neuromedin U receptor agonists, and the like.

Rimonabant (SR141716A also known under the tradename Acomplia™ available from Sanofi-Synthelabo) can be prepared as described in U.S. Pat. No. 5,624,941. Other suitable CB-1 antagonists include those described in U.S. Pat. Nos. 5,747,524, 6,432,984 and 6,518,264; U.S. Patent Publication Nos. US2004/0092520, US2004/0157839, US2004/0214855, and US2004/0214838; U.S. patent application Ser. No. 10/971599 filed on Oct. 22, 2004; and PCT Patent Publication Nos. WO 02/076949, WO 03/075660, WO04/048317, WO04/013120, and WO 04/012671.

Preferred apolipoprotein-B secretion/microsomal triglyceride transfer protein (apo-B/MTP) inhibitors for use as anti-obesity agents are gut-selective MTP inhibitors, such as dirlotapide described in U.S. Pat. No. 6,720,351; 4-(4-(4-(4-((2-((4-methyl-4H-1,2,4-triazol-3-ylthio)methyl)-2-(4-chlorophenyl)-1,3-dioxolan-4-yl)methoxy)phenyl)piperazin-1-yl)phenyl)-2-sec-butyl-2H-1,2,4-triazol-3(4H)-one (R103757) described in U.S. Pat. Nos. 5,521,186 and 5,929,075; and implitapide (BAY 13-9952) described in U.S. Pat. No. 6,265,431. As used herein, the term "gut-selective" means that the MTP inhibitor has a higher exposure to the gastro-intestinal tissues versus systemic exposure.

Any thyromimetic can be used as the second agent in combination with a compound of the present invention. Such thyromimetic activity is readily determined by those skilled in the art according to standard assays (e.g., Atherosclerosis (1996) 126: 53–63). A variety of thyromimetic agents are known to those skilled in the art, for example those disclosed in U.S. Pat. Nos. 4,766,121; 4,826,876; 4,910,305; 5,061,798; 5,284,971; 5,401,772; 5,654,468; and 5,569,674. Other antiobesity agents include sibutramine which can be prepared as described in U.S. Pat. No. 4,929,629. and bromocriptine which can be prepared as described in U.S. Pat. Nos. 3,752,814 and 3,752,888.

The compounds of the present invention can also be used in combination with other antihypertensive agents. Any anti-hypertensive agent can be used as the second agent in such combinations and examples are provided herein. Such antihypertensive activity is readily determined by those skilled in the art according to standard assays (e.g., blood pressure measurements).

Amlodipine and related dihydropyridine compounds are disclosed in U.S. Pat. No. 4,572,909, which is incorporated herein by reference, as potent anti-ischemic and antihypertensive agents. U.S. Pat. No. 4,879,303, which is incorporated herein by reference, discloses amlodipine benzenesulfonate salt (also termed amlodipine besylate). Amlodipine and amlodipine besylate are potent and long lasting calcium channel blockers. As such, amlodipine, amlodipine besylate, amlodipine maleate and other pharmaceutically acceptable acid addition salts of amlodipine have utility as antihypertensive agents and as antiischemic agents. Amlodipine besylate is currently sold as Norvasc®. Amlodipine has the formula

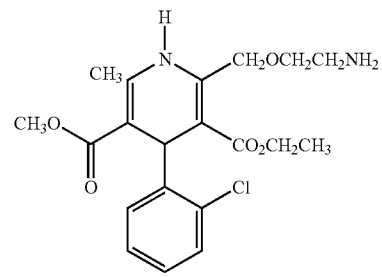

Calcium channel blockers which are within the scope of this invention include, but are not limited to: bepridil, which may be prepared as disclosed in U.S. Pat. Nos. 3,962,238 or U.S. Reissue No. 30,577; clentiazem, which may be prepared as disclosed in U.S. Pat. No. 4,567,175; diltiazem, which may be prepared as disclosed in U.S. Pat. No. 3,562, fendiline, which may be prepared as disclosed in U.S. Pat. No. 3,262,977; gallopamil, which may be prepared as disclosed in U.S. Pat. No. 3,261,859; mibefradil, which may be prepared as disclosed in U.S. Pat. No. 4,808,605; prenylamine, which may be prepared as disclosed in U.S. Pat. No.

3,152,173; semotiadil, which may be prepared as disclosed in U.S. Pat. No. 4,786,635; terodiline, which may be prepared as disclosed in U.S. Pat. No. 3,371,014; verapamil, which may be prepared as disclosed in U.S. Pat. No. 3,261,859; aranipine, which may be prepared as disclosed in U.S. Pat. No. 4,572,909; barnidipine, which may be prepared as disclosed in U.S. Pat. No. 4,220,649; benidipine, which may be prepared as disclosed in European Patent Application Publication No. 106,275; cilnidipine, which may be prepared as disclosed in U.S. Pat. No. 4,672,068; efonidipine, which may be prepared as disclosed in U.S. Pat. No. 4,885,284; elgodipine, which may be prepared as disclosed in U.S. Pat. No. 4,952,592; felodipine, which may be prepared as disclosed in U.S. Pat. No. 4,264,611; isradipine, which may be prepared as disclosed in U.S. Pat. No. 4,466,972; lacidipine, which may be prepared as disclosed in U.S. Pat. No. 4,801,599; lercanidipine, which may be prepared as disclosed in U.S. Pat. No. 4,705,797; manidipine, which may be prepared as disclosed in U.S. Pat. No. 4,892,875; nicardipine, which may be prepared as disclosed in U.S. Pat. No. 3,985,758; nifedipine, which may be prepared as disclosed in U.S. Pat. No. 3,485,847; nilvadipine, which may be prepared as disclosed in U.S. Pat. No. 4,338,322; nimodipine, which may be prepared as disclosed in U.S. Pat. No. 3,799,934; nisoldipine, which may be prepared as disclosed in U.S. Pat. No. 4,154,839; nitrendipine, which may be prepared as disclosed in U.S. Pat. No. 3,799,934; cinnarizine, which may be prepared as disclosed in U.S. Pat. No. 2,882,271; flunarizine, which may be prepared as disclosed in U.S. Pat. No. 3,773,939; lidoflazine, which may be prepared as disclosed in U.S. Pat. No. 3,267,104; lomerizine, which may be prepared as disclosed in U.S. Pat. No. 4,663,325; bencyclane, which may be prepared as disclosed in Hungarian Patent No. 151,865; etafenone, which may be prepared as disclosed in German Patent No. 1,265,758; and perhexiline, which may be prepared as disclosed in British Patent No. 1,025,578. The disclosures of all such U.S. patents are incorporated herein by reference. Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop® Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®.

Angiotensin Converting Enzyme Inhibitors (ACE-Inhibitors) which are within the scope of this invention include, but are not limited to: alacepril, which may be prepared as disclosed in U.S. Pat. No. 4,248,883; benazepril, which may be prepared as disclosed in U.S. Pat. No. 4,410,520; captopril, which may be prepared as disclosed in U.S. Pat. Nos. 4,046,889 and 4,105,776; ceronapril, which may be prepared as disclosed in U.S. Pat. No. 4,452,790; delapril, which may be prepared as disclosed in U.S. Pat. No. 4,385,051; enalapril, which may be prepared as disclosed in U.S. Pat. No. 4,374,829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S. Pat. No. 4,344,949; ramipril, which may be prepared as disclosed in U.S. Pat. No. 4,587,258; spirapril, which may be prepared as disclosed in U.S. Pat. No. 4,470,972; temocapril, which may be prepared as disclosed in U.S. Pat. No. 4,699,905; and trandolapril, which may be prepared as disclosed in U.S. Pat. No. 4,933,361. The disclosures of all such U.S. patents are incorporated herein by reference.

Angiotensin-II receptor antagonists (A-II antagonists) which are within the scope of this invention include, but are not limited to: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S. Pat. No. 5,138,069; and valsartan, which may be prepared as disclosed in U.S. Pat. No. 5,399,578. The disclosures of all such U.S. patents are incorporated herein by reference.

Beta-adrenergic receptor blockers (beta- or β-blockers) which are within the scope of this invention include, but are not limited to: acebutolol, which may be prepared as disclosed in U.S. Pat. No. 3,857,952; alprenolol, which may be prepared as disclosed in Netherlands patent application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., Journal of Medicinal Chemistry, 1982, 25, 670; epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176; mepindolol, which may be prepared as disclosed in Seeman et al., Helv. Chim. Acta, 1971, 54, 241; metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Pat. No. 3,501,7691; nadolol, which maybe prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362;

nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., Journal of Medicinal Chemistry, 1966, 9, 88; sufinalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824. The disclosures of all such U.S. patents are incorporated herein by reference.

Alpha-adrenergic receptor blockers (alpha- or α-blockers) which are within the scope of this invention include, but are not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol, which may be prepared as disclosed above; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art. The disclosures of all such U.S. patents are incorporated herein by reference.

The term "vasodilator," where used herein, is meant to include cerebral vasodilators, coronary vasodilators and peripheral vasodilators. Cerebral vasodilators within the scope of this invention include, but are not limited to: bencyclane, which may be prepared as disclosed above; cinnarizine, which may be prepared as disclosed above; citicoline, which may be isolated from natural sources as disclosed in Kennedy et al., Journal of the American Chemical Society, 1955, 77, 250 or synthesized as disclosed in Kennedy, Journal of Biological Chemistry, 1956, 222, 185; cyclandelate, which may be prepared as disclosed in U.S. Pat. No. 3,663,597; ciclonicate, which may be prepared as disclosed in German Patent No. 1,910,481; diisopropylamine dichloroacetate, which may be prepared as disclosed in British Patent No. 862,248; eburnamonine, which may be prepared as disclosed in Hermann et al., Journal of the American Chemical Society, 1979, 101, 1540; fasudil, which may be prepared as disclosed in U.S. Pat. No. 4,678,783; fenoxedil, which may be prepared as disclosed in U.S. Pat. No. 3,818,021; flunarizine, which may be prepared as disclosed in U.S. Pat. No. 3,773,939; ibudilast, which may be prepared as disclosed in U.S. Pat. No. 3,850,941; ifenprodil, which may be prepared as disclosed in U.S. Pat. No. 3,509,164; lomerizine, which may be prepared as disclosed in U.S. Pat. No. 4,663,325; nafronyl, which may be prepared as disclosed in U.S. Pat. No. 3,334,096; nicametate, which may be prepared as disclosed in Blicke et al., Journal of the American Chemical Society, 1942, 64, 1722; nicergoline, which may be prepared as disclosed above; nimodipine, which may be prepared as disclosed in U.S. Pat. No. 3,799,934; papaverine, which may be prepared as reviewed in Goldberg, Chem. Prod. Chem. News, 1954, 17, 371; pentifylline, which may be prepared as disclosed in German Patent No. 860,217; tinofedrine, which may be prepared as disclosed in U.S. Pat. No. 3,563,997; vincamine, which may be prepared as disclosed in U.S. Pat. No. 3,770,724; vinpocetine, which may be prepared as disclosed in U.S. Pat. No. 4,035,750; and viquidil, which may be prepared as disclosed in U.S. Pat. No. 2,500,444. The disclosures of all such U.S. patents are incorporated herein by reference.

Coronary vasodilators within the scope of this invention include, but are not limited to: amotriphene, which may be prepared as disclosed in U.S. Pat. No. 3,010,965; bendazol, which may be prepared as disclosed in J. Chem. Soc. 1958, 2426; benfurodil hemisuccinate, which may be prepared as disclosed in U.S. Pat. No. 3,355,463; benziodarone, which may be prepared as disclosed in U.S. Pat. No. 3,012,042; chloracizine, which may be prepared as disclosed in British Patent No. 740,932; chromonar, which may be prepared as disclosed in U.S. Pat. No. 3,282,938; clobenfural, which may be prepared as disclosed in British Patent No. 1,160,925; clonitrate, which may be prepared from propanediol according to methods well known to those skilled in the art, e.g., see *Annalen,* 1870, 155, 165; cloricromen, which may be prepared as disclosed in U.S. Pat. No. 4,452,811; dilazep, which may be prepared as disclosed in U.S. Pat. No. 3,532,685; dipyridamole, which may be prepared as disclosed in British Patent No. 807,826; droprenilamine, which may be prepared as disclosed in German Patent No. 2,521,113; efloxate, which may be prepared as disclosed in British Patent Nos. 803,372 and 824,547; erythrityl tetranitrate, which may be prepared by nitration of erythritol according to methods well-known to those skilled in the art; etafenone, which may be prepared as disclosed in German Patent No. 1,265,758; fendiline, which may be prepared as disclosed in U.S. Pat. No. 3,262,977; floredil, which may be prepared as disclosed in German Patent No. 2,020,464; ganglefene, which may be prepared as disclosed in U.S.S.R. Patent No. 115,905; hexestrol, which may be prepared as disclosed in U.S. Pat. No. 2,357,985; hexobendine, which may be prepared as disclosed in U.S. Pat. No. 3,267,103; itramin tosylate, which may be prepared as disclosed in Swedish Patent No. 168,308; khellin, which may be prepared as disclosed in Baxter et al., Journal of the Chemical Society, 1949, S 30; lidoflazine, which may be prepared as disclosed in U.S. Pat. No. 3,267,104; mannitol hexanitrate, which may be prepared by the nitration of mannitol according to methods well-known to those skilled in the art; medibazine, which may be prepared as disclosed in U.S. Pat. No. 3,119,826; nitroglycerin; pentaerythritol tetranitrate, which may be prepared by the nitration of pentaerythritol according to methods well-known to those skilled in the art; pentrinitrol, which may be prepared as disclosed in German Patent No. 638,422-3; perhexilline, which may be prepared as disclosed above; pimefylline, which may be prepared as disclosed in U.S. Pat. No. 3,350,400; prenylamine, which may be prepared as disclosed in U.S. Pat. No. 3,152,173;

propatyl nitrate, which may be prepared as disclosed in French Patent No. 1,103,113; trapidil, which may be prepared as disclosed in East German Patent No. 55,956; tricromyl, which may be prepared as disclosed in U.S. Pat. No. 2,769,015; trimetazidine, which may be prepared as disclosed in U.S. Pat. No. 3,262,852; trolnitrate phosphate, which may be prepared by nitration of triethanolamine followed by precipitation with phosphoric acid according to methods well-known to those skilled in the art; visnadine, which may be prepared as disclosed in U.S. Pat. Nos. 2,816,118 and 2,980,699. The disclosures of all such U.S. patents are incorporated herein by reference.

Peripheral vasodilators within the scope of this invention include, but are not limited to: aluminum nicotinate, which may be prepared as disclosed in U.S. Pat. No. 2,970,082; bamethan, which may be prepared as disclosed in Corrigan et al., Journal of the American Chemical Society, 1945, 67, 1894; bencyclane, which may be prepared as disclosed above; betahistine, which may be prepared as disclosed in Walter et al.; Journal of the American Chemical Society, 1941, 63, 2771; bradykinin, which may be prepared as disclosed in Hamburg et al., Arch. Biochem. Biophys., 1958, 76, 252; brovincamine, which may be prepared as disclosed in U.S. Pat. No. 4,146,643; bufeniode, which may be prepared as disclosed in U.S. Pat. No. 3,542,870; buflomedil, which may be prepared as disclosed in U.S. Pat. No. 3,895,030; butalamine, which may be prepared as disclosed in U.S. Pat. No. 3,338,899; cetiedil, which may be prepared as disclosed in French Patent Nos. 1,460,571; ciclonicate, which may be prepared as disclosed in German Patent No. 1,910,481; cinepazide, which may be prepared as disclosed in Belgian Patent No. 730,345; cinnarizine, which may be prepared as disclosed above; cyclandelate, which may be prepared as disclosed above; diisopropylamine dichloroacetate, which may be prepared as disclosed above; eledoisin, which may be prepared as disclosed in British Patent No. 984,810; fenoxedil, which may be prepared as disclosed above; flunarizine, which may be prepared as disclosed above; hepronicate, which may be prepared as disclosed in U.S. Pat. No. 3,384,642; ifenprodil, which may be prepared as disclosed above; iloprost, which may be prepared as disclosed in U.S. Pat. No. 4,692,464; inositol niacinate, which may be prepared as disclosed in Badgett et al., Journal of the American Chemical Society, 1947, 69, 2907; isoxsuprine, which may be prepared as disclosed in U.S. Pat. No. 3,056,836; kallidin, which may be prepared as disclosed in *Biochem. Biophys. Res. Commun.,* 1961, 6, 210; kallikrein, which may be prepared as disclosed in German Patent No. 1,102,973; moxisylyte, which may be prepared as disclosed in German Patent No. 905,738; nafronyl, which may be prepared as disclosed above; nicametate, which may be prepared as disclosed above; nicergoline, which may be prepared as disclosed above; nicofuranose, which may be prepared as disclosed in Swiss Patent No. 366,523; nylidrin, which may be prepared as disclosed in U.S. Pat. Nos. 2,661,372 and 2,661,373; pentifylline, which may be prepared as disclosed above; pentoxifylline, which may be prepared as disclosed in U.S. Pat. No. 3,422,107; piribedil, which may be prepared as disclosed in U.S. Pat. No. 3,299,067; prostaglandin $E_1$, which may be prepared by any of the methods referenced in the Merck Index, Twelfth Edition, Budaveri, Ed., New Jersey, 1996, p. 1353; suloctidil, which may be prepared as disclosed in German Patent No. 2,334,404; tolazoline, which may be prepared as disclosed in U.S. Pat. No. 2,161,938; and xanthinol niacinate, which may be prepared as disclosed in German Patent No. 1,102,750 or Korbonits et al., Acta. Pharm. Hung., 1968, 38, 98. The disclosures of all such U.S. patents are incorporated herein by reference.

The term "diuretic," within the scope of this invention, is meant to include diuretic benzothiadiazine derivatives, diuretic organomercurials, diuretic purines, diuretic steroids, diuretic sulfonamide derivatives, diuretic uracils and other diuretics such as amanozine, which may be prepared as disclosed in Austrian Patent No. 168,063; amiloride, which may be prepared as disclosed in Belgian Patent No. 639,386; arbutin, which may be prepared as disclosed in Tschitschibabin, Annalen, 1930, 479, 303; chlorazanil, which may be prepared as disclosed in Austrian Patent No. 168,063; ethacrynic acid, which may be prepared as disclosed in U.S. Pat. No. 3,255,241; etozolin, which may be prepared as disclosed in U.S. Pat. No. 3,072,653; hydracarbazine, which may be prepared as disclosed in British Patent No. 856,409; isosorbide, which may be prepared as disclosed in U.S. Pat. No. 3,160,641; mannitol; metochalcone, which may be prepared as disclosed in Freudenberg et al., Ber., 1957, 90, 957; muzolimine, which may be prepared as disclosed in U.S. Pat. No. 4,018,890; perhexiline, which may be prepared as disclosed above; ticrynafen, which may be prepared as disclosed in U.S. Pat. No. 3,758,506; triamterene which may be prepared as disclosed in U.S. Pat. No. 3,081,230; and urea. The disclosures of all such U.S. patents are incorporated herein by reference.

Diuretic benzothiadiazine derivatives within the scope of this invention include, but are not limited to: althiazide, which may be prepared as disclosed in British Patent No. 902,658; bendroflumethiazide, which may be prepared as disclosed in U.S. Pat. No. 3,265,573; benzthiazide, McManus et al., 136th Am. Soc. Meeting (Atlantic City, September 1959), Abstract of papers, pp 13-O; benzylhydrochlorothiazide, which may be prepared as disclosed in U.S. Pat. No. 3,108,097; buthiazide, which may be prepared as disclosed in British Patent Nos. 861,367 and 885,078; chlorothiazide, which may be prepared as disclosed in U.S. Pat. Nos. 2,809,194 and 2,937,169; chlorthalidone, which may be prepared as disclosed in U.S. Pat. No. 3,055,904; cyclopenthiazide, which may be prepared as disclosed in Belgian Patent No. 587,225; cyclothiazide, which may be prepared as disclosed in Whitehead et al., Journal of Organic Chemistry, 1961, 26, 2814; epithiazide, which may be prepared as disclosed in U.S. Pat. No. 3,009,911; ethiazide, which may be prepared as disclosed in British Patent No. 861,367; fenquizone, which may be prepared as disclosed in U.S. Pat. No. 3,870,720; indapamide, which may be prepared as disclosed in U.S. Pat. No. 3,565,911; hydrochlorothiazide, which may be prepared as disclosed in U.S. Pat. No. 3,164,588; hydroflumethiazide, which may be prepared as disclosed in U.S. Pat. No. 3,254,076; methyclothiazide, which may be prepared as disclosed in Close et al., Journal of the American Chemical Society, 1960, 82, 1132; meticrane, which may be prepared as disclosed in French Patent Nos. M2790 and 1,365,504; metolazone, which may be prepared as disclosed in U.S. Pat. No. 3,360,518; paraflutizide, which may be prepared as disclosed in Belgian Patent No. 620,829; polythiazide, which may be prepared as disclosed in U.S. Pat. No. 3,009,911; quinethazone, which may be prepared as disclosed in U.S. Pat. No. 2,976,289; teclothiazide, which may be prepared as disclosed in Close et al., Journal of the American Chemical Society, 1960, 82, 1132; and trichlormethiazide, which may be prepared as dislcosed in deStevens et al., Experientia, 1960, 16, 113. The disclosures of all such U.S. patents are incorporated herein by reference.

Diuretic sulfonamide derivatives within the scope of this invention include, but are not limited to: acetazolamide, which may be prepared as disclosed in U.S. Pat. No. 2,980,679; ambuside, which may be prepared as disclosed in U.S. Pat. No. 3,188,329; azosemide, which may be prepared as disclosed in U.S. Pat. No. 3,665,002; bumetanide, which may be prepared as disclosed in U.S. Pat. No. 3,634,583; butazolamide, which may be prepared as disclosed in British Patent No. 769,757; chloraminophenamide, which may be prepared as disclosed in U.S. Pat. Nos. 2,809,194, 2,965,655 and 2,965,656; clofenamide, which may be prepared as disclosed in Olivier, Rec. Trav. Chim., 1918, 37, 307; clopamide, which may be prepared as disclosed in U.S. Pat. No. 3,459,756; clorexolone, which may be prepared as disclosed in U.S. Pat. No. 3,183,243; disulfamide, which may be prepared as disclosed in British Patent No. 851,287; ethoxolamide, which may be prepared as disclosed in British Patent No. 795,174; furosemide, which may be prepared as disclosed in U.S. Pat. No. 3,058,882; mefruside, which may be prepared as disclosed in U.S. Pat. No. 3,356,692; methazolamide, which may be prepared as disclosed in U.S. Pat. No. 2,783,241; piretanide, which may be prepared as disclosed in U.S. Pat. No. 4,010,273; torasemide, which may be prepared as disclosed in U.S. Pat. No. 4,018,929; tripamide, which may be prepared as disclosed in Japanese Patent No. 73 05,585; and xipamide, which may be prepared as disclosed in U.S. Pat. No. 3,567,777. The disclosures of all such U.S. patents are incorporated herein by reference.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecasted to increase three-fold over the next 60 years, and one study has estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- or 17β-ethynyl estradiol) may be used in conjunction with the compounds of the present invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol.

Preferred progestins are medroxyprogestrone, norethindrone and norethynodrel.

Exemplary bone resorption inhibiting polyphosphonates include polyphosphonates of the type disclosed in U.S. Pat. No. 3,683,080, the disclosure of which is incorporated herein by reference. Preferred polyphosphonates are geminal diphosphonates (also referred to as bis-phosphonates). Tiludronate disodium is an especially preferred polyphosphonate. Ibandronic acid is an especially preferred polyphosphonate. Alendronate and resindronate are especially preferred polyphosphonates. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid,N,N-dimethylamino methane diphosphonic acid, N(2-hydroxyethyl) amino methane diphosphonic acid, butane-4-amino-1-hydroxy-1, 1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used in the combination aspect of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art of standard assays including estrogen receptor binding assays, standard bone histomorphometric and densitometer methods, and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below.

Another preferred estrogen agonist/antagonist is 3-(4-(1, 2-diphenyl-but-1-enyl)-phenyl)-acrylic acid, which is disclosed in Willson et al., Endocrinology, 1997, 138, 3901–3911.

Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516, the disclosure of which is incorporated herein by reference.

Another related compound is 4-hydroxy tamoxifen, which is disclosed in U.S. Pat. No. 4,623,660, the disclosure of which is incorporated herein by reference.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)-hydrochloride) which is disclosed in U.S. Pat. No. 4,418,068, the disclosure of which is incorporated herein by reference.

Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225, the disclosure of which is incorporated herein by reference.

Another preferred estrogen agonist/antagonist is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287, the disclosure of which is incorporated herein by reference. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155, the disclosure of which is incorporated herein by reference.

Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058, the disclosure of which is incorporated herein by reference.

Another preferred estrogen agonist/antagonist is 6-(4-hydroxy-phenyl)-5-(4-(2-piperidin-1-yl-ethoxy)-benzyl)-naphthalen-2-ol, which is disclosed in U.S. Pat. No. 5,484,795, the disclosure of which is incorporated herein by reference.

Another preferred estrogen agonist/antagonist is (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc.

Other preferred estrogen agonist/antagonists include the compounds, TSE-424 (Wyeth-Ayerst Laboratories) and arazoxifene.

Other preferred estrogen agonist/antagonists include compounds as described in commonly assigned U.S. Pat. No. 5,552,412, the disclosure of which is incorporated herein by reference. Especially preferred compounds described therein are:

cis-6-(4-fluoro-phenyl)-5-(4-(2-piperidin-1-yl-ethoxy)-phenyl)-5,6,7,8-tetrahydro-naphthalene-2-ol;

(−)-cis-6-phenyl-5-(4-(2-pyrrolidin-1-yl-ethoxy)-phenyl)-5,6,7,8-tetrahydro-naphthalene-2-ol (also known as lasofoxifene);

cis-6-phenyl-5-(4-(2-pyrrolidin-1-yl-ethoxy)-phenyl)-5,6,7,8-tetrahydro-naphthalene-2-ol;

cis-1-(6'-pyrrolodinoethoxy-3'-pyridyl)-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-(4-(2-piperidin-1-yl-ethoxy)-phenyl)-5,6,7,8-tetrahydro-naphthalene-2-ol; and 1-(4'-pyrrolidinolethoxyphenyl)-2-phenyl-6-hydroxy-1,2,3,4-tetrahydroisoquinoline.

Other estrogen agonists/antagonists are described in U.S. Pat. No. 4,133,814 (the disclosure of which is incorporated herein by reference). U.S. Pat. No. 4,133,814 discloses derivatives of 2-phenyl-3-aroyl-benzothiophene and 2-phenyl-3-aroylbenzothiophene-1-oxide.

Other anti-osteoporosis agents, which can be used as the second agent in combination with a compound of the present invention, include, for example, the following: parathyroid hormone (PTH) (a bone anabolic agent); parathyroid hormone (PTH) secretagogues (see, e.g., U.S. Pat. No. 6,132,774), particularly calcium receptor antagonists; calcitonin; and vitamin D and vitamin D analogs.

Any selective androgen receptor modulator (SARM) can be used in combination with a compound of the present invention. A selective androgen receptor modulator (SARM) is a compound that possesses androgenic activity and which exerts tissue-selective effects. SARM compounds can function as androgen receptor agonists, partial agonists, partial antagonists or antagonists. Examples of suitable SARMs include compounds such as cyproterone acetate, chlormadinone, flutamide, hydroxyflutamide, bicalutamide, nilutamide, spironolactone, 4-(trifluoromethyl)-2(1H)-pyrrolidino [3,2-g]quinoline derivatives, 1,2-dihydropyridino [5,6-g] quinoline derivatives and piperidino[3,2-g]quinolinone derivatives.

Cypterone, also known as (1b,2b)-6-chloro-1,2-dihydro-17-hydroxy-3'H-cyclopropa[1,2]pregna-1,4,6-triene-3,20-dione is disclosed in U.S. Pat. No. 3,234,093. Chlormadinone, also known as 17-(acetyloxy)-6-chloropregna-4,6-diene-3,20-dione, in its acetate form, acts as an antiandrogen and is disclosed in U.S. Pat. No. 3,485,852. Nilutamide, also known as 5,5-dimethyl-3-[4-nito-3-(trifluoromethyl)phenyl]-2,4-imidazolidinedione and by the trade name Nilandron® is disclosed in U.S. Pat. No. 4,097,578. Flutamide, also known as 2-methyl-N-[4-nitro-3-(trifluoromethyl)phenyl]propanamide and the trade name Eulexin® is disclosed in U.S. Pat. No. 3,847,988. Bicalutamide, also known as 4'-cyano-a',a',a'-trifluoro-3-(4-fluorophenylsulfonyl)-2-hydroxy-2-methylpropiono-m-toluidide and the trade name Casodex® is disclosed in EP-100172. The enantiomers of biclutamide are discussed by Tucker and Chesterton, *J. Med. Chem.* 1988, 31, 885–887. Hydroxyflutamide, a known androgen receptor antagonist in most tissues, has been suggested to function as a SARM for effects on IL-6 production by osteoblasts as disclosed in Hofbauer et al. *J. Bone Miner. Res.* 1999, 14, 1330–1337. Additional SARMs have been disclosed in U.S. Pat. No. 6,017,924; WO 01/16108, WO 01/16133, WO 01/16139, WO 02/00617, WO 02/16310, U.S. Patent Application Publication No. US 2002/0099096, U.S. Patent Application Publication No. US 2003/0022868, WO 03/011302 and WO 03/011824. All of the above references are hereby incorporated by reference herein.

The starting materials and reagents for the above-described compounds of the present invention and combination agents, are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

Some of the compounds of the present invention or intermediates in their synthesis have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by, for example, chiral HPLC methods or converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, an enantiomeric mixture of the compounds or an intermediate in their synthesis which contain an acidic or basic moiety may be separated into their compounding pure enantiomers by forming a diastereomeric salt with an optically pure chiral baseor acid (e.g., 1-phenyl-ethyl amine or tartaric acid) and separating the diasteromers by fractional crystallization followed by neutralization to break the salt, thus providing the corresponding pure enantiomers. All such isomers, including diastereomers, enantiomers and mixtures thereof are considered as part of the present invention. Also, some of the compounds of the present invention are atropisomers (e.g., substituted biaryls) and are considered as part of the present invention.

More specifically, the compounds of the present invention can be obtained by fractional crystallization of the basic intermediate with an optically pure chiral acid to form a diastereomeric salt. Neutralization techniques are used to remove the salt and provide the enantiomerically pure compounds. Alternatively, the compounds of the present invention may be obtained in enantiomerically enriched form by resolving the racemate of the final compound or an intermediate in its synthesis (preferably the final compound) employing chromatography (preferably high pressure liquid chromatography [HPLC]) on an asymmetric resin (preferably Chiralcel™ AD or OD (obtained from Chiral Technologies, Exton, Pa.)) with a mobile phase consisting of a hydrocarbon (preferably heptane or hexane) containing between 0 and 50% isopropanol (preferably between 2 and 20%) and between 0 and 5% of an alkyl amine (preferably 0.1% of diethylamine). Concentration of the product containing fractions affords the desired materials.

Some of the compounds of the present invention are acidic and they form a salt with a pharmaceutically acceptable cation. Some of the compounds of the present invention are basic and they form a salt with a pharmaceutically acceptable anion. All such salts are within the scope of the present invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

The compounds of the present invention, their prodrugs and the salts of such compounds and prodrugs are all adapted to therapeutic use as agents that activate peroxisome proliferator activator receptor (PPAR) activity in mammals, particularly humans. Thus, it is believed the compounds of the present invention, by activating the PPAR receptor, stimulate transcription of key genes involved in fatty acid oxidation and also those involved in high density lipoprotein (HDL) assembly (for example apolipoprotein AI gene transcription), accordingly reducing whole body fat and increasing HDL cholesterol. By virtue of their activity, these agents also reduce plasma levels of triglycerides, VLDL cholesterol, LDL cholesterol and their associated components in mammals, particularly humans, as well as increasing HDL cholesterol and apolipoprotein AI. Hence, these compounds are useful for the treatment and correction of the various dyslipidemias observed to be associated with the development and incidence of atherosclerosis and cardiovascular disease, including hypoalphalipoproteinemia and hypertriglyceridemia.

The present compounds are also useful for modulation of plasma and or serum or tissue lipids or lipoproteins, such as HDL subtypes (e.g., increase, including pre-beta HDL, HDL-1,-2 and 3 particles) as measured by precipitation or by apo-protein content, size, density, NMR profile, FPLC and charge and particle number and its constituents; and LDL subtypes (including LDL subtypes e.g., decreasing small dense LDL, oxidized LDL, VLDL, apo(a) and Lp(a)) as measured by precipitation, or by apo-protein content, size density, NMR profile, FPLC and charge; IDL and remnants (decrease); phospholipids (e.g., increase HDL phospholipids); apo-lipoproteins (increase A-I, A-II, A-IV, decrease total and LDL B-100, decrease B-48, modulate C-II, C-III, E, J); paraoxonase (increase, anti-oxidant effects, anti-inflammatory effects); decrease post-prandial (hyper)lipemia; decrease triglycerides, decrease non-HDL; elevate HDL in subjects with low HDL and optimize and increase ratios of HDL to LDL (e.g., greater than 0.25).

Given the positive correlation between triglycerides, LDL cholesterol, and their associated apolipoproteins in blood with the development of cardiovascular, cerebral vascular and peripheral vascular diseases, the compounds of the present invention, their prodrugs and the salts of such compounds and prodrugs, by virtue of their pharmacologic action, are useful for the prevention, arrestment and/or regression of atherosclerosis and its associated disease states. These include cardiovascular disorders (e.g., cerebrovascular disease, coronary artery disease, ventricular dysfunction, cardiac arrhythmia, pulmonary vascular disease, vascular hemostatic disease, cardiac ischemia and myocardial infarction), complications due to cardiovascular disease, and cognitive dysfunction (including, but not limited to, dementia secondary to atherosclerosis, transient cerebral ischemic attacks, neurodegeneration, neuronal deficient, and delayed onset or procession of Alzheimer's disease).

Thus, given the ability of the compounds of the present invention, their prodrugs and the salts of such compounds and prodrugs to reduce plasma triglycerides and total plasma cholesterol, and increase plasma HDL cholesterol, they are of use in the treatment of diabetes, including impaired glucose tolerance, diabetic complications, insulin resistance and metabolic syndrome, as described previously. In addition, the compounds are useful for the treatment of polycystic ovary syndrome. Also, the compounds are useful in the treatment of obesity given the ability of the compounds of this invention, their prodrugs and the salts of such compounds and prodrugs to increase hepatic fatty acid oxidation.

The utility of the compounds of the present invention, their prodrugs and the salts of such compounds and prodrugs as medical agents in the treatment of the above described disease/conditions in mammals (e.g. humans, male or female) is demonstrated by the activity of the compounds of the present invention in one or more of the conventional assays and in vivo assays described below. The in vivo assays (with appropriate modifications within the skill in the art) can be used to determine the activity of other lipid or triglyceride controlling agents as well as the compounds of the present invention. Thus, the protocols described below can also be used to demonstrate the utility of the combinations of the agents (i.e., the compounds of the present invention) described herein. In addition, such assays provide a means whereby the activities of the compounds of the present invention, their prodrugs and the salts of such compounds and prodrugs (or the other agents described herein) can be compared to each other and with the activities of other known compounds. The results of these comparisons are useful for determining dosage levels in mammals, including humans, for the treatment of such diseases. The following protocols can of course be varied by those skilled in the art.

PPAR FRET Assay

Measurement of coactivator recruitment by a nuclear receptor-ligand association is a method for evaluating the ability of a ligand to produce a functional response through a nuclear receptor. The PPAR FRET (Fluorescence Resonance Energy Transfer) assay measures the ligand-dependent interaction between nuclear receptor and coactivator. GST/PPAR ($\alpha,\beta$, and $\gamma$) ligand binding domain (LBD) is labeled with a europium-tagged anti-GST antibody, while an SRC-1 (Sterol Receptor Coactivator-1) synthetic peptide containing an amino terminus long chain biotin molecule is labeled with streptavidin-linked allophycocyanin (APC). Binding of ligand to the PPAR LBD causes a conformational change that allows SRC-1 to bind. Upon SRC-1 binding, the donor FRET molecule (europium) comes in close proximity to the acceptor molecule (APC), resulting in fluorescence energy transfer between donor (337 nm excitation and 620 nm emission) and acceptor (620 nm excitation and 665 nm emission). Increases in the ratio of 665 nm emission to 620 nm emission is a measure of the ability of the ligand-PPAR LBD to recruit SRC-1 synthetic peptide and therefore a measure of the ability of a ligand to produce a functional response through the PPAR receptor.

[1] GST/PPAR LBD Expression. The human PPAR$\alpha$ LBD (amino acids 235–507) is fused to the carboxy terminus of glutathione S-transferase (GST) in pGEX-6P-1 (Pfizer, Inc.). The GST/PPAR$\alpha$ LBD fusion protein is expressed in BL21[DE3]pLysS cells using a 50 uM IPTG induction at room temperature for 16 hr (cells induced at an $Ar_{600}$ of ~0.6). Fusion protein is purified on glutathione sepharose 4B beads, eluted in 10 mM reduced glutathione, and dialyzed against 1× PBS at 4° C. Fusion protein is quantitated by Bradford assay (M. M. Bradford, Analst. Biochem. 72:248–254; 1976), and stored at −20° C. in 1× PBS containing 40% glycerol and 5 mM dithiothreitol.

[2] FRET Assay. The FRET assay reaction mix consists of 1× FRET buffer (50 mM Tris-Cl pH 8.0, 50 mM KCl, 0.1 mg/ml BSA, 1 mM EDTA, and 2 mM dithiothreitol) containing 20 nM GST/PPAR$\alpha$ LBD, 40 nM of SRC-1 peptide (amino acids 676–700, 5'-long chain biotin-CPSSHSS-LTERHKILHRLLQEGSPS-NH$_2$, purchased from American Peptide Co., Sunnyvale, Calif.), 2 nM of europium-conjugated anti-GST antibody (Wallac, Gaithersburg, Md.), 40 nM of streptavidin-conjugated APC (Wallac), and control and test compounds. The final volume is brought to 100 ul with water and transferred to a black 96-well plate (Microfuor B, Dynex (Chantilly, Va.)). The reaction mixes are incubated for 1 hr at 4° C. and fluorescence is read in Victor 2 plate reader (Wallac). Data is presented as a ratio of the emission at 665 nm to the emission at 615 nm.

Assessment of Lipid-modulating Activity in Mice

[1] Triglyceride lowering. The hypolipidemic treating activity of the compounds of the present invention can be demonstrated by methods based on standard procedures. For example, the in vivo activity of these compounds in decreasing plasma triglyceride levels may be determined in hybrid B6CBAF1/J mice.

Male B6CVAF1/J mice (8–11 week old) are obtained from The Jackson Laboratory and housed 4–5/cage and maintained in a 12 hr light/12 hr dark cycle. Animals have ad lib. access to Purina rodent chow and water. The animals are dosed daily (9 AM) by oral gavage with vehicle (water or 0.5% methyl cellulose 0.05% Tween 80) or with vehicle containing test compound at the desired concentration. Plasma triglycerides levels are determined 24 hours after the administration of the last dose (day 3) from blood collected retro-orbitally with heparinized hematocrit tubes. Triglyceride determinations are performed using a commercially available Triglyceride E kit from Wako (Osaka, Japan).

[2] HDL cholesterol elevation. The activity of the compounds of the present invention for raising the plasma level of high density lipoprotein (HDL) in a mammal can be demonstrated in transgenic mice expressing the human apoAI and CETP transgenes (HuAICETPTg). The transgenic mice for use in this study are described previously in Walsh et al., J. Lipid Res. 1993, 34: 617–623, Agellon et al., J. Biol. Chem. 1991, 266: 10796–10801. Mice expressing the human apoAI and CETP transgenes are obtained by mating transgenic mice expressing the human apoAI transgene (HuAITg) with CETP mice (HuCETPTg).

Male HuAICETPTg mice (8–11 week old) are grouped according to their human apo AI levels and have free access to Purina rodent chow and water. Animals are dosed daily by oral gavage with vehicle (water or 0.5% methylcellulose 0.05% Tween 80) or with vehicle containing test compound at the desired dose for 5 days. HDL-cholesterol and human apoAI are determined initially (day 0) and 90 minutes post dose (day 5) using methods based on standard procedures. Mouse HDL is separated from apoB-containing lipoproteins by dextran sulfate precipitation as described elsewhere (Francone et al., J. Lipid. Res. 1996, 37:1268–1277). Cholesterol is measured enzymatically using a commercially available cholesterol/HP Reagent kit (Boehringer MannHeim, Indianapolis, Ind.) and spectrophotometrically quantitated on a microplate reader. Human apoAI is measured by a sandwich enzyme-linked immunosorbent assay as previously described (Francone et al., J. Lipid. Res. 1996, 37:1268–1277).

Measurement of Glucose Lowering in the ob/ob Mouse

The hypoglycemic activity of the compounds of the present invention can be determined by the amount of test compound that reduces glucose levels relative to a vehicle without test compound in male ob/ob mice. The test also allows the determination of an approximate minimal effective dose (MED) value for the in vivo reduction of plasma glucose concentration in such mice for such test compounds.

Five to eight week old male C57BL/6J-ob/ob mice (obtained from Jackson Laboratory, Bar Harbor, Me.) are housed five per cage under standard animal care practices. After a one-week acclimation period, the animals are weighed and 25 microliters of blood are collected from the retro-orbital sinus prior to any treatment. The blood sample is immediately diluted 1:5 with saline containing 0.025% sodium heparin, and held on ice for metabolite analysis. Animals are assigned to treatment groups so that each group has a similar mean for plasma glucose concentration. After group assignment, animals are dosed orally each day for four days with the vehicle consisting of either: (1) 0.25% w/v methyl cellulose in water without pH adjustment; or (2) 0.1% Pluronic® P105 Block Copolymer Surfactant (BASF Corporation, Parsippany, N.J.) in 0.1% saline without pH adjustment. On day 5, the animals are weighed again and then dosed orally with a test compound or the vehicle alone. All compounds are administered in vehicle consisting of either: (1) 0.25% w/v methyl cellulose in water; (2) 10% DMSO/0.1% Pluronic® in 0.1% saline without pH adjustment; or 3) neat PEG 400 without pH adjustment. The animals are then bled from the retro-orbital sinus three hours later for determination of blood metabolite levels. The freshly collected samples are centrifuged for two minutes at 10,000×g at room temperature. The supernatant is analyzed for glucose, for example, by the Abbott VP™ (Abbott Laboratories, Diagnostics Division, Irving, Tex.) and VP Super System® Autoanalyzer (Abbott Laboratories, Irving, Tex.), or by the Abbott Spectrum CCX™ (Abbott Laboratories, Irving, Tex.) using the A-Gent™Glucose-UV Test reagent system (Abbott Laboratories, Irving, Tex.) (a modification of the method of Richterich and Dauwalder, *Schweizerische Medizinische Wochenschrift*, 101: 860 (1971)) (hexokinase method) using a 100 mg/dl standard. Plasma glucose is then calculated by the equation: Plasma glucose (mg/dl)=Sample value×8.14 where 8.14 is the dilution factor, adjusted for plasma hematocrit (assuming the hematocrit is 44%).

The animals dosed with vehicle maintain substantially unchanged hyperglycemic glucose levels (e.g., greater than or equal to 250 mg/dl), animals treated with compounds having hypoglycemic activity at suitable doses have significantly depressed glucose levels. Hypoglycemic activity of the test compounds is determined by statistical analysis (unpaired t-test) of the mean plasma glucose concentration between the test compound group and vehicle-treated group on day 5. The above assay carried out with a range of doses of a test compound allows the determination of an approximate minimal effective dose (MED) value for the in vivo reduction of plasma glucose concentration.

Measurement of Insulin, Triglyceride, and Cholesterol Levels in the ob/ob Mouse

The compounds of the present invention are readily adapted to clinical use as hyperinsulinemia reversing agents, triglyceride lowering agents and hypocholesterolemic agents. Such activity can be determined by the amount of test compound that reduces insulin, triglycerides or cholesterol levels relative to a control vehicle without test compound in male ob/ob mice.

Since the concentration of cholesterol in blood is closely related to the development of cardiovascular, cerebral vascular or peripheral vascular disorders, the compounds of the present invention, by virtue of their hypocholesterolemic action, prevent, arrest and/or regress atherosclerosis.

Since the concentration of insulin in blood is related to the promotion of vascular cell growth and increased renal sodium retention, (in addition to the other actions, e.g., promotion of glucose utilization) and these functions are known causes of hypertension, the compounds of the present invention, by virtue of their hypoinsulinemic action, prevent, arrest and/or regress hypertension.

Since the concentration of triglycerides in blood contributes to the overall levels of blood lipids, the compounds of the present invention, by virtue of their triglyceride lowering and/or free fatty acid lowering activity prevent, arrest and/or regress hyperlipidemia.

Free fatty acids contribute to the overall level of blood lipids and independently have been negatively correlated with insulin sensitivity in a variety of physiologic and pathologic states.

Five to eight week old male C57BL/6J-ob/ob mice (obtained from Jackson Laboratory, Bar Harbor, Me.) are housed five per cage under standard animal care practices and fed standard rodent diet ad libitum. After a one-week acclimation period, the animals are weighed and 25 microliters of blood are collected from the retro-orbital sinus prior to any treatment. The blood sample is immediately diluted 1:5 with saline containing 0.025% sodium heparin, and held on ice for plasma glucose analysis. Animals are assigned to treatment groups so that each group has a similar mean for plasma glucose concentration. The compound to be tested is administered by oral gavage as an about 0.02% to 2.0% solution (weight/volume (w/v)) in either (1) 10% DMSO/0.1% Pluronic® P105 Block Copolymer Surfactant (BASF Corporation, Parsippany, N.J.) in 0.1% saline without pH adjustment or (2) 0.25% w/v methylcellulose in water without pH adjustment. Alternatively, the compound to be tested can be administered by oral gavage dissolved in or in suspension in neat PEG 400. Single daily dosing (s.i.d.) or twice daily dosing (b.i.d.) is maintained for 1 to, for example, 15 days. Control mice receive the 10% DMSO/0.1% Pluronic® P105 in 0.1% saline without pH adjustment or the 0.25% w/v methylcellulose in water without pH adjustment, or the neat PEG 400 without pH adjustment.

Three hours after the last dose is administered, the animals are sacrificed and blood is collected into 0.5 ml serum separator tubes containing 3.6 mg of a 1:1 weight/weight sodium fluoride: potassium oxalate mixture. The freshly collected samples are centrifuged for two minutes at 10,000×g at room temperature, and the serum supernatant is transferred and diluted 1:1 volume/volume with a 1 TIU/ml aprotinin solution in 0.1% saline without pH adjustment.

The diluted serum samples are then stored at −80° C. until analysis. The thawed, diluted serum samples are analyzed for insulin, triglycerides, free fatty acids and cholesterol levels. Serum insulin concentration is determined using Equate® RIA INSULIN kits (double antibody method; as specified by the manufacturer) available from Binax, South Portland, Me. The interassay coefficient of variation is ≦10%. Serum triglycerides are determined using the Abbott VP™ and VP Super System® Autoanalyzer (Abbott Laboratories, Irving, Tex.), or the Abbott Spectrum CCX™ (Abbott Laboratories, Irving, Tex.) using the A-Gent™ Triglycerides Test reagent system (Abbott Laboratories, Diagnostics Division, Irving, Tex.) (lipase-coupled enzyme method; a modification of the method of Sampson, et al., *Clinical Chemistry* 21: 1983 (1975)). Serum total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al. *Clinical Chemistry* 20: 470 (1974)) using 100 and 300 mg/dl standards. Serum free fatty acid concentration is determined utilizing a kit from WAKO (Osaka, Japan), as adapted for use with the Abbott VP™ and VP Super System® Autoanalyzer (Abbott Laboratories, Irving, Tex.), or the Abbott Spectrum CCX™ (Abbott Laboratories, Irving, Tex.). Serum insulin, triglycerides, free fatty acids and total cholesterol levels are then calculated by the equations: Serum insulin (µU/ml)=Sample value×2; Serum triglycerides (mg/dl)=Sample value×2; Serum total cholesterol (mg/dl)=Sample value×2; Serum free fatty acid (μEq/l)=Sample value×2; where 2 is the dilution factor.

The animals dosed with vehicle maintain substantially unchanged, elevated serum insulin (e.g., 275 μU/ml), serum triglycerides (e.g., 235 mg/dl), serum free fatty acid (1500 mEq/ml) and serum total cholesterol (e.g., 190 mg/dl) levels. The serum insulin, triglycerides, free fatty acid and total cholesterol lowering activity of the test compounds are determined by statistical analysis (unpaired t-test) of the mean serum insulin, triglycerides, or total cholesterol concentration between the test compound group and the vehicle-treated control group.

Measurement of Energy Expenditure in Rats

As would be appreciated by those skilled in the relevant art, during increased energy expenditure, animals generally consume more oxygen. In addition, metabolic fuels such as, for example, glucose and fatty acids, are oxidized to $CO_2$ and $H_2O$ with the concomitant evolution of heat, commonly referred to in the art as thermogenesis. Thus, the measurement of oxygen consumption in animals, including humans and companion animals, is an indirect measure of thermogenesis. Indirect calorimetry is commonly used in animals, e.g., humans, by those skilled in the relevant art to measure such energy expenditures.

Those skilled in the art understand that increased energy expenditure and the concomitant burning of metabolic fuels resulting in the production of heat may be efficacious with respect to the treatment of, e.g., obesity.

The ability of the compounds of the present invention to generate a thermogenic response can be demonstrated according to the following protocol: This in vivo screen is designed to evaluate the efficacy of compounds that are PPAR agonists, using as an efficacy endpoint measurement of whole body oxygen consumption. The protocol involves: (a) dosing fatty Zucker rats for about 6 days, and (b) measuring oxygen consumption. Male fatty Zucker rats having a body weight range of from about 400 g to about 500 g are housed for from about 3 to about 7 days in individual cages under standard laboratory conditions prior to the initiation of the study. A compound of the present invention and a vehicle is administered by oral gavage as a single daily dose given between about 3 p.m. to about 6 p.m. for about 6 days. A compound of the present invention is dissolved in vehicle containing about 0.25% of methyl cellulose. The dosing volume is about 1 ml.

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment. The subject rats are removed from their home cages and their body weights recorded. The rats are placed into the sealed chambers (43×43×10 cm) of the Oxymax, the chambers are placed in the activity monitors, and the air flow rate through the chambers is then set at from about 1.6 L/min to about 1.7 L/min. The Oxymax software then calculates the oxygen consumption (mL/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 min for from about 5 h to about 6.5 h. Resting oxygen consumption is calculated on individual rats by averaging the values excluding the first 5 values and the values obtained during time periods where ambulatory activity exceeds about 100 counts.

In Vivo Atherosclerosis Assay

Anti-atherosclerotic effects of the compounds of the present invention can be determined by the amount of compound required to reduce the lipid deposition in rabbit aorta. Male New Zealand White rabbits are fed a diet containing 0.2% cholesterol and 10% coconut oil for 4 days (meal-fed once per day). Rabbits are bled from the marginal ear vein and total plasma cholesterol values are determined from these samples. The rabbits are then assigned to treatment groups so that each group has a similar mean±SD for total plasma cholesterol concentration, HDL cholesterol concentration and triglyceride concentration. After group assignment, rabbits are dosed daily with compound given as a dietary admix or on a small piece of gelatin based confection. Control rabbits receive only the dosing vehicle, be it the food or the gelatin confection. The cholesterol/coconut oil diet is continued along with the compound administration throughout the study. Plasma cholesterol, HDL-cholesterol, LDL cholesterol and triglyceride values can be determined at any point during the study by obtaining blood from the marginal ear vein. After 3–5 months, the rabbits are sacrificed and the aortae are removed from the thoracic arch to the branch of the iliac arteries. The aortae are cleaned of adventitia, opened longitudinally and then stained with Sudan IV as described by Holman et. al. (Lab. Invest. 1958, 7, 42–47). The percent of the surface area stained is quantitated by densitometry using an Optimas Image Analyzing System (Image Processing Solutions; North Reading Mass.). Reduced lipid deposition is indicated by a reduction in the percent surface area stained in the compound-receiving group in comparison with the control rabbits.

The utility of the formula I compounds useful in the present invention, their prodrugs and the salts of such compounds and prodrugs as agents in the treatment of the above described disease/conditions in ruminants is additionally demonstrated by the activity of the compounds of the present invention in the assays described below.

Negative Energy Balance

To determine negative energy balance, serum concentrations of NEFAs or ketone bodies, or levels of triglycerides in liver tissues, are measured. Higher than 'normal' levels of NEFA's and/or triglycerides and/or ketone bodies are indicators of negative energy balance. Levels considered 'higher than normal' or 'excessive' are:

NEFA's >800 μmol/L in serum.
Triglycerides >10% w/w in liver tissue.
Ketone bodies >1.2 □mol/L in serum.

Determination of Chances in Blood Non-esterified Fatty Acid (NEFA) Concentrations and Liver Triglycerides Levels:

Compounds are administered once or several times in the transition period at dose levels predicted to be effective by comparing results of in-vitro receptor affinity tests in laboratory species and pharmacokinetic evaluations in cattle. NEFA levels are determined via standard laboratory methods, for example, using the commercial WAKO NEFA kit (Wako Chemical Co., USA, Dallas, Tex., 994-75409), and liver triglyceride content is determined using the method as described in the literature (J. K. Drackley, J. J. Veenhuizen, M. J. Richard and J. W. Young, J Dairy Sci, 1991, 74, 4254)).

All animals may be obtained from a commercial dairy farm approximately thirty days prior to anticipated calving date. The cows are moved into separate building, approximately 10–14 days prior to their anticipated calving dates and switched to the TMR-Close-Up dry diet. Enrolment of animals in the study begins approximately 7 days prior to their anticipated calving dates. The animals may be moved to the "on-test" pen, weighed and are locked each AM into feed stanchions. At that time, appropriate doses are administered and appropriate blood samples obtained (see table below for sample data for a PPAR alpha agonist, compound Z, 2-Methyl-5-(4'-trifluoromethoxy-biphenyl-4-ylsulfamoyl)-benzoic acid (EXAMPLE 193). Animals enrolled in T01 were treated with vehicle control every other day (eod) beginning at the estimated Day −7 prior to calving, and once again at calving. Animals enrolled in T02 were treated with compound Z, 2-Methyl-5-(4'-trifluoromethoxy-biphenyl-4-ylsulfamoyl)-benzoic acid (EXAMPLE 193) every other day beginning at the estimated Day −7 prior to calving, and once again at calving.

| Treatment | Dosage | Animals per Treatment | Pre Partum Dosing (every other day = eod − beginning targeted day -7) | Treatment at Calving |
|---|---|---|---|---|
| T01 Vehicle Control | — | 11 | X | X |
| T02 Compound Z | 0.5 mg/kg | 9 | X | X |

As soon as possible post-calving (~30 minutes) the cow is transferred to the freestall barn for the next scheduled milking (6:00 hrs and 19:00 hrs). Treatments on postpartum animals are administered every other day through day 8. Pre and post-calving NEFA samples are analyzed using the WAKO NEFA-C test kit (#994-75409). Post-calving liver biopsies are performed on all cows on days 5, 10 and 14 post-calving. Tissues are transported on ice and stored frozen at −70° F. At the conclusion of the study, samples are analysed of liver triglyceride levels using the method described by Drackley, J. K. et al. (1991, J Dairy Sci (74):4254–4264).

All animals treated with test article (T02) exhibited significantly lower ($p<0.10$) serum NEFA levels as compared to control on days 1–8, with the exceptions of T02 on day 5($p=0.17$). All treatment regimens significantly lowered liver triglyceride levels compared to placebo at all time points measured (Days 5, 10 and 14 postcalving).

Ketone Bodies

Levels of ketone bodies in serum can be measured by standard methods well known to the person skilled in the art, for example, by using the commercially available kits for this purpose, including Sigma BHBA kit of order number 310-A.

Milk Content:

Machines to assay for milk protein, fat, or lactose content are commercially available (MilkoScan™ 50, MilkoScan™ 4000, MilkoScan™ FT 6000 available from Foss Group). Machines to assay for somatic cell content are also commercially available (Fossomatic™ FC, Fossomatic™ Minor available from Foss Group).

Compounds used in this invention may be administered alone or in combination with one or more other compounds of the invention or in combination with one or more other drugs (or as any combination thereof).

For example, compounds of this invention can also be mixed with one or more biologically active compounds or agents selected from sedatives, analgesics, antiinflammatories, analeptics, antibacterials, antidiarrhoeals, anti-endotoxin, antifungals, respiratory stimulants, corticosteroids, diuretics, parasiticides, electrolyte preparations and nutritional supplements, growth promoters, hormones, and metabolic disease treatments, giving an even broader spectrum of veterinary or agricultural utility.

Examples of suitable active compounds or agents are found below:

Amylase inhibitors: Acarbose;

Glucosidase Inhibitors: Acarbose;

Sedatives: xylazine;

Analgesics and antiinflammatories: Lignocaine, Procaine, flunixin, oxytetracycline, ketoprofen, meloxicam and carprofen;

Analeptics :Etamiphylline, Doxapram, Diprenorphine, Hyoscine, Ketoprofen, Meloxicam, Pethidine, Xylazine and Butorphanol;

Antibacterials: Chlortetracycline, Tylosin, Amoxycillin, Ampicillin, Aproamycin, Cefquinome, Cephalexin, Clavulanic acid, Florfenicol, Danofloxacin, Enrofloxacin, Marbofloxacin, Framycetin, Procaine penicillin, procaine benzylpenicillin, Benzathine penicillin, sulfadoxine, Trimethoprim, sulphadimidine, baquiloprim,streptomycin, dihydrostreptomycin, sulphamethoxypyridazine, sulphamethoxypuridazine, oxytetracycline, flunixin, tilmicosin, cloxacillin, ethyromycin, neomycin, nafcillin, Aureomycin, lineomycin, cefoperazone, cephalonium, oxytetracycline, formosulphathiazole, sulphadiazine and zinc.;

Antidiarrhoeals: Hyoscine, Dipyrone, charcoal, attapulgite, kaolin, Isphaghula husk;

Anti-endotoxins: Flunixin, ketoprofen;

Antifungals: Enilconazole, Natamycin;

Respiratory stimulants: florfenicol;

Corticosteroids: dexamethasone, betamethasone;

Diuretics: frusemide;

Parasiticides—amitraz, deltamethrin, moxidectin, doramectin, alpha cypermethrin, fenvalerate, eprinomectin, permethrin, ivermectin, abamectin, ricobendazole, levamisole, febantel, triclabendazole, fenbendazole, albendazole, netobimin, oxfenazole, oxyclozanide, nitroxynil, morantel;

Electrolyte preparations and nutritional supplements: dextrose, lactose, propylene glycol, whey, glucose, glycine, calcium, cobalt, copper, iodine, iron, magnesium, manganese, phosphorous, selenium, zinc, Biotin, vitamin $B_{12}$, Vitamin E, and other vitamins;

Growth Promoters: monensin, flavophospholipol, bambermycin, salinomycin, tylosin;

Hormones: chorionic gonadotrophin, serum gonadotrophin, atropine, melatonin, oxytocin, dinoprost, cloprostenol, etiproston, luprostiol, buserelin, oestradiol, progesterone, and bovine somatotropin; and Metabolic Disease Treatments: calcium gluconate, calcium borogluconate, propylene glycol, magnesium sulphate.

Compounds of this invention can also be mixed with one or more biologically active compounds or agents selected from antiprotozoals such as imidocarb, bloat remedies such as dimethicone and poloxalene, and probiotics such as Lactobacilli and streptococcus.

Administration of the compounds of the present invention can be via any method which delivers a compound of this invention systemically and/or locally.

These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate or where the patient is unable to ingest the drug.

In general an amount of a compound of the present invention is used that is sufficient to achieve the therapeutic effect desired (e.g., lipid lowering).

In general an effective dosage for the compounds of the present invention, their prodrugs and the salts of such compounds and prodrugs is in the range of about 0.001 to about 100 mg/kg/day, preferably about 0.005 to about 5 mg/kg/day.

A dosage of the combination pharmaceutical agents to be used in conjuction with the PPAR agonists is used that is effective for the indication being treated. Such dosages can be determined by standard assays such as those referenced above and provided herein. The combination agents may be administered simultaneously or sequentially in any order.

For example, typically an effective dosage for HMG-CoA reductase inhibitors is in the range of about 0.01 to about 100 mg/kg/day.

The compounds of the present invention are generally administered in the form of a pharmaceutical composition comprising at least one of the compounds of this invention together with a pharmaceutically acceptable vehicle, diluent or carrier. Thus, the compounds of the present invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol™ or Capmul™, in a soft gelatin capsule. Antioxidants may be added to prevent long term degradation as appropriate. When aqueous suspensions and/or elixirs are desired for oral administration, the compounds of the present invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 19th Edition (1995).

Pharmaceutical compositions according to the present invention may contain 0.1%–95% of the compound(s) of the present invention, preferably 1%–70%. In any event, the composition or formulation to be administered will contain a quantity of a compound(s) according to the present invention in an amount effective to treat the disease/condition of the subject being treated, e.g., atherosclerosis.

Since the present invention has an aspect that relates to the treatment of the disease/conditions described herein with a combination of active ingredients, which may be administered separately, the invention also relates to combining separate pharmaceutical compositions in kit form. The kit comprises two separate pharmaceutical compositions: a compound of the present invention, a prodrug thereof or a salt of such compound or prodrugs and a second compound as described above. The kit for example comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention either alone or in combination with each other or other compounds generally will be administered in a convenient formulation. The following formulation examples only are illustrative and are not intended to limit the scope of the present invention.

In the formulations which follow, "active ingredient" means a compound of the present invention.

Formulation 1: Gelatin Capsules
Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7: Intravenous Solution | |
|---|---|
| Ingredient | Quantity |
| Active ingredient dissolved in ethanol 1% | 20 mg |
| Intralipid ™ emulsion | 1,000 mL |

The solution of the above ingredients is intravenously administered to a patient at a rate of about 1 mL per minute.

Soft gelatin capsules are prepared using the following:

| Formulation 8: Soft Gelatin Capsule with Oil Formulation | |
|---|---|
| Ingredient | Quantity (mg/capsule) |
| Active ingredient | 10–500 |
| Olive Oil or Miglyol ™ Oil | 500–1000 |

The active ingredient above may also be a combination of therapeutic agents.

General Experimental Procedures

The following examples are put forth so as to provide those of ordinary skill in the art with a disclosure and description of how the compounds, compositions, and methods claimed herein are made and evaluated, and are intended to be purely exemplary of the invention and are not intended to limit the scope of what the inventors regard as their invention. Unless indicated otherwise, percent is percent by weight given the component and the total weight of the composition, temperature is in ° C. or is at ambient temperature, and pressure is at or near atmospheric. Commercial reagents were utilized without further purification. Room or ambient temperature refers to 20–25° C. All non-aqueous reactions were run under a nitrogen atmosphere for convenience and to maximize yields. Concentration in vacuo means that a rotary evaporator was used. The names for the compounds of the invention were created by the Autonom 2.0 PC-batch version from Beilstein Informationssysteme GmbH (ISBN 3-89536-976-4). "DMSO" means dimethyl sulfoxide.

NMR spectra were recorded on a Varian Unity 400 (Varian Co., Palo Alto, Calif.) NMR spectrometer at ambient temperature. Chemical shifts are expressed in parts per million (δ) relative to an external standard (tetramethylsilane). The peak shapes are denoted as follows: s, singlet; d, doublet, t, triplet, q, quartet, m, multiplet with the prefix br indicating a broadened signal. The coupling constant (J) data given have a maximum error of ±0.41 Hz due to the digitization of the spectra that are acquired. Mass spectra were obtained by (1) atmospheric pressure chemical ionization (APCI) in alternating positive and negative ion mode using a Fisons Platform II Spectrometer or a Micromass MZD Spectrometer (Micromass, Manchester, UK) or (2) electrospray ionization in alternating positive and negative ion mode using a Micromass MZD Spectrometer (Micromass, Manchester, UK) with a Gilson LC-MS interface (Gilson Instruments, Middleton, Wisc.) or (3) a QP-8000 mass spectrometer (Shimadzu Corporation, Kyoto, Japan) operating in positive or negative single ion monitoring mode, utilizing electrospray ionization or atmospheric pressure chemical ionization. Where the intensity of chlorine- or bromine-containing ions are described, the expected intensity ratio was observed (approximately 3:1 for $^{35}Cl/^{37}Cl$-containing ions and 1:1 for $^{79}Br/^{81}Br$-containing ions) and the position of only the lower mass ion is given.

Column chromatography was performed with either Baker Silica Gel (40 µm) (J. T. Baker, Phillipsburg, N.J.) or Silica Gel 60 (40–63 µm)(EM Sciences, Gibbstown, N.J.). Flash chromatography was performed using a Flash 12 or Flash 40 column (Biotage, Dyar Corp., Charlottesville, Va.). Preparative HPLC purification was performed on a Shimadzu 10A preparative HPLC system (Shimadzu Corporation, Kyoto, Japan) using a model SIL-10A autosampler and model 8A HPLC pumps. Preparative HPLC-MS was performed on an identical system, modified with a QP-8000 mass spectrometer operating in positive or negative single ion monitoring mode, utilizing electrospray ionization or atmospheric pressure chemical ionization. Elution was carried out using water/acetonitrile gradients containing either 0.1% formic acid or ammonium hydroxide as a modifier. In acidic mode, typical columns used include Waters Symmetry C8, 5 µm, 19×50 mm or 30×50 mm, Waters XTerra C18, 5 µm, 50×50 (Waters Corp, Milford, Mass.) or Phenomenex Synergi Max-RP 4 µm, 50×50 mm (Phenomenex Inc., Torrance, Calif.). In basic mode, the Phenomenex Synergi Max-RP 4 µm, 21.2×50 mm or 30×50 mm columns (Phenomenex Inc., Torrance, Calif.) were used.

Optical rotations were determined using a Jasco P-1020 Polarimeter Jasco Inc., Easton, Md.)

Dimethylformamide, tetrahydrofuran, toluene and dichloromethane were the anhydrous grade supplied by Aldrich Chemical Company (Milwaukee, Wisc.). Unless otherwise specified, reagents were used as obtained from commercial sources. The terms "concentrated" and "evaporated" refer to removal of solvent at 1–200 mm of mercury pressure on a rotary evaporator with a bath temperature of less than 45° C. The abbreviation "min" stand for "minutes" and "h" or "hr" stand for "hours." The abbreviation "gm" or "g" stand for grams. The abbreviation "µl" or "µL" stand for microliters.

EXAMPLE 1

5-(4-Benzyloxy-phenylsulfamoyl)-2-methyl-benzoic acid

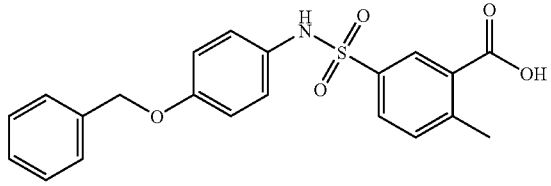

To a solution of 5-chlorosulfonyl-2-methylbenzoic acid (200 mg, 0.85 mmol) and p-benzyloxyaniline (187 mg, 0.94 mmol) in 6 ml acetone and 3 ml dimethylformamide was added a solution of sodium bicarbonate (215 mg, 0.56 mmol) in 2 ml water. The resulting mixture was stirred overnight at room temperature. The acetone was then removed under reduced pressure and the residual mixture was partitioned between 25 ml 1N aqueous hydrochloric acid solution and 25 ml ethyl acetate. The aqueous phase was separated and extracted with 2×25 ml ethyl acetate. The combined ethyl acetate extracts were dried (anhydrous sodium sulfate) and concentrated under reduced pressure.

The residue was purified by flash column chromatography (silica gel, 15 gm) eluting with 9:1 chloroform/methanol to yield a white solid (154 mg). The solid was triturated with dichloromethane to yield the title compound (93 mg, 28% yield) as a white solid. MS: 395.6 (M−1); $^1$H NMR (400 MHz, CD$_3$OD): δ2.57(s, 3H), 4.96 (s, 2H), 6.81 (m, 2H), 6.93 (m, 2H), 7.30 (m, 6H), 7.60 (m, 1H), 8.20 (m, 1H).

The title compounds of EXAMPLES 2–26 were prepared using procedures analogous to that of EXAMPLE 1 from appropriate starting materials.

EXAMPLE 2

2-Methyl-5-[4-(6-methyl-benzothiazol-2-yl)-phenyl-sulfamoyl]benzoic acid

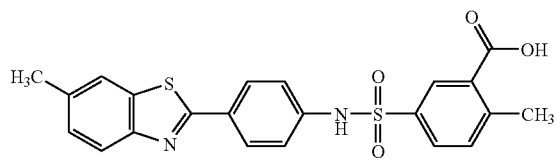

8% yield. MS: 439.4 (M+1); $^1$H NMR (400 MHz, CD$_3$OD): δ62.44 (s, 3H), 2.53 (s, 3H), 7.23 (m, 2H), 7.29 (m, 1H), 7.34 (m, 1H), 7.72 (m, 1H), 7.75 (m, 1H), 7,80 (m, 1H), 7.88 (m, 2H), 8.19 (m, 1H).

EXAMPLE 3

2-Methyl-5-[4-(5-methyl-benzooxazol-2-yl)-phenyl-sulfamoyl]benzoic acid

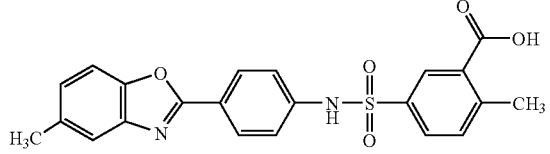

4% yield. MS: 423.4 (M+1); $^1$H NMR (400 MHz, CD$_3$OD): δ2.42 (s, 3H), 2.51 (s, 3H), 7.17 (m, 1H), 7.26 (m, 2H), 7.35(m, 1H), 7.44 (m, 2H), 7.56 (m, 1H), 8.0 (m, 2H), 8.15 (m, 1H).

EXAMPLE 4

5-(4-Benzooxazol-2-yl-phenylsulfamoyl)-2-methyl-benzoic acid

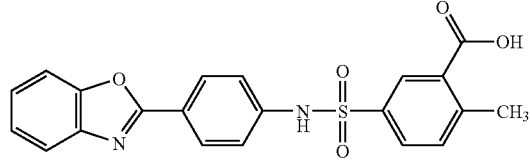

10% yield. MS: 407.1 (M−1); $^1$H NMR (400 MHz, CD$_3$OD): δ2.48 (s, 3H), 7.38 (m, 3H), 7.65 (m, 1H), 7.7 (m, 1H), 7.92 (m, 3H), 8.22 (m, 1H).

EXAMPLE 5

2-Methyl-5-[4-(5-phenyl-benzooxazol-2-yl)-phenyl-sulfamoyl]-benzoic acid

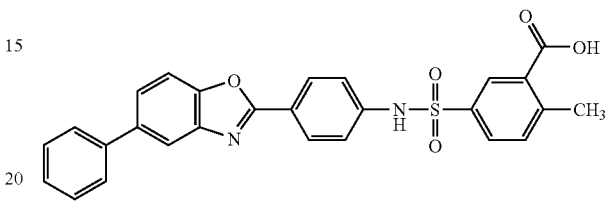

7% yield. MS: 483.2 (M−1); $^1$H NMR (400 MHz, CD$_3$OD): δ2.48 (s, 3H), 7.35 (m, 2H), 7.44 (m, 2H), 7.64 (m, 3H), 7.71 (d, 1H), 7.82 (m, 1H), 7.92 (m, 4H), 8.23 (m, 2H).

EXAMPLE 6

5-[4-(5-Chloro-benzooxazol-2-yl)-phenylsulfamoyl]-2-methyl-benzoic acid

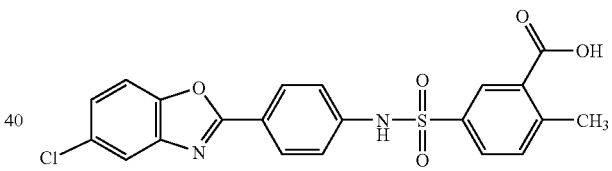

10% yield. MS: 441.1 (M−1); $^1$H NMR (400 MHz, CD$_3$OD): δ2.47 (s, 3H), 7.37 (m, 2H), 7.63 (d, 1H), 7.7 (b, 1H), 7.81 (m, 1H), 7.92 (m, 3H), 8.21 (m, 2H).

EXAMPLE 7

5-(4-Benzothiazol-2-yl-phenylsulfamoyl)-2-methyl-benzoic acid

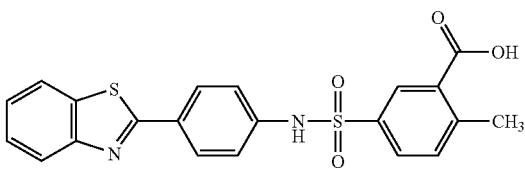

7% yield. MS: 425.1 (M+1); $^1$H NMR (400 MHz, CD$_3$OD): δ246 (s, 3H), 7.26 (m, 3H), 7.37 (t, 1H), 7.47 (t, 1H), 7.62 (d, 1H), 7.91 (m 4H)), 7.98 (b, 1H).

EXAMPLE 8

2-Methyl-5-[4-(4-trifluoromethyl-benzylsulfanyl)-phenylsulfamoyl]-benzoic acid

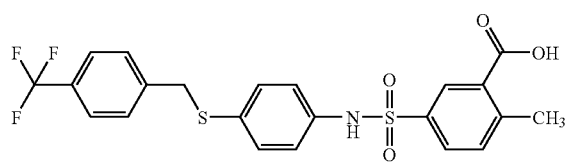

33% yield. MS: 480.2 (M−1); $^1$H NMR (400 MHz, CD$_3$OD): δ2.49 (s, 3H), 4.04 (s, 2H), 6.96 (d, 2H), 7.1 (d, 2H), 7.23 (d, 1H), 7.29 (m, 2H), 7.47 (m, 3H), 7.94 (b, 1H).

EXAMPLE 9

2-Methyl-5-[4-(4-trifluoromethyl-benzyloxy)-phenylsulfamoyl]-benzoic acid

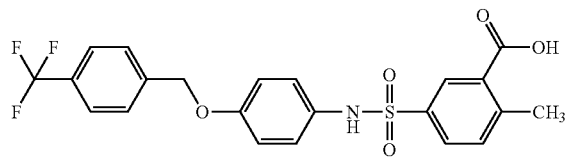

28% yield. MS: 464.1 (M−1); $^1$H NMR (400 MHz, CD$_3$OD): δ2.56 (s, 3H), 5.07 (s, 2H), 6.83 (m, 2H), 6.95 (m, 2H), 7.30 (d, 1H), 7.57 (m, 3H), 7.63 (d, 2H), 8.13 (s, 1H).

EXAMPLE 10

2-Methyl-5-(4-styryl-phenylsulfamoyl)-benzoic acid

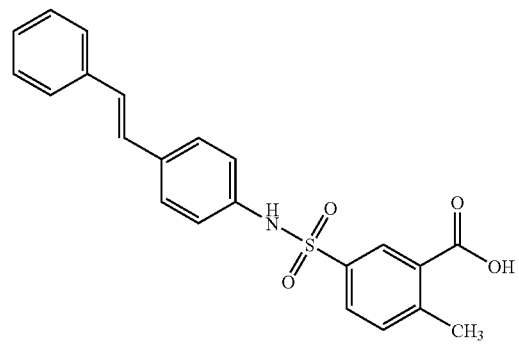

33% yield. MS: 392.2 (M−1); $^1$H NMR (400 MHz, CD$_3$OD): δ2.54 (s, 3H), 7.05 (m, 4H), 7.18 (t, 1H), 7.26–7.4 (m, 5H), 7.46 (m, 2H), 7.67 (m, 1H), 8.18 (s, 1H).

EXAMPLE 11

2-Methyl-5-[4-(3-trifluoromethyl-benzylsulfanyl)-phenylsulfamoyl]-benzoic acid

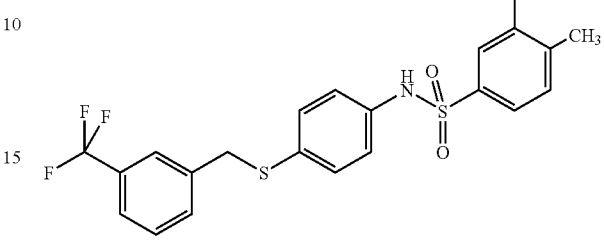

21% yield. MS: 480.1 (M−1); $^1$H NMR (400 MHz, CD$_3$OD): δ2.59 (s, 3H), 4.06 (s, 2H), 6.98 (m, 2H), 7.13 (m, 2H), 7.34 (m, 3H), 7.44 (m, 2H), 7.68 (m, 2H), 8.26 (d, 1H).

EXAMPLE 12

5-[4-(4-tert-Butyl-benzylsulfanyl)-phenylsulfamoyl]-2-methyl-benzoic acid

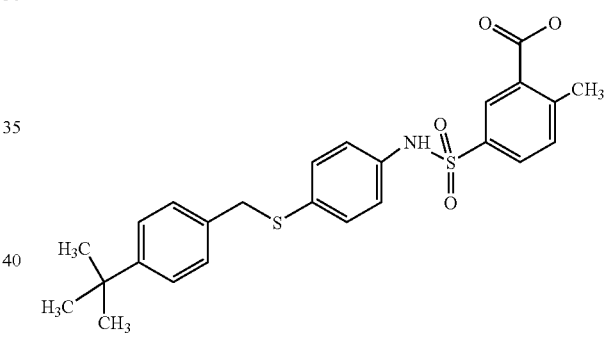

31% yield. MS: 468.2 (M−1); $^1$H NMR (400 MHz, CD$_3$OD): δ1.24 (s, 9H), 2.57 (s, 3H), 3.95 (s, 2H), 6.95 (m, 2H), 7.05 (d, 1H), 7.11 (m, 1H), 7.21 (d, 1H), 734 (d, 1H), 7.66 (m, 1H), 8.22 (d, 1H).

EXAMPLE 13

5-(4-Benzothiazol-2-yl-phenylsulfamoyl)-2-ethyl-benzoic acid

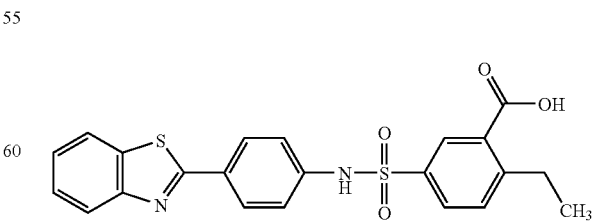

6% yield. MS: 439.1 (M+1); $^1$H NMR (400 MHz, CD$_3$OD): δ1.18 (t, 3H), 2.96 (q, 2H), 7.27 (d, 2H), 7.39 (t, 2H), 7.49 (t, 1H), 7.79 (d, 1H), 7.94 (m, 4H), 8.15 (d, 1H).

EXAMPLE 14

2-Ethyl-5-[4-(5-methyl-benzooxazol-2-yl)-phenyl-sulfamoyl]-benzoic acid

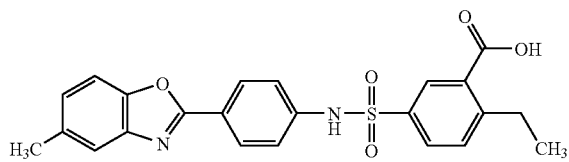

9% yield. MS: 437.1 (M+1); $^1$H NMR (400 MHz, CD$_3$OD): δ1.18 (t, 3H), 2.45 (s, 3H), 2.95 (q, 2H), 7.19 (m, 1H), 7.29 (m, 2H), 7.38 (d, 1H), 7.47 (d, 2H), 7.78 (m, 1H), 8.04 (d, 2H), 8.2 (d, 1H).

EXAMPLE 15

2-Ethyl-5-[4-(4-trifluoromethyl-benzylsulfanyl)-phenylsulfamoyl]-benzoic acid

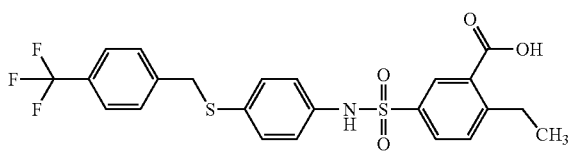

32% yield. MS: 495.2 (M−1); $^1$H NMR (400 MHz, CD$_3$OD): δ1.17 (t, 3H), 2.93 (q, 2H), 4.04 (s, 2H), 6.97 (m, 2H), 7.11 (m, 2H), 7.3 (m, 3H), 7.46 (d, 2H), 7.59 (m, 1H), 8.0 (d, 1H).

EXAMPLE 16

5-[4-(4-Isopropyl-benzylsulfanyl)-phenylsulfamoyl]-2-methyl-benzoic acid

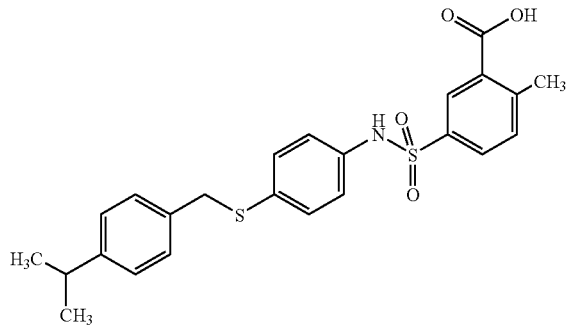

10% yield. MS: 454.2 (M−1); $^1$H NMR (400 MHz, CD$_3$OD): δ1.17 (d, 6H), 2.8 (m, 1H), 10 3.94 (s, 2H), 6.95 (d, 2H), 7.04 (s, 4H), 7.1 (m, 2H), 7.31 (d, 1H), 7.61 (d, 1H), 8.16 (s, 1H).

EXAMPLE 17

2-Methyl-5-[4-(4-trifluoromethoxy-benzylsulfanyl)-phenylsulfamoyl]-benzoic acid

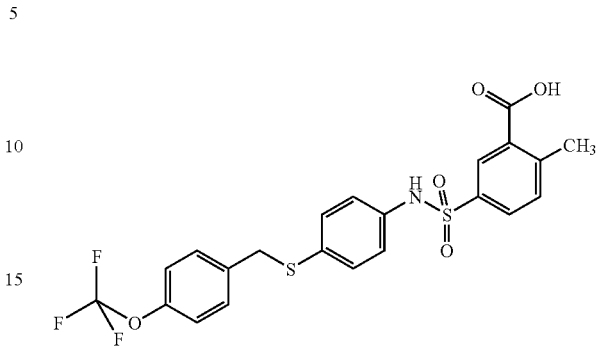

29% yield. MS: 496.1 (M−1); $^1$H NMR (400 MHz, CD$_3$OD): δ2.59 (s, 3H), 4.01 (s, 2H), 6.98 (m, 2H), 7.06 (d, 2H), 7.14 (m, 2H), 7.20 (d, 2H), 7.36 (d, 1H), 7.67 (d, 1H), 8.22 (s, 1H).

EXAMPLE 18

5-[4-(4-Chloro-benzylsulfanyl)-phenylsulfamoyl]-2-methyl-benzoic acid

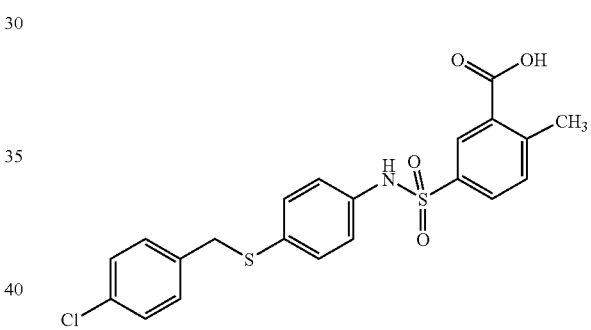

7% yield. MS: 448.1 (M+1); $^1$H NMR (400 MHz, CD$_3$OD): δ2.53 (s, 3H), 3.95 (s, 2H), 6.95 (d, 2H), 7.09 (t, 4H), 7.14 (d, 2H), 7.28 (d, 1H), 7.55 (m, 1H), 8.07 (d, 1H).

EXAMPLE 19

2-Methyl-5-[4-(3-phenoxy-benzylsulfanyl)-phenyl-sulfamoyl]-benzoic acid

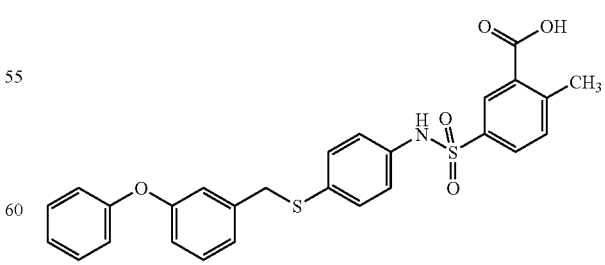

25% yield. MS: 504.2 (M+1); $^1$H NMR (400 MHz, CD$_3$OD): δ2.54 (s, 3H), 3.94 (s, 2H), 6.77 (m, 4H), 6.89 (d, 1H), 6.95 (d, 2H), 7.09 (m, 4H), 7.28 (m, 3H), 7.63 (m, 1H), 8.24 (d, 1H).

EXAMPLE 20

2-Methyl-5-(4-{2-[2-(4-trifluoromethyl-phenyl)-thiazol-4-yl]-ethoxy}-phenylsulfamoyl)-benzoic acid

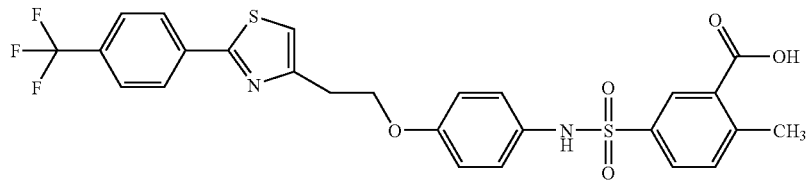

72% yield. MS: 563.1 (M+1); $^1$H NMR (400 MHz, CD$_3$OD): δ2.54 (s, 3H), 3.22 (t, 2H), 4.27 (t, 2H), 6.77 (m, 2H), 6.93 (m, 2H), 7.29 (d, 1H), 7.34 (s, 1H), 7.55 (m, 1H), 7.74 (d, 2H), 8.09 (d, 3H).

EXAMPLE 21

2-Methyl-5-(4-{2-[2-(4-trifluoromethoxy-phenyl)-thiazol-4-yl]-ethoxy}-phenylsulfamoyl)-benzoic acid

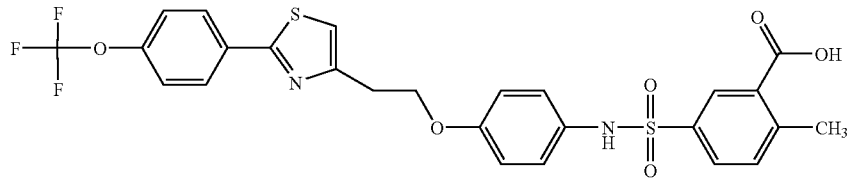

31% yield. MS: 579.1 (M+1); $^1$H NMR (400 MHz, CD$_3$OD): δ2.48 (s, 3H), 3.20 (t, 2H), 4.25 (t, 2H), 6.75 (d, 2H), 6.94 (d, 2H), 7.22 (m, 1H), 7.29 (s, 1H), 7.35 (m, 2H), 7.44 (m, 1H), 7.89 (s, 1H), 8.00 (d, 2H).

EXAMPLE 22

2,3-Dimethyl-5-[4-(5-methyl-benzooxazol-2-yl)-phenylsulfamoyl]-benzoic acid

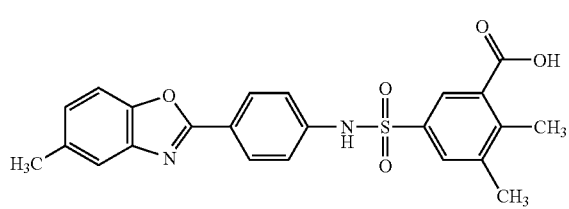

7% yield. MS: 437.3 (M+1); $^1$H NMR (400 MHz, CD$_3$OD): δ2.38 (s, 3H), 2.39 (s, 3H), 2.48 (s, 3H), 7.23 (d, 1H), 7.53 (m, 2H), 7.74 (s, 2H), 7.94 (d, 2H), 8.21 (d, 2H).

EXAMPLE 23

2,6-Dimethyl-3-[4-(6-methyl-benzothiazol-2-yl)-phenylsulfamoyl]-benzoic acid

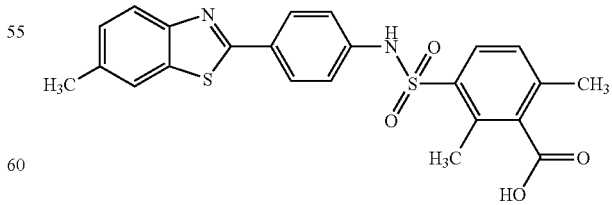

16% yield. MS: 453.1 (M+1); $^1$H NMR (400 MHz, CD$_3$OD): δ2.33 (s, 3H,), 2.46 (s, 3H), 2.63 (s, 3H), 7.2–7.3 (c, 3H), 7.32 (d, 1H), 7.73 (s, 1H), 7.8 (d, 1H), 7.88 (m, 2H), 8.0 (d, 1H).

EXAMPLE 24

2,6-Dimethyl-3-[4-(3-trifluoromethoxy-benzylsulfanyl)-phenylsulfamoyl]-benzoic acid

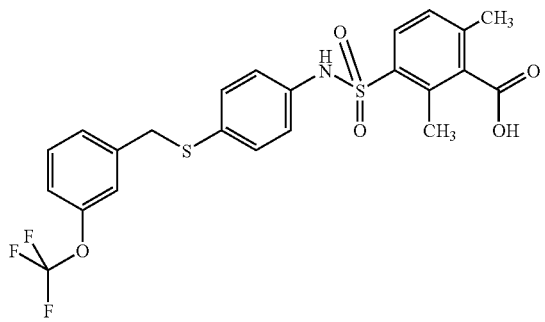

6% yield. MS: 510.1 (M−1); $^1$H NMR (400 MHz, CD$_3$OD): δ2.34 (s, 3H), 2.57 (s, 3H), 4.02 (s, 2H), 6.95 (m, 2H), 7.07 (d, 1H) 7.12 (m, 4H), 7.22 (m, 2H), 7.85 (d, 1H).

EXAMPLE 25

2,6-Dimethyl-3-[4-(4-trifluoromethoxy-benzylsulfanyl)-phenylsulfamoyl]-benzoic acid

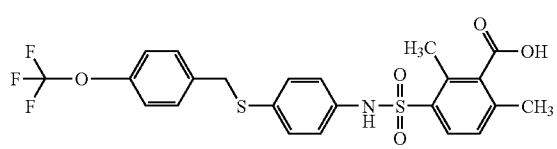

32% yield. MS: 510.3 (M−1); $^1$H NMR (400 MHz, CD$_3$OD): δ2.35 (s, 3H), 2.62 (s, 3H), 4.01 (s, 2H), 6.97 (m, 2H), 7.12 (m, 5H), 7.24 (d, 2H), 7.77 (d, 1H).

EXAMPLE 26

2,6-Dimethyl-3-(4'-trifluoromethoxy-biphenyl-4-ylsulfamoyl)-benzoic acid

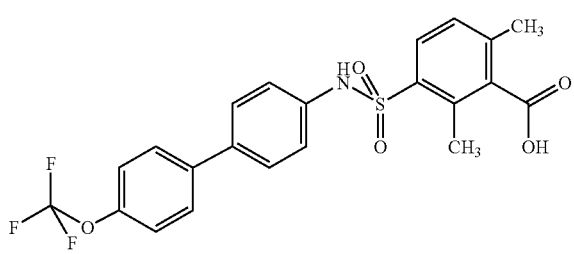

13% yield. $^1$H NMR (400 MHz, CD$_3$OD): δ2.33 (s, 3H), 2.62 (s, 3H), 7.17 (m, 2H), 7.22 (d, 1H), 7.28 (d, 2H), 7.47 (m, 2H), 7.60 (m, 2H), 7.93 (d, 1H).

EXAMPLE 27

5-[4-(4-tert-Butyl-phenoxy)-phenylsulfamoyl]-2-methyl-benzoic acid

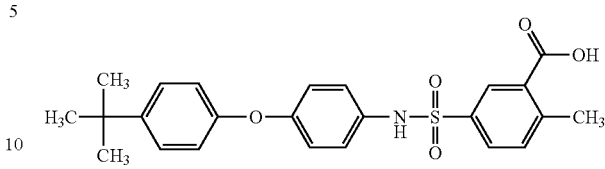

A solution of 4-(4-tert-butyl-phenoxy)-phenylamine (0.1 g, 0.41 mmol). 5-chlorosulfonyl-2-methylbenzoic acid (0.097 g, 0.41 mmol) and pyridine (0.1 ml, 1.24 mmol) in 2 ml anhydrous tetrahydrofuran was heated at 60° C. for 2 hr. The reaction mixture was cooled to room temperature and diluted with 30 ml ethyl acetate. The ethyl acetate solution was washed sequentially with 25 ml 1N aqueous hydrochloric acid solution and 25 ml brine, dried (anhydrous sodium sulfate) and concentrated to dryness under reduced pressure. The crude product was purified by preparative thick layer chromatography (silica gel), eluting with 9:1 chloroform/methanol to yield the title compound.

82% yield. MS: 438.3 (M−1); $^1$H NMR (400 MHz, CD$_3$OD): δ1.30 (s, 9H), 2.58 (s, 3H), 6.82 (m, 4H), 7.02 (d, 2H), 7.36 (d, 3H), 7.63 (d, 1H), 8.1 (b, 1H).

The title compounds of EXAMPLES 28–40 were prepared using procedures analogous to that of EXAMPLE 27 from appropriate starting materials.

EXAMPLE 28

5-[4-(4-Ethyl-benzylsulfanyl)-phenylsulfamoyl]-2-methyl-benzoic acid

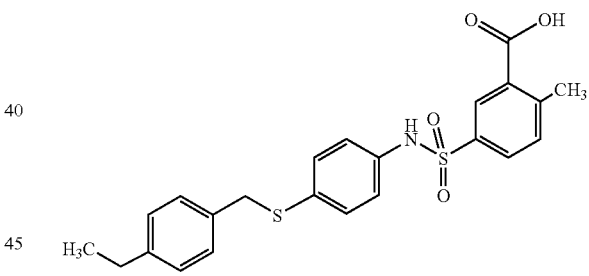

78% yield. MS: 442.1 (M+1); $^1$H NMR (400 MHz, CD$_3$OD): δ1.15 (t, 3H), 2.54 (q, 2H), 2.57 (s, 3H), 3.94 (s, 2H), 6.94 (m, 3H), 7.01 (m , 3H), 7.10 (d, 2H). 7.33 (d, 1H), 7.64 (m, 1H), 8.20 (d, 1H).

EXAMPLE 29

2-Methyl-5-[3-methyl-4-(4-trifluoromethyl-benzyloxy)-phenylsulfamoyl]-benzoic acid

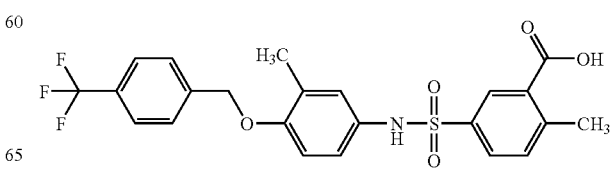

6% yield. MS: 478.2 (M−1); ¹H NMR (400 MHz, CD₃OD): δ2.17 (s, 3H), 2.60 (s, 3H), 5.11 (s, 2H), 6.80 (m, 2H), 6.88 (s, 1H), 7.36 (d, 1H), 7.63 (m, 5H), 8.20 (d, 1H).

EXAMPLE 30

2-Methyl-5-[2-methyl-4-(4-trifluoromethyl-benzyloxy)-phenylsulfamoyl]-benzoic acid

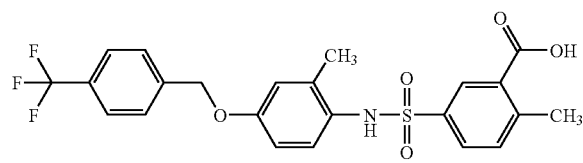

65% yield. ¹H NMR (400 MHz, CD₃OD): δ2.00 (s, 3H), 2.62 (s, 3H), 5.10 (s, 2H), 6.71 (m, 1H), 6.79 (d, 1), 6.87 (d, 1H), 7.36 (d, 1H), 7.59 (m, 3H), 7.66 (d, 2H).

EXAMPLE 31

5-(4-{2-[5-(3,5-Dimethyl-phenyl)-[1,3,4]oxadiazol-2-ylsulfanyl]-ethyl}-phenylsulfamoyl)-2-methyl-benzoic acid

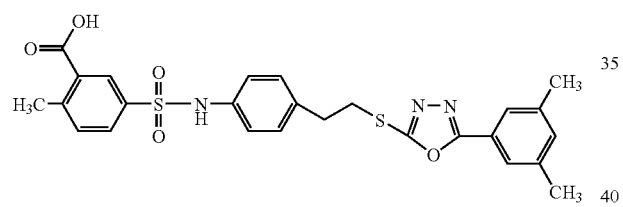

49% yield. MS: 524.4 (M+1); ¹H NMR (400 MHz, CDCl₃): δ2.36 (s, 3H), 2.59 (s, 3H), 3.03 (t, 2H), 3.41 (t, 2H), 7.05 (d, 2H), 7.13 (d, 3H), 7.27, (b, 1H), 7.61 (s, 2H), 7.75 (b, 1H), 8.14 (b, 1H).

EXAMPLE 32

5-(4-{2-[5-(3,5-Dichloro-phenyl)-[1,3,4]oxadiazol-2-ylsulfanyl]-ethyl}-phenylsulfamoyl)-2-methyl-benzoic acid

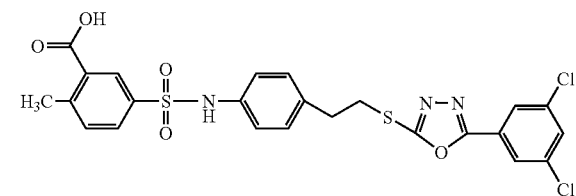

90% yield. MS: 566.3 (M+1); ¹H NMR (400 MHz, CDCl₃): δ2.55 (s, 3H), 2.97 (t, 2H), 3.38 (t, 2H), 7.03 (m, 5H), 7.18 (d, 1H), 7.53 (d, 1H), 7.63 (m, 1H), 7.77 (m, 1H), 8.02 (d, 1H).

EXAMPLE 33

5-[4-(3-Difluoromethoxy-benzylsulfanyl)-phenylsulfamoyl]-2-methyl-benzoic acid

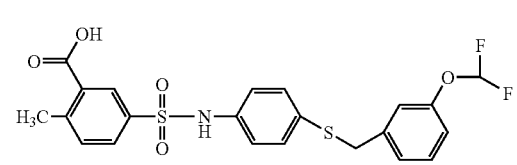

40% yield. MS: 478.2 (M−1); ¹H NMR (400 MHz, CD₃OD): δ2.58 (s, 3H), 4.01 (s, 2H), 6.98 (c, 5H), 7.14 (m, 2H), 7.20 (t, 1H), 7.33 (d, 1H), 7.63 (m, 1H), 7.87 (s, 1H), 8.19 (d, 1H).

EXAMPLE 34

2-Methyl-5-[4-(2-trifluoromethoxy-benzylsulfanyl)-phenylsulfamoyl]-benzoic acid

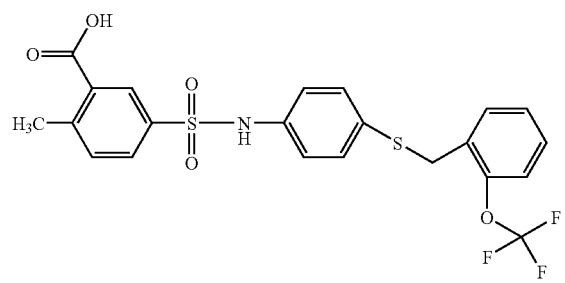

27% yield. MS: 498.3 (M+1); ¹H NMR (400 MHz, CDCl₃): δ2.60 (s, 3H), 3.98 (s, 2H), 7.01 (d, 2H), 7.10 (c, 5H), 7.23 (c, 2H), 7.68 (m, 1H), 8.41 (d, 1H).

EXAMPLE 35

2-Methyl-5-[4-(4-trifluoromethyl-phenylsulfamoyl)-phenylsulfamoyl]-benzoic acid

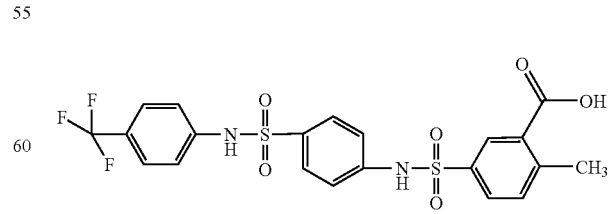

6% yield. MS: 512.9 (M−1); ¹H NMR (400 MHz, CD₃OD): δ2.55 (s, 3H), 7.20 (m, 3H), 7.30 (d, 1H), 7.48 (d, 2H), 7.66 (m, 3H), 7.90 (s, 1H), 8.20 (d, 1H).

EXAMPLE 36

5-{4-[5-(4-Ethyl-phenyl)-[1,3,4]oxadiazol-2-yl]-phenylsulfamoyl}-2-methyl-benzoic acid

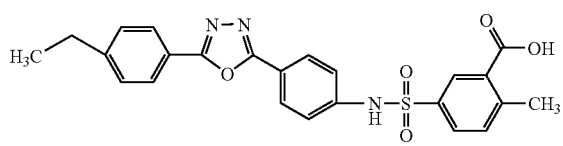

34% yield. $^1$H NMR (400 MHz, CD$_3$OD): δ1.28 (t, 3H), 2.60 (s, 3H), 2.74 (q, 2H), 7.34 (m, 2H), 7.43 (m, 3H), 7.87 (m, 2H), 8.03 (m, 3H), 8.38 (d, 1H).

EXAMPLE 37

5-[4-(5-tert-Butyl-[1,3,4]oxadiazol-2-yl)-phenylsulfamoyl]-2-methyl-benzoic acid

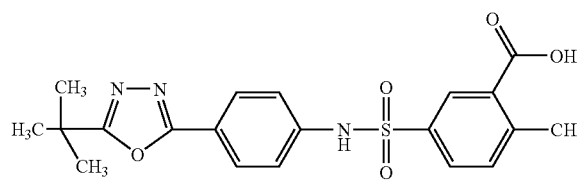

51% yield. MS: 416.7 (M+1); $^1$H NMR (400 MHz, CD$_3$OD): δ1.46 (s, 9H), 2.60 (s, 3H), 7.30 (m, 2H), 7.42 (d, 1H), 7.84 (m, 1H), 7.89 (m, 2H), 8.35 (d, 1H).

EXAMPLE 38

2-Methyl-5-{4-[5-(4-trifluoromethoxy-phenyl)-[1,3,4]oxadiazol-2-yl]-phenylsulfamoyl}-benzoic acid

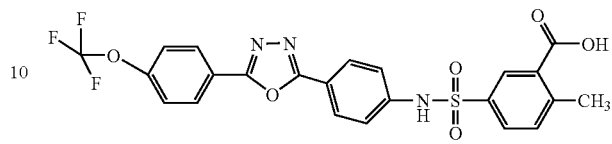

6% yield. MS: 518.0 (M+1); $^1$H NMR (400 MHz, CD$_3$OD): δ2.47 (s, 3H), 7.2–7.34 (m, 4H), 7.50 (d, 1H), 7.67 (m, 1H), 7.92–8.04 (m, 4H), 8.22 (d, 1H).

EXAMPLE 39

2-Methyl-5-[4-(5-trifluoromethyl-pyridin-2-ylcarbamoyl)-phenylsulfamoyl]-benzoic acid methyl ester

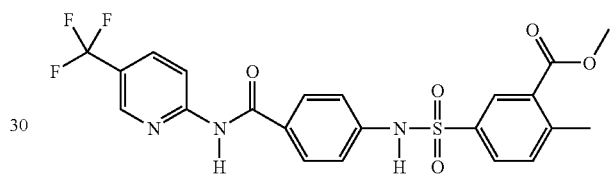

60% yield. MS: 492.0 (M−1)

EXAMPLE 40

5-[4-(5-Cyclohexyl-[1,3,4]oxadiazol-2-yl)-phenylsulfamoyl]-2-methyl-benzoic acid methyl ester

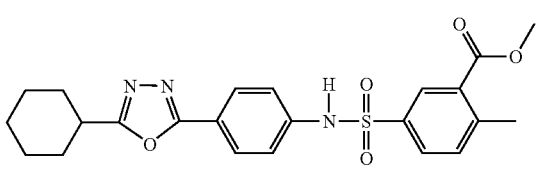

32% yield. MS: 454.1 (M−1)

The title compounds of EXAMPLES 41–82 were prepared using procedures analogous to that of EXAMPLE 1 from appropriate starting materials.

| Ex. | Chemical Structure | Chemical Name | Data |
|---|---|---|---|
| 41 | 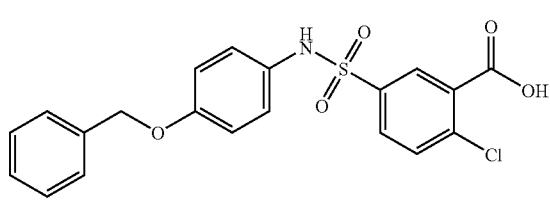 | 5-(4-Benzyloxy-phenylsulfamoyl)-2-chloro-benzoic acid | 29% yield. MS: 416.2 (M − 1) |

-continued

| Ex. | Chemical Structure | Chemical Name | Data |
|---|---|---|---|
| 42 | 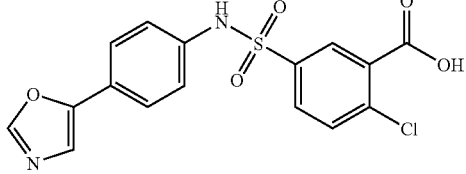 | 2-Chloro-5-(4-oxazol-5-yl-phenylsulfamoyl)-benzoic acid | 36% yield. MS: 379.2 (M + 1) |
| 43 | 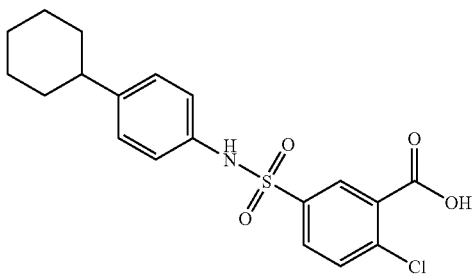 | 2-Chloro-5-(4-cyclohexyl-phenylsulfamoyl)-benzoic acid | 44% yield. MS: 392.0 (M − 1) |
| 44 | 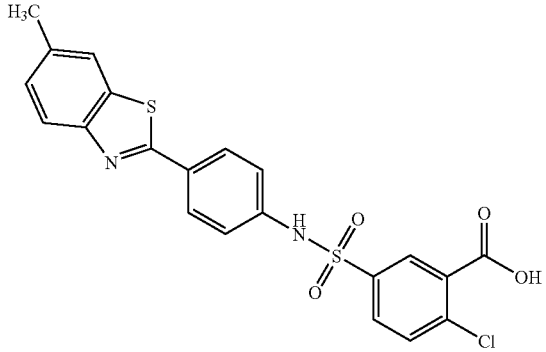 | 2-Chloro-5-[4-(6-methyl-benzothiazol-2-yl)-phenylsulfamoyl]-benzoic acid | 4% yield. MS: 459.2 (M + 1) |
| 45 | 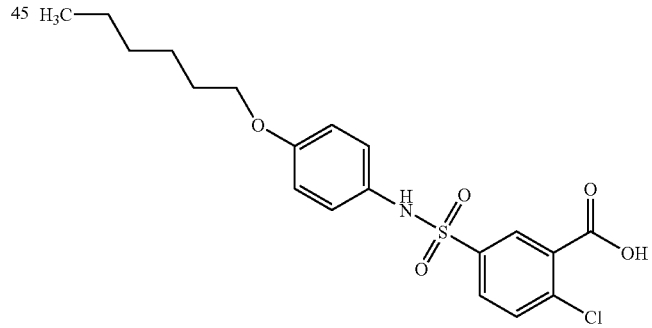 | 2-Chloro-5-(4-hexyloxy-phenylsulfamoyl)-benzoic acid | 46% yield. MS: 410.3 (M − 1) |
| 46 | 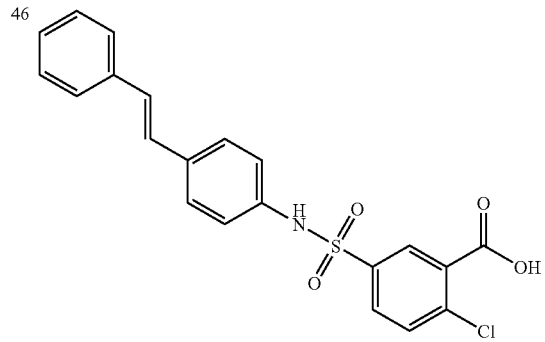 | 2-Chloro-5-(4-styryl-phenylsulfamoyl)-benzoic acid | 29% yield. MS: 411.9 (M − 1) |

| Ex. | Chemical Structure | Chemical Name | Data |
| --- | --- | --- | --- |
| 47 | 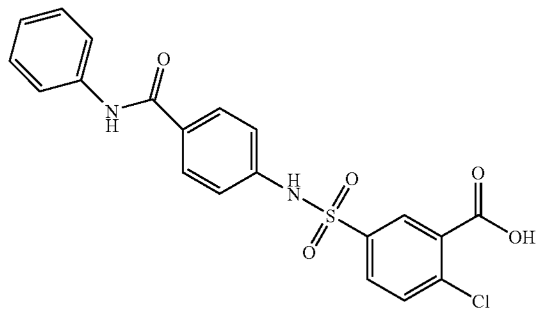 | 2-Chloro-5-(4-phenylcarbamoyl-phenylsulfamoyl)-benzoic acid | 41% yield. MS: 431.2 (M + 1) |
| 48 | 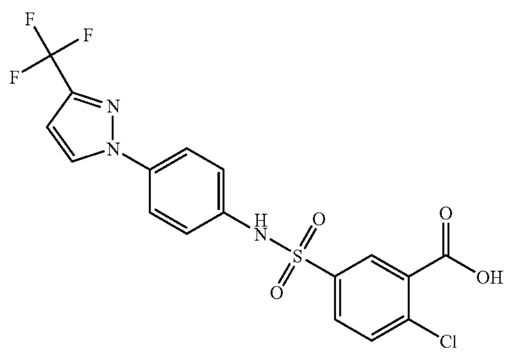 | 2-Chloro-5-[4-(3-trifluoromethyl-pyrazol-1-yl)-phenylsulfamoyl]-benzoicacid | 25% yield. MS: 446.2 (M + 1) |
| 49 | 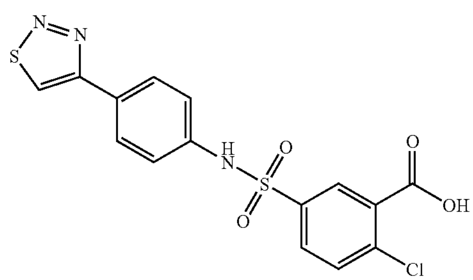 | 2-Chloro-5-(4-[1,2,3]thiadiazol-4-yl-phenylsulfamoyl)-benzoic acid | 17% yield. MS: 394.3 (M − 1) |
| 50 | 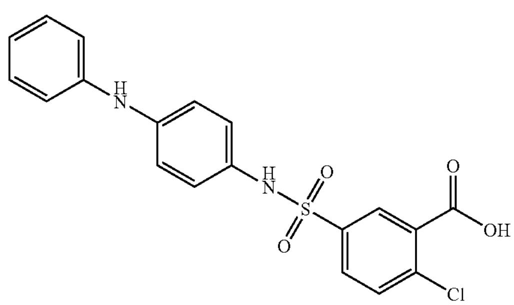 | 2-Chloro-5-(4-phenylamino-phenylsulfamoyl)-benzoic acid | 36% yield. MS: 403.1 (M + 1) |
| 51 | 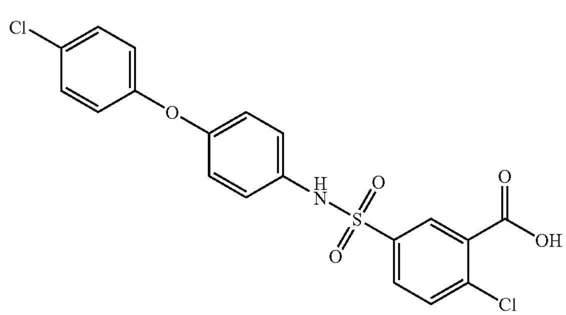 | 2-Chloro-5-[4-(4-chloro-phenoxy)-phenylsulfamoyl]-benzoic acid | 41% yield. MS: 436.0 (M − 1) |

| Ex. | Chemical Structure | Chemical Name | Data |
|---|---|---|---|
| 52 | 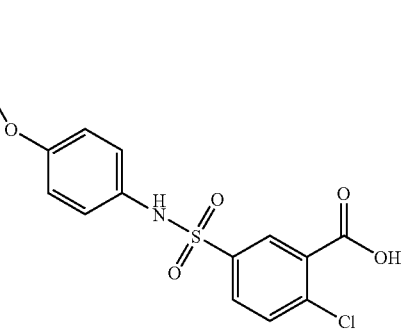 | 2-Chloro-5-(4-pentyloxy-phenylsulfamoyl)-benzoic acid | 51% yield. MS: 396.0 (M − 1) |
| 53 | 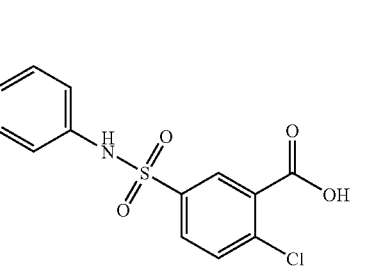 | 5-(4-Benzoyl-phenylsulfamoyl)-2-chloro-benzoic acid | 7% yield. MS: 416.1 (M + 1) |
| 54 | 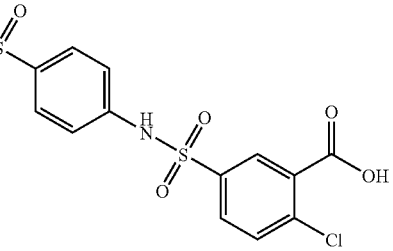 | 2-Chloro-5-(4-phenylsulfamoyl-phenylsulfamyoyl)-benzoic acid | 5% yield. MS: 465.0 (M − 1) |
| 55 | 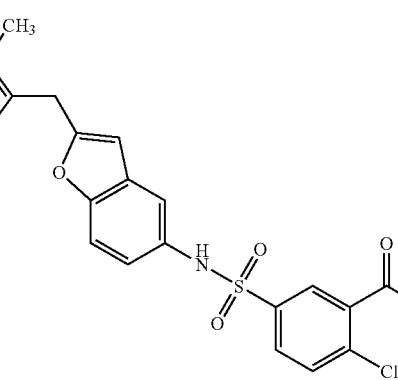 | 2-Chloro-5-[2-(5-methyl-2-phenyl-oxazol-4-ylmethyl)-benzofuran-5-ylsulfamoyl]-benzoic acid | 5% yield. MS: 524.3 (M + 1) |
| 56 | 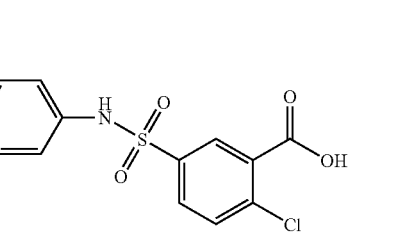 | 2-Chloro-5-(4-phenylsulfanyl-phenylsulfamoyl)-benzoic acid | 38% yield. MS: 418.0 (M − 1) |

| Ex. | Chemical Structure | Chemical Name | Data |
|---|---|---|---|
| 57 | 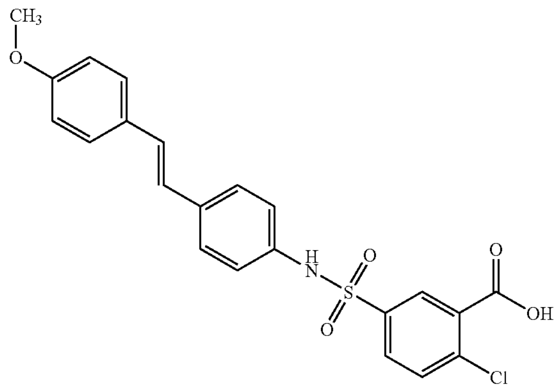 | 2-Chloro-5-{4-[2-(4-methoxy-phenyl)-vinyl]-phenylsulfamoyl}-benzoic acid | 13% yield. MS: 442.1 (M − 1) |
| 58 | 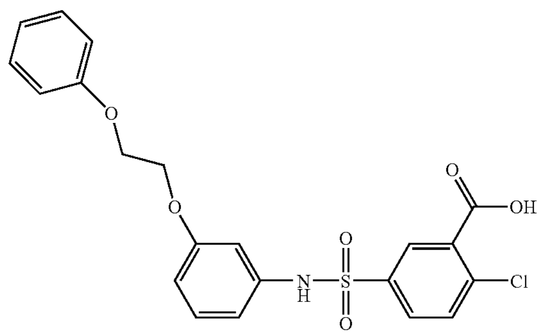 | 2-Chloro-5-[3-(2-phenoxy-ethoxy)-phenylsulfamoyl]-benzoic acid | 54% yield. MS: 446.1 (M − 1) |
| 59 | 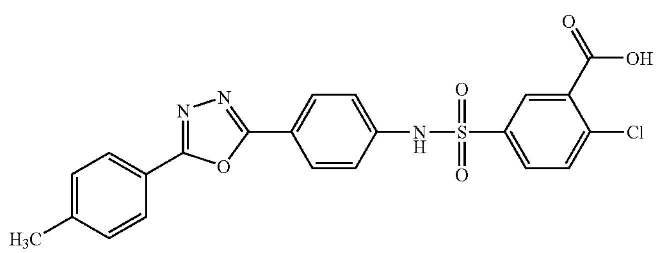 | 2-Chloro-5-[4-(5-p-tolyl-[1,3,4]oxadiazol-2-yl)-phenylsulfamoyl]-benzoic acid | 4% yield MS: 470.2 (M + 1) |
| 60 | 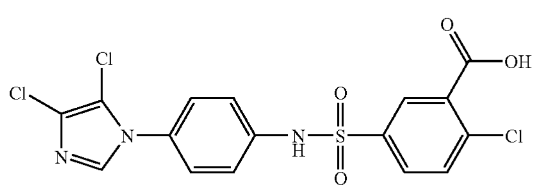 | 2-Chloro-5-[4-(4,5-dichloro-imidazol-1-yl)-phenylsulfamoyl]-benzoic acid | 31% yield MS: 448.0 (m + 1) |
| 61 | 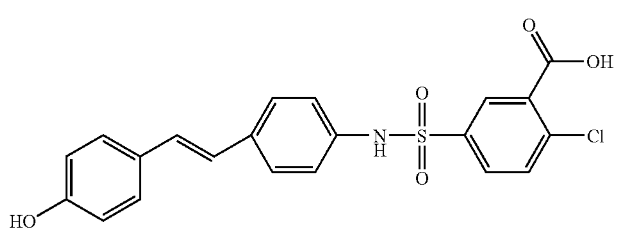 | 2-Chloro-5-{4-[2-(4-hydroxy-phenyl)-vinyl]-phenylsulfamoyl}-benzoic acid | 45% yield MS: 428.1 (M − 1) |
| 62 | 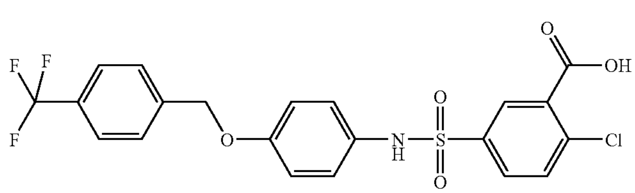 | 2-Chloro-5-[4-(4-trifluoromethyl-benzyloxy)-phenylsulfamoyl]-benzoic acid | 15% yield MS: 484.1 (M − 1) |

-continued

| Ex. | Chemical Structure | Chemical Name | Data |
|---|---|---|---|
| 63 | 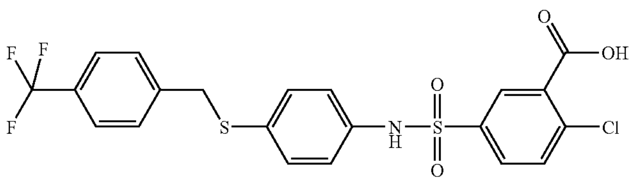 | 2-Chloro-5-[4-(4-trifluoromethyl-benzylsulfanyl)-phenylsulfamoyl]-benzoic acid | 35% yield MS: 500.1 (M − 1) |
| 64 | 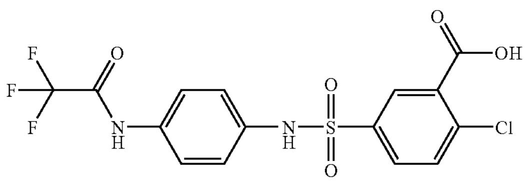 | 2-Chloro-5-[4-(2,2,2-trifluoro-acetylamino)-phenylsulfamoyl]-benzoic acid | 39% yield MS: 421.0 (M − 1) |
| 65 | 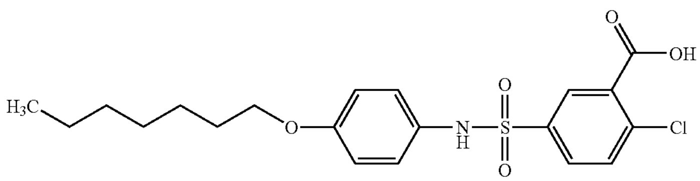 | 2-Chloro-5-(4-heptyloxy-phenylsulfamoyl)-benzoic acid | 50% yield MS: 423.6 (M − 1) |
| 66 | 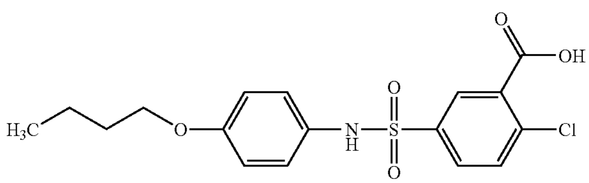 | 5-(4-Butoxy-phenylsulfamoyl)-2-chloro-benzoic acid | 47% yield. MS: 382.4 (M − 1) |
| 67 | 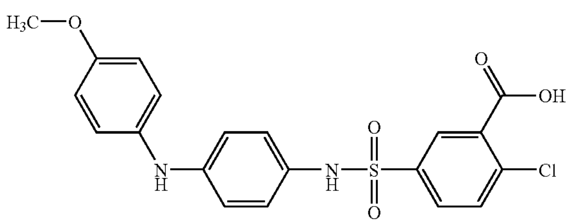 | 2-Chloro-5-[4-(4-methoxy-phenylamino)-phenylsulfamoyl]-benzoic acid | 43% yield MS: 433.0 (M + 1) |
| 68 | 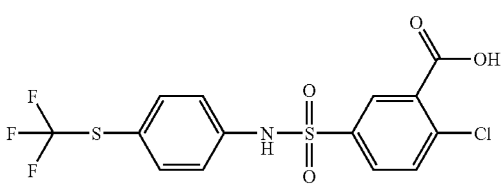 | 2-Chloro-5-(4-trifluoromethylsulfanyl-phenylsulfamoyl)-benzoic acid | 14% yield MS: 410.0 (M − 1) |
| 69 | 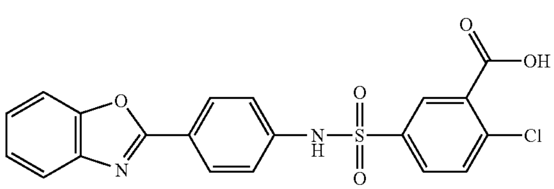 | 5-(4-Benzooxazol-2-yl-phenylsulfamoyl)-2-chloro-benzoic acid | 5% yield MS: 429.1 (M + 1) |
| 70 | 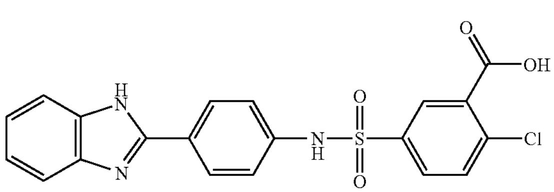 | 5-[4-(1H-Benzoimidazol-2-yl)-phenylsulfamoyl]-2-chloro-benzoic acid | 2% yield MS: 428.1 (M + 1) |

-continued

| Ex. | Chemical Structure | Chemical Name | Data |
|---|---|---|---|
| 71 | 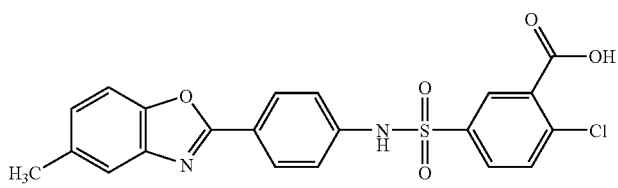 | 2-Chloro-5-[4-(5-methyl-benzooxazol-2-yl)-phenylsulfamoyl]-benzoic acid | 13% yield MS: 443.1 (M + 1) |
| 72 | 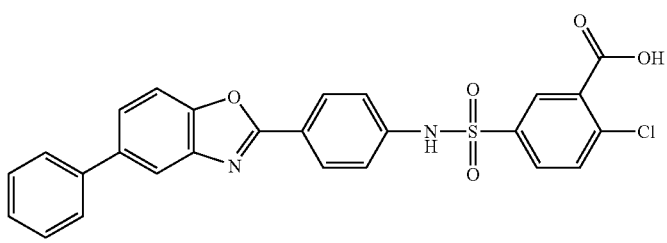 | 2-Chloro-5-[4-(5-phenyl-benzooxazol-2-yl)-phenylsulfamoyl]-benzoic acid | 14% yield MS: 505.0 (M + 1) |
| 73 | 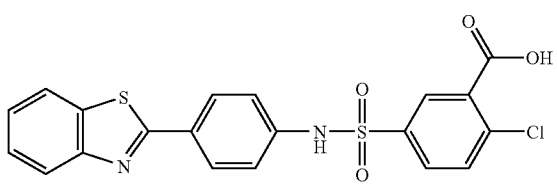 | 5-(4-Benzothiazol-2-yl-phenylsulfamoyl)-2-chloro-benzoic acid | 5% yield MS: 445.1 (M − 1) |
| 74 | 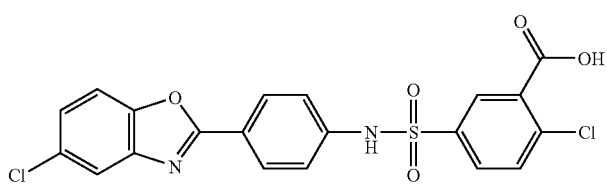 | 2-Chloro-5-[4-(5-chloro-benzooxazol-2-yl)-phenylsulfamoyl]-benzoic acid | 7% yield MS: 463.0 (M − 1) |
| 75 | 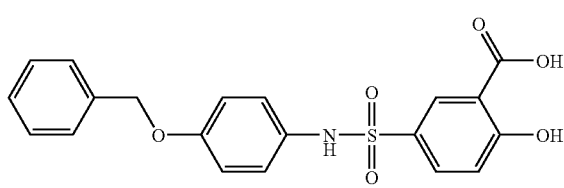 | 5-(4-Benzyloxy-phenylsulfamoyl)-2-hydroxy-benzoic acid | 58% yield MS: 398.3 (M − 1) |
| 76 | 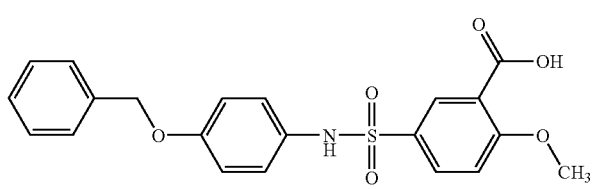 | 5-(4-Benzyloxy-phenylsulfamoyl)-2-methoxy-benzoic acid | 58% yield MS: 411.6 (M − 1) |
| 77 | 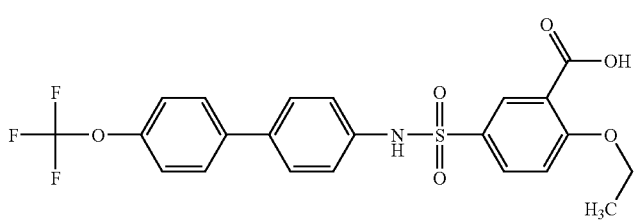 | 2-Ethoxy-5-(4'-trifluoromethoxy-biphenyl-4-ylsulfamoyl)-benzoic acid | 88% yield MS: 480.3 (M − 1) |

| Ex. | Chemical Structure | Chemical Name | Data |
|---|---|---|---|
| 78 | 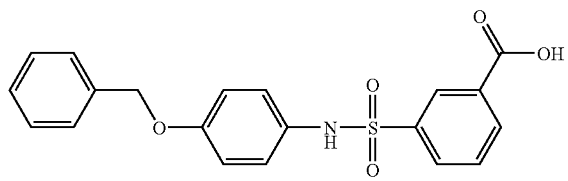 | 3-(4-Benzyloxy-phenylsulfamoyl)-benzoic acid | 60% yield<br>MS: 381.6<br>(M − 1) |
| 79 | 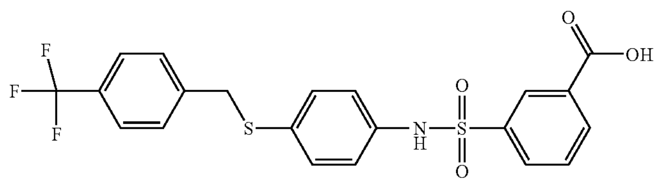 | 3-[4-(4-Trifluoromethyl-benzylsulfanyl)-phenylsulfamoyl]-benzoic acid | 49% yield<br>MS: 466.3<br>(M − 1) |
| 80 | 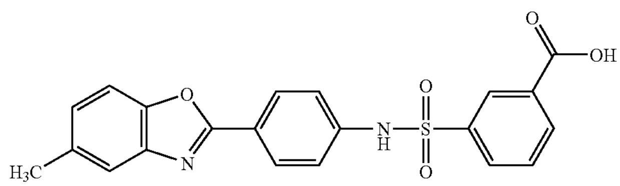 | 3-[4-(5-Methyl-benzooxazol-2-yl)-phenylsulfamoyl]-benzoic acid | 12% yield<br>MS: 409.0<br>(M + 1) |
| 81 | 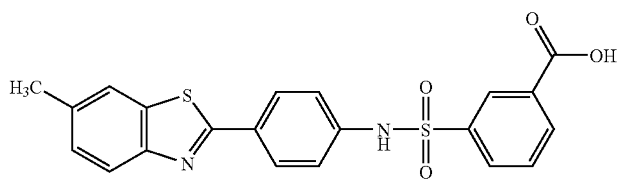 | 3-[4-(6-Methyl-benzothiazol-2-yl)-phenylsulfamoyl]-benzoic acid | 17% yield<br>MS: 425.1<br>(M + 1) |
| 82 | 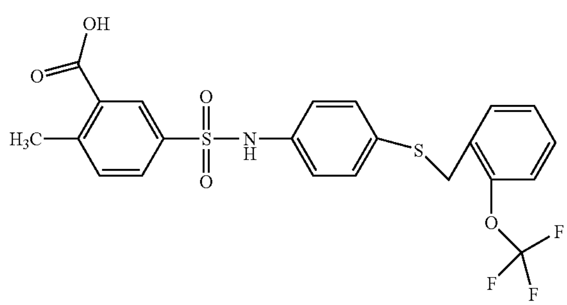 | 2-Methyl-5-[4-(2-trifluoromethoxy-benzylsulfanyl)-phenylsulfamoyl]-benzoic acid | 27% yield.<br>MS: 498.3<br>(M + 1) |

EXAMPLE 83

2-Methyl-5-[4-(4-trifluoromethyl-benzylsulfanyl)-phenylsulfamoyl]-benzoic acid methyl ester

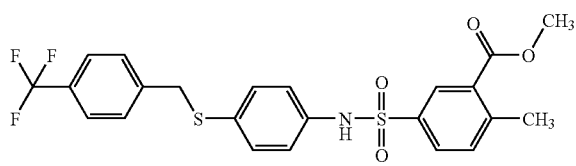

A solution of sodium bicarbonate (667 mg, 7.94 mmol) in 4.5 ml water was added to a solution of 4-(4-trifluoromethyl-benzylsulfanyl)-phenylamine (750 mg, 2.65 mmol) and 5-chlorosulfonyl-2-methyl-benzoic acid methyl ester (855 mg, 3.44 mmol) in 14 ml acetone and the resulting mixture was stirred at room temperature overnight. The reaction mixture was then diluted with 60 ml chloroform and washed sequentially with 1N aqueous hydrochloric acid solution (2×50 ml), water (50 ml) and brine (40 ml). The chloroform solution was dried (anhydrous sodium sulfate) and concentrated under reduced pressure to a brownish oil (1.59 g). The crude product was purified by flash column chromatography (silica gel, 40 g), eluting with 8:2 hexane/ethyl acetate to yield a yellowish oil (1.3 g). Trituration of the oil in 5 ml of a mixture of 98:2 hexane/diethyl ether and filtration of the resulting solid yielded the title compound as a white solid (1.13 g, 86% yield). MS: 480.2 (M−1)

The title compounds of EXAMPLES 84–153 were prepared using procedures analogous to that of EXAMPLE 83 from appropriate starting materials and are shown in the table that follows.

| Ex. | Chemical Structure | Chemical Name | Data |
|---|---|---|---|
| 84 | 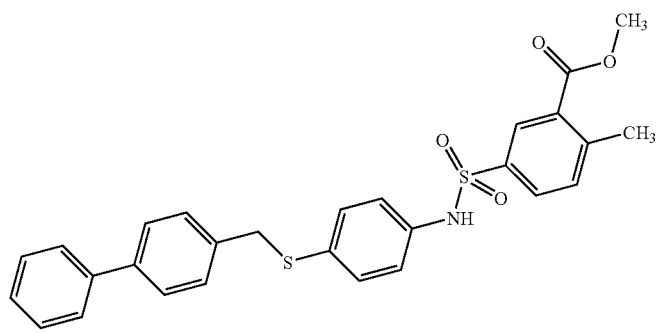 | 5-[4-(Biphenyl-4-ylmethylsulfanyl)-phenylsulfamoyl]-2-methyl-benzoic acid methyl ester | 18% yield. MS: 502.2 (M − 1) |
| 85 | 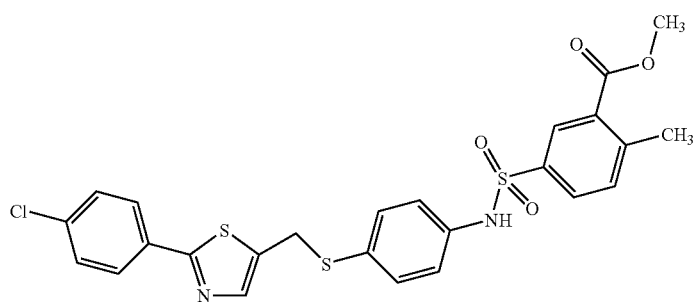 | 5-{4-[2-(4-Chloro-phenyl)-thiazol-5-ylmethylsulfanyl]-phenylsulfamoyl}-2-methyl-benzoic acid methyl ester | 8% yield. MS: 545.1 (M − 1) |
| 86 | 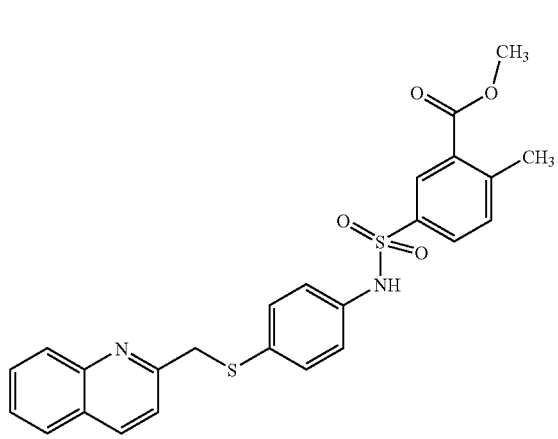 | 2-Methyl-5-[4-(quinolin-2-ylmethylsulfanyl)-phenylsulfamoyl]-benzoic acid methyl ester | 10% yield. MS: 479.2 (M + 1) |
| 87 | 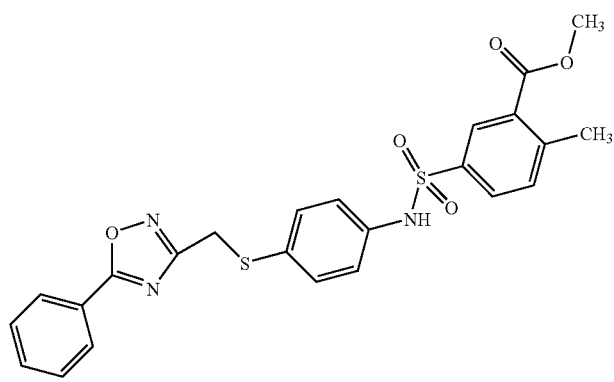 | 2-Methyl-5-[4-(5-phenyl-[1,2,4]oxadiazol-3-ylmethylsulfanyl)-phenylsulfamoyl]-benzoic acid methyl ester | 55% yield. MS: 496.2 (M + 1) |

-continued

| Ex. | Chemical Structure | Chemical Name | Data |
|---|---|---|---|
| 88 | 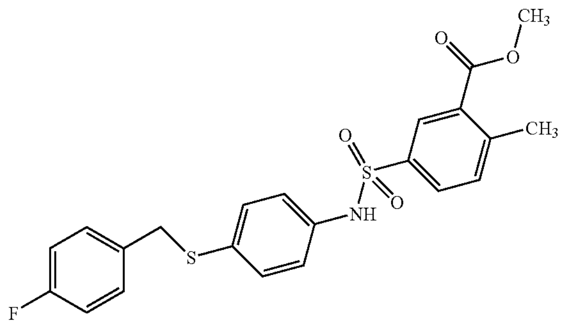 | 5-[4-(4-Fluoro-benzylsulfanyl)-phenylsulfamoyl]-2-methyl-benzoic acid methyl ester | 67% yield. MS: 446.2 (M + 1) |
| 89 | 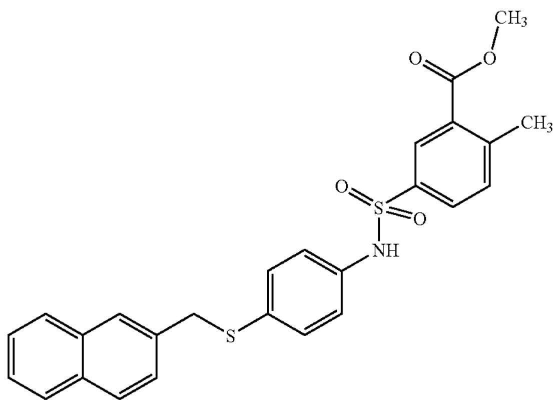 | 2-Methyl-5-[4-(naphthalen-2-ylmethylsulfanyl)-phenylsulfamoyl]-benzoic acid methyl ester | 49% yield. MS: 478.2 (M + 1) |
| 90 | 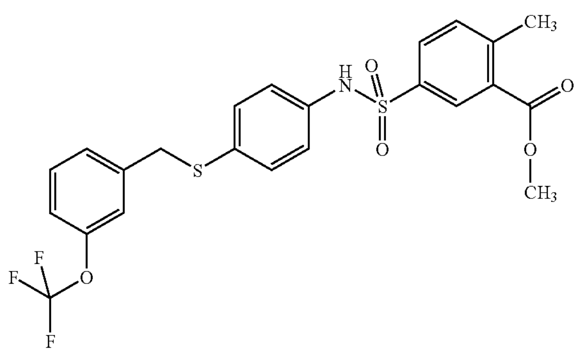 | 2-Methyl-5-[4-(3-trifluoromethoxy-benzylsulfanyl-phenylsulamoyl]-benzoic acid methyl ester | 76% yield. MS: 511.9 (M + 1) |
| 91 | 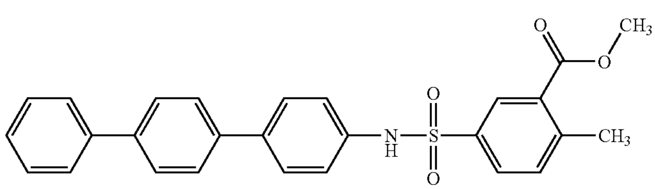 | 2-Methyl-5-([1,1';4',1'']terphenyl-4-ylsulfamoyl)-benzoic acid methyl ester | 70% yield. MS: 458.3 (M + 1) |
| 92 | 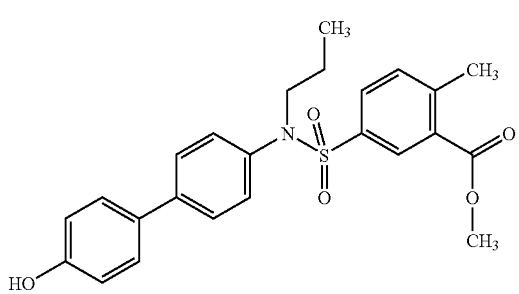 | 5-[(4'-Hydroxy-biphenyl-4-yl)-propyl-sulfamoyl]-2-methyl-benzoic acid methyl ester | 60% yield. MS: 440.2 (M + 1) |

-continued

| Ex. | Chemical Structure | Chemical Name | Data |
|---|---|---|---|
| 93 | 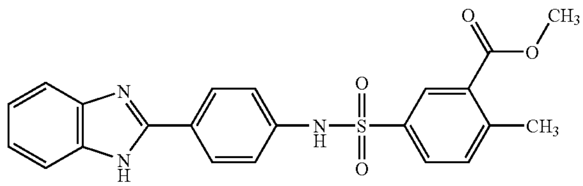 | 5-[4-(1H-Benzoimidazol-2-yl)-phenylsulfamoyl]-2-methyl-benzoic acid methyl ester | 41% yield. MS: 420.0 (M − 1) |
| 94 | 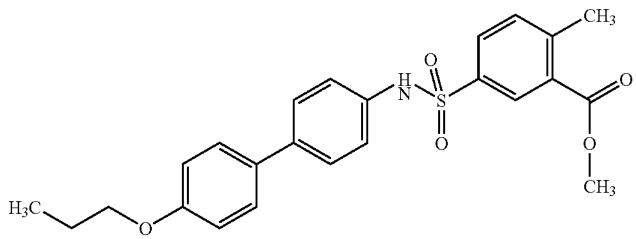 | 2-Methyl-5-(4'-propoxy-biphenyl-4-ylsulfamoyl)-benzoic acid methyl ester | 80% yield. MS: 438.3 (M − 1) |
| 95 | 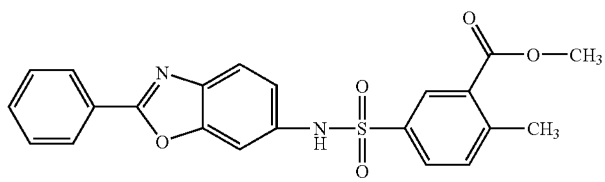 | 2-Methyl-5-(2-phenyl-benzooxazol-6-ylsulfamoyl)-benzoic acid methyl ester | 64% yield. MS: 423.3 (M + 1) |
| 96 | 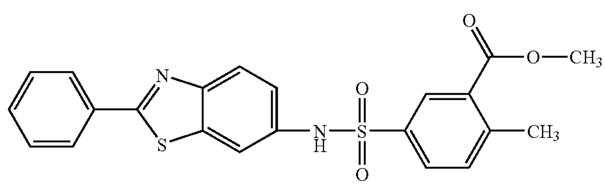 | 2-Methyl-5-(2-phenyl-benzothiazol-6-ylsulfamoyl)-benzoic acid methyl ester | 49% yield. MS: 439.3 (M + 1) |
| 97 | 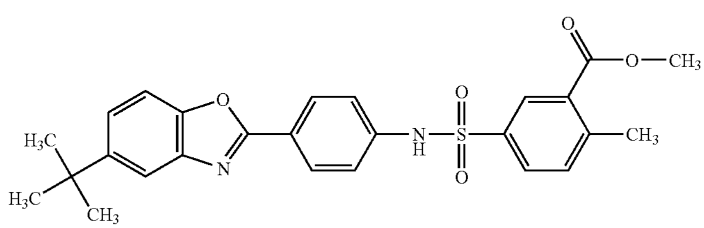 | 5-[4-(5-tert-Butyl-benzooxazol-2-yl)-phenylsulfamoyl]-2-methyl-benzoic acid methyl ester | 50% yield. MS: 479.5 (M + 1) |
| 98 | 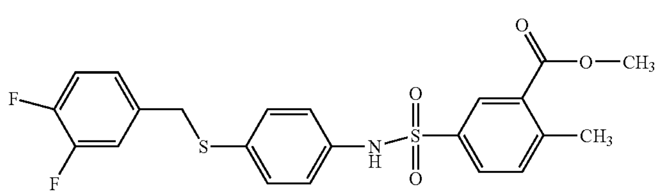 | 5-[4-(3,4-Difluoro-benzylsulfanyl)-phenylsulfamoyl]-2-methyl-benzoic acid methyl ester | 83% yield. MS: 462.2 (M − 1) |
| 99 | 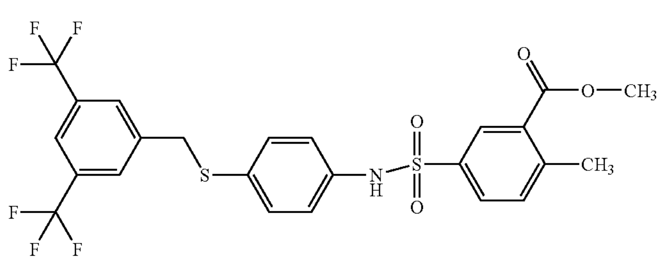 | 5-[4-(3,5-Bis-trifluoromethyl-benzylsulfanyl)-phenylsulfamoyl]-2-methyl-benzoic acid methyl ester | 85% yield. MS: 562.2 (M − 1) |

-continued

| Ex. | Chemical Structure | Chemical Name | Data |
|---|---|---|---|
| 100 | 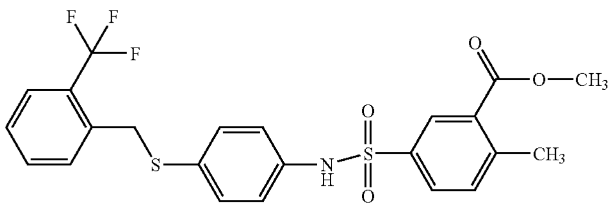 | 2-Methyl-5-[4-(2-trifluoromethyl-benzylsulfanyl)-phenylsulfamoyl]-benzoic acid methyl ester | 74% yield. MS: 494.2 (M − 1) |
| 101 | 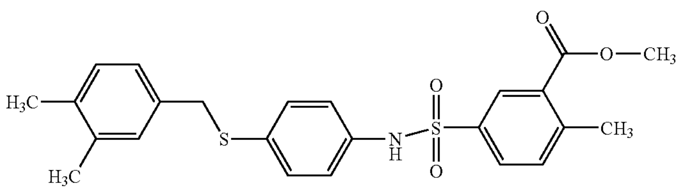 | 5-[4-(3,4-Dimethyl-benzylsulfanyl)-phenylsulfamoyl]-2-methyl-benzoic acid methyl ester | 92% yield. MS: 454.3 (M − 1) |
| 102 | 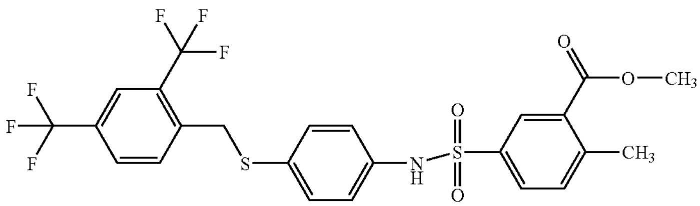 | 5-[4-(2,4-Bis-trifluoromethyl-benzylsulfanyl)-phenylsulfamoyl]-2-methyl-benzoic acid methyl ester | 88% yield. MS: 561.8 (M − 1) |
| 103 | 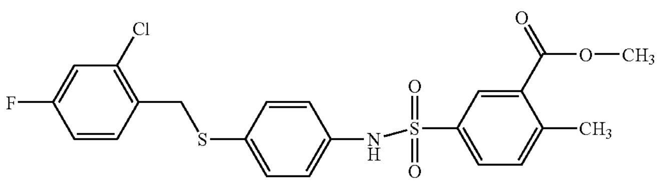 | 5-[4-(2-Chloro-4-fluoro-benzylsulfanyl)-phenylsulfamoyl]-2-methyl-benzoic acid methyl ester | 93% yield. MS: 477.9 (M − 1) |
| 104 | 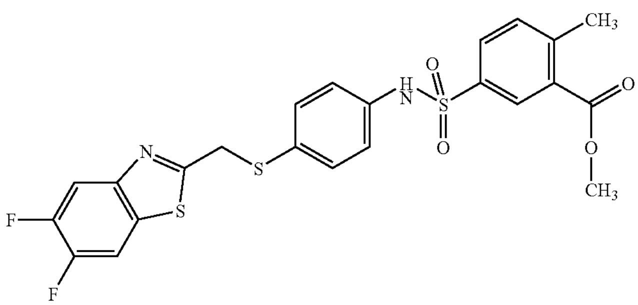 | 5-[4-(5,6-Difluoro-benzothiazol-2-ylmethylsulfanyl)-phenylsulfamoyl]-2-methyl-benzoic acid methyl ester | 65% yield MS: 522.1 (M + 1) |
| 105 | 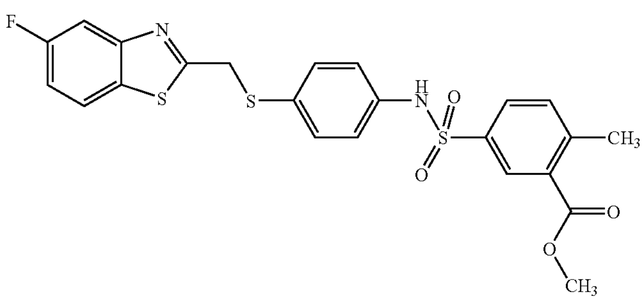 | 5-[4-(5-Fluoro-benzothiazol-2-ylmethylsulfanyl)-phenylsulfamoyl]-2-methyl-benzoic acid methyl ester | 65% yield. MS: 503.0 (M + 1) |
| 106 | 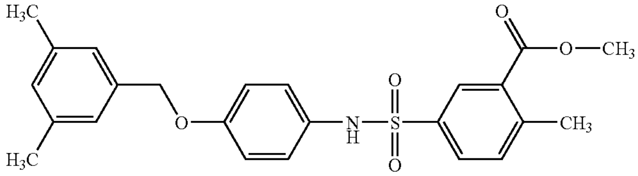 | 5-[4-(3,5-Dimethyl-benzyloxy)-phenylsulfamoyl]-2-methyl-benzoic acid methyl ester | 93% yield. MS: 438.0 (M − 1) |

-continued

| Ex. | Chemical Structure | Chemical Name | Data |
|---|---|---|---|
| 107 | 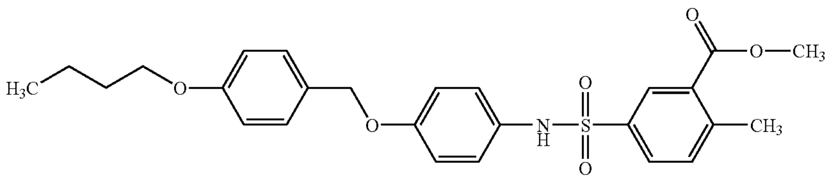 | 5-[4-(4-Butoxy-benzyloxy)-phenylsulfamoyl]-2-methyl-benzoic acid methyl ester | 61% yield. MS: 482.1 (M − 1) |
| 108 | 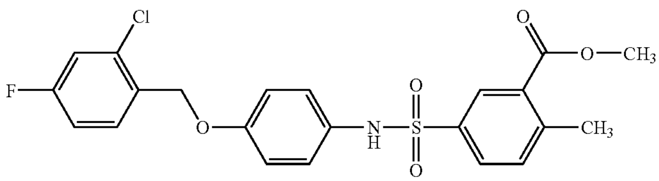 | 5-[4-(2-Chloro-4-fluoro-benzyloxy)-phenylsulfamoyl]-2-methyl-benzoic acid methyl ester | 93% yield. MS: 462.0 (M − 1) |
| 109 | 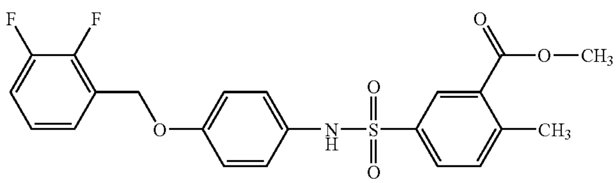 | 5-[4-(2,3-Difluoro-benzyloxy)-phenylsulfamoyl]-2-methyl-benzoic acid methyl ester | 67% yield. MS: 445.9 (M − 1) |
| 110 | 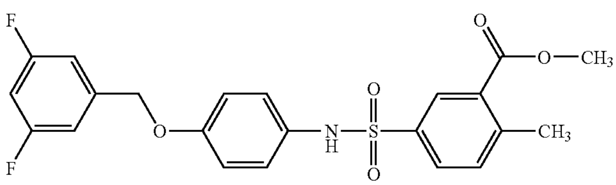 | 5-[4-(3,5-Difluoro-benzyloxy)-phenylsulfamoyl]-2-methyl-benzoic acid methyl ester | 91% yield. MS: 446.1 (M − 1) |
| 111 | 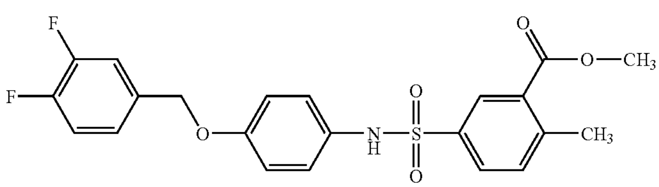 | 5-[4-(3,4-Difluoro-benzyloxy)-phenylsulfamoyl]-2-methyl-benzoic acid methyl ester | 77% yield. MS: 446.2 (M − 1) |
| 112 | 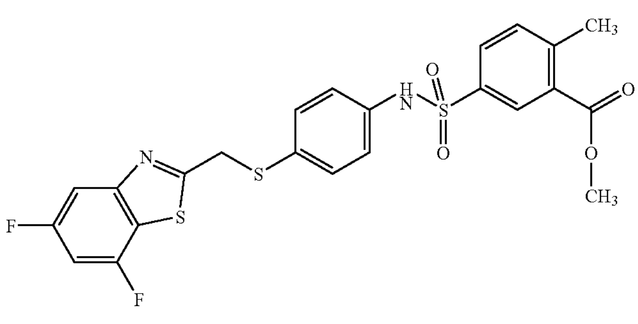 | 5-[4-(5,7-Difluoro-benzothiazol-2-ylmethylsulfanyl)-phenylsulfamoyl]-2-methyl-benzoic acid methyl ester | 59% yield. MS: 521.0 (M + 1) |
| 113 | 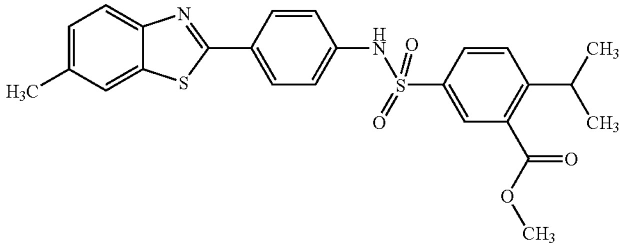 | 2-Isopropyl-5-[4-(6-methyl-benzothiazol-2-yl)-phenylsulfamoyl]-benzoic acid methyl ester | 48% yield. MS: 481.1 (M + 1) |

-continued

| Ex. | Chemical Structure | Chemical Name | Data |
|---|---|---|---|
| 114 | 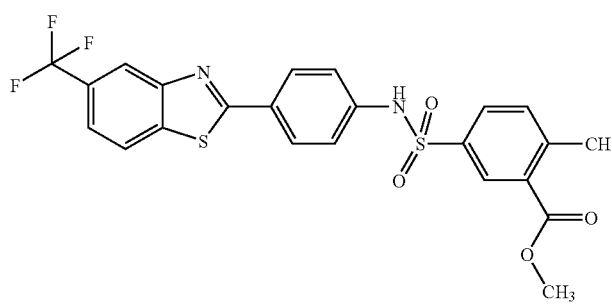 | 2-Methyl-5-[4-(5-trifluoromethyl-benzothiazol-2-ylmethylsulfanyl)-phenylsulfamoyl]-benzoic acid methyl ester | 27% yield. MS: 553.0 (M + 1) |
| 115 | 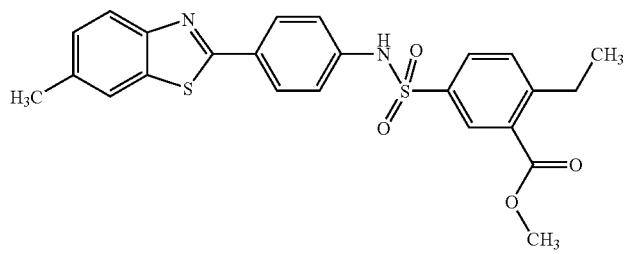 | 2-Ethyl-5-[4-(6-methyl-benzothiazol-2-yl)-phenylsulfamoyl]-benzoic acid methyl ester | 70%.yield. MS: 467.1 (M + 1) |
| 116 | 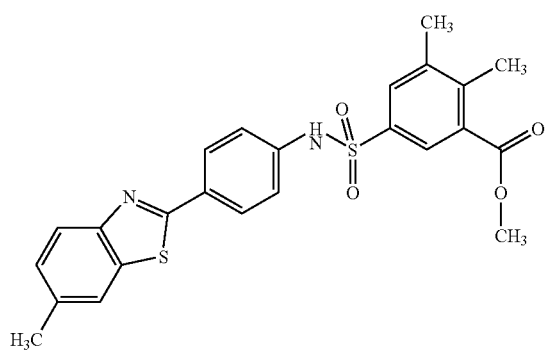 | 2,3-Dimethyl-5-[4-(6-methyl-benzothiazol-2-yl)-phenylsulfamoyl]-benzoic acid methyl ester | 64% yield. MS: 467.1 (M + 1) |
| 117 | 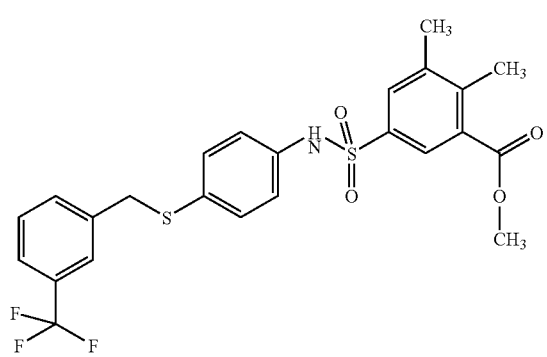 | 2,3-Dimethyl-5-[4-(3-trifluoromethyl-benzylsulfanyl)-phenylsulfamoyl]-benzoic acid methyl ester | 60% yield. MS: 510.1 (M + 1) |
| 118 | 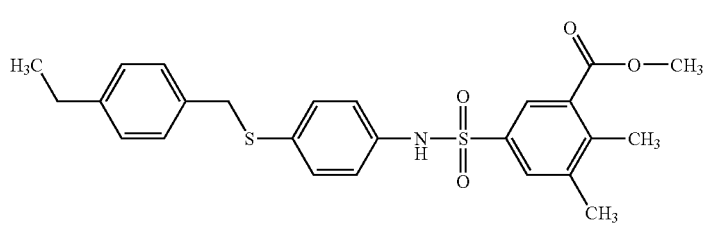 | 5-[4-(4-Ethyl-benzylsulfanyl)-phenylsulfamoyl]-2,3-dimethyl-benzoic acid methyl ester | 60% yield. MS: 470.1 (M + 1) |

| Ex. | Chemical Structure | Chemical Name | Data |
|---|---|---|---|
| 119 | 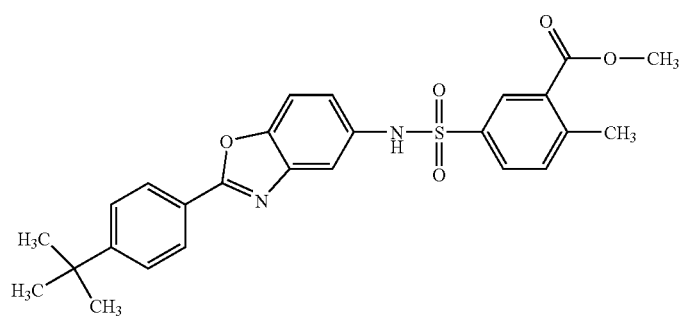 | 5-[2-(4-tert-Butyl-phenyl)-benzooxazol-5-ylsulfamoyl]-2-methyl-benzoic acid methyl ester | 77% yield. MS: 479.1 (M + 1) |
| 120 | 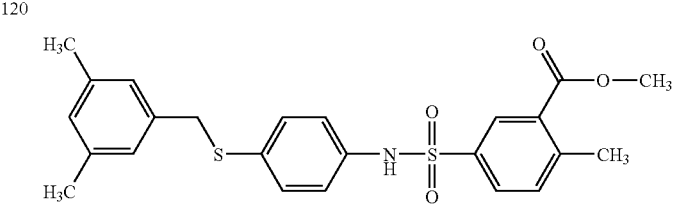 | 5-[4-(3,5-Dimethyl-benzylsulfanyl)-phenylsulfamoyl]-2-methyl-benzoic acid methyl ester | 97% yield. MS: 454.2 (MS − 1) |
| 121 | 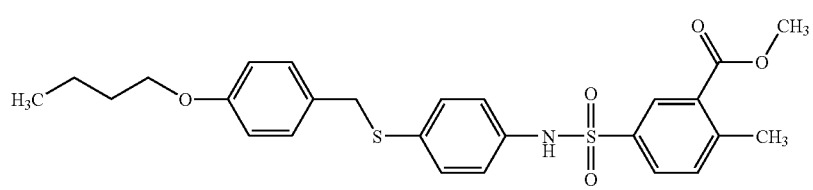 | 5-[4-(4-Butoxy-benzylsulfanyl)-phenylsulfamoyl]-2-methyl-benzoic acid methyl ester | 78% yield. MS: 498.2 (M − 1) |
| 122 | 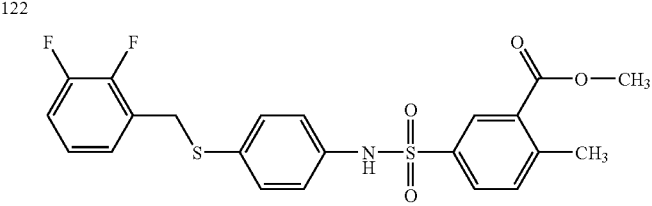 | 5-[4-(2,3-Difluoro-benzylsulfanyl)-phenylsulfamoyl]-2-methyl-benzoic acid methyl ester | 79% yield. MS: 463.8 (M + 1) |
| 123 | 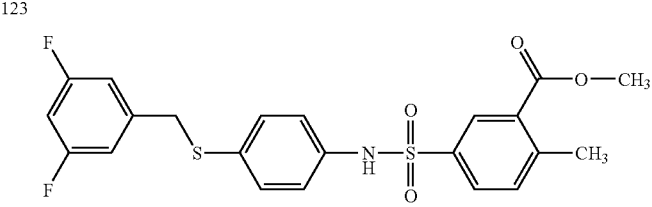 | 5-[4-(3,5-Difluoro-benzylsulfanyl)-phenylsulfamoyl]-2-methyl-benzoic acid methyl ester | 81% yield. MS: 462.2 (M − 1) |
| 124 | 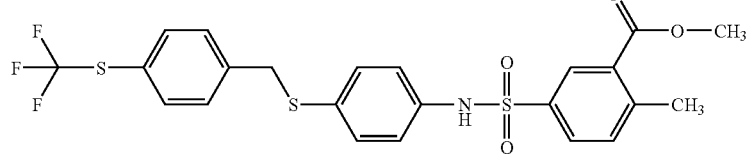 | 2-Methyl-5-[4-(4-trifluoromethyl-sulfanyl-benzylsulfanyl)-phenylsulfamoyl]-benzoic acid methyl ester | 98% yield. MS: 528.3 (M + 1) |

-continued

| Ex. | Chemical Structure | Chemical Name | Data |
|---|---|---|---|
| 125 | 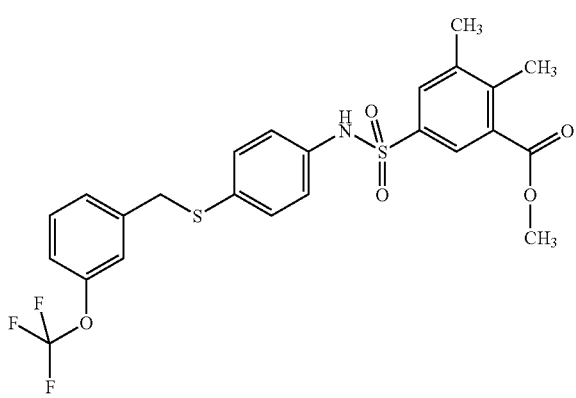 | 2,3-Dimethyl-5-[4-(3-trifluoromethoxy-benzylsulfanyl)-phenylsulfamoyl]-benzoic acid methyl ester | 48% yield. MS: 526.0 (M + 1) |
| 126 | 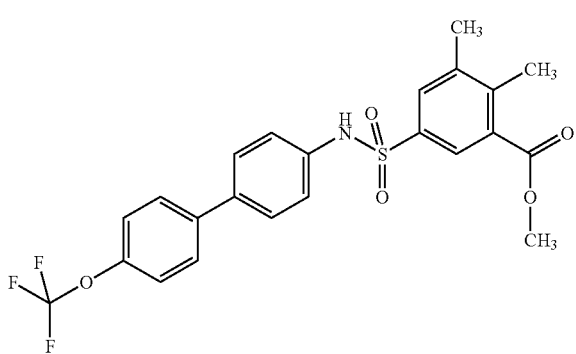 | 2,3-Dimethyl-5-(4'-trifluoromethoxy-biphenyl-4-ylsulfamoyl)-benzoic acid methyl ester | 74% yield. MS: 480.0 (M + 1) |
| 127 | 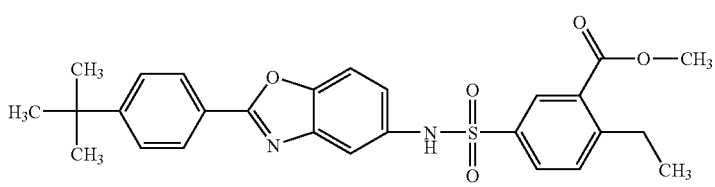 | 5-[2-(4-tert-Butyl-phenyl)-benzooxazol-5-ylsulfamoyl]-2-ethyl-benzoic acid methyl ester | 67% yield. MS: 493.4 (M + 1) |
| 128 | 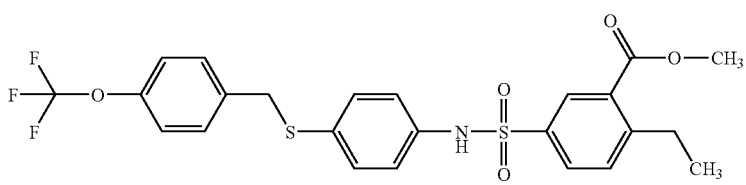 | 2-Ethyl-5-[4-(4-trifluoromethoxy-benzylsulfanyl)-phenylsulfamoyl]-benzoic acid methyl ester | 56% yield. MS: 524.2 (M − 1) |
| 129 | 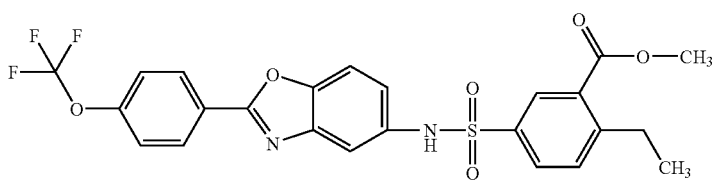 | 2-Ethyl-5-[2-(4-trifluoromethoxy-phenyl)-benzooxazol-5-ylsulfamoyl]-benzoic acid methyl ester | 40% yield. MS: 521.3 (M + 1) |

-continued

| Ex. | Chemical Structure | Chemical Name | Data |
|---|---|---|---|
| 130 | 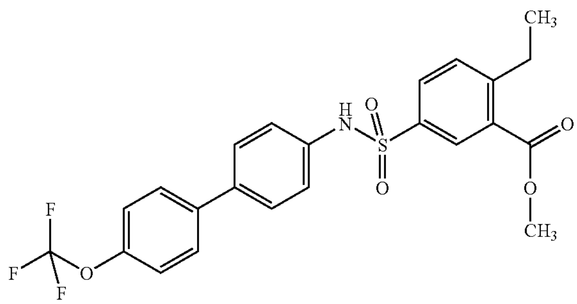 | 2-Ethyl-5-(4'-trifluoromethoxy-biphenyl-4-ylsulfamoyl)-benzoic acid methyl ester | 21% yield. MS: 480.0 (M + 1) |
| 131 | 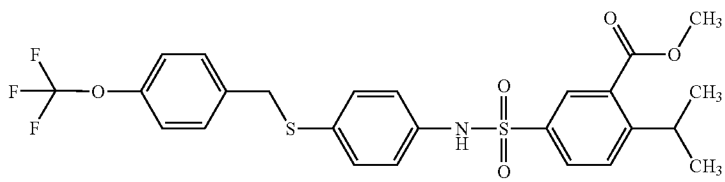 | 2-Isopropyl-5-[4-(4-trifluoromethoxy-benzylsulfanyl)-phenylsulfamoyl]-benzoic acid methyl ester | 62% yield. MS: 538.2 (M − 1) |
| 132 | 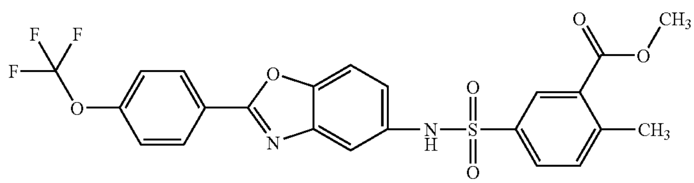 | 2-Methyl-5-[2-(4-trifluoromethoxy-phenyl)-benzooxazol-5-ylsulfamoyl]-benzoic acid methyl ester | 63% yield. MS: 507.2 (M + 1) |
| 133 | 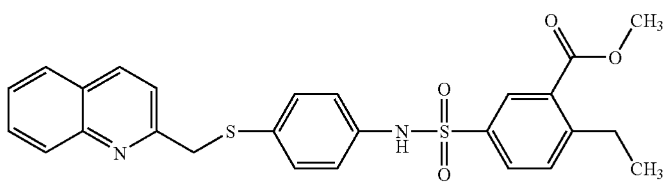 | 2-Ethyl-5-[4-(quinolin-2-ylmethylsulfanyl)-phenylsulfamoyl]-benzoic acid methyl ester | 35% yield. MS: 493.3 (M + 1) |
| 134 | 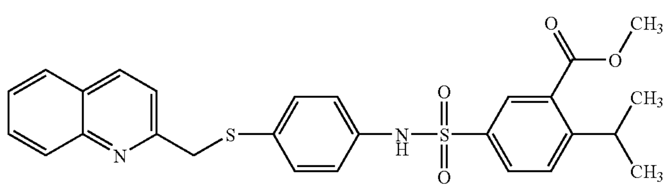 | 2-Isopropyl-5-[4-(quinolin-2-ylmethylsulfanyl)-phenylsulfamoyl]-benzoic acid methyl ester | 55% yield. MS: 507.1 (M + 1) |
| 135 | 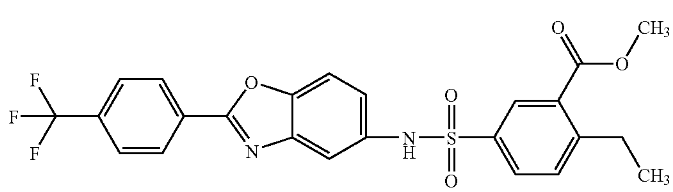 | 2-Ethyl-5-[2-(4-trifluoromethyl-phenyl)-benzooxazol-5-ylsulfamoyl]-benzoic acid methyl ester | 52% yield. MS: 505.3 (M + 1) |
| 136 | 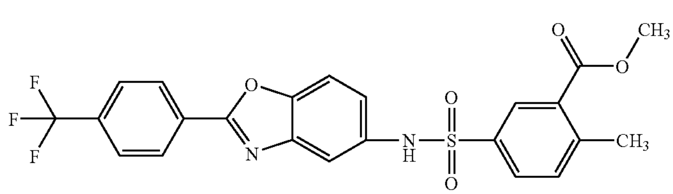 | 2-Methyl-5-[2-(4-trifluoromethyl-phenyl)-benzooxazol-5-ylsulfamoyl]-benzoic acid methyl ester | 93% yield. MS: 489.2 (M − 1) |

-continued

| Ex. | Chemical Structure | Chemical Name | Data |
|---|---|---|---|
| 137 | 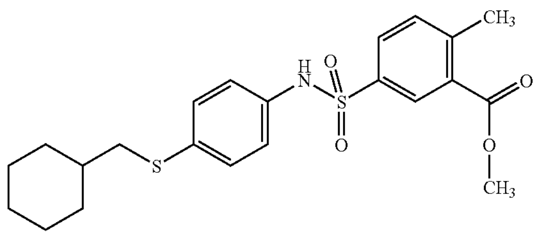 | 5-(4-Cyclohexylmethyl-sulfanyl-phenylsulfamoyl)-2-methyl-benzoic acid methyl ester | 79% yield. MS: 434.0 (M + 1) |
| 138 | 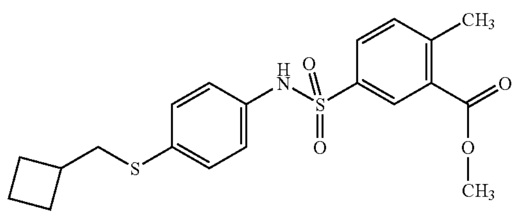 | 5(4-Cyclobutylmethyl-sulfanyl-phenylsulfamoyl)-2-methyl-benzoic acid methyl ester | 81% yield. MS: 406.1 (M + 1) |
| 139 | 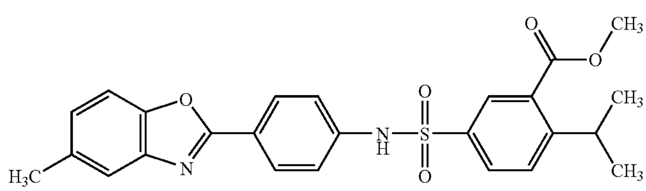 | 2-Isopropyl-5-[4-(5-methyl-benzooxazol-2-yl-phenylsulfamoyl]-benzoic acid methyl ester | 31% yield. MS: 465.4 (M + 1) |
| 140 | 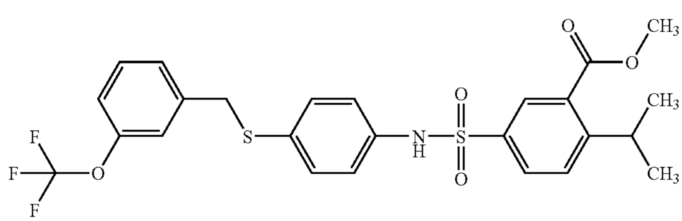 | 2-Isopropyl-5-[4-(3-trifluoromethoxy-benzylsulfanyl)-phenylsulfamoyl]-benzoic acid methyl ester | 46% yield. MS: 538.3 (M − 1) |
| 141 | 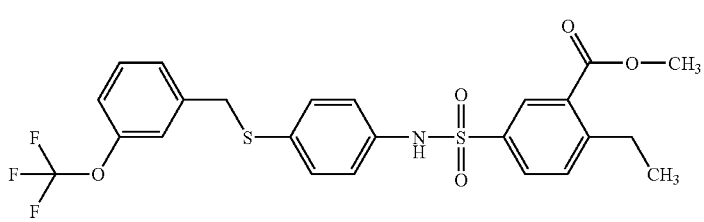 | 2-Ethyl-5-[4-(3-trifluoromethoxy-benzylsulfanyl)-phenylsulfamoyl]-benzoic acid methyl ester | 42% yield. MS: 524.3 (M − 1) |
| 142 | 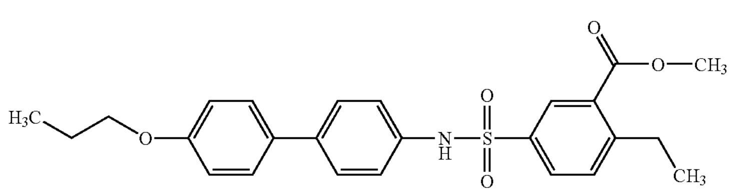 | 2-Ethyl-5-(4'-propoxy-biphenyl-4-ylsulfamoyl)-benzoic acid methyl ester | 46% yield. MS: 452.4 (M − 1) |
| 143 | 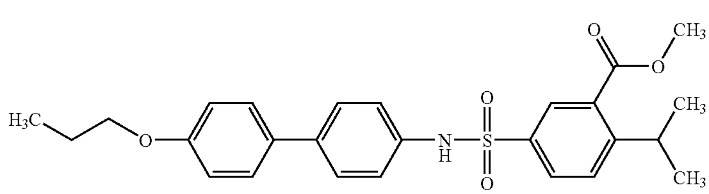 | 2-Isopropyl-5-(4'-propoxy-biphenyl-4-ylsulfamoyl)-benzoic acid methyl ester | 61% yield. MS: 466.4 (M − 1) |

| Ex. | Chemical Structure | Chemical Name | Data |
|---|---|---|---|
| 144 | 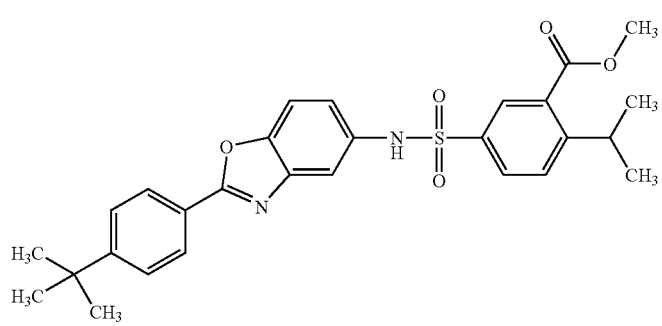 | 5-[2-(4-tert-Butyl-phenyl)-benzooxazol-5-ylsulfamoyl]-2-isopropyl-benzoic acid methyl ester | 72% yield. MS: 505.3 (M − 1) |
| 145 | 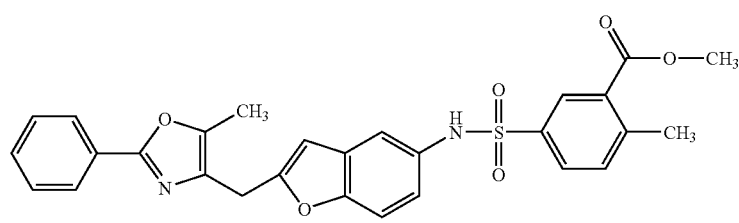 | 2-Methyl-5-[2-(5-methyl-2-phenyl-oxazol-4-ylmethyl)-benzofuran-5-ylsulfamoyl]-benzoic acid methyl ester | 98% yield. MS: 517.4 (M + 1) |
| 146 | 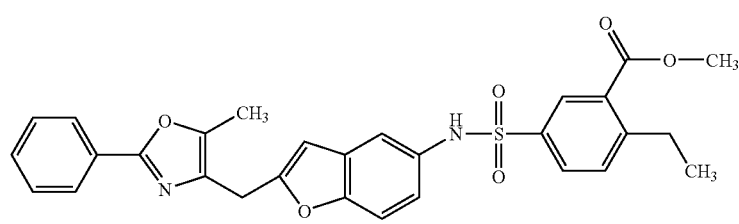 | 2-Ethyl-5-[2-(5-methyl-2-phenyl-oxazol-4-ylmethyl)-benzofuran-5-ylsulfamoyl]-benzoic acid methyl ester | 52% yield. MS: 531. (M + 1) |
| 147 | 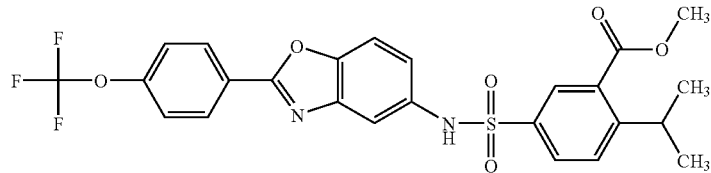 | 2-Isopropyl-5-[2-(4-trifluoromethoxy-phenyl)-benzooxazol-5-ylsulfamoyl]-benzoic acid methyl ester | 55% yield. MS: 535.3 (M + 1) |
| 148 | 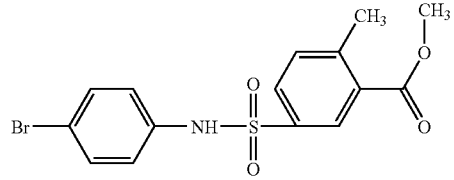 | 5-(4-Bromo-phenylsulfamoyl)-2-methyl-benzoic acid methyl ester | 79% yield. MS: 531.4 (M − 1) |

| Ex. | Chemical Structure | Chemical Name | Data |
|---|---|---|---|
| 149 | 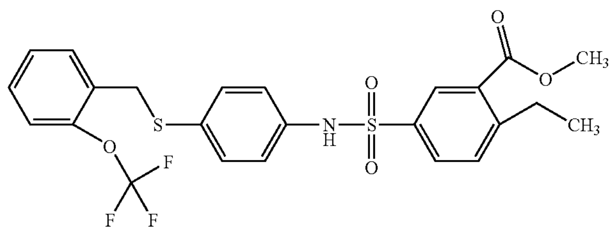 | 2-Ethyl-5-[4-(2-trifluoromethoxy-benzylsulfanyl)-phenylsulfamoyl]-benzoic acid methyl ester | 37% yield. MS 526.3 (M + 1) |
| 150 | 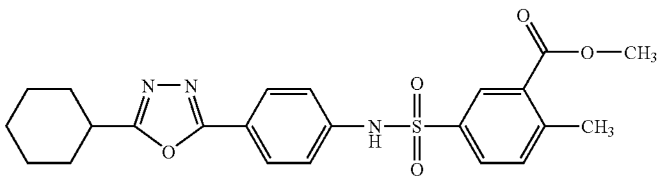 | 5-[4-(5-Cyclohexyl-[1,3,4]oxadiazol-2-yl)-phenylsulfamoyl]-2-methyl-benzoic acid methyl ester | 95% yield. MS: 456.1 (M + 1) |
| 151 | 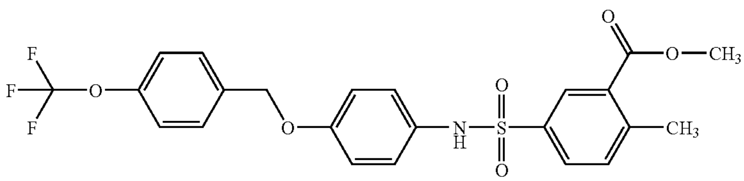 | 2-Methyl-5-[4-(4-trifluoromethoxy-benzyloxy)-phenylsulfamoyl]-benzoic acid methyl ester | 36% yield. MS: 494.9 (M − 1) |

EXAMPLE 152

2,3-Dimethyl-5-[4-(4-trifluoromethoxy-benzylsulfanyl)-phenylsulfamoyl]-benzoic acid methyl ester

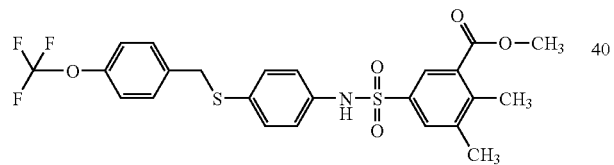

41% yield. $^1$H NMR (400 MHz, CD$_3$Cl): δ2.31 (s, 3H), 2.48 (s, 3H), 3.88 (s, 3H), 4.01 (s, 2H), 6.95 (d, 2H), 7.08 (d, 2H), 7.16 (d, 2H), 7.21 (d, 2H), 7.61 (s, 1H), 8.04 (s, 1H).

EXAMPLE 153

5-[4-(1H-Benzoimidazol-2-yl)-phenylsulfamoyl]-2-isopropyl-benzoic acid methyl ester

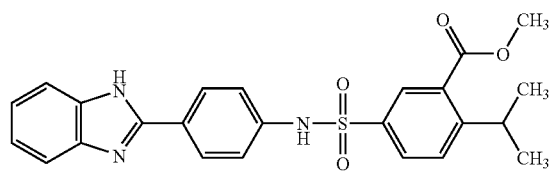

41% yield. $^1$H NMR (400 MHz, CD$_3$Cl): δ1.16 (d, 6H), 3.67 (m, 1H), 3.83 (s, 3H), 7.11 (d, 2H), 7.23 (c, 2H), 7.42 (d, 1H), 7.61 (c, 2H), 7.85 (c, 3H), 8.23 (d, 1H).

EXAMPLE 154

5-(4'-Butyl-biphenyl-4-ylsulfamoyl)-2-methyl-benzoic acid methyl ester

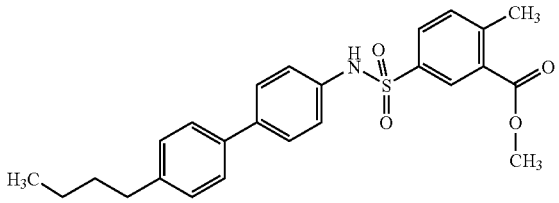

A mixture of 4-butylbenzeneboronic acid (174 mg, 0.975 mmol), 5-(4-bromo-phenylsulfamoyl)-2-methyl-benzoic acid methyl ester (150 mg, 0.39 mmol), dichloro[1,1'-bis(diphenylphosphino)ferrocene]palladium(II) dichloromethane adduct (16 mg, 0.019 mmol), 1,1'-bis(diphenylphosphino)ferrocene (11 mg, 0.019 mmol) and potassium carbonate (0.39 ml of a 2M aqueous solution, 0.78 mmol) in 15 ml 1,4-dioxane was heated at reflux under nitrogen for 20 hr. The reaction mixture was cooled to room temperature, diluted with 80 ml water and extracted with 2×70 ml ethyl acetate. The combined ethyl acetate extracts were washed with 60 ml brine, dried over anhydrous sodium sulfate and concentrated under reduced pressure. The crude product was purified by flash column chromatography (silica gel, 15 g), eluting with 6:1 hexane/ethyl acetate to yield the title compound as a white solid (109 mg, 64% yield).

MS: 422.1 (M−1)

The title compounds of EXAMPLES 155–173 were prepared using procedures analogous to that of EXAMPLE 154 from appropriate starting materials and the results are presented below.

| Ex. | Chemical Structure | Chemical Name | Data |
|---|---|---|---|
| 155 | 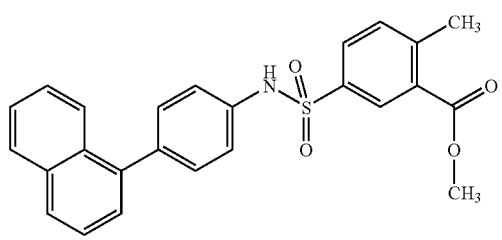 | 2-Methyl-5-(4-naphthalen-1-yl-phenylsulfamoyl)-benzoic acid methyl ester | 50% yield. MS: 416.0 (M − 1) |
| 156 | 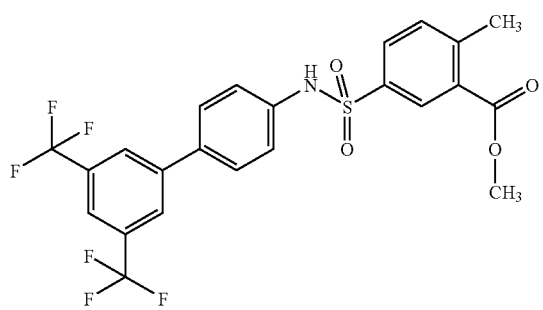 | 5-(3',5'-Bis-trifluoromethyl-biphenyl-4-ylsulfamoyl)-2-methyl-benzoic acid methyl ester | 80% yield. MS: 501.9 (M − 1) |
| 157 | 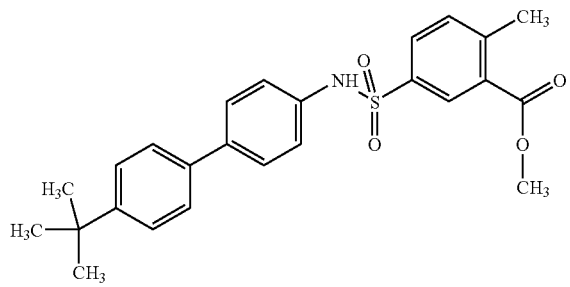 | 5-(4'-tert-Butyl-biphenyl-4-ylsulfamoyl)-2-methyl-benzoic acid methyl ester | 14% yield. MS: 422.0 (M − 1) |
| 158 | 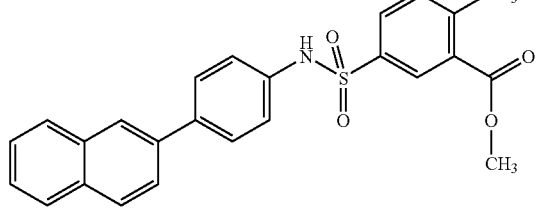 | 2-Methyl-5-(4-naphthalen-2-yl-phenylsulfamoyl)-benzoic acid methyl ester | 43% yield. MS: 416.0 (M − 1) |
| 159 | 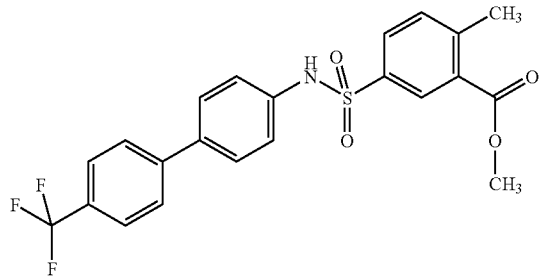 | 2-Methyl-5-(4'-trifluoromethyl-biphenyl-4-ylsulfamoyl)-benzoic acid methyl ester | 78% yield. MS: 434.0 (M − 1) |

-continued

| Ex. | Chemical Structure | Chemical Name | Data |
|---|---|---|---|
| 160 | 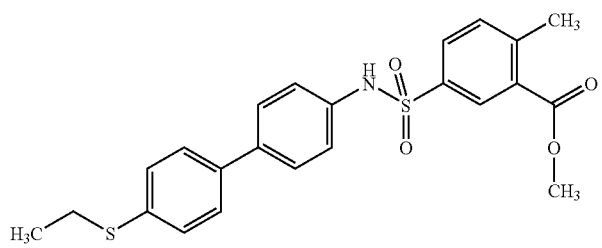 | 5-(4'-Ethylsulfanyl-biphenyl-4-ylsulfamoyl)-2-methyl-benzoic acid methyl ester | 85% yield. MS: 426.0 (M − 1) |
| 161 | 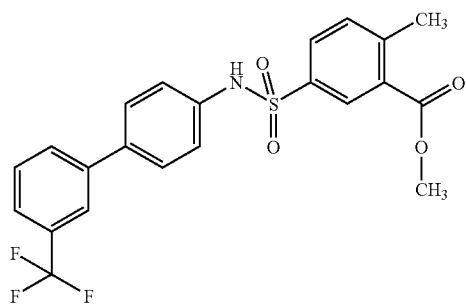 | 2-Methyl-5-(3'-trifluoromethyl-biphenyl-4-ylsulfamoyl)-benzoic acid methyl ester | 63% yield. MS: 434.0 (M − 1) |
| 162 | 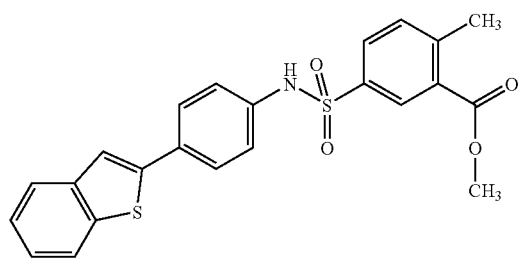 | 5-(4-Benzo[b]thiophen-2-yl-phenylsulfamoyl)-2-methyl-benzoic acid methyl ester | 70% yield. MS: 422.0 (M − 1) |
| 163 | 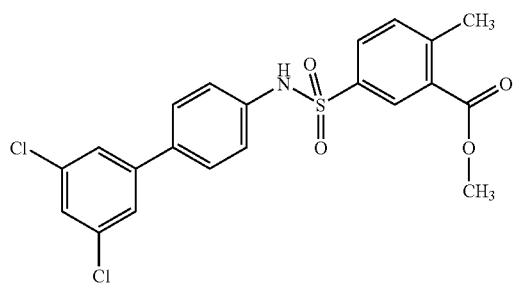 | 5-(3',5'-Dichloro-biphenyl-4-ylsulfamoyl)-2-methyl-benzoic acid methyl ester | 99% yield. MS: 436 (M − 1) |
| 164 | 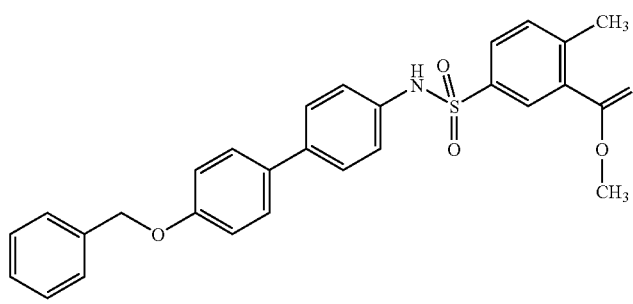 | 5-(4'-Benzyloxy-biphenyl-4-ylsulfamoyl)-2-methyl-benzoic acid methyl ester | 17% yield. MS: 472.3 (M − 1) |

| Ex. | Chemical Structure | Chemical Name | Data |
|---|---|---|---|
| 165 | 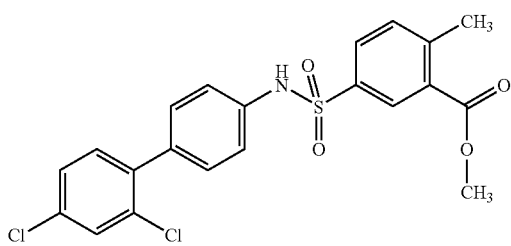 | 5-(2',4'-Dichloro-biphenyl-4-ylsulfamoyl)-2-methyl-benzoic acid methyl ester | 95% yield. MS: 435.9 (M − 1) |
| 166 | 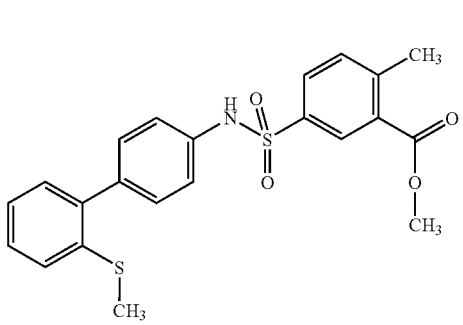 | 2-Methyl-5-(2'-methylsulfanyl-biphenyl-4-ylsulfamoyl)-benzoic acid methyl ester | 73% yield. MS: 412.3 (M − 1) |
| 167 | 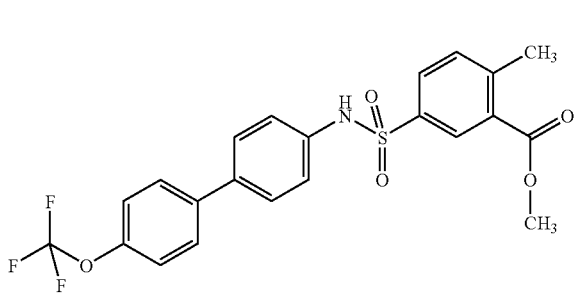 | 2-Methyl-5-(4'-trifluoromethoxy-biphenyl-4-ylsulfamoyl)-benzoic acid methyl ester | 76% yield. MS: 450.2 (M − 1) |
| 168 | 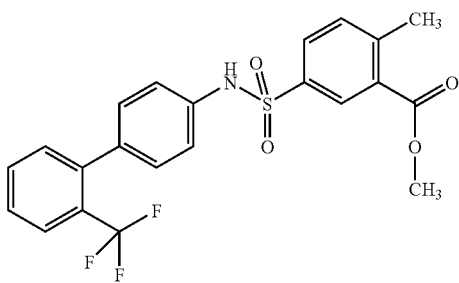 | 2-Methyl-5-(2'-trifluoromethyl-biphenyl-4-ylsulfamoyl)-benzoic acid methyl ester | 95% yield. MS: 434.3 (M − 1) |
| 169 | 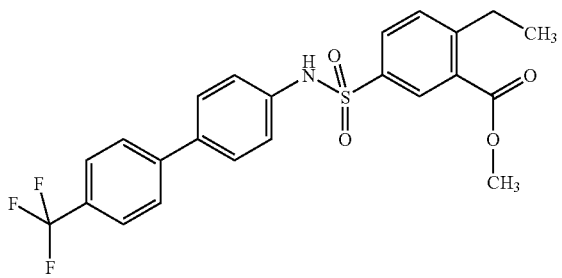 | 2-Ethyl-5-(4'-trifluoromethyl-biphenyl-4-ylsulfamoyl)-benzoic acid methyl ester | 81% yield. MS: 448.3 (M − 1) |

| Ex. | Chemical Structure | Chemical Name | Data |
|---|---|---|---|
| 170 | 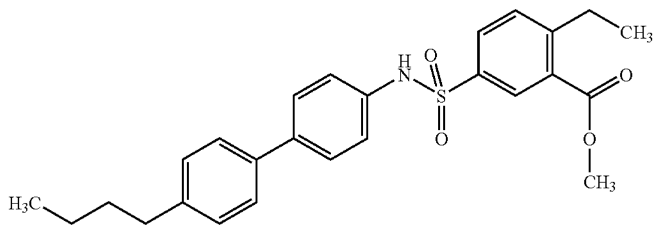 | 5-(4'-Butyl-biphenyl-4-ylsulfamoyl)-2-ethyl-benzoic acid methyl ester | 72% yield. MS: 436.3 (M − 1) |
| 171 | 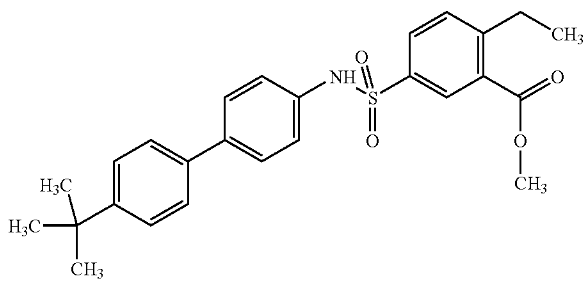 | 5-(4'-tert-Butyl-biphenyl-4-ylsulfamoyl)-2-ethyl-benzoic acid methyl ester | 72% yield. MS: 438.2 (M + 1) |
| 172 | 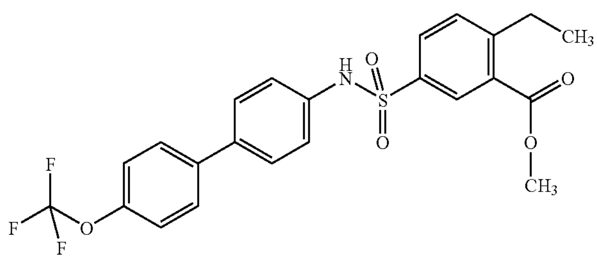 | 2-Isopropyl-5-(4'-trifluoromethoxy-biphenyl-4-ylsulfamoyl)-benzoic acid methyl ester | 39%.yield. MS: 492.0 (M − 1) |
| 173 | 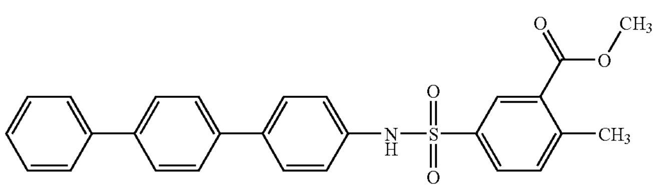 | 2-Methyl-5-([1,1';4',1'']terphenyl-4-ylsulfamoyl)-benzoic acid methyl ester | 58% yield. MS: 458.3 (M + 1) |

EXAMPLE 174

2-Methyl-5-[4-(4-trifluoromethyl-benzylsulfanyl)-phenylsulfamoyl]-benzoic acid

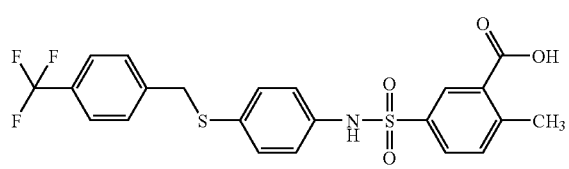

A solution of 1.0N aqueous sodium hydroxide (9.1 ml, 9.16 mmol) was added to a solution of 2-methyl-5-[4-(4-trifluoromethyl-benzylsulfanyl)-phenylsulfamoyl]-benzoic acid methyl ester (1.13 g, 2.29 mmol) in 100 ml methanol and the resulting solution was heated at reflux overnight under nitrogen. The reaction solution was then cooled to room temperature and concentrated under reduced pressure. The residue was stirred in 1.0N aqueous hydrochloric acid solution (25 ml) and filtered to yield the title compound as a white solid (1.03 g, 94% yield). MS: 480.2 (M−1); $^1$H NMR (400 MHz, CD$_3$OD): δ2.49 (s, 3H), 4.04 (s, 2H), 6.96 (d, 2H), 7.1 (d, 2H), 7.29 (m, 2H), 7.33 (d, 1H), 7.47 (m, 3H), 7.94 (b, 1H).

The title compounds of EXAMPLES 175–258 were prepared using procedures analogous to that of EXAMPLE 174 from appropriate starting materials.

EXAMPLE 175

5-[4-(Biphenyl-4-ylmethylsulfanyl)-phenylsulfamoyl]-2-methyl-benzoic acid

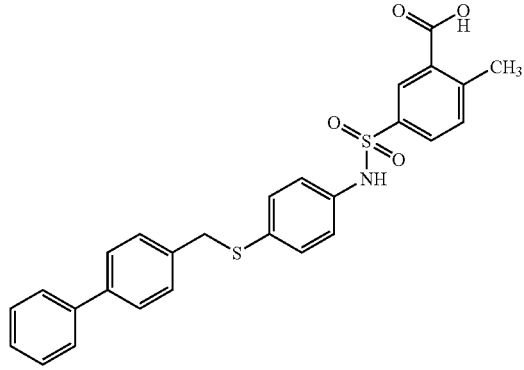

30% yield. MS: 488.2 (M−1); $^1$H NMR (400 MHz, CD$_3$OD): δ2.48 (s, 3H), 4.15 (s, 2H), 6.99 (d, 2H), 7.22 (m, 2H), 7.32 (m, 3H), 7.43 (m, 3H), 7.52 (m, 2H), 7.61 (m, 2H), 7.70 (m, 1H), 8.18 (d, 1H).

EXAMPLE 176

5-{4-[2-(4-Chloro-phenyl)-thiazol-5-ylmethylsulfanyl]-phenylsulfamoyl}-2-methyl-benzoic acid

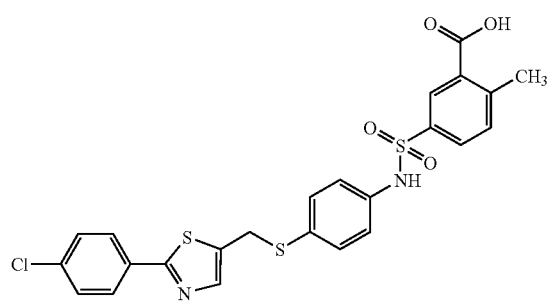

99% yield. MS: 529.0 (M−1); $^1$H NMR (400 MHz, CD$_3$OD): δ2.60 (s, 3H), 4.15 (s, 2H), 6.99 (m, 2H), 7.19 (m, 2H), 7.3–7.5 (c, 5H), 7.87 (d, 2H), 8.27 (d, 1H).

EXAMPLE 177

2-Methyl-5-[4-(quinolin-2-ylmethylsulfanyl)-phenylsulfamoyl]-benzoic acid

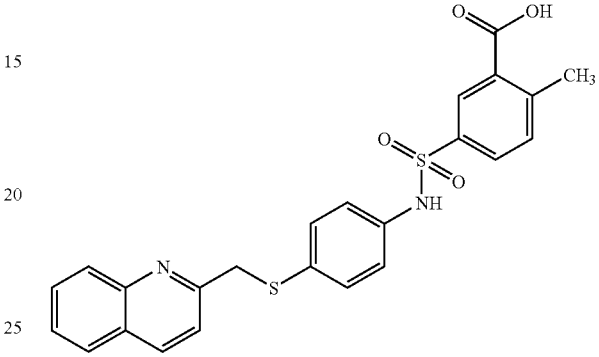

56% yield. MS: 465.2 (M+1); $^1$H NMR (400 MHz, CD$_3$OD): δ2.59 (s, 3H), 4.29 (s, 2H), 6.95 (d, 2H), 7.18 (d, 2H), 7.29 (d, 1H), 7.41 (d, 1H), 7.56(m, 1H), 7.64 (d, 1H), 7.73 (m, 1H), 7.88 (c, 2H), 8.19 (d, 1H), 8.26 (s, 1H).

EXAMPLE 178

2-Methyl-5-[4-(5-phenyl-[1,2,4]oxadiazol-3-ylmethylsulfanyl)-phenylsulfamoyl]-benzoic acid

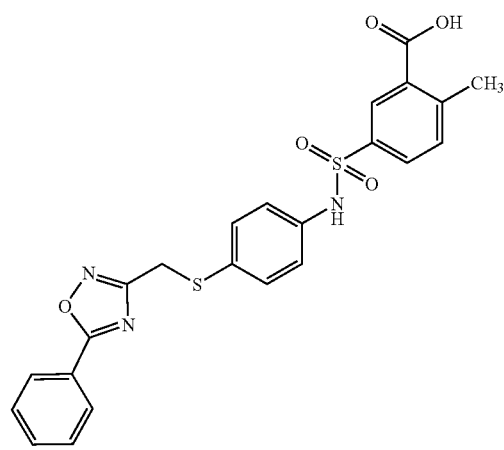

85% yield. MS: 481.0 (M−1); $^1$H NMR (400 MHz, DMSO-D$_6$): δ2.51 (s, 3H), 4.28 (s, 2H), 7.02 (d, 2H), 7.31 (d, 2H), 7.43 (d, 1H), 7.61 (m, 2H), 7.70 (m, 2H), 8.04 (m, 2H), 8.19 (s, 1H).

EXAMPLE 179

5-[4-(4-Fluoro-benzylsulfanyl)-phenylsulfamoyl]-2-methyl-benzoic acid

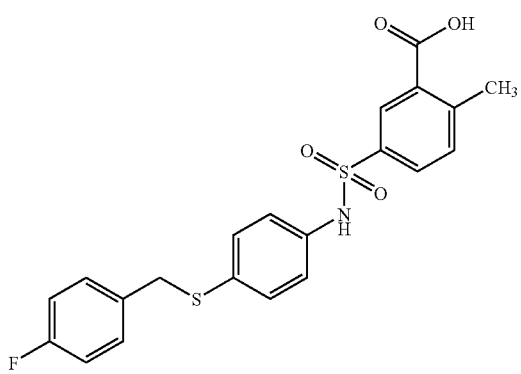

85% yield. MS: 430.0 (M−1); $^1$H NMR (400 MHz, DMSO-D$_6$): δ2.53 (s, 3H), 4.08(s, 2H), 7.01 (m, 4H), 7.17 (m, 2H), 7.23 (m, 2H), 7.46 (d, 1H), 7.71 (m, 1H), 8.17 (d, 1H).

EXAMPLE 180

2-Methyl-5-[4-(naphthalen-2-ylmethylsulfanyl)-phenylsulfamoyl]-benzoic acid

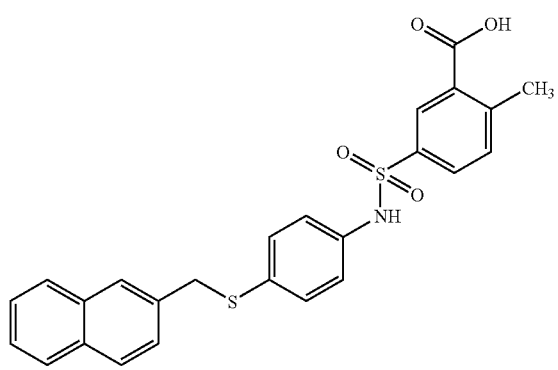

82% yield. MS: 462.0 (M−1); $^1$H NMR (400 MHz, DMSO-D$_6$): δ2.49 (s, 3H), 4.27 (s, 2H), 6.97 (d, 2H), 7.21 (m, 2H), 7.39 (m, 2H), 7.46 (m, 2H), 7.68 (m, 1H), 7.72–7.87 (m, 4H), 8.18 (d, 1H).

EXAMPLE 181

2-Methyl-5-[4-(3-trifluoromethoxy-benzylsulfanyl)-phenylsulfamoyl]-benzoic acid

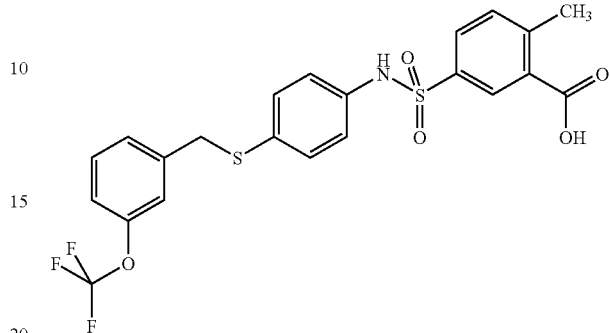

74% yield. MS: 496.3 (M−1); $^1$H NMR (400 MHz, DMSO-D$_6$): δ2.49 (s, 3H), 4.15 (s, 2H), 6.97 (m, 2H), 7.19 (c, 5H), 7.33 (m, 1H), 7.44 (d, 1H), 7.71 (m, 1H), 8.17 (d, 1H).

EXAMPLE 182

2-Methyl-5-(4-naphthalen-1-yl-phenylsulfamoyl)-benzoic acid

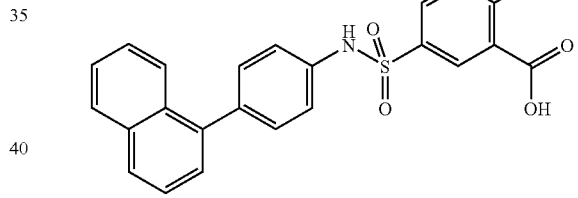

69% yield. MS: 416.0 (M−1); $^1$H NMR (400 MHz, DMSO-D$_6$): δ2.49 (s, 3H), 7.22 (d, 2H), 7.34 (m, 3H), 7.48 (m, 4H), 7.67 (d, 1H), 7.91 (m, 3H), 8.23 (d, 1H).

EXAMPLE 183

5-(3′,5′-Bis-trifluoromethyl-biphenyl-4-ylsulfamoyl)-2-methyl-benzoic acid

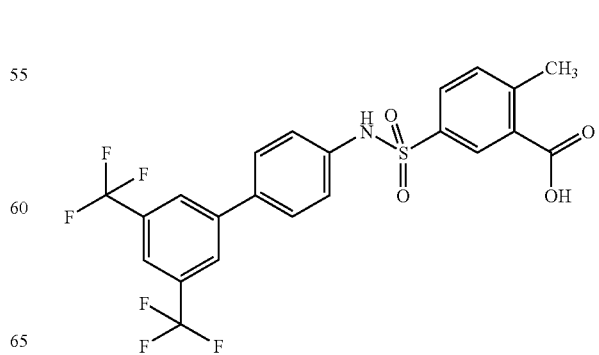

81% yield. MS: 501.9 (M−1); ¹H NMR (400 MHz, CD₃OD): δ2.59 (s, 3H), 7.27 (m, 2H), 7.40 (d, 1H), 7.59 (m, 2H), 7.80 (d, 1H), 7.82 (d, 1H), 8.08 (s, 2H), 8.35 (d, 1H).

EXAMPLE 184

2-Methyl-5-(4-naphthalen-2-yl-phenylsulfamoyl)-benzoic acid

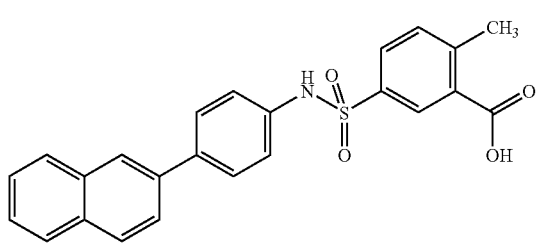

65% yield. MS: 416.0 (M−1); ¹H NMR (400 MHz, DMSO-D₆): δ2.53 (s, 3H), 7.21 (d, 2H), 7.49 (m, 3H), 7.70 (d, 2H), 7.75 (m, 1H), 7.81 (m, 1H), 7.92 (m, 2H), 8.11 (s, 1H), 8.24 (d, 1H).

EXAMPLE 185

2-Methyl-5-(4'-trifluoromethyl-biphenyl-4-ylsulfamoyl)-benzoic acid

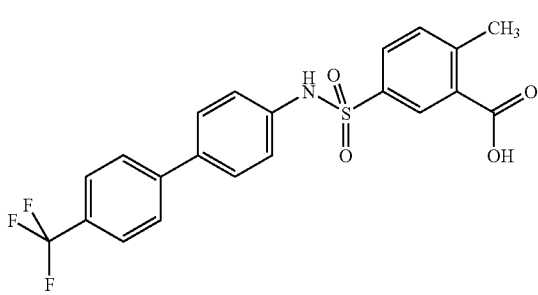

81% yield. MS: 434.0 (M−1); ¹H NMR (400 MHz, DMSO-D₆): δ2.53 (s, 3H), 7.20 (m, 2H), 7.49 (d, 1H), 7.63 (d, 2H), 7.72–7.84 (m, 5H), 8.24 (d, 1H).

EXAMPLE 186

5-(4'-Ethylsulfanyl-biphenyl-4-ylsulfamoyl)-2-methyl-benzoic acid

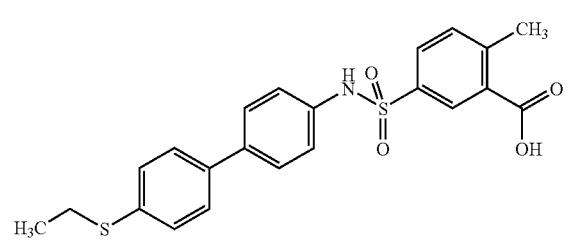

79% yield. MS: 426.0 (M−1); ¹H NMR (400 MHz, DMSO-D₆): δ1.22 (t, 3H), 2.53 (s,3H), 2.98 (q, 2H), 7.15 (d, 2H), 7.32 (d, 2H), 7.51 (m, 5H), 7.79 (m, 1H), 8.22 (d, 1H).

EXAMPLE 187

5-[4-(1H-Benzoimidazol-2-yl)-phenylsulfamoyl]-2-methyl-benzoic acid

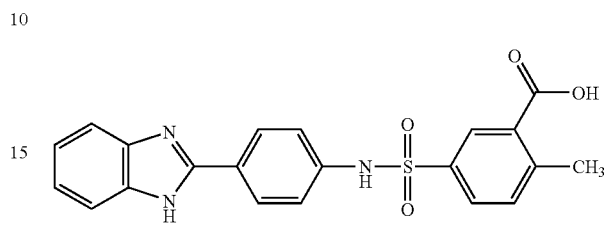

94% yield. MS: 408.2 (M+1); ¹H NMR (400 MHz, CD₃OD): δ2.60 (s, 3H), 7.46 (m, 3H), 7.59 (m, 2H), 7.76 (m, 2H), 7.92 (m,1H), 8.00 (m, 2H), 8.40 (d, 1H).

EXAMPLE 188

2-Methyl-5-(3'-trifluoromethyl-biphenyl-4-ylsulfamoyl)-benzoic acid

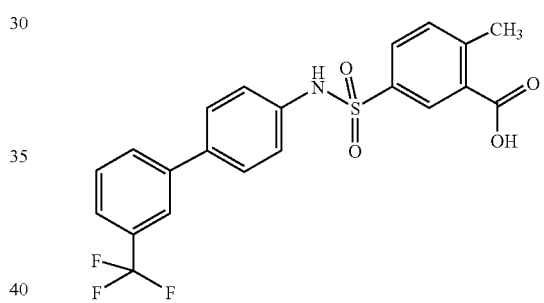

43% yield. MS: 434.0 (M−1); ¹H NMR (400 MHz, DMSO-D₆): δ2.53 (s, 3H), 7.19 (d, 2H), 7.48 (d, 1H), 7.64 (c, 4H), 7.81 (m, 1H), 7.88 (c, 2H), 8.23 (d, 1H).

EXAMPLE 189

5-(4-Benzo[b]thiophen-2-yl-phenylsulfamoyl)-2-methyl-benzoic acid

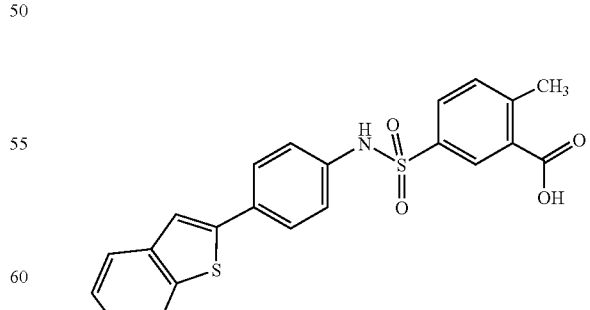

80% yield. MS: 422.0 (M−1); ¹H NMR (400 MHz, DMSO-D₆): δ2.53 (s, 3H), 7.18 (d, 2H), 7.33 (m, 2H), 7.49 (d, 1H), 7.65 (m, 2H), 7.73 (s, 1H), 7.80 (m, 2H), 7.92 (m, 1H), 8.23 (d, 1H).

EXAMPLE 190

5-(4'-Benzyloxy-biphenyl-4-ylsulfamoyl)-2-methyl-benzoic acid

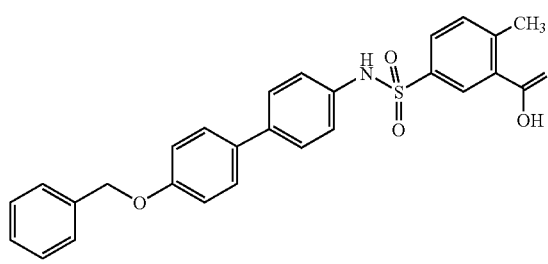

74% yield. MS: 472.3 (M−1); ¹H NMR (400 MHz, DMSO-D$_6$): δ2.52 (s, 3H), 5.11 (s, 2H), 7.03 (m, 2H), 7.12 (d, 2H), 7.28–7.52 (c, 10H), 7.78 (m, 1H), 8.21 (d, 1H).

EXAMPLE 191

2-Methyl-5-(4'-propoxy-biphenyl-4-ylsulfamoyl)-benzoic acid

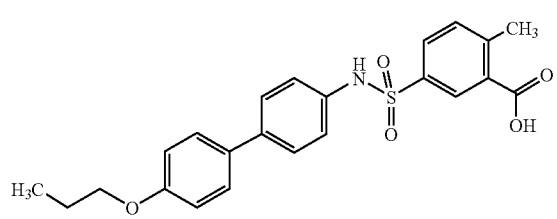

61% yield. ¹H NMR (400 MHz, DMSO-D$_6$): δ0.95 (t, 3H), 1.7 (m, 2H), 2.52 (s, 3H), 3.91 (t, 2H), 6.93 (d, 2H), 7.11 (d, 2H), 7.47 (d, 5H), 7.77 (d, 1H), 8.31 (s, 1H).

EXAMPLE 192

2-Methyl-5-(2'-methylsulfanyl-biphenyl-4-ylsulfamoyl)-benzoic acid

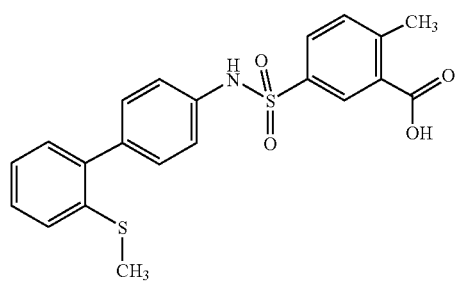

87% yield. MS: 412.3 (M−1); ¹H NMR (400 MHz, DMSO-D$_6$): δ2.48 (s 3H), 2.54 (s, 3H), 7.06–7.17 (c, 4H), 7.17–7.34 (c, 4H), 7.49 (d, 1H), 7.81 (m, 1H), 8.22 (d, 1H).

EXAMPLE 193

2-Methyl-5-(4'-trifluoromethoxy-biphenyl-4-ylsulfamoyl)-benzoic acid

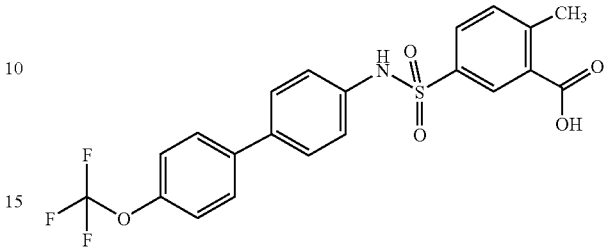

69% yield. MS: 450.2 (M−1); ¹H NMR (400 MHz, DMSO-D$_6$): δ2.48 (s, 3H), 7.17 (d, 2H), 7.38 (d, 2H), 7.48 (d, 1H), 7.56 (d, 2H), 7.68 (d, 2H), 7.80 (m, 1H), 8.22 (d, 1H).

EXAMPLE 194

2-Methyl-5-(2'-trifluoromethyl-biphenyl-4-ylsulfamoyl)-benzoic acid

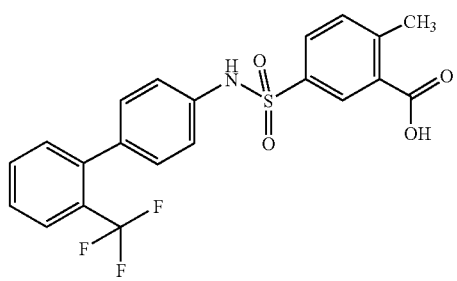

64% yield. MS: 434.3 (M−1); ¹H NMR (400 MHz, DMSO-D$_6$): δ□□□ (s, 3H), 7.11 (d, 2H), 7.17 (d, 2H), 7.30 (d, 1H), 7.48 (d, 1H), 7.55 (m, 1H), 7.65 (m, 1H), 7.78 (m, 2H), 8.20 (d, 1H), 7.78 (d, 2H).

EXAMPLE 195

2-Ethyl-5-(4'-trifluoromethyl-biphenyl-4-ylsulfamoyl)-benzoic acid

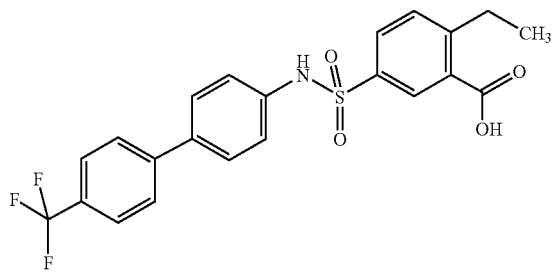

90% yield. MS: 448.3 (M−1); ¹H NMR (400 MHz, CD$_3$OD): δ1.19 (t, 3H), 3.01 (q, 2H), 7.23 (d, 2H), 7.43 (d, 1H), 7.56 (d, 2H), 7.68 (d, 2H), 7.73 (d, 2H), 7.82 (m, 1H), 8.28 (d, 1H).

EXAMPLE 196

2-Methyl-5-(2-phenyl-benzooxazol-6-ylsulfamoyl)-benzoic acid

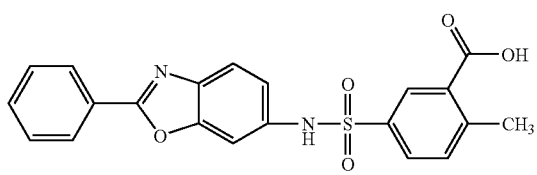

85% yield. MS: 409.3 (M+1); ¹H NMR (400 MHz, CD₃OD): δ2.58 (s, 3H), 7.07 (m, 1H), 7.38 (d, 1H), 7.5–7.6 (c, 5H), 7.75 (m,1H), 8.18 (m, 2H), 8.29 (d, 1H).

EXAMPLE 197

2-Methyl-5-(2-phenyl-benzothiazol-6-ylsulfamoyl)-benzoic acid

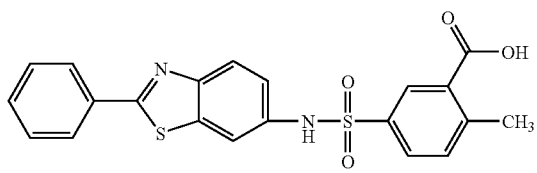

93% yield. MS: 425.3 (M+1); ¹H NMR (400 MHz, CD₃OD): δ2.58 (s, 3H), 7.23 (m, 1H), 7.38 (d, 1H), 7.51 (c, 3H), 7.76 (c, 2H), 7.85 (d, 1H), 8.04 (c, 2H), 8.30 (d, 1H).

EXAMPLE 198

5-[4-(5-tert-Butyl-benzooxazol-2-yl)-phenylsulfamoyl]-2-methyl-benzoic acid

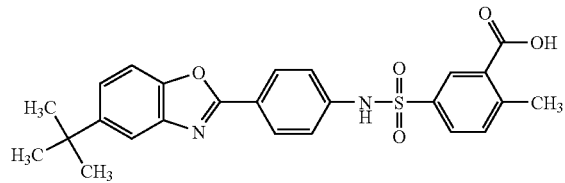

62% yield. MS: 465.4 (M+1); ¹H NMR (400 MHz, CD₃OD): δ1.38 (s, 9H), 2.59 (s, 3H), 7.31 (m, 2H), 7.42 (d, 1H), 7.46 (d, 1H), 7.49 d, 1H), 7.53 (d, 1H), 7.69 (d, 1H), 7.85 (m, 1H).

EXAMPLE 199

5-[4-(3,4-Difluoro-benzylsulfanyl)-phenylsulfamoyl]-2-methyl-benzoic acid

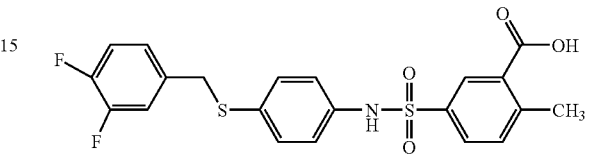

77% yield. MS: 448.2 (M−1); ¹H NMR (400 MHz, CD₃OD): δ2.61 (s, 3H), 3.98 (s, 2H), 6.89 (c, 1H), 6.97–7.12 (c, 3H), 7.18 (m, 2H), 7.38 (d, 1H),7.69 (m, 1H), 8.27 (d, 1H).

EXAMPLE 200

5-[4-(3,5-Bis-trifluoromethyl-benzylsulfanyl)-phenylsulfamoyl]-2-methyl-benzoic acid

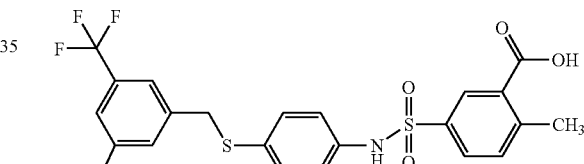

80% yield. MS: 548.2 (M−1); ¹H NMR (400 MHz, CD₃OD): δ2.61 (s, 3H), 7.02 (m, 2H), 7.16 (m, 2H), 7.37 (d, 1H), 7.71 (m, 2H), 8.30 (d, 1H).

EXAMPLE 201

2-Methyl-5-[4-(2-trifluoromethyl-benzylsulfanyl)-phenylsulfamoyl]-benzoic acid

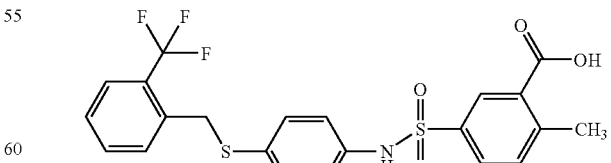

86% yield. MS: 480.2 (M−1); ¹H NMR (400 MHz, CD₃OD): δ2.62 (s, 3H), 4.15 (s, 2H), 7.02 (m,2H), 7.14–7.25 (c, 3H), 7.34–7.42 (c, 3H), 7.61 (m, 1H), 7.73 (m, 1H), 8.29 (d, 1H).

EXAMPLE 202

5-[4-(3,4-Dimethyl-benzylsulfanyl)-phenylsulfamoyl]-2-methyl-benzoic acid

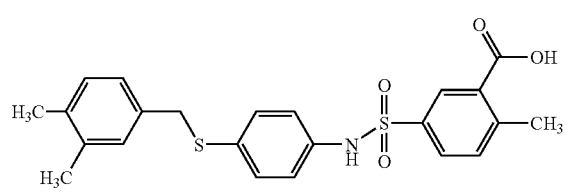

85% yield. MS: 439.9 (M−1); $^1$H NMR (400 MHz, CD$_3$OD): δ2.15 (s, 3H), 2.19 (3, 3H), 2.61 (s, 3H), 3.94 (s, 2H), 6.83(d, 1H), 6.95 (c, 2H), 6.98 (m, 2H), 7.14 (m, 2H), 7.38 (d, 1H), 7.70 (m, 1H), 8.28 (d, 1H).

EXAMPLE 203

5-[4-(2,4-Bis-trifluoromethyl-benzylsulfanyl)-phenylsulfamoyl]-2-methyl-benzoic acid

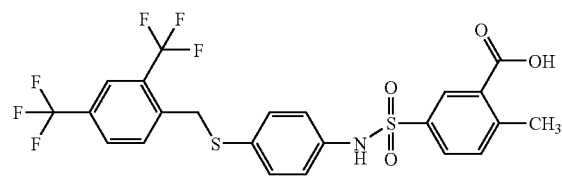

80% yield. MS: 548.1 (M−1); $^1$H NMR (400 MHz, CD$_3$OD): δ2.61 (s, 3H), 4.21 (s, 2H), 7.04 (m, 2H), 7.19 (m, 2H), 7.39 (m, 2H), 7.67 (d, 1H), 7.74 (m, 1H), 7.87 (s, 1H), 8.28 (d, 1H).

EXAMPLE 204

5-[4-(2-Chloro-4-fluoro-benzylsulfanyl)-phenylsulfamoyl]-2-methyl-benzoic acid

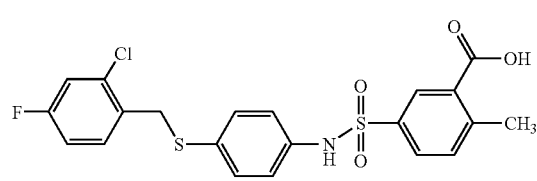

84% yield. MS: 464.0 (M−1)

EXAMPLE 205

5-[4-(5,6-Difluoro-benzothiazol-2-ylmethylsulfanyl)-phenylsulfamoyl]-2-methyl-benzoic acid

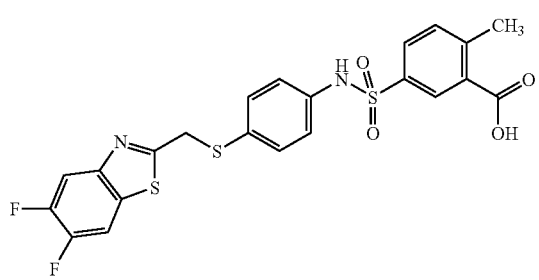

49% yield. MS: 507.0 (M−1); $^1$H NMR (400 MHz, CD$_3$OD): δ2.58 (s, 3H), 4.46 (s, 2H), 7.01 (d, 2H), 7.29 (m, 3H), 7.70 (m, 2H), 7.85 (m, 1H), 8.26 (d, 1H).

EXAMPLE 206

5-[4-(5-Fluoro-benzothiazol-2-ylmethylsulfanyl)-phenylsulfamoyl]-2-methyl-benzoic acid

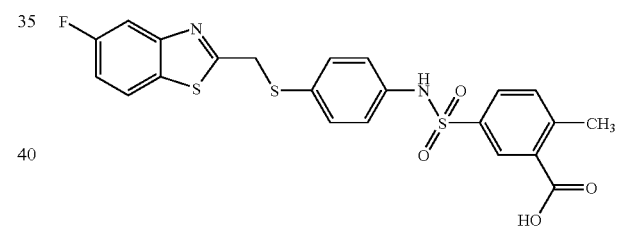

80% yield. MS: 489.1 (M+1); $^1$H NMR (400 MHz, CD$_3$OD): δ2.58 (s, 3H), 4.47 (s, 2H), 7.02 (m, 2H), 7.21 (m, 1H), 7.28 (c, 3H), 7.55 (m, 1H), 7.65 (m, 1H), 7.89 (m, 1H), 8.27 (d, 1H).

EXAMPLE 207

5-[4-(3,5-Dimethyl-benzyloxy)-phenylsulfamoyl]-2-methyl-benzoic acid

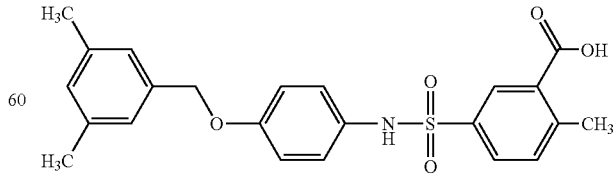

87% yield. MS: 424.2 (M−1); $^1$H NMR (400 MHz, CD$_3$OD): δ2.28 (s, 6H), 2.60 (s, 3H), 4.90 (s, 2H), 6.83 (m, 2H), 6.95 (c, 5H), 7.35 (d, 1H), 7.62 (m, 1H), 8.22 (d, 1H).

EXAMPLE 208

5-[4-(4-Butoxy-benzyloxy)-phenylsulfamoyl]-2-methyl-benzoic acid

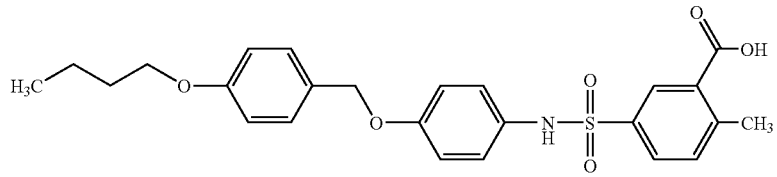

88% yield. MS: 468.1 (M−1); ¹H NMR (400 MHz, CD₃OD): δ0.98 (s, 3H), 1.50 (m, 2H), 1.73 (m, 2H), 2.60 (s, 3H), 3.96 (t, 2H), 4.90 (s, 2H), 6.83 (d, 2H), 6.88 (d, 2H), 6.95 (d, 2H), 7.28 (d, 2H), 7.35 (d, 1H), 7.62 (m, 1H), 8.21 (d, 1H).

EXAMPLE 209

5-[4-(2-Chloro-4-fluoro-benzyloxy)-phenylsulfamoyl]-2-methyl-benzoic acid

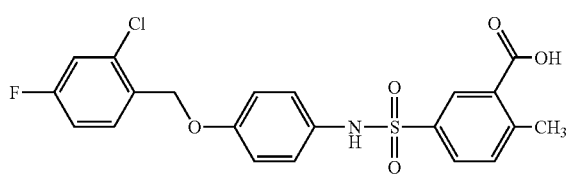

84% yield; MS: 448.0 (M−1); ¹H NMR (400 MHz, CD₃OD): δ2.60 (s, 3H), 5.05 (s, 2H), 6.86 (m, 2H), 6.98 (m, 2H), 7.08 (m, 1H), 7.25 (m, 1H), 7.36 (d, 1H), 7.53 (m, 1H), 7.64 (m, 1H), 8.21 (d, 1H).

EXAMPLE 210

5-[4-(2,3-Difluoro-benzyloxy)-phenylsulfamoyl]-2-methyl-benzoic acid

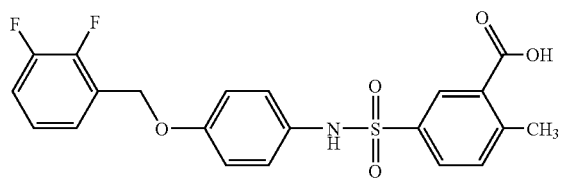

82% yield. MS: 432.2 (M−1); ¹H NMR (400 MHz, CD₃OD): δ2.60 (s, 3H), 5.08 (s, 2H), 6.87 (m, 2H), 6.99 (m, 2H), 7.17 (c, 1H), 7.24 (c, 2H), 7.36 (d, 1H), 7.64 (m, 1H), 8.22 (d, 1H).

EXAMPLE 211

5-[4-(3,5-Difluoro-benzyloxy)-phenylsulfamoyl]-2-methyl-benzoic acid

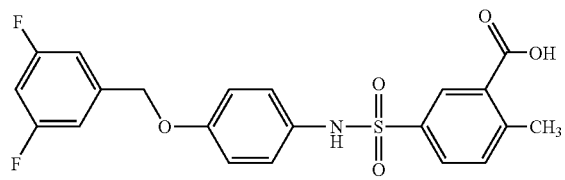

56% yield. MS: 432.2 (M−1); ¹H NMR (400 MHz, CD₃OD): δ2.60 (s, 3H), 5.02 (s, 2H), 6.86 (c, 3H), 6.99 (c, 4H), 7.36 (d, 1H), 7.63 (m, 1H), 8.22 (d, 1H).

EXAMPLE 212

5-[4-(3,4-Difluoro-benzyloxy)-phenylsulfamoyl]-2-methyl-benzoic acid

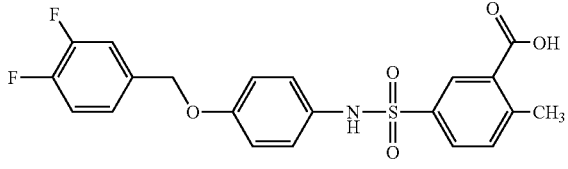

66% yield. MS: 432.2 (M−1); ¹H NMR (400 MHz, CD₃OD): δ2.60 (s, 3H), 4.97 (s, 2H), 6.85 (c, 2H), 6.97 (c, 2H), 7.17–7.38 (c, 4H), 7.63 (m, 1H), 8.21 (d, 1H).

EXAMPLE 213

5-[4-(5,7-Difluoro-benzothiazol-2-ylmethylsulfanyl)-phenylsulfamoyl]-2-methyl-benzoic acid

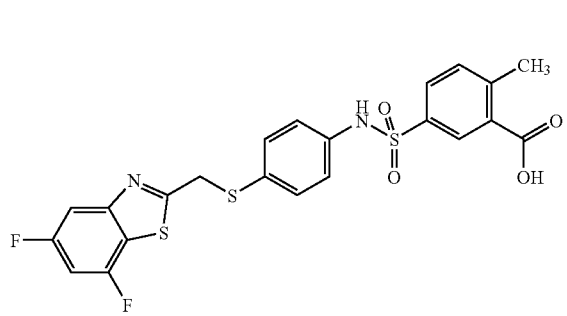

19% yield. MS: 507.0 (M+1); ¹H NMR (400 MHz, CD₃OD): δ2.47 (s, 3H), 4.49 (s, 2H), 7.02 (m, 2H), 7.12 (m, 2H), 7.26 (m, 2H), 7.46 (c, 2H), 7.97 (d, 1H).

EXAMPLE 214

2-Isopropyl-5-[4-(6-methyl-benzothiazol-2-yl)-phenylsulfamoyl]-benzoic acid

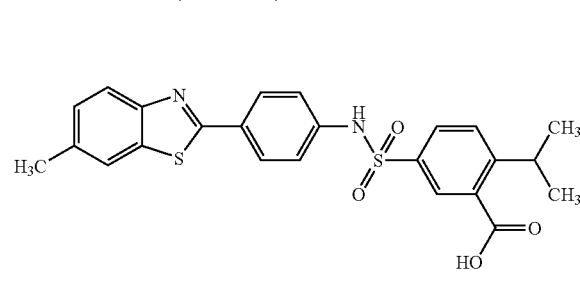

84% yield. MS: 467.1 (M+1); ¹H NMR (400 MHz, CD₃OD): δ1.21 (d, 6H), 2.47 (s, 3H), 3.81 (m, 1H), 7.28 (m, 2H), 7.32 (m, 1H), 7.60 (d, 1H), 7.75 (s, 1H) 7.82 (d, 1H), 7.92 (c, 3H), 8.20 (d, 1H).

EXAMPLE 215

2-Methyl-5-[4-(5-trifluoromethyl-benzothiazol-2-ylmethylsulfanyl)-phenylsulfamoyl]-benzoic acid

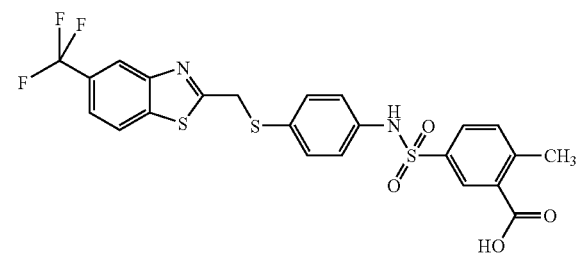

17% yield. MS: 539.0 (M+1); ¹H NMR (400 MHz, CD₃OD): δ2.55 (s, 3H), 4.52 (s, 2H), 7.01 (d, 2H), 7.27 (c, 4H), 7.64 (m, 2H), 8.12 (d, 1H), 8.22 (b, 1H).

EXAMPLE 216

2-Ethyl-5-[4-(6-methyl-benzothiazol-2-yl)-phenylsulfamoyl]-benzoic acid

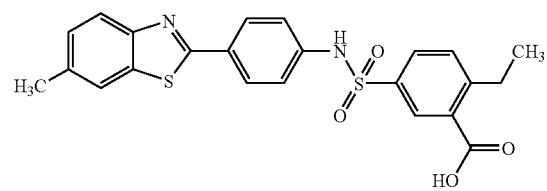

83% yield. MS: 453.0 (M+1); ¹H NMR (400 MHz, CD₃OD): δ1.18 (t, 3H), 2.47 (s, 3H), 3.01 (q, 2H), 7.27 (m, 2H), 7.32 (m, 1H), 7.45 (d, 1H), 7.84 (m, 2H), 7.93 (m, 2H), 8.32 (d, 1H).

EXAMPLE 217

2,3-Dimethyl-5-[4-(6-methyl-benzothiazol-2-yl)-phenylsulfamoyl]-benzoic acid

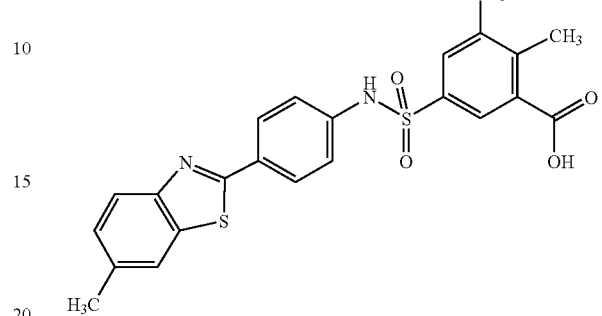

75% yield. MS: 453.0 (M+1); ¹H NMR (400 MHz, DMSO-D₆): δ2.30 (s, 3H), 2.38 (s, 3H), 2.42 (s, 3H), 7.26 (m, 2H), 7.31 (m, 1H), 7.76 (s, 1H).

EXAMPLE 218

2,3-Dimethyl-5-[4-(3-trifluoromethyl-benzylsulfanyl)-phenylsulfamoyl]-benzoic acid

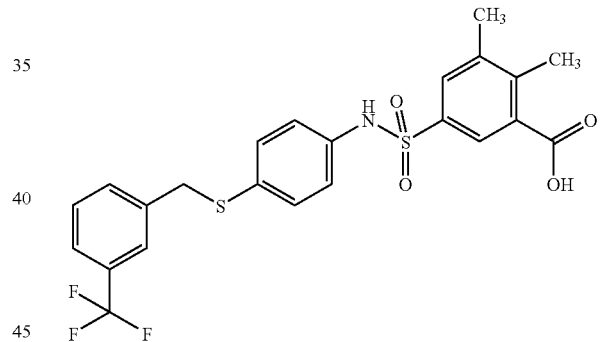

75% yield. MS: 494.2 (M−1); ¹H NMR (400 MHz, CD₃OD): δ2.32 (s, 3H), 2.48 (s, 3H), 4.07 (s, 2H), 7.0 (m, 2H), 7.14 (d, 2H), 7.34 (c, 2H), 7.46 (c, 2H), 7.63 (s, 1H), 8.0 (s, 1H).

EXAMPLE 219

5-[4-(4-Ethyl-benzylsulfanyl)-phenylsulfamoyl]-2,3-dimethyl-benzoic acid

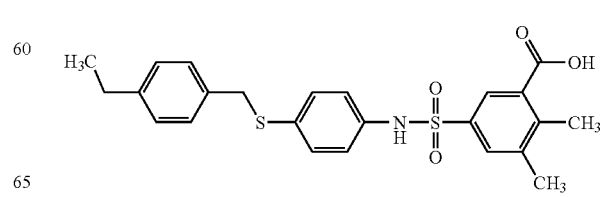

80% yield. MS: 456.3 (M+1); $^1$H NMR (400 MHz, CD$_3$OD): δ1.17 (t, 3H), 2.33 (s, 3H), 2.49 (s, 3H), 2.57 (q, 2H), 3.97 (s, 2H), 6.96–7.06 (c, 6H), 7.13 (c, 1H), 7.63 (d, 1H), 8.00 (d, 1H).

EXAMPLE 220

2-Isopropyl-5-(4'-trifluoromethoxy-biphenyl-4-ylsulfamoyl)-benzoic acid

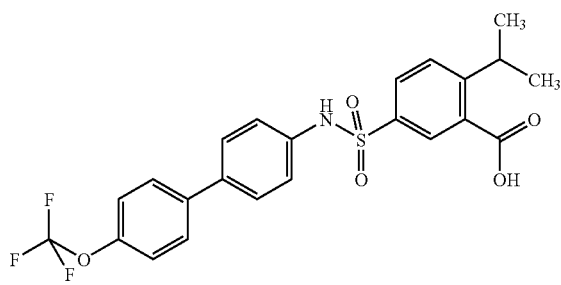

37%.yield. MS: 480.0 (M+1); $^1$H NMR (400 MHz, CD$_3$OD): δ1.22 (d, 6H), 3.81 (m, 1H), 7.20 (m, 2H), 7.29 (d, 2H), 7.51 (m, 2H), 7.58 (d, 1H), 7.63 (m, 2H), 7.84 (m, 1H), 8.14 (d, 1H).

EXAMPLE 221

5-[2-(4-tert-Butyl-phenyl)-benzooxazol-5-ylsulfamoyl]-2-methyl-benzoic acid

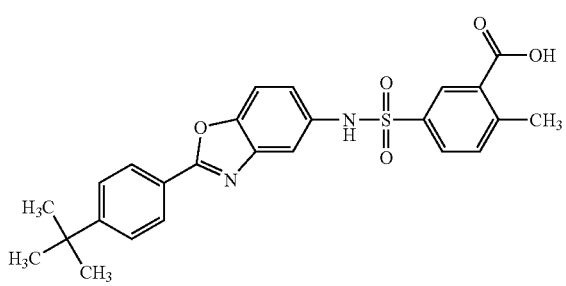

90% yield. MS: 465.3 (M+1); $^1$H NMR (400 MHz, CD$_3$OD): δ1.37 (s, 9H), 2.58 (s, 3H), 7.13 (m, 1H), 7.37 (d, 1H), 7.43 (d, 1H), 7.53 (d, 1H), 7.61 (m, 2H), 7.72 (m, 1H), 8.11 (m, 2H), 8.27 (d, 1H).

EXAMPLE 222

5-[4-(3,5-Dimethyl-benzylsulfanyl)-phenylsulfamoyl]-2-methyl-benzoic acid

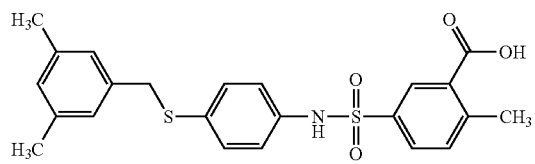

74% yield. MS: 440.2 (M+1); $^1$H NMR (400 MHz, CD$_3$OD): δ2.19 (s, 6H), 2.56 (s, 3H), 3.93 (s, 2H), 6.78 (s, 2H), 6.82 (s, 1H), 6.98 (d, 2H), 7.12 (d, 2H), 7.30 (d, 1H), 7.58 (d, 1H), 8.08 (b, 1H).

EXAMPLE 223

5-[4-(4-Butoxy-benzylsulfanyl)-phenylsulfamoyl]-2-methyl-benzoic acid

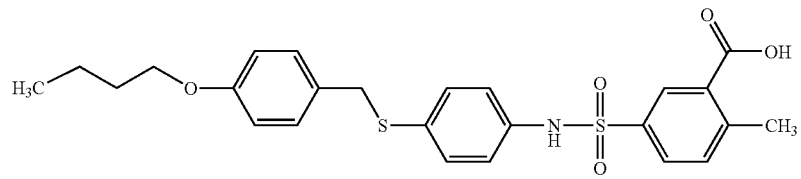

82% yield. MS: 484.2 (M−1); $^1$H NMR (400 MHz, CD$_3$OD): δ0.97 (t, 3H), 1.49 (m, 2H), 1.72 (m, 2H), 2.61 (s, 3H), 3.91 (t, 2H), 3.95 (s, 2H), 6.72 (m, 2H), 6.97 (m, 2H), 7.03 (m, 2H), 7.13 (m, 2H), 7.38 (d, 1H), 7.68 (m, 1H), 8.28 (d, 1H).

EXAMPLE 224

5-[4-(2,3-Difluoro-benzylsulfanyl)-phenylsulfamoyl]-2-methyl-benzoic acid

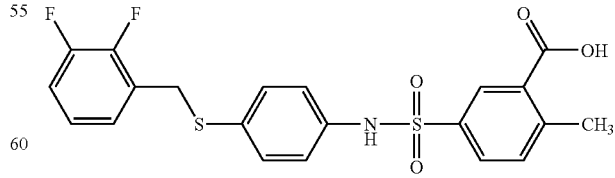

81% yield. MS: 448.2 (M−1); $^1$H NMR (400 MHz, CD$_3$OD): δ2.57 (s, 3H), 4.03 (s, 2H), 6.81 (c, 1H), 6.92 (c, 1H), 7.00 (d, 2H), 7.07 (m, 1H), 7.16 (d, 1H), 7.34 (d, 1H), 7.61 (d, 1H), 8.14 (b, 1H).

EXAMPLE 225

5-[4-(3,5-Difluoro-benzylsulfanyl)-phenylsulfamoyl]-2-methyl-benzoic acid

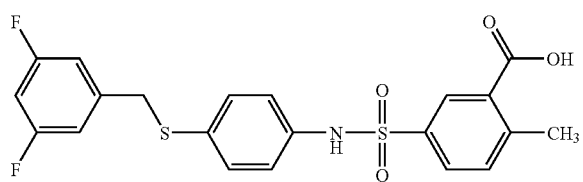

84% yield. MS: 448.2 (M−1); $^1$H NMR (400 MHz, CD$_3$OD): δ2.60 (s, 3H), 4.01 (s, 2H), 6.74 (c, 3H), 7.00 (c, 2H), 7.17 (c, 2H), 7.37, (d, 1H), 7.68 (m, 1H), 8.28 (d, 1H).

EXAMPLE 226

2-Methyl-5-[4-(4-trifluoromethylsulfanyl-benzylsulfanyl)-phenylsulfamoyl]-benzoic acid

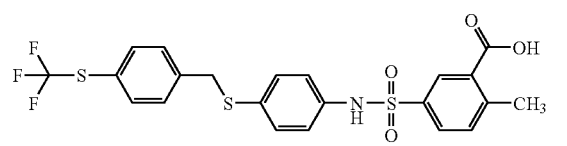

84% yield. MS: 512.2 (M−1); $^1$H NMR (400 MHz, CD$_3$OD): δ2.63 (s, 3H), 4.78 (s, 2H), 6.98 (m, 2H), 7.13 (m, 2H), 7.21 (d, 2H), 7.40 (d, 1H), 7.47 (d, 2H), 7.72 (m, 1H), 8,28 (d, 1H).

EXAMPLE 227

2,3-Dimethyl-5-[4-(3-trifluoromethoxy-benzylsulfanyl)-phenylsulfamoyl]-benzoic acid

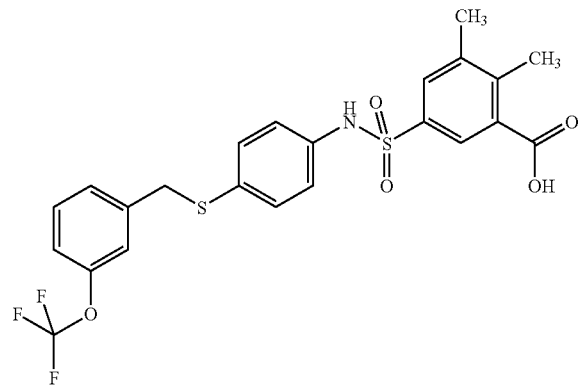

77% yield. MS: 510.2 (M−1); $^1$H NMR (400 MHz, CD$_3$OD): δ2.32 (s, 3H), 2.48 (s, 3H), 4.04 (s, 2H), 6.98 (d, 2H), 7.08 (c, 3H), 7.15 (d, 2H), 7.24 (t, 1H), 7.62 (s, 1H), 7.99 (s, 1H).

EXAMPLE 228

2,3-Dimethyl-5-(4'-trifluoromethoxy-biphenyl-4-ylsulfamoyl)-benzoic acid

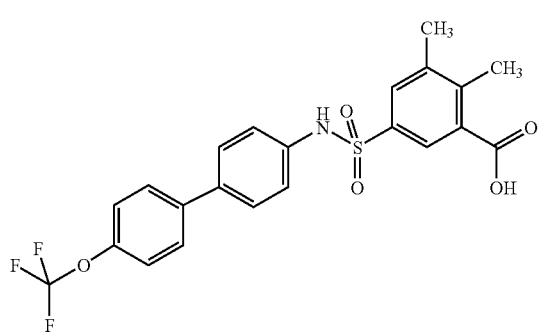

77% yield. MS: 464.2 (M−1); $^1$H NMR (400 MHz, CD$_3$OD): δ2.33 (s, 3H), 2.47 (s, 3H), 7.18 (d, 2H), 7.29 (d, 2H), 7.50 (m, 2H), 7.62 (m, 2H), 7.68 (s, 1H), 8.03 (s, 1H).

EXAMPLE 229

5-[2-(4-tert-Butyl-phenyl)-benzooxazol-5-ylsulfamoyl]-2-ethyl-benzoic acid

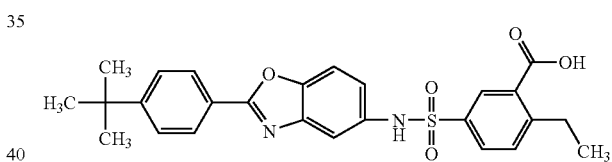

84% yield. MS: 479.4 (M+1); $^1$H NMR (400 MHz, CD$_3$OD): δ1.17 (t, 3H), 1.37 (s, 9H), 3.00 (q, 2H), 7.13 (m, 1H), 7.42 (m, 2H), 7.53 (d, 1H), 7.61 (m, 2H), 7.75 (m, 1H), 8.11 (m, 2H), 8.23 (d, 1H).

EXAMPLE 230

2-Ethyl-5-[4-(4-trifluoromethoxy-benzylsulfanyl)-phenylsulfamoyl]-benzoic acid

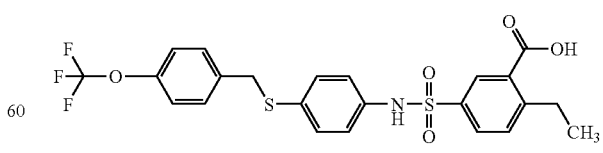

67% yield. MS: 510.3 (M−1); $^1$H NMR (400 MHz, CD$_3$OD): δ1.20 (t, 3H), 2.97 (q, 2H), 4.03 (s, 2H), 7.01 (m, 2H), 7.09 (d, 2H), 7.14 (m, 2H), 7.23 (m, 2H), 7.34 (d, 1H), 7.63 (m, 1H), 8.06 (d, 1H).

EXAMPLE 231

2,3-Dimethyl-5-[4-(4-trifluoromethoxy-benzylsulfanyl)-phenylsulfamoyl]-benzoic acid

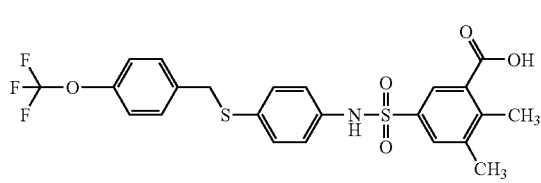

49% yield. MS: 510.2 (M−1); $^1$H NMR (400 MHz, CD$_3$OD): δ2.32 (s, 3H), 2.48 (s, 3H), 4.02 (s, 2H), 6.99 (m, 2H), 7.06 (d, 2H), 7.14 (m, 2H), 7.21 (m, 2H), 7.62 (t, 1H), 7.96 (d, 1H).

EXAMPLE 232

2-Ethyl-5-[2-(4-trifluoromethoxy-phenyl)-benzooxazol-5-ylsulfamoyl]-benzoic acid

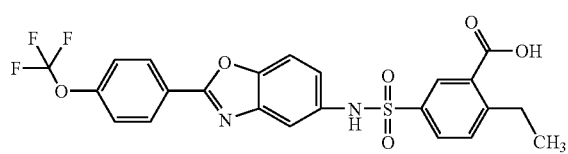

77% yield. MS: 507.3 (M+1); $^1$H NMR (400 MHz, CD$_3$OD): δ1.17 (t, 3H), 2.97 (q, 2H), 7.16 (m, 1H), 7.38 (d, 1H), 7.48 (m, 3H), 7.54 (d, 1H), 7.71 (m, 1H), 8.14 (d, 1H), 8.29 (m, 2H).

EXAMPLE 233

2-Ethyl-5-(4'-trifluoromethoxy-biphenyl-4-ylsulfamoyl)-benzoic acid

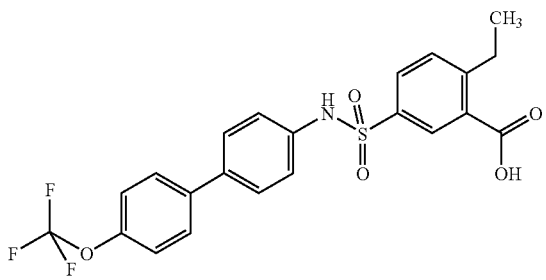

82% yield. MS: 464.2 (M−1); $^1$H NMR (400 MHz, CD$_3$OD): δ1.19 (t, 3H), 3.0 (q, 2H), 7.20 (m, 2H), 7.29 (d, 2H), 7.43 (d, 1H), 7.50 (m, 2H), 7.62 (m, 1H), 7.81 (m, 1H), 8.27 (d, 1H).

EXAMPLE 234

2-Isopropyl-5-[4-(4-trifluoromethoxy-benzylsulfanyl)-phenylsulfamoyl]-benzoic acid

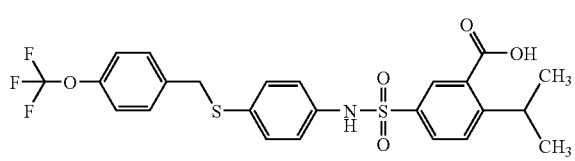

71% yield. MS: 524.2 (M−1); $^1$H NMR (400 MHz, CD$_3$OD): δ1.23 (d, 6H), 3.75 (m, 1H), 7.02 (m, 2H), 7.09 (d, 2H), 7.15 (m, 2H), 7.23 (m, 2H), 7.51 (d, 1H), 7.71 (m, 1H), 8.01 (d, 1H).

EXAMPLE 235

2-Methyl-5-[2-(4-trifluoromethoxy-phenyl)-benzooxazol-5-ylsulfamoyl]-benzoic acid

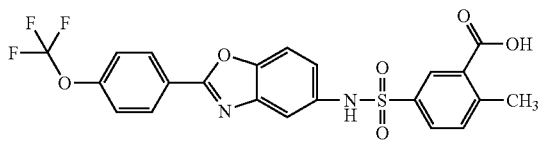

71% yield. MS: 493.2 (M+1); $^1$H NMR (400 MHz, CD$_3$OD): δ2.56 (s, 3H), 7.15 (m, 1H), 7.35 (d, 1H), 7.48 (c, 3H), 7.54 (c, 1H), 7.68 (m, 1H), 8.19 (d, 1H), 8.31 (d, 2H),

EXAMPLE 236

2-Ethyl-5-[4-(quinolin-2-ylmethylsulfanyl)-phenylsulfamoyl]-benzoic acid

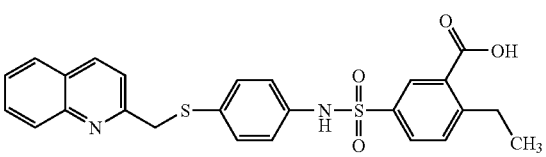

100% yield. MS: 479.4 (M+1); $^1$H NMR (400 MHz, CD$_3$OD): δ1.20 (t, 3H), 3.03 (q, 2H), 4.5 (d, 2H), 7.01 (m, 2H), 7.20 (m, 2H), 7.42 (d, 1H), 7.78 (c, 2H), 7.93 (m, 1H), 7.99 (d, 1H), 8.12 (m, 1H), 8.23 (d, 1H), 8.26 (d, 1H), 8.94 (d, 1H).

EXAMPLE 237

2-Isopronyl-5-[4-(quinolin-2-ylmethylsulfanyl)-phenylsulfamoyl]-benzoic acid

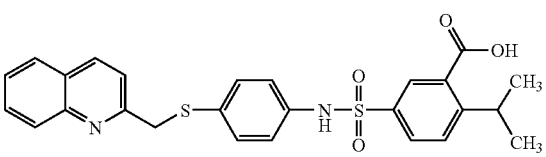

96% yield. MS: 493.3 (M+1); $^1$H NMR (400 MHz, CD$_3$OD): δ1.23 (d, 6H), 3.82 (m, 1H), 4.49 (s, 2H), 7.02 (m, 2H), 7.2 (m, 2H), 7.58 (d, 1H), 7.76 (d, 1H), 7.82 (m, 1H), 7.95 (m, 1H), 8.04 (m, 1H), 8.11 (c 2H), 8.25 (d, 1H), 8.92 (d, 1H).

EXAMPLE 238

2-Ethyl-5-[2-(4-trifluoromethyl-phenyl)-benzooxazol-5-ylsulfamoyl]-benzoic acid

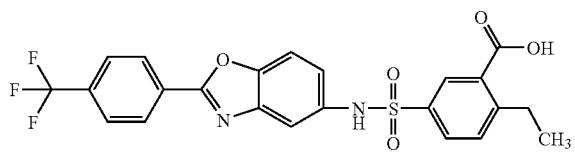

85% yield. MS: 491.3 (M+1); $^1$H NMR (400 MHz, CD$_3$OD): δ1.17 (t, 3H), 3.00 (q, 2H), 7.19 (m, 1H), 7.41 (d, 1H), 7.51 (d, 1H), 7.58 (d, 1H), 7.76 (m, 1H), 7.87 (d, 2H), 8.23 (d, 1H), 8.37 (d, 2H).

EXAMPLE 239

2-Methyl-5-[2-(4-trifluoromethyl-phenyl)-benzooxazol-5-ylsulfamoyl]-benzoic acid

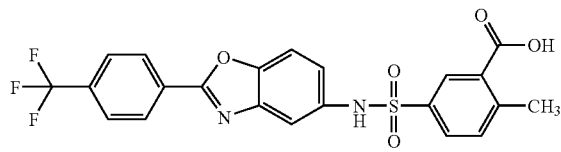

92% yield. MS: 477.3 (M+1); $^1$H NMR (400 MHz, CD$_3$OD): δ2.58 (s, 3H), 7.18 (m, 1H), 7.38 (d, 1H), 7.50 (d, 1H), 7.38 (d, 1H), 7.50 (d, 1H), 7.58 (d, 1H), 7.73 (m, 1H), 7.88 (d, 2H), 8.27 (d, 1H), 8.38 (d, 2H).

EXAMPLE 240

5-(4-Cyclohexylmethylsulfanyl-phenylsulfamoyl)-2-methyl-benzoic acid

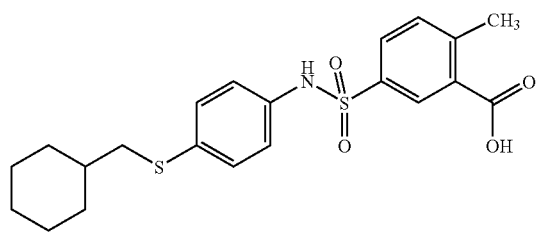

74% yield. MS: 418.0 (M−1); $^1$H NMR (400 MHz, CD$_3$OD): δ0.95 (c, 2H), 1.19 (c, 3H), 1.40 (c, 1H), 1.67 (c, 3H), 1.83 (c, 2H), 2.60 (s, 3H), 2.72 (d, 2H), 7.00 (m, 2H), 7.17 (m, 2H), 7.38 (d, 1H), 7.70 (m, 1H), 8.27 (d, 1H).

EXAMPLE 241

5-(4-Cyclobutylmethylsulfanyl-phenylsulfamoyl)-2-methyl-benzoic acid

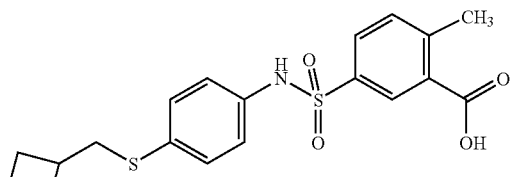

83% yield. MS: 390 (M−1); $^1$H NMR (400 MHz, CDCl$_3$): δ1.70 (c, 2H), 1.85 (c, 2H), 2.06 (c, 2H), 2.47 (m, 1H), 2.68 (s, 3H), 2.93 (d, 2H), 6.99 (m, 2), 7.20 (m, 2H), 7.34 (d, 1H), 7.75 (m, 1H), 8.47 (d, 1H).

EXAMPLE 242

2-Isopropyl-5-[4-(5-methyl-benzooxazol-2-yl)-phenylsulfamoyl]-benzoic acid

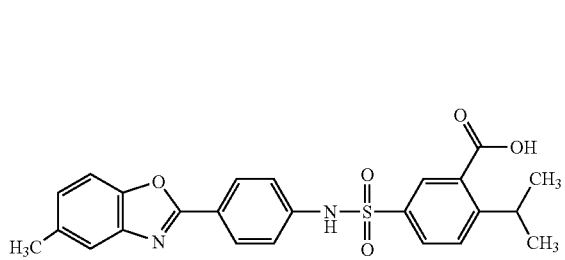

89% yield. MS: 451.3 (M+1); $^1$H NMR (400 MHz, CD$_3$OD): δ1.21 (d, 6H), 2.45 (s, 3H), 3.81 (m, 1H), 7.20 (d, 1H), 7.32 (d, 2H), 7.48 (d, 2H), 7.61 (d, 1H), 7.91 (m, 1H), 8.07 (d, 2H), 8.21 (d, 1H).

EXAMPLE 243

5-[4-(1H-Benzoimidazol-2-yl)-phenylsulfamoyl]-2-isopropyl-benzoic acid

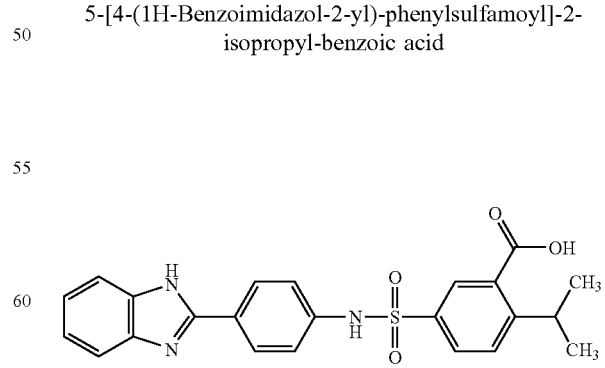

94% yield. MS: 436.3 (M+1); $^1$H NMR (400 MHz, CD$_3$OD): δ1.22 (d, 6H), 3.81 (m, 1H), 7.48 (m, 2H), 7.61 (c, 3H), 7.77 (c, 2H), 8.00 (c, 3H), 8.23 (d, 1H).

EXAMPLE 244

2-Isopropyl-5-[4-(3-trifluoromethoxy-benzylsulfanyl)-phenylsulfamoyl]-benzoic acid

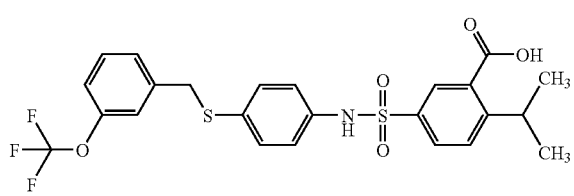

91% yield. MS: 524.3 (M−1); ¹H NMR (400 MHz, CD₃OD): δ1.23 (d, 6H), 3.82 (m, 1H), 7.00 (m, 2H), 7.08 (c, 3H), 7.16 (m, 2H), 7.25 (m, 1H), 7.55 (d, 1H), 7.76 (m, 1H), 8.11 (d, 1H).

EXAMPLE 245

2-Ethyl-5-[4-(3-trifluoromethoxy-benzylsulfanyl)-phenylsulfamoyl]-benzoic acid

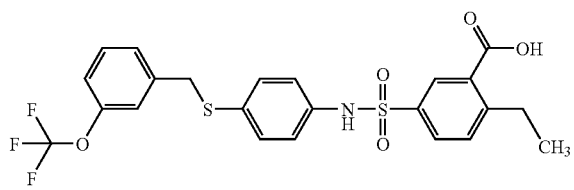

72% yield. MS: 510.1 (M−1); ¹H NMR (400 MHz, CD₃OD): δ1.20 (t, 3H), 3.03 (q, 2H), 4.04 (s, 2H), 6.99 (m, 2H), 7.08 (c, 3H), 7.16 (m, 2H), 7.25 (m, 1H), 7.40 (d, 1H), 7.73 (m, 1H), 8.24 (d, 1H).

EXAMPLE 246

2-Ethyl-5-(4'-propoxy-biphenyl-4-ylsulfamoyl)-benzoic acid

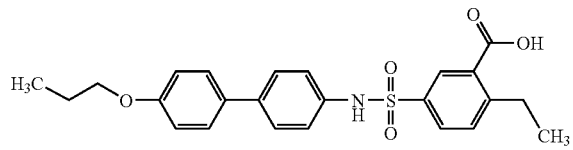

92% yield. MS: 438.3 (M−1); ¹H NMR (400 MHz, CD₃O(D): δ1.04 (t, 3H), 1.19 (t, 3H), 1.79 (m, 2H), 3.02 (q, 2H), 3.94 (t, 2H), 6.92 (m,2H), 7.13 (m, 2H), 7.43 (c, 5H), 7.78 (m, 1H), 8.26 (d, 1H).

EXAMPLE 247

2-Isopropyl-5-(4'-propoxy-biphenyl-4-ylsulfamoyl)-benzoic acid

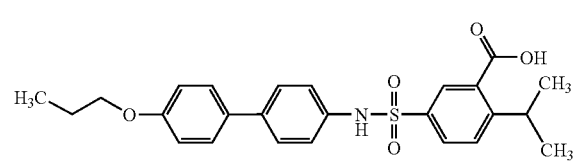

93% yield. MS: 452.3 (M−1); ¹H NMR (400 MHz, CD₃OD): δ1.04 (t, 3H), 1.22 (d, 6H), 1.79 (m, 2H), 3.81 (m, 1H), 3.94 (m, 2H), 6.93 (m, 2H), 7.14 (m, 2H), 7.44 (c, 4H), 7.57 (d, 1H), 7.80 (m, 1H), 8.13 (d, 1H).

EXAMPLE 248

5-[2-(4-tert-Butyl-phenyl)-benzooxazol-5-ylsulfamoyl]-2-isopropyl-benzoic acid

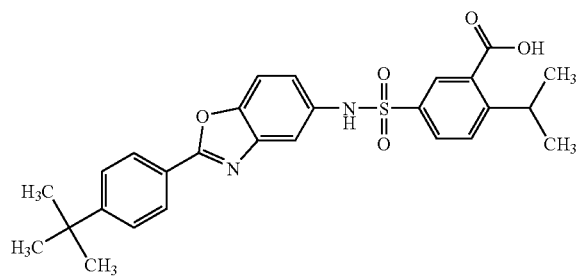

93% yield. MS: 493.4 (M+1); ¹H NMR (400 MHz, CD₃OD): δ1.20 (d, 6H), 1.37 (s, 9H), 3.80 (c, 1H), 7.13 (m,1H), 7.45 (d, 1H), 7.54 (t, 2H), 7.62 (d, 2H), 7.78 (m, 1H), 8.11 (m, 3H).

EXAMPLE 249

2-Methyl-5-[4-(5-trifluoromethyl-pyridin-2-ylcarbamoyl)-phenylsulfamoyl]-benzoic acid

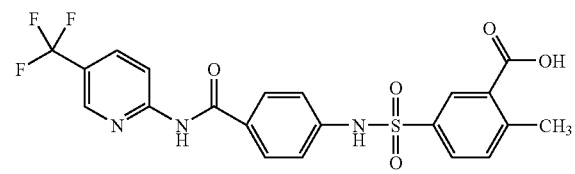

2% yield (material lost). MS: 478.0 (M−1); ¹H NMR (400 MHz, CD₃OD): δ2.49 (s, 3H), 7.19 (d, 1H), 7.28 (m, 4H), 7.67 (m, 1H), 7.85 (m, 2H), 8.05 (m, 2H).

EXAMPLE 250

5-[4-(5-Cyclohexyl-[1,3,4]oxadiazol-2-yl)-phenyl-sulfamoyl]-2-methyl-benzoic acid

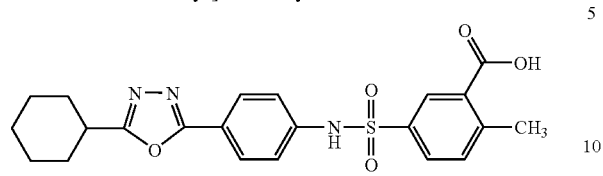

86% yield. MS: 442.0 (M+1); $^1$H NMR (400 MHz, CDCl$_3$): δ1.15–1.4 (c, 3H), 1.49–1.7 (c, 3H), 1.76 (c, 2H), 2.02 (c, 2H), 2.53 (s, 3H), 2.86 (c, 1H), 7.20 (m, 3H), 7.73 (m, 3H), 8.39 (d, 1H).

| Ex. | Chemical Structure | Chemical Name | Data |
|---|---|---|---|
| 251 | 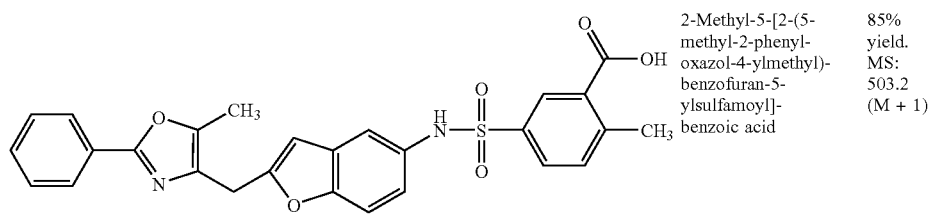 | 2-Methyl-5-[2-(5-methyl-2-phenyl-oxazol-4-ylmethyl)-benzofuran-5-ylsulfamoyl]-benzoic acid | 85% yield. MS: 503.2 (M + 1) |
| 252 | 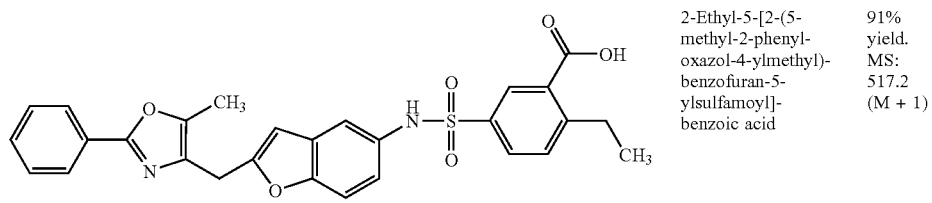 | 2-Ethyl-5-[2-(5-methyl-2-phenyl-oxazol-4-ylmethyl)-benzofuran-5-ylsulfamoyl]-benzoic acid | 91% yield. MS: 517.2 (M + 1) |
| 253 | 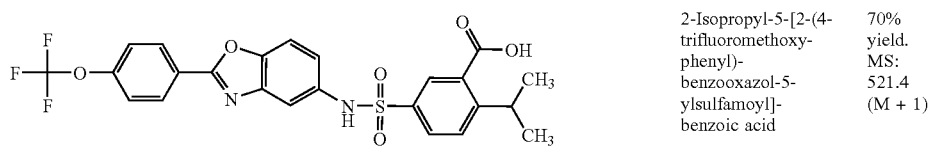 | 2-Isopropyl-5-[2-(4-trifluoromethoxy-phenyl)-benzooxazol-5-ylsulfamoyl]-benzoic acid | 70% yield. MS: 521.4 (M + 1) |
| 254 | 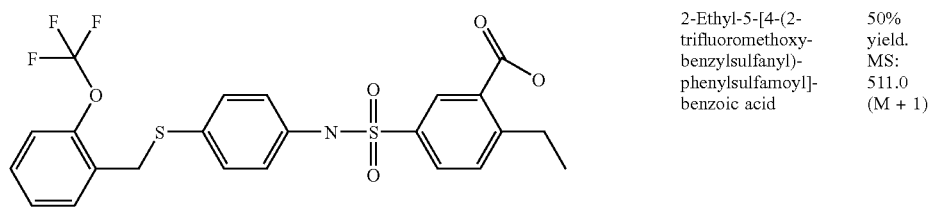 | 2-Ethyl-5-[4-(2-trifluoromethoxy-benzylsulfanyl)-phenylsulfamoyl]-benzoic acid | 50% yield. MS: 511.0 (M + 1) |
| 255 | 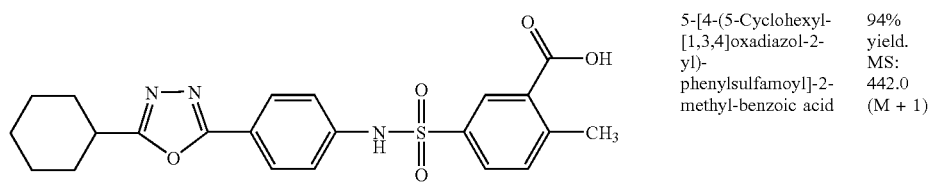 | 5-[4-(5-Cyclohexyl-[1,3,4]oxadiazol-2-yl)-phenylsulfamoyl]-2-methyl-benzoic acid | 94% yield. MS: 442.0 (M + 1) |

| Ex. | Chemical Structure | Chemical Name | Data |
|---|---|---|---|
| 256 | 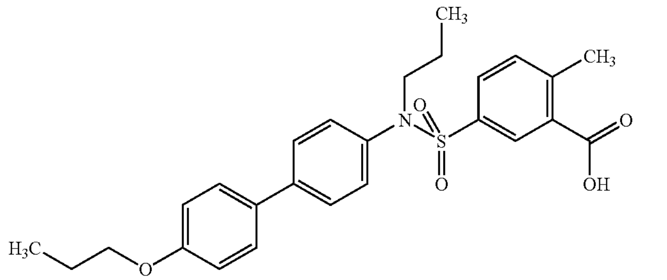 | 2-Methyl-5-[(4'-propoxy-biphenyl-4-yl)-propyl-sulfamoyl]-benzoic acid | 75% yield. MS: 468.1 (M + 1) |
| 257 | 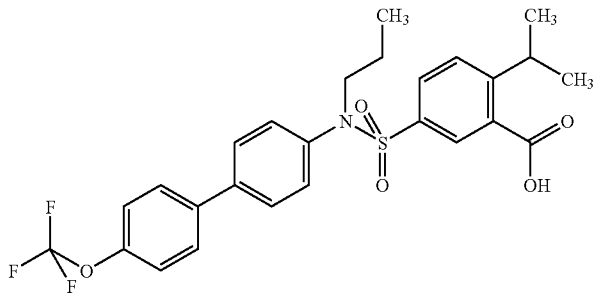 | 2-Isopropyl-5-[propyl-(4'-trifluoromeethoxy-biphhenyl-4-yl)-sulfamoyl]-benzoic acid | 75% yield. MS: 522.2 (M + 1) |
| 258 | 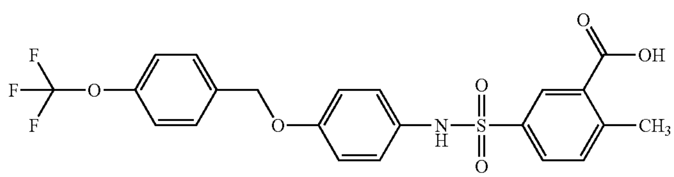 | 2-Methyl-5-[4-(4-trifluoromethoxy-benzyloxy)-phenylsulfamoyl]-benzoic acid | 95% yield. MS: 480.9 (M − 1) |

EXAMPLE 259

2-Methyl-5-[(4'-propoxy-biphenyl-4-yl)-propyl-sulfamoyl]-benzoic acid methyl ester

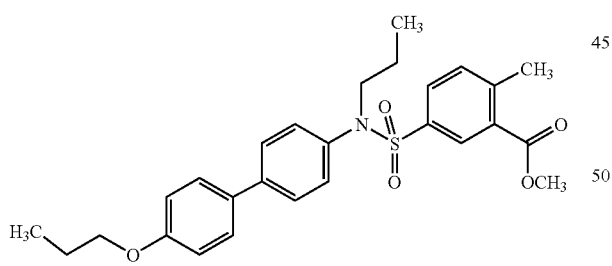

A mixture of 5-[(4'-hydroxy-biphenyl-4-yl)-propyl-sulfamoyl]-2-methyl-benzoic acid methyl ester (100 mg, 0.25 mmol), 1-iodopropane (36.7 μl, 0.38 mmol) and potassium carbonate (52 mg, 38 mmol) in 5 ml acetone was heated at 56° C. under nitrogen overnight. Additional 1-iodopropane was added (35.7 μl, 0.38 mmol) and the mixture was heated at 56° C. under nitrogen overnight. The reaction mixture was then cooled to room temperature and diluted with 40 ml ethyl acetate. The ethyl acetate solution was washed sequentially with 30 ml water and 30 ml brine, dried (anhydrous sodium sulfate) and concentrated under reduced pressure. The residue was purified by preparative thick layer chromatography (silica gel), eluting with 3:1 toluene/ethyl acetate to yield the title compound as an off-white solid (21 mg, 17% yield) along with 5-[(4'-hydroxy-biphenyl-4-yl)-propyl-sulfamoyl]-2-methyl-benzoic acid methyl ester (64 mg, 58% yield).

MS: 482.2 (M+1) 2-Methyl-5-[(4'-propoxy-biphenyl-4-yl)-propyl-sulfamoyl]-benzoic acid methyl ester MS: 440.1 (M+1) 5-[(4'-hydroxy-biphenyl-4-yl)-propyl-sulfamoyl]-2-methyl-benzoic acid methyl ester

EXAMPLE 260

2-Isopropyl-5-[propyl-(4'-trifluoromethoxy-biphenyl-4-yl)-sulfamoyl]-benzoic acid methyl ester

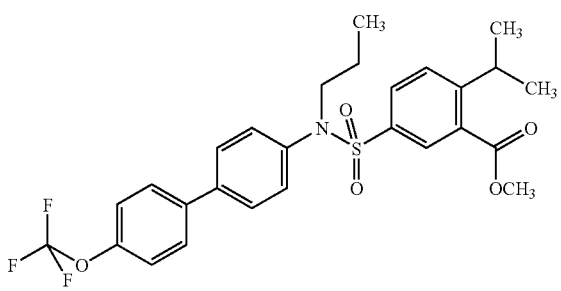

The title compound was prepared using a procedure analogous to that of EXAMPLE 257 but using 2-isopropyl- 5-(4'-trifluoromethoxy-biphenyl-4-ylsulfamoyl)-benzoic acid methyl ester in place of 5-[(4'-hydroxy-biphenyl-4-yl)-propyl-sulfamoyl]-2-methyl-benzoic acid methyl ester. 80% yield. MS: 564.2 (M+1).

EXAMPLE 261

4-(5-Methyl-benzooxazol-2-yl)-phenylamine

A mixture of 2-amino-p-cresol (1.5 g, 12 mmol), 4-aminobenzoic acid (1.67 g, 12 mmol) and 40 g polyphosphoric acid was heated at 190° C. under nitrogen for 6 h. The reaction mixture was cooled to room temperature and 300 ml water was added to the viscous liquid. The solid that precipitated was collected by filtration and dissolved in 200 ml ethyl acetate. The ethyl acetate solution was washed sequentially with 100 ml saturated aqueous sodium bicarbonate solution, 100 ml water and 100 ml brine, dried (anhydrous sodium sulfate) and concentrated under reduced pressure to yield the title compound as an off-white solid (2.43 g, 89% yield).

MS: 225.0 (M+1)

The title compounds of EXAMPLES 262–268 were prepared using procedures analogous to that of EXAMPLE 261 from appropriate starting materials.

| Ex. | Chemical Name | Data |
| --- | --- | --- |
| 262 | 4-Benzooxazol-2-yl-phenylamine | 85% yield. MS: 211.1 (M + 1) |
| 263 | 4-(5-Phenyl-benzooxazol-2-yl)-phenylamine | 92% yield. MS: 287.2 (M + 1) |
| 264 | 4-(5-Chloro-benzooxazol-2-yl)-phenylamine | 77% yield. MS: 245.1 (M + 1) |
| 265 | 4-Benzothiazol-2-yl-phenylamine | 59% yield. MS: 227.2 (M + 1) |
| 266 | 4-(1H-Benzoimidazol-2-yl)-phenylamine | 79% yield. MS: 210.2 (M + 1) |
| 267 | 3-(5-Methyl-benzooxazol-2-yl)-phenylamine | 83% yield. MS: 225.1 (M + 1) |
| 268 | 3-Benzothiazol-2-yl-phenylamine | 39% yield. MS: 227.1 (M + 1) |

EXAMPLE 269

4-(4-Trifluoromethyl-benzyloxy)-phenylamine

To a solution of p-aminophenol (0.200 g, 1.83 mmol), 4-trifluoromethylbenzyl alcohol (025 ml, 1.83 mmol) and triphenylphosphine (0.529 g, 2.02 mmol) in 5 ml anhydrous tetrahydrofuran was added diethyl azodicarboxylate (0.318 ml, 2.02 mmol). The reaction mixture was stirred overnight at room temperature under nitrogen. It was then diluted with 70 ml ethyl acetate and the resulting solution was washed sequentially with 50 ml saturated aqueous sodium bicarbonate solution, 50 ml water and 50 ml brine, dried (anhydrous sodium sulfate) and concentrated under reduced pressure. The solid residue was purified by flash column chromatography (silica gel, 15 g), eluting with 8:2 hexane/ethyl acetate to yield the title compound as an off-white solid (0.272 g, 55% yield). MS: 284.1 (M+1)

The title compounds of EXAMPLES 270–276 were prepared using procedures analogous to that of EXAMPLE 269 from appropriate starting materials.

| Ex. | Chemical Name | Data |
| --- | --- | --- |
| 270 | 4-(3,5-Dimethyl-benzyloxy)-phenylamine | 21% yield. MS: 228.3 (M + 1) |
| 271 | 4-(4-Butoxy-benzyloxy)-phenylamine | 19% yield. MS: 272.4 (M + 1) |
| 272 | 4-(2-Chloro-4-fluoro-benzyloxy)-phenylamine | 27% yield. MS: 252.2 (M + 1) |
| 273 | 4-(2,3-Difluoro-benzyloxy)-phenylamine | 29% yield. MS: 236.2 (M + 1) |
| 274 | 4-(3,5-Difluoro-benzyloxy)-phenylamine | 19% yield. MS: 236.2 (M + 1) |
| 275 | 4-(3,4-Difluoro-benzyloxy)-phenylamine | 29% yield. MS: 236.2 (M + 1) |
| 276 | 4-(4-Trifluoromethoxy-benzyloxy)-phenylamine | 26% yield. MS: 284.2 (M + 1) |

EXAMPLE 277

4-(4-Trifluoromethyl-benzylsulfanyl)-phenylamine

Sodium hydride [0.153 g (50% in mineral oil), 3.2 mmol] was added to a solution of 4-aminothiophenol (0.20 g, 1.6 mmol) in 5 ml anhydrous tetrahydrofuran. The resulting mixture was stirred at room temperature under nitrogen for 15 min, then 4-trifluoromethylbenzyl chloride (0.236 ml, 1.6 mmol) was added. The reaction mixture was stirred overnight at room temperature under nitrogen. Water (50 ml) was then added and the resulting mixture was extracted with 2×50 ml ethyl acetate. The combined ethyl acetate extracts were washed sequentially with 60 ml saturated aqueous sodium bicarbonate solution, 60 ml water and 60 ml brine, dried (anhydrous sodium sulfate) and concentrated under reduced pressure. The solid residue was purified by flash column chromatography (silica gel, 15 g), eluting with 85:15 hexane/ethyl acetate to yield the title compound as an off-white solid (0.318 g, 70% yield). MS: 284.1 (M+1)

The title compounds of EXAMPLE 278–304 were prepared using procedures analogous to that of EXAMPLE 277 from appropriate starting materials.

| Ex. | Chemical Name | Data |
| --- | --- | --- |
| 278 | 3-(4-Trifluoromethyl-benzylsulfanyl)-phenylamine | 66% yield. MS: 284.1 (M + 1) |
| 279 | 4-(3-Trifluoromethyl-benzylsulfanyl)-phenylamine | 58% yield. MS: 284.1 (M + 1) |
| 280 | 4-(4-t-Butyl-benzylsulfanyl)-phenylamine | 42% yield. MS: 272.2 (M + 1) |
| 281 | 4-(4-Isopropyl-benzylsulfanyl)-phenylamine | 56% yield. MS: 258.2 (M + 1) |

-continued

| Ex. | Chemical Name | Data |
|---|---|---|
| 282 | 4-(4-Trifluoromethoxy-benzylsulfanyl)-phenylamine | 46% yield.<br>MS: 300.1 (M + 1) |
| 283 | 4-(4-Chloro-benzylsulfanyl)-phenylamine | 45% yield.<br>250.1 (M + 1) |
| 284 | 4-(4-Ethyl-benzylsulfanyl)-phenylamine | 45% yield.<br>MS: 244.1 (M + 1) |
| 285 | 4-(4-Phenyl-benzylsulfanyl)-phenylamine | 21% yield.<br>MS: 292.1 (M + 1) |
| 286 | 4-(3-Phenoxy-benzylsulfanyl)-phenylamine | 50% yield.<br>MS: 308.1 (M + 1) |
| 287 | 4-[2-(4-Chloro-phenyl)-thiazol-4-ylmethylsulfanyl]-phenylamine | 25% yield.<br>MS: 333.1 (M + 1) |
| 288 | 4-(Quinolin-2-ylmethylsulfanyl)-phenylamine | 53% yield.<br>MS: 267.1 (M + 1) |
| 289 | 4-(5-Phenyl-[1,2,4]oxadiazol-3-ylmethylsulfanyl)-phenylamine | 46% yield.<br>MS: 284.2 (M + 1) |
| 290 | 4-(Naphthalen-2-ylmethylsulfanyl)-phenylamine | 53% yield.<br>MS: 266.3 (M + 1) |
| 291 | 4-(4-Fluoro-benzylsulfanyl)-phenylamine | 41% yield.<br>MS: 234.3 (M + 1) |
| 292 | 4-(3,4-Difluoro-benzylsulfanyl)-phenylamine | 66% yield.<br>MS: 252.2 (M + 1) |
| 293 | 4-(3,5-Bis-trifluoromethyl-benzylsulfanyl)-phenylamine | 45% yield.<br>MS: 352.2 (M + 1) |
| 294 | 4-(3-Trifluoromethyl-benzylsulfanyl)-phenylamine | 22% yield.<br>MS: 284.3 (M + 1) |
| 295 | 4-(3,4-Dimethyl-benzylsulfanyl)-phenylamine | 84% yield.<br>MS: 244.3 (M + 1) |
| 296 | 4-(2,4-Bis-trifluoromethyl-benzylsulfanyl)-phenylamine | 39% yield.<br>MS: 251.3 (M + 1) |
| 297 | 4-(2-Chloro-4-fluoro-benzylsulfanyl)-phenylamine | 65% yield.<br>MS: 268.2 (M + 1) |
| 298 | 4-(5,6-Difluoro-benzothiazol-2-ylmethylsulfanyl)-phenylamine | 22% yield.<br>MS: 309.2 (M + 1) |
| 299 | 4-(5-Fluoro-benzothiazol-2-ylmethylsulfanyl)-phenylamine | 38% yield.<br>MS: 291.1 (M + 1) |
| 300 | 4-(5,7-Difluoro-benzothiazol-2-ylmethylsulfanyl)-phenylamine | 36% yield.<br>MS: 309.0 (M + 1) |
| 301 | 4-(5-Trifluoromethyl-benzothiazol-2-ylmethylsulfanyl)-phenylamine | 17% yield.<br>MS: 341.2 (M + 1) |
| 302 | 4-(3-Trifluoromethoxy-benzylsulfanyl)-phenylamine | 39% yield.<br>MS: 300.1 (M + 1) |
| 303 | 4-(4-Cyclohexylmethylsulfanyl)-phenylamine | 49% yield.<br>MS: 222.1 (M + 1) |
| 304 | 4-(2-trifluoromethoxy-benzylsulfanyl)-phenylamine | 43% yield.<br>MS: 300.3 (M + 1) |

EXAMPLE 305

4-(3,5-Dimethyl-benzylsulfanyl)-nitrobenzene

To a solution of 4-nitrothiophenol (0.400 g, 2.57 mmol), 3,5-dimethylbenzyl alcohol (0.38 ml, 2.57 mmol) and triphenylphosphine (0.743 g, 2.84 mmol) in 10 ml anhydrous tetrahydrofuran was added diethyl azodicarboxylate (0.446 ml, 2.84 mmol). The reaction mixture was stirred overnight at room temperature under nitrogen. It was then diluted with 90 ml ethyl acetate and the resulting solution was washed sequentially with 70 ml saturated aqueous sodium bicarbonate solution, 70 ml water and 70 ml brine, dried (anhydrous sodium sulfate) and concentrated under reduced pressure. The solid residue was triturated with 95:5 hexane/ethyl acetate (20 ml) and filtered. The filtrate was concentrated under reduced pressure and the residue was purified by column chromatography (silica gel, 15 g), eluting with 95:5 hexane/ethyl acetate to yield title compound as a yellow solid (0.35 g, 50% yield). $^1$H NMR (400 MHz, CD$_3$Cl): $\delta$2.30 (s, 6H), 4.18 (s, 2H), 6.92 (s, 1H), 7.0 (s, 2H), 7.33 (d, 2H), 8.10 (d, 2H).

The title compounds of EXAMPLE 306–309 were prepared using procedures analogous to that of EXAMPLE 305 from appropriate starting materials.

EXAMPLE 306

4-(4-Butoxy-benzylsulfanyl)-nitrobenzene

26% yield. $^1$H NMR (400 MHz, CD$_3$Cl): $\delta$0.97 (t, 3H), 1.4–1.53 (c, 2H), 1.7–1.8 (c, 2H), 3.95 (m, 2H), 4.2 (s, 2H), 6.85 (d, 2H), 7.27 (d, 2H), 7.33 (d, 2H), 8.1 (d, 2H).

EXAMPLE 307

4-(2,3-Difluoro-benzylsulfanyl)-nitrobenzene

55% yield. $^1$H NMR (400 MHz, CD$_3$Cl): $\delta$4.28 (s, 2H), 7.0–7.16 (c, 3H), 7.37 (d, 2H), 8.13 (d, 2H).

EXAMPLE 308

4-(3,5-Difluoro-benzylsulfanyl)-nitrobenzene

33% yield. ¹H NMR (400 MHz, CD₃Cl): δ4.20 (s, 2H), 6.73 (m, 2H), 6.92 (m, 2H), 7.32 (m, 2H), 8.12 (m, 2H).

EXAMPLE 309

4-(4-Trifluoromethylsulfanyl-benzylsulfanyl)-nitrobenzene

55% yield. MS: 344.1 (M−1).

The title compounds of EXAMPLE 310–312 were prepared using procedures analogous to that of EXAMPLE 305 from appropriate starting materials but using 4-nitrophenol or 3-nitrophenol in place of 4-nitrothiophenol.

EXAMPLE 310

4-[2-(4-Nitro-phenoxy)-ethyl]-2-(4-trifluoromethoxy-phenyl)-thiazole

78% yield. MS: 411.1 (M+1)

EXAMPLE 311

4-[2-(4-Nitro-phenoxy)-ethyl]-2-(4-trifluoromethyl-phenyl)-thiazole

70% yield. MS: 395.1 (M+1)

EXAMPLE 312

3-(4-trifluoromethylbenzyloxy)-nitrobenzene

22% yield. MS: 296.1 (M−1)

EXAMPLE 313

4-(4-tert-butylphenoxy)nitrobenzene

Sodium hydride [0.16 g (50% in mineral oil), 3.33 mmol] was added to a solution of 4-tert-butylphenol (0.5 g, 3.33 mmol) in 5 ml dimethylformamide at room temperature. After 15 min 1-chloro-4-nitrobenzene (0.262 g, 1.66 mmol) was added and the reaction mixture was heated at 80° C. overnight. The reaction mixture was cooled to room temperature and diluted with 50 ml ethyl acetate. The ethyl acetate solution was washed sequentially with 3×40 ml water and 40 ml brine, dried (anhydrous sodium sulfate) and concentrated under reduced pressure.

The crude product (0.9 g) was purified by flash column chromatography (15 g silica gel), eluting with 98:2 hexane/ethyl acetate to yield the title compound as a yellowish solid (0.499 g, quantitative yield).

¹H NMR (400 MHz, CD₃Cl): δ1.35 (s, 9H), 7.0 (d, 2H), 7.43 (d, 2H), 8.19 (d, 2H).

EXAMPLE 314

4-(3,5-Dimethyl-benzylsulfanyl)-phenylamine

A mixture of 4-(3,5-dimethyl-benzylsulfanyl)-nitrobenzene (0.35 g, 1.28 mmol) calcium chloride (0.071 g, 0.64 mmol) and iron powder (−325 mesh) (0.573 g, 10.3 mmol) in 4 ml water and 17 ml ethanol was heated at reflux under nitrogen for 4.5 h. The reaction mixture was then cooled to room temperature, filtered through Celite and the filtrate was concentrated under reduced pressure. The residual oil was purified by column chromatography, eluting with 9:1 hexane/ethyl acetate to yield the title compound as a yellowish oil (0.29 g, 91% yield). MS: 244.3 (M+1)

The title compounds of EXAMPLE 315–327 were prepared using procedures analogous to that of EXAMPLE 314 from appropriate starting materials.

EXAMPLE 315

4-(4-Butoxy-benzylsulfanyl)-phenylamine

80% yield. ¹H NMR (400 MHz, CD₃Cl): δ0.96 (m, 3H), 1.4–1.52 (c, 2H), 1.7–1.8 (c, 2H), 3.85–3.96 (m, 4H), 6.57 (d, 2H), 6.77 (d, 2H), 7.07 (d, 2H), 7.13 (d, 2H).

| Ex. | Chemical Name | Data |
|---|---|---|
| 316 | 4-(2,3-Difluoro-benzylsulfanyl)-phenylamine | 91% yield. MS: 252.2 (M + 1) |
| 317 | 4-(3,5-Difluoro-benzylsulfanyl)-phenylamine | 84% yield. MS: 252.2 (M + 1) |
| 318 | 4-(4-Trifluoromethylsulfanyl-benzylsulfanyl)-phenylamine | 88% yield. MS: 316.1 (M + 1) |
| 319 | 4'-Propoxy-biphenyl-4-ylamine | 55% yield. MS: 228.3 (M + 1) |
| 320 | 4-(5-Cyclohexyl-[1,3,4]oxadiazol-2-yl)-phenylamine | 29% yield. MS: 244.2 (M + 1) |
| 321 | 2-(4-tert-Butyl-phenyl)-benzooxazol-5-ylamine | 97% yield. MS: 267.3 (M + 1) |
| 322 | 2-(4-Trifluoromethoxy-phenyl)-benzooxazol-5-ylamine | 99% yield. MS: 295.3 (M + 1) |
| 323 | 2-(4-Trifluoromethyl-phenyl)-benzooxazol-5-ylamine | 90% yield. MS (279.3 (M + 1) |
| 324 | 4-{2-[2-(4-Trifluoromethoxy-phenyl)-thiazol-4-yl]-ethoxy}-phenylamine | 90% yield. MS: 381.2 (M + 1) |
| 325 | 4-{2-[2-(4-Trifluoromethyl-phenyl)-thiazol-4-yl]-ethoxy}-phenylamine | 70% yield. MS: 365.2 (M + 1) |

-continued

| Ex. | Chemical Name | Data |
|---|---|---|
| 326 | 4-(4-tert-Butyl-phenoxy)-phenylamine | 80% yield.<br>MS: 242.4 (M + 1) |
| 327 | 3-(4-trifluoromethylbenzyloxy)-phenylamine | 77% yield.<br>MS: 268.1 (M + 1) |

EXAMPLE 328

4'-Trifluoromethoxy-biphenyl-4-ylamine

A mixture of 4-trifluoromethoxylbenzeneboronic acid (300 mg, 1.45 mmol), p-bromoaniline (100 mg, 0.58 mmol), dichloro[1,1'-bis(diphenylphosphino)ferrocene]palladium (II) dichloromethane adduct (24 mg,0.029 mmol), 1,1'-bis(diphenylphosphino)ferrocene (16 mg, 0.029 mmol) and potassium carbonate (0.58 ml of a 2M aqueous solution, 1.16 mmol) in 5 ml 1,4-dioxane was heated at reflux under nitrogen for 20 hr. The reaction mixture was cooled to room temperature, diluted with 40 ml water and extracted with 2×40 ml ethyl acetate. The combined ethyl acetate extracts were washed with 40 ml brine, dried over anhydrous sodium sulfate and concentrated under reduced pressure. The crude product was purified by flash column chromatography (silica gel, 15 g), eluting with 10:1 hexane/ethyl acetate to yield the title compound as a tan solid (70 mg, 48% yield). MS: 254.1 (M+1)

EXAMPLE 329

2-Cyclohexyl-5-(4-nitro-phenyl)-[1,3,4]oxadiazole

A mixture of 5-(4-nitro-phenyl)-1H-tetrazole (0.5 g, 2.62 mmol) and cyclohexane carbonyl chloride (0.35 ml, 2.62 mmol) in 3 ml anhydrous pyridine was stirred at room temperature under nitrogen for 20 min, then heated to 60° C. for 1 hr and finally heated to 100° C. for 2 h. The reaction mixture was cooled to room temperature then poured onto ice (30 g) and the aqueous mixture was extracted with 30 ml ethyl acetate. The ethyl acetate solution was washed sequentially with 30 ml water, 30 ml 1N aqueous hydrochloric acid solution and 30 ml brine, dried (anhydrous sodium sulfate) and concentrated under reduced pressure. The crude produce was purified by flash column chromatography (silica gel, 40 g), eluting with 4:1 hexane/ethyl acetate to yield the title compound as a yellowish solid (0.5 g, 100% yield). MS: 274.2 (M+1)

EXAMPLE 330

4-Nitro-4'propoxybiphenyl

To a solution of 4-hydroxy-4'nitrobiphenyl in 5 ml acetone was added potassium carbonate (240 mg, 1.74 mmol) and 1-iodopropane (0.17 ml, 1.74 mmol). The reaction mixture was heated at reflux for 24 h. Additional potassium carbonate (240 mg, 1.74 mmol) and 1-iodopropane (0.17 ml, 1.74 mmol) was added and the reaction mixture was heated at reflux for 24 h. The reaction mixture was cooled to room temperature and diluted with 30 ml ethyl acetate. The ethyl acetate solution was washed sequentially with 25 ml water and 25 ml brine, dried (anhydrous sodium sulfate) and concentrated under reduced pressure. The crude product was purified by column chromatography (silica gel), eluting with 14:1 hexane/ethyl acetate to yield the title compound (0.267 g, 89% yield) MS: 258.3 (M−1)

EXAMPLE 331

2-(4-tert-Butyl-phenyl)-5-nitro-benzooxazole 4-tert-Butyl-N-(2-hydroxy-5-nitro-phenyl)-benzamide 4-Dimethylaminopyridine (2.62 g, 21.4 mmol) was added portionwise with stirring to a solution of 4-tert-butylbenzoyl chloride (3.8 ml, 19.5 mmol) and 2-amino-4-nitrophenol (3.0 g, 19.5 mmol) in 60 ml methylene chloride. The resulting solution was stirred overnight at room temperature. The reaction solution was diluted with 60 ml methylene chloride and washed with 3×50 ml water. The methylene chloride solution was separated, filtered to remove precipitated solid, dried (anhydrous sodium sulfate) and concentrated to dryness under reduced pressure to yield the title compound as a brownish solid (5.01 g, 82% yield).

2-(4-tert-Butyl-phenyl)-5-nitro-benzooxazole

Diethyl azodicarboxylate (0.275 ml, 1.75 mmol) was added dropwise with stirring to a solution of 4-tert-butyl-N-(2-hydroxy-5-nitro-phenyl)-benzamide (0.5 g, 1.59 mmol) and triphenylphosphine (0.458 g, 1.75 mmol) in 15 ml anhydrous tetrahydrofuran. The reaction mixture was stirred overnight at room temperature, then diluted with 75 ml ethyl acetate. The ethyl acetate solution was washed sequentially with 50 ml water and 50 ml brine, dried (anhydrous sodium sulfate) and concentrated to dryness under reduced pressure. The residue was purified by flash column chromatography (40 g silica gel), eluting with 9:1 hexane/ethyl acetate to yield a yellowish solid (0.305 g), which was further purified by column chromatography (15 g silica gel), eluting with 95:5 hexane/ethyl acetate, to yield the title compound as a yellowish solid (0.125 g, 27% yield). MS: 297.3 (M+1)

The title compounds of EXAMPLE 332–333 were prepared using procedures analogous to that of EXAMPLE 331 from appropriate starting materials.

EXAMPLE 332

2-(4-Trifluoromethoxy-phenyl)-5-nitro-benzooxazole

4-Trifluoromethoxy-N-(2-hydroxy-5-nitro-phenyl)-benzamide

100% yield 2-(4-Trifluoromethoxy-phenyl)-5-nitro-benzooxazole

66% yield. MS: 325.2 (M+1)

EXAMPLE 333

2-(4-Trifluoromethoxy-phenyl)-5-nitro-benzooxazole

4-Trifluoromethyl-N-(2-hydroxy-5-nitro-phenyl)-benzamide

83% yield 2-(4-Trifluoromethyl-phenyl)-5-nitro-benzooxazole

93% yield. MS: 309.3 (M+1).

EXAMPLE 334

5-Chlorosulfonyl-2-methyl-benzoic acid

A mixture of o-toluic acid (15 g, 0.11 mol) and chlorosulfonic acid (30 ml) was heated at 100° C. under nitrogen for 2.5 h. The reaction mixture was then poured onto ice (500 ml) and the resulting precipitate was filtered, yielding the title compound as an off-white solid (20 g, 78% yield). MP 151–155° C.

The title compounds of EXAMPLE 335–337 were prepared using a procedure analogous to that of EXAMPLE 334 from appropriate starting materials.

EXAMPLE 335

3-Chlorosulfonyl-2,6-dimethyl-benzoic acid

28% yield. $^1$H NMR (400 MHz, CD$_3$OD) δ 2.44 (s, 3H), 2.72 (s, 3H), 7.41 (d, 1H), 8.02 (d, 1H),

EXAMPLE 336

5-Chlorosulfonyl-2,3-dimethyl-benzoic acid

77% yield. $^1$H NMR (400 MHz, CDCl$_3$) δ 2.49 (s, 3H), 2.66 (s, 3H), 7.98 (s, 1H), 8.47 (s, 1H).

EXAMPLE 337

5-Chlorosulfonyl-2-ethyl-benzoic acid

76% yield. MS: 247.0 (M−1).

EXAMPLE 338

5-Chlorosulfonyl-2-methyl-benzoic acid methyl ester

Chlorosulfonic acid (106.2 ml) was carefully added over 1 min with stirring under nitrogen to 2-methyl-benzoic acid methyl ester (55.9 ml, 0.4 mol). The reaction mixture was placed in an oil bath preheated to 100° C. for 15 min, then poured onto ice (1000 ml). The resulting precipitate was filtered and dissolved in ethyl acetate (400 ml). The ethyl acetate solution was washed sequentially with 10×300 ml saturated aqueous sodium bicarbonate, 300 ml water and 300 ml brine, dried (anhydrous sodium sulfate) and concentrated under reduced pressure to yield the title compound as a yellowish oil (37.3 g, 37% yield). $^1$H NMR (400 MHz, CDCl$_3$) δ, 2.74 (s, 3H), 3.96 (s, 3H), 7.52 (d, 1H), 8.04 (m, 1H), 8.58 (d, 1H).

The title compounds of EXAMPLE 339–343 were prepared using procedures analogous to that of EXAMPLE 338 from appropriate starting materials.

EXAMPLE 339

5-Chlorosulfonyl-2-ethyl-benzoic acid methyl ester

42% yield. $^1$H NMR (400 MHz, CDCl$_3$) δ 1.29 (t, 3H), 3.11 (q, 2H), 3.96 (s, 3H), 7.54 (d, 1H), 8.06 (m, 1H), 8.53 (d, 1H).

EXAMPLE 340

5-Chlorosulfonyl-2-isopropyl-benzoic acid methyl ester

47% yield. $^1$H NMR (400 MHz, CDCl$_3$)δ 1.3 (d, 6H), 3.87 (m, 1H), 3.96 (s, 3H), 7.67 (d, 1H), 8.08 (m, 1H), 8.41 (d, 1H).

EXAMPLE 341

5-Chlorosulfonyl-2,3-dimethyl-benzoic acid methyl ester

41% yield. $^1$H NMR (400 MHz, CDCl$_3$) δ 2.45 (s, 3H), 2.58 (s, 3H), 3.95 (s, 3H), 7.92 (d, 1H), 8.31 (d, 1H).

EXAMPLE 342

5-Chlorosulfonyl-2-ethoxy-benzoic acid ethyl ester

10% yield. $^1$H NMR (400 MHz, CDCl3) d 1.43 (t, 3H), 1.52 (t, 3H), 4.24 (q, 2H), 4.40 (q, 2H), 7.10 (d, 1H), 8.09 (m, 1H), 8.43 (d, 1H).

EXAMPLE 343

5-Chlorosulfonyl-2-methylsulfanyl-benzoic acid methyl ester

58% yield. $^1$H NMR (400 MHz, CDCl3) d 2.55 (s, 3H), 3.98 (s, 3H), 7.47 (d, 1H), 8.05 (m, 1H), 8.64 (d, 1H).

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A compound
   5-[4-(4-Ethyl-benzylsulfanyl)-phenylsulfamoyl]-2-methyl-benzoic acid;
   or a pharmaceutically acceptable salt of said compound.
2. A method for treating dyslipidemia, obesity, overweight condition, hypertriglyceridemia, hyperlipidemia, hypoalphalipoproteinemia, metabolic syndrome, diabetes mellitus (Type I and/or Type II), hyperinsulinemia, impaired glucose tolerance, insulin resistance, diabetic complications, athero- sclerosis, hypertension, coronary heart disease, hypercholesterolemia, inflammation, osteoporosis, thrombosis, peripheral vascular disease, cognitive dysfunction, or congestive heart failure in a mammal by administering to a mammal in need of such treatment a therapeutically effective amount of a compound of claim 1, or a pharmaceutically acceptable salt of said compound.

3. A pharmaceutical composition which comprises a therapeutically effective amount of a compound of claim 1, or a pharmaceutically acceptable salt of said compound and a pharmaceutically acceptable carrier, vehicle or diluent.

4. A pharmaceutical combination composition comprising: a therapeutically effective amount of a composition comprising
a first compound, said first compound being a compound of claim 1, or a pharmaceutically acceptable salt of said compound;
a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor, a bile acid sequestrant, or a prodrug of said compound or a pharmaceutically acceptable salt of said compound or prodrug; and
a pharmaceutically acceptable carrier, vehicle or diluent.

5. A pharmaceutical combination composition of claim 4 wherein the second compound is an HMG-CoA reductase inhibitor or a CETP inhibitor.

6. A pharmaceutical combination composition of claim 5 wherein the second compound is rosuvastatin, rivastatin, pitavastatin, lovastatin, simvastatin, pravastatin, fluvastatin, atorvastatin, cerivastatin, or [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester or a prodrug of said compound or a pharmaceutically acceptable salt of said compound or prodrug.

7. A method for treating atherosclerosis in a mammal comprising administering to a mammal in need of treatment thereof;
a first compound, said first compound being a compound of claim 1, or a pharmaceutically acceptable salt of said compound; and
a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor or a bile acid sequestrant
wherein the amounts of first and second compounds result in a therapeutic effect.

8. A method for treating atherosclerosis of claim 7 wherein the second compound is an HMG-CoA reductase inhibitor or a CETP inhibitor.

9. A method for treating atherosclerosis of claim 8 wherein the second compound is rosuvastatin, pitavastatin, lovastatin, simvastatin, pravastatin, fluvastatin, atorvastatin, cerivastatin, or [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester or a prodrug of said compound or a pharmaceutically acceptable salt of said compound or prodrug.

10. A kit for achieving a therapeutic effect in a mammal comprising packaged in association a first therapeutic agent comprising a therapeutically effective amount of a compound of claim 1, or a pharmaceutically acceptable salt of said compound and a pharmaceutically acceptable carrier, a second therapeutic agent comprising a therapeutically effective amount of an HMG CoA reductase inhibitor, a CETP inhibitor, a cholesterol absorption inhibitor, a cholesterol synthesis inhibitor, a fibrate, niacin, slow-release niacin, a combination of niacin and lovastatin, an ion-exchange resin, an antioxidant, an ACAT inhibitor or a bile acid sequestrant and a pharmaceutically acceptable carrier and directions for administration of said first and second agents to achieve the therapeutic effect.

11. A kit of claim 10 wherein said second compound is an HMG-CoA reductase inhibitor or CETP inhibitor.

12. A kit of claim 11 wherein said second compound is rosuvastatin, pitavastatin, lovastatin, simvastatin, pravastatin, fluvastatin, atorvastatin, cerivastatin, or [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester or a prodrug of said compound or a pharmaceutically acceptable salt of said compound or prodrug.

13. A method for treating negative energy balance in ruminants by administering to a ruminant in need of such treatment a therapeutically effective amount of a compound of claim 1, or a pharmaceutically acceptable salt of said compound.

* * * * *